US012570650B2

(12) United States Patent
Abbineni et al.

(10) Patent No.: US 12,570,650 B2
(45) Date of Patent: Mar. 10, 2026

(54) 6-SUBSTITUTED PYRIDAZINE COMPOUNDS AS SMARCA2 AND/OR SMARCA4 DEGRADERS

(71) Applicant: Aurigene Oncology Limited, Bangalore (IN)

(72) Inventors: Chandrasekhar Abbineni, Hyderabad (IN); Susanta Samajdar, Bangalore (IN); Bilash Kuila, Howrah (IN); Subhendu Mukherjee, Hooghly (IN); Suraj Tatyasaheb Gore, Taluka: Rahata (IN)

(73) Assignee: Aurigene Oncology Limited, Bangalore (IN)

( * ) Notice: Subject to any disclaimer, the term of this patent is extended or adjusted under 35 U.S.C. 154(b) by 509 days.

(21) Appl. No.: 18/019,721

(22) PCT Filed: Aug. 3, 2021

(86) PCT No.: PCT/IB2021/057089
§ 371 (c)(1),
(2) Date: Feb. 3, 2023

(87) PCT Pub. No.: WO2022/029617
PCT Pub. Date: Feb. 10, 2022

(65) Prior Publication Data

US 2024/0018134 A1 Jan. 18, 2024

(30) Foreign Application Priority Data

Aug. 4, 2020 (IN) ............................ 202041033326

(51) Int. Cl.
*C07D 417/14* (2006.01)
*A61P 35/00* (2006.01)

(52) U.S. Cl.
CPC ............ *C07D 417/14* (2013.01); *A61P 35/00* (2018.01)

(58) Field of Classification Search
CPC .................................................... C07D 417/14
See application file for complete search history.

(56) References Cited

U.S. PATENT DOCUMENTS

| | | | |
|---|---|---|---|
| 2019/0300521 A1 | 10/2019 | Crew et al. | |
| 2021/0253564 A1 | 8/2021 | Sasmal et al. | |

FOREIGN PATENT DOCUMENTS

| | | | |
|---|---|---|---|
| WO | 2016105518 A1 | 6/2016 | |
| WO | 2016138114 A1 | 9/2016 | |
| WO | 2017007612 A1 | 1/2017 | |
| WO | 2017011371 A1 | 1/2017 | |
| WO | 2017030814 A1 | 2/2017 | |
| WO | 2019195201 A1 | 10/2019 | |
| WO | WO-2019207538 A1 * | 10/2019 | ......... C07K 5/06052 |

OTHER PUBLICATIONS

Hoffman et al., Functional epigenetics approach identifies BRM/SMARCA2 as a critical synthetic lethal target in BRG1-deficient cancers, Feb. 25, 2014, PNAS, 111(8): 3128-3133.
Karnezis et al., Dual loss of the SWI/SNF complex ATPases SMARCA4/BRG1 and SMARCA2/BRM is highly sensitive and specific for small cell carcinoma of the ovary, hypercalcaemic type, J Pathol 2016, 238:389-400.
Vangamudi et al., The SMARCA2/4 ATPase Domain Surpasses the Bromodomain as a Drug Target in SWI/SN-Mutant Cancers: Insights from cDNA Rescue and PFI-3 Inhibitor Studies, Sep. 15, 2015, Cancer Research, 75(18):3865-3878.
Nandi et al., The ubiquitin-proteasome system, J. Biosci 2006, 31:137-155.
Shen et al., Targeting the ubiquitin-proteasome system for cancer therapy, Sep. 2013, Expert Opin Ther Targets, 17(9):1091-1108.
Huang, X. and Dixit, V.M., Drugging the undruggables: exploring the ubiquitin system for drug development, Cell Research 2016, 26:484-498.
Bondeson et al., Lessons in PROTAC Design from Selective Degradation with a Promiscuous Warhead, Jan. 18, 2018, Cell Chemical Biology, 25:78-87.
Gerstenberger et al., Identification of a chemical probe for family VIII bromodomains through optimization of a fragment hit, May 26, 2016, J Med Chem., 59(10):4800-4811.
Sutherell et al., Identification and Development of 2,3-Dihydorpyrrolo[1,2-a]-5(1H)-one Inhibitors Targeting Bromodomains within the Switch/Sucrose Nonfermenting Complex, Journal of Medicinal Chemistry 2016, 59:5095-5101.

* cited by examiner

*Primary Examiner* — James D. Anderson
(74) *Attorney, Agent, or Firm* — Benjamin Aaron Adler

(57) ABSTRACT

The present invention provides 6-substituted pyridazine compounds of formula (I)

(I)

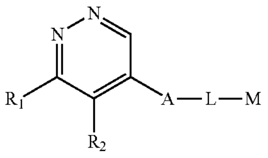

which are therapeutically useful as SMARCA2 and/or SMARCA4 degraders. These compounds are useful in the treatment and/or delaying progression of diseases or disorders dependent upon SMARCA2 and/or SMARCA4 in a subject. The present invention also provides preparation of the compounds and pharmaceutical compositions comprising at least one of the compounds of formula (I) or a pharmaceutically acceptable salt, or a stereoisomer or a tautomer or a prodrug thereof.

27 Claims, No Drawings

6-SUBSTITUTED PYRIDAZINE COMPOUNDS AS SMARCA2 AND/OR SMARCA4 DEGRADERS

RELATED APPLICATION

This application is a national stage application under 35 U.S.C. § 371 of pending international application PCT/IB2021/057089, filed on 3 Aug. 2021, which claims the benefit of Indian provisional application No. 20/204, 1033326, filed on 4 Aug. 2020, now abandoned; the specifications of which are hereby incorporated by reference in their entireties.

FIELD OF THE INVENTION

The present invention relates to 6-substituted pyridazine compounds, a pharmaceutically acceptable salt or a stereoisomer or a tautomer or a prodrug thereof which are useful as SMARCA2 and/or SMARCA4 degraders for the treatment of diseases or disorders dependent upon SMARCA2 and/or SMARCA4. The present invention also relates to a method of preparation of the said pyridazine compounds and pharmaceutical compositions comprising the said compounds.

BACKGROUND OF THE INVENTION

One of the most significant findings from the cancer genome profiling is the discovery of frequent mutations in various subunits of the mammalian SWI/SNF (SWItch/Sucrose Non-Fermentable) chromatin remodelling complex. Approximately 20% of human cancers are associated with somatic mutations in subunits of the SWI/SNF complex, a chromatin remodelling complex that influences gene regulation by disrupting histone-DNA contacts (PNAS Feb. 25, 2014. 111 (8) 3128-3133).

SWI/SNF complexes contain either of two closely related and evolutionarily conserved catalytic ATPase subunits: Brahma (BRM/SMARCA2) or Brahma-related gene 1 (BRG1/SMARCA4). They share approximately 75% identity at the protein level. Although BRG1- and BRM-containing complexes show some redundancy, they may function distinctively. In human cancer, BRG1 seems to be one of the most frequently mutated subunit genes, whereas the BRM gene is rarely mutated. BRG1/SMARCA4 mutations occurring in ~10-15% of lung adenocarcinomas. BRM/SMARCA2 is essential for the growth of tumour cells that harbour loss of function mutations in BRG1/SMARCA4. Depletion of BRM in BRG1-deficient cancer cells leads to a cell cycle arrest, induction of senescence, and increased levels of global H3K9me31 (PNAS Feb. 25, 2014, 111 (8), 3128-3133).

In some tumour types, mutations within the SWI/SNF complex lead to context specific vulnerabilities such as the requirement of SMARCA2 for survival of tumour cells lacking SMARCA4. This finding of SMARCA2/4 synthetic lethal relationship translates in vivo which emphasizes SMARCA2 as a promising therapeutic target for the treatment of SMARCA4-deficient cancers. Moreover, the SMARCA4-deficient patient population generally lacks targetable oncogenes (such as mutant EGFR or ALK translocations), which further emphasizes the potential of developing SMARCA2 inhibitors. Characterization of SMARCA4 function in tumours with high SMARCA4 levels, shows effects on signalling pathways that result in increased proliferation and survival. SMARCA4 knockdown in tumours that show elevated levels known to inhibit proliferation and other cancer cell properties. Studies have also shown that SMARCA4 knockdown/modulation increases sensitivity to known chemotherapeutic agents, thereby indicating that SMARCA4 targeting could also be an adjuvant therapy to existing chemotherapeutic approaches (PNAS Feb. 25, 2014. 111 (8) 3128-3133; J Pathol. 2016 February; 238(3): 389-400).

Contrary to genetic silencing of SMARCA2 leading to potent anti-proliferative activity in SMARCA4-deficient cancer cell lines, PFI-3, a selective cell permeable SMARCA2/4 bromodomain inhibitor capable of binding to SMARCA2 and SMARCA4 bromodomain, fails to display an antiproliferative phenotype which indicates that bromodomain function of SMARCA2/4 is dispensable for tumor cell proliferation, while the catalytic ATPase activity is essential (Cancer Res. 2015 Sep. 15; 75(18): 3865-3878). In order to mimic the phenotype achieved by genetic silencing, approaches that lead to reduction or complete elimination of SMARCA2/4 may be needed.

The ubiquitin-proteasome system (UPS) is a major pathway that regulates the levels of intracellular proteins and provides a fine balance between protein synthesis and degradation required for normal maintenance of cellular function, including proliferation, differentiation, and cell death. Ubiquitination is a post-translational modification, where a small protein, ubiquitin, is covalently attached to lysine residues on a substrate protein carried out sequentially by a cascade of enzymatic reactions involving an intimate collaboration between E1 activating, E2 conjugating and E3 ligating enzymes and subsequent degradation of the tagged proteins (J. Biosci. 31(1), March 2006, 137-155; Expert Opin Ther Targets. 2013 September; 17(9): 1091-1108 and Cell Research (2016) 26:484-498).

Proteolysis targeting chimeras are the heterobifunctional molecules contain a ligand for a target protein of interest connected via a linker to a ligand for an E3 ubiquitin ligase. Upon such bi-functional molecule-mediated heterodimerization of the two bound proteins, the target protein is ubiquitinated and degraded by the proteasome in cells. Many such bi-functional molecules have been developed to recruit E3 ubiquitin ligases to a variety of substrates using high-affinity ligands for the protein of interest. Proteins effectively degraded using these approaches include RIPK2 and ERRα, BRD4, BRD9, BCR/Abl and Abl and Erα (Cell Chemical Biology 25, 1-10, Jan. 18, 2018). E3 ubiquitin ligases (of which over 600 are known in humans) confer substrate specificity for ubiquitination and are more attractive therapeutic targets than general proteasome inhibitors due to their specificity for certain protein substrates.

Small molecule ligands targeting the bromodomains of SMARCA2 and SMARCA4 have been reported (Gerstenberger et al., Journal of Medicinal Chemistry 2016, 59, 4800-4811; Hoffman et al., PNAS, 2014b, 777, 3128-3133; Sutherell et al., 2016, Journal of Medicinal Chemistry 59, 5095-5101; WO2016138114). Although cells lacking SMARCA4 activity are vulnerable to the loss of SMARCA2 (Hoffman et al., 2014a, PNAS 777, 3128-3133), SMARCA2/4 inhibitors have failed to phenocopy these anti-proliferative effects (Vangamudi et al., 2015). In agreement with this, re-expression of SMARCA2 variants in cells, where the endogenous protein had been suppressed, showed that an intact bromodomain is not required to maintain proliferation (Vangamudi et al., 2015, Cancer Research 75, 3865-3878). SMARCA2/4BD inhibitors are thus precluded from use for the treatment of SMARCA4 mutant cancers but could provide attractive ligands for PROTAC conjugation.

It is therefore reasoned that a PROTAC targeting the non-functional bromodomain of SMARCA2/4 should offer an opportunity to exploit the vulnerability of SMARCA2 in SMARCA4 mutated cancer cells for therapeutic purposes. The principle of conjugation of a suitable SMARCA ligand with an E3 ligase binder has been described in WO 2016/105518; WO2017/007612 and WO2017/011371. However, in none of the publications a concrete example and corresponding degradation of SMARCA proteins has been demonstrated.

SUMMARY OF THE INVENTION

Provided herein are 6-substituted pyridazine compounds and pharmaceutical compositions thereof that are useful as SMARCA2 and/or SMARCA4 degraders and for the treatment of diseases or disorders dependent upon or mediated by SMARCA2 and/or SMARCA4.

In one aspect, the present invention provides compounds of formula (I):

(I)

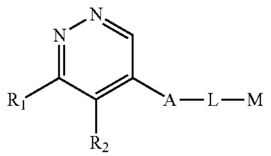

or a pharmaceutically acceptable salt or a stereoisomer or a tautomer or a prodrug thereof;

wherein

A represents 5- to 6-membered heteroarylenyl or 6-membered arylenyl; wherein the arylenyl and heteroarylenyl are substituted with 1, 2 or 3 occurrences of Ra;

Ra is hydrogen, hydroxy, hydroxyalkyl, halogen, alkoxy, alkyl, haloalkyl, haloalkoxy, amino, alkylamino or cyano;

$R_1$ is halogen, alkyl, haloalkyl, alkenyl, alkoxy, hydroxy, hydroxyalkyl, —COORb, —$CON(Rb)_2$, 6- to 10-membered aryl or 5- to 10-membered heteroaryl; wherein the aryl and heteroaryl are optionally substituted with 1, 2 or 3 groups independently selected from oxo, hydroxy, alkoxy, halogen, alkyl, haloalkyl, amino, —ONa, —COORc and —OCORc;

Rb and Rc, at each occurrence, independently represents hydrogen, alkyl or aminoalkyl;

$R_2$ is hydrogen, hydroxy, hydroxyalkyl, halogen, alkoxy, alkyl, haloalkyl or cyano; L is a bond, —O—$(CH_2)$p-, —O—$(CH_2)$p-O—, —C≡C-alkylenyl-, —NRx-$(CH_2)$p-, —NRx-$(CH_2)$p-O—, —NRx-$(CH_2)$p-C≡C—, —NRx-(3- to 10-membered heterocycloalkylenyl)-(CRxRy)n-, -(3- to 10-membered cycloalkylenyl)-(CRxRy)n-, -(3- to 10-membered heterocycloalkylenyl)-(CRxRy)n- or —O—(3- to 10-membered heterocycloalkylenyl)-(CRxRy)n-; wherein the cycloalkylenyl and heterocycloalkylenyl are substituted with 1, 2 or 3 occurrences of Rd; and wherein the left side of L is attached with A and right side of the L is attached with M;

Rd, at each occurrence, is independently selected from hydrogen, hydroxy, halogen, alkoxy, alkyl, haloalkyl, amino, alkylamino and cyano;

Rx and Ry, at each occurrence, are independently selected from hydrogen, alkyl and halogen;

M is selected from M-1 and M-2:

M-1

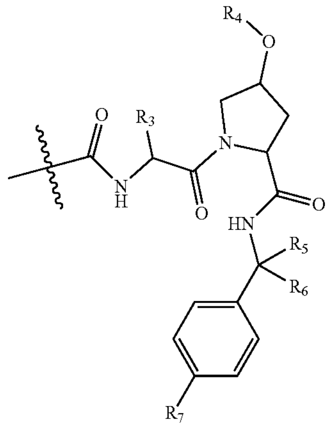

or

M-2

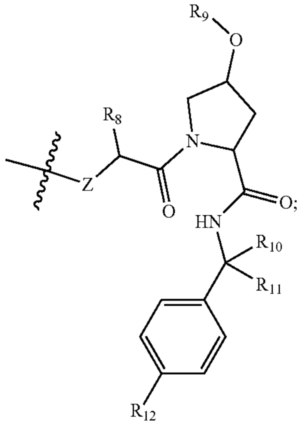

wherein,

Z is 5- to 6-membered heteroarylenyl optionally substituted with 1, 2 or 3 groups independently selected from hydroxy, halogen, alkyl, heteroalkyl, haloalkyl, hydroxyalkyl, aminoalkyl and aminoalkynyl; wherein the aminoalkyl and aminoalkynyl are optionally substituted with 1 or 2 substituents selected from alkyl and —$COCH_3$;

$R_3$ and $R_8$ independently represents alkyl, acyl, heteroalkyl, haloalkyl, hydroxyalkyl or aminoalkyl;

$R_4$ and $R_9$ independently represents hydrogen, alkyl, heteroalkyl, haloalkyl, hydroxyalkyl, aminoalkyl, —CO-aminoalkyl or acyl; wherein the alkyl is optionally substituted with —OCOR' or —$OP(O)(OR'')_2$;

R' and R'' are independently selected from hydrogen and alkyl;

$R_5$, $R_6$, $R_{10}$ and $R_{11}$ independently represents hydrogen, alkyl, halogen, heteroalkyl, haloalkyl, hydroxyalkyl, aminoalkyl-, —CONRuRv, acyl, —Na, -alkyl-heterocycloalkyl and -heteroalkyl-heterocycloalkyl; wherein the aminoalkyl and heterocycloalkyl are optionally substituted with 1 or 2 substituents selected from alkyl and —$COCH_3$; or $R_5$ and $R_6$ together combine with the C atom to which they are attached form a 4- to 6-membered heterocycloalkyl optionally substituted with alkyl or —$COCH_3$; or $R_{10}$ and $R_{11}$ together combine with the C atom to which they are attached form a 4- to 6-membered heterocycloalkyl optionally substituted with alkyl or —$COCH_3$;

Ru and Rv independently represents hydrogen, alkyl, 4- to 6-membered cycloalkyl or 6-membered aryl;

$R_7$ and $R_{12}$ represents thiazolyl substituted with alkyl, hydroxy, amino or haloalkyl;

p is an integer selected from 1, 2, 3 and 4; and n is an integer selected from 0, 1, 2 and 3.

In another aspect, the present invention provides a pharmaceutical composition comprising a compound of formula (I) or a pharmaceutically acceptable salt or a stereoisomer or a tautomer or a prodrug thereof and at least one pharmaceutically acceptable excipient (such as a pharmaceutically acceptable carrier or diluent).

In yet another aspect, the present invention relates to the preparation of compounds of formula (I).

In another aspect, the present invention provides a pharmaceutical composition comprising a compound of formula (I) or a pharmaceutically acceptable salt or a stereoisomer or a tautomer or a prodrug thereof for treating diseases or disorders that are dependent upon or mediated by SMARCA2 and/or SMARCA4.

In another aspect, the present invention provides a pharmaceutical composition comprising a compound of formula (I) or a pharmaceutically acceptable salt or a stereoisomer or a tautomer or a prodrug thereof for treating or delaying progression of a disease or disorder wherein degradation of SMARCA2 and/or SMARCA4 proteins provides a benefit, e.g., cancer.

In another aspect, the present invention provides a method of degrading a target protein comprising administering to a subject a therapeutically effective amount of a compound of formula (I) or a pharmaceutically acceptable salt or a stereoisomer or a tautomer or a prodrug thereof, wherein the compound is effective for degrading the target protein.

In another aspect, the present invention provides a method for treating a subject afflicted with cancer comprising administering a therapeutically effective amount of a compound of formula (I) or a pharmaceutically acceptable salt or a stereoisomer or a tautomer or a prodrug thereof.

In another aspect, the present invention provides a method for inhibiting tumor growth in a subject afflicted with cancer comprising administering a therapeutically effective amount of a compound of formula (I) or a pharmaceutically acceptable salt or a stereoisomer or a tautomer or a prodrug thereof.

In another aspect, the present invention provides a use of a compound of formula (I) or a pharmaceutically acceptable salt or a stereoisomer or a tautomer or a prodrug thereof, in the manufacture of a medicament for treating a disease or disorder that are dependent upon or mediated by SMARCA2 and/or SMARCA4.

DETAILED DESCRIPTION OF THE INVENTION

The present invention provides 6-substituted pyridazine compounds, referred as a compound of formula (I), which are useful as SMARCA2 and/or SMARCA4 degraders and for the treatment of conditions dependent upon or mediated by SMARCA2 and/or SMARCA4. The present invention further provides pharmaceutical compositions comprising the said compound or a stereoisomer or a tautomer or a prodrug thereof as therapeutic agents.

Each embodiment is provided by way of explanation of the invention and not by way of limitation of the invention. In fact, it will be apparent to those skilled in the art that various modifications and variations can be made to the compounds, compositions and methods described herein without departing from the scope or spirit of the invention. For instance, features illustrated or described as part of one embodiment can be applied to another embodiment to yield a still further embodiment. Thus, it is intended that the present invention includes such modifications and variations and their equivalents. Other objects, features and aspects of the present invention are disclosed in or are obvious from, the following detailed description. It is to be understood by one of ordinary skill in the art that the present discussion is a description of exemplary embodiments only and is not to be construed as limiting the broader aspects of the present invention.

In one embodiment, the present invention provides compounds of formula (I),

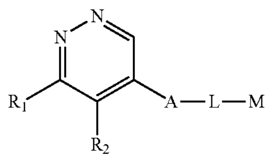

(I)

or a pharmaceutically acceptable salt or a stereoisomer or a tautomer or a prodrug thereof;

wherein

A represents 5- to 6-membered heteroarylenyl or 6-membered arylenyl; wherein the arylenyl and heteroarylenyl are substituted with 1, 2 or 3 occurrences of Ra;

Ra is hydrogen, hydroxy, hydroxyalkyl, halogen, alkoxy, alkyl, haloalkyl, haloalkoxy, amino, alkylamino or cyano;

$R_1$ is halogen, alkyl, haloalkyl, alkenyl, alkoxy, hydroxy, hydroxyalkyl, —COORb, —CON(Rb)$_2$, 6- to 10-membered aryl or 5- to 10-membered heteroaryl; wherein the aryl and heteroaryl are optionally substituted with 1, 2 or 3 groups independently selected from oxo, hydroxy, alkoxy, halogen, alkyl, haloalkyl, amino, —ONa, —COORc and —OCORc;

Rb and Rc, at each occurrence, independently represents hydrogen, alkyl or aminoalkyl;

$R_2$ is hydrogen, hydroxy, hydroxyalkyl, halogen, alkoxy, alkyl, haloalkyl or cyano; L is a bond, —O—(CH$_2$)p-, —O—(CH$_2$)p-O—, —C≡C-alkylenyl-, —NRx-(CH$_2$)p-, —NRx-(CH$_2$)p-O—, —NRx-(CH$_2$)p-C≡C—, —NRx-(3- to 10-membered heterocycloalkylenyl)-(CRxRy)n-, -(3- to 10-membered cycloalkylenyl)-(CRxRy)n-, -(3- to 10-membered heterocycloalkylenyl)-(CRxRy)n- or —O-(3- to 10-membered heterocycloalkylenyl)-(CRxRy)n-; wherein the cycloalkylenyl and heterocycloalkylenyl are substituted with 1, 2 or 3 occurrences of Rd; and wherein the left side of L is attached with A and right side of the L is attached with M;

Rd, at each occurrence, is independently selected from hydrogen, hydroxy, halogen, alkoxy, alkyl, haloalkyl, amino, alkylamino and cyano;

Rx and Ry, at each occurrence, are independently selected from hydrogen, alkyl and halogen;

M is selected from M-1 and M-2:

M-1

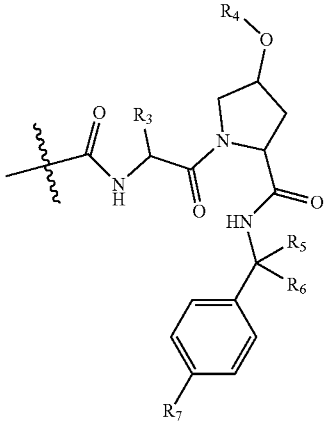

or

M-2

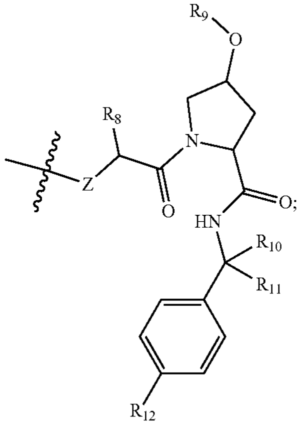

wherein,

Z is 5- to 6-membered heteroarylenyl optionally substituted with 1, 2 or 3 groups independently selected from hydroxy, halogen, alkyl, heteroalkyl, haloalkyl, hydroxyalkyl, aminoalkyl and aminoalkynyl; wherein the aminoalkyl and aminoalkynyl are optionally substituted with 1 or 2 substituents selected from alkyl and —$COCH_3$;

$R_3$ and $R_8$ independently represents alkyl, acyl, heteroalkyl, haloalkyl, hydroxyalkyl or aminoalkyl;

$R_4$ and $R_9$ independently represents hydrogen, alkyl, heteroalkyl, haloalkyl, hydroxyalkyl, aminoalkyl, —CO-aminoalkyl or acyl; wherein the alkyl is optionally substituted with —OCOR' or —OP(O)(OR")$_2$;

R' and R" are independently selected from hydrogen and alkyl;

$R_5$, $R_6$, $R_{10}$ and $R_{11}$ independently represents hydrogen, alkyl, halogen, heteroalkyl, haloalkyl, hydroxyalkyl, aminoalkyl-, —CONRuRv, acyl, —Na, -alkyl-heterocycloalkyl and -heteroalkyl-heterocycloalkyl; wherein the aminoalkyl and heterocycloalkyl are optionally substituted with 1 or 2 substituents selected from alkyl and —$COCH_3$; or $R_5$ and $R_6$ together combine with the C atom to which they are attached form a 4- to 6-membered heterocycloalkyl optionally substituted with alkyl or —$COCH_3$; or $R_{10}$ and $R_{11}$ together combine with the C atom to which they are attached form a 4- to 6-membered heterocycloalkyl optionally substituted with alkyl or —$COCH_3$;

Ru and Rv independently represents hydrogen, alkyl, 4- to 6-membered cycloalkyl or 6-membered aryl;

$R_7$ and $R_{12}$ represents thiazolyl substituted with alkyl, hydroxy, amino or haloalkyl;

p is an integer selected from 1, 2, 3 and 4; and n is an integer selected from 0, 1, 2 and 3.

In one embodiment, $R_1$ is halogen, alkyl, haloalkyl, alkoxy, hydroxy, hydroxyalkyl, 6- to 10-membered aryl or 5- to 10-membered heteroaryl; wherein the aryl and heteroaryl are optionally substituted with 1, 2 or 3 groups independently selected from oxo, hydroxy, alkoxy, halogen, alkyl, haloalkyl and amino;

In one embodiment, $R_1$ is halogen, hydroxy, —$CH_2OH$, —COOH, —$COOCH_3$, —$CONH_2$, —$CONHCH_3$, 6- to 10-membered aryl or 5- to 10-membered heteroaryl; wherein, the aryl and heteroaryl are optionally substituted with 1, 2 or 3 groups independently selected from hydroxy, alkoxy, halogen, alkyl and haloalkyl.

In one embodiment, $R_1$ is halogen, hydroxy, 6- to 10-membered aryl or 5- to 10-membered heteroaryl; wherein the aryl and heteroaryl are optionally substituted with 1, 2 or 3 groups independently selected from hydroxy, alkoxy, halogen, alkyl, haloalkyl, —$OCOCH_3$ and —CH($NH_2$)(CH($CH_3$)$_2$).

In one embodiment, $R_1$ represents halogen, hydroxy, 6- to 10-membered aryl or 5- to 10-membered heteroaryl; wherein the aryl and heteroaryl are optionally substituted with 1 or 2 groups independently selected from alkyl, hydroxy, alkoxy, halogen and haloalkyl.

In one embodiment, $R_1$ is 6- to 10-membered aryl or 5- to 10-membered heteroaryl; wherein the aryl and heteroaryl are optionally substituted with 1, 2 or 3 groups independently selected from alkyl, hydroxy, alkoxy, halogen and haloalkyl.

In one embodiment, $R_1$ is 6- to 10-membered aryl optionally substituted with 1, 2 or 3 groups independently selected from alkyl, hydroxy, alkoxy, halogen and haloalkyl.

In one embodiment, $R_1$ represents phenyl optionally substituted with 1 or 2 groups independently selected from hydroxy, alkyl, haloalkyl and halogen.

In one embodiment, $R_1$ is 5- to 10-membered heteroaryl optionally substituted with 1, 2 or 3 groups independently selected from alkyl, hydroxy, alkoxy, halogen and haloalkyl.

In one embodiment, $R_1$ represents

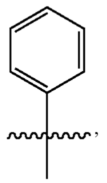,
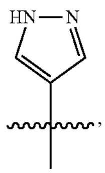,
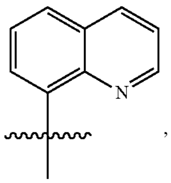,
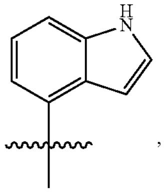,
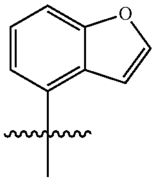
or
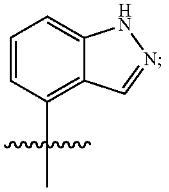

and wherein each group is optionally substituted with 1, 2 or 3 groups independently selected from hydroxy, alkyl, haloalkyl and halogen.

In one embodiment, $R_2$ is hydrogen, hydroxy, hydroxyalkyl, halogen, alkoxy, alkyl or haloalkyl.

In one embodiment, $R_2$ is hydrogen, hydroxy, halogen, alkoxy, alkyl or haloalkyl.

In one embodiment, $R_2$ independently represent hydrogen or halogen.

In one embodiment, A represents phenylenyl substituted with 1 or 2 occurrences of Ra.

In one embodiment, A represents 5- to 6-membered heteroarylenyl substituted with 1 or 2 occurrences of Ra.

In one embodiment, A represents phenylenyl, furanylenyl, thienylenyl, pyrrolylenyl, imidazolylenyl, oxazolylenyl, isoxazolylenyl, thiazolylenyl, isothiazolylenyl, 1H-tetrazolylenyl, oxadiazolylenyl, triazolylenyl, pyrazolylenyl, pyridylenyl, pyrimidinylenyl, pyrazinylenyl, pyridazinylenyl, 1,2,3-triazinylenyl, 1,2,4-triazinylenyl, or 1,3,5-triazinylenyl; wherein each group is optionally substituted with 1 or 2 occurrences of Ra.

In one embodiment, A represents phenylenyl, pyridylenyl, pyrimidinylenyl, pyrazinylenyl, or pyridazinylenyl; wherein each group is optionally substituted with 1, 2 or 3 occurrences of Ra.

In one embodiment, A represents phenylenyl, furanylenyl, thienylenyl, pyrrolylenyl, imidazolylenyl, oxazolylenyl, isoxazolylenyl, thiazolylenyl, isothiazolylenyl, 1H-tetrazolylenyl, oxadiazolylenyl, triazolylenyl, pyrazolylenyl, pyridylenyl, pyrimidinylenyl, pyrazinylenyl, pyridazinylenyl, 1,2,3-triazinylenyl, 1,2,4-triazinylenyl, or 1,3,5-triazinylenyl; wherein each of said group is substituted with 1 or 2 substituents selected from hydrogen, hydroxy, hydroxyalkyl, halogen, alkoxy, alkyl, haloalkyl, haloalkoxy, amino, alkylamino or cyano.

In one embodiment, A represents phenylenyl, pyridylenyl, pyrimidinylenyl or pyrazinylenyl, wherein the phenylenyl, pyridylenyl, pyrimidinylenyl and pyrazinylenyl are optionally substituted with 1 or 2 substituents selected from hydroxy, hydroxyalkyl, halogen, alkoxy, alkyl, haloalkyl, haloalkoxy, amino, alkylamino or cyano.

In one embodiment, A represents

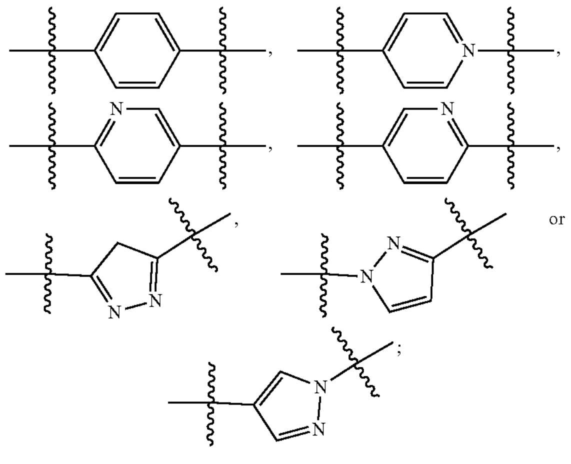

or wherein each ring is optionally substituted with 1 or 2 occurrences of Ra; and wherein the left side of A is attached with pyridazine ring and right side of the ring is attached with L.

In one embodiment, A represents

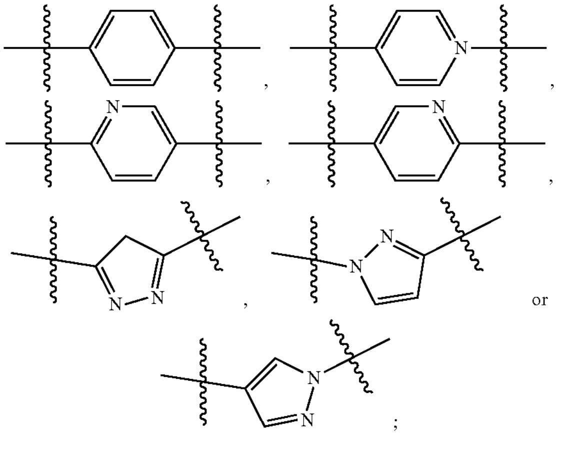

or wherein each group is optionally substituted with 1 or 2 substituents selected from hydrogen, hydroxy, hydroxyalkyl, halogen, alkoxy, alkyl, haloalkyl, haloalkoxy, amino, alkylamino and cyano; and wherein the left side of A is attached with pyridazine ring and right side of the ring is attached with L.

In one embodiment, L is a bond, —O—$(CH_2)$p-, —O—$(CH_2)$p-O—, —NRx-$(CH_2)$p-, —NRx-$(CH_2)$p-O—, —NRx-(3- to 10-membered heterocycloalkylenyl)-(CRxRy)n-, (3- to 10-membered cycloalkylenyl)-(CRxRy)n-, (3- to 10-membered heterocycloalkylenyl)-(CRxRy)n or —O-(3- to 10-membered heterocycloalkylenyl)-(CRxRy)n-; wherein the cycloalkylenyl and heterocycloalkylenyl are substituted with 1 or 2 occurrences of Rd.

In one embodiment, L is a bond and M is attached to A. In one embodiment, L is —O—$(CH_2)$p-. In one embodiment, L is —O—$CH_2$—. In one embodiment, L is —O—$CH_2CH_2$—. In one embodiment, L is —O—$CH_2CH_2CH_2$—. In one embodiment, L is —O—$CH_2CH_2CH_2CH_2$—. In one embodiment, L is —O—$(CH_2)$p-O—, or —C≡C-alkylenyl-. In one embodiment, L is —O—$CH_2CH_2CH_2CH_2$—O—. In one embodiment, L is —O—$CH_2CH_2CH_2$—O—. In one embodiment, L is —O—$CH_2CH_2$—O—. In one embodiment, L is —O—$CH_2$—O—. In one embodiment, L is —C≡C—$(CH_2)_{1-4}$—. In one embodiment, L is —C≡C—$CH_2$—. In one embodiment, L is —C≡C—$CH_2CH_2$—. In one embodiment, L is —C≡C—$CH_2CH_2CH_2$—. In one embodiment, L is —C≡C—$CH_2CH_2CH_2CH_2$—.

In one embodiment, L is —NRx-$(CH_2)$p-. In one embodiment, L is —NRx-$(CH_2)_{1-4}$. In one embodiment L is —NRx-$CH_2$—. In one embodiment, L is —NRx-$CH_2CH_2$—. In one embodiment, L is —NRx-$CH_2CH_2CH_2$—. In one embodiment, L is —NRx-$CH_2CH_2CH_2CH_2$—. In one embodiment, L is —NH—$(CH_2)_{1-4}$—. In one embodiment, L is —NH—$CH_2$—. In one embodiment L is —NH—$CH_2CH_2$—. In one embodiment, L is —NH—$CH_2CH_2CH_2$—. In one embodiment —NH—$CH_2CH_2CH_2CH_2$—. In one embodiment, L is —$N(CH_3)$—$CH_2$—. In one embodiment L is —$N(CH_3)$—$CH_2CH_2$—. In one embodiment, L is —$N(CH_3)$—$CH_2CH_2CH_2$—. In one embodiment —$N(CH_3)$—$CH_2CH_2CH_2CH_2$—.

In one embodiment, L is —NRx-$(CH_2)$p-O—. In one embodiment, L is —NRx-$(CH_2)_{1-4}$—O—. In one embodiment, L is —NRx-$CH_2$—O—. In one embodiment, L is —NRx-$CH_2CH_2$—O—. In one embodiment, L is —NRx- $CH_2CH_2CH_2$—O—. In one embodiment, L is —NRx-$CH_2CH_2CH_2CH_2$—O—. In one embodiment, L is —NH—$CH_2$—O—. In one embodiment, L is —NH—$CH_2CH_2$—O—. In one embodiment, L is —NH—$CH_2CH_2CH_2$—O—. In one embodiment, L is —NH—$CH_2CH_2CH_2CH_2$—O—. In one embodiment, L is —N($CH_3$)—$CH_2$—O—. In one embodiment, L is —N($CH_3$)—$CH_2CH_2$—O—. In one embodiment, L is —N($CH_3$)—$CH_2CH_2CH_2$—O—. In one embodiment, L is —N($CH_3$)—$CH_2CH_2CH_2CH_2$—O—.

In one embodiment, L is a bond, —O—$CH_2$—, —O—$CH_2CH_2$—, —O—$CH_2CH_2CH_2$—, —O—$CH_2CH_2$—$CH_2CH_2$—, —O—$CH_2$O—, —O—$CH_2CH_2$—O—, —O—$CH_2CH_2CH_2$—O—, —O—$CH_2CH_2CH_2CH_2$—O—, —NH—$CH_2$—, —NH—$CH_2CH_2$—, —NH—$CH_2CH_2CH_2$—, —NH—$CH_2CH_2CH_2CH_2$—, —N($CH_3$)—$CH_2$—, —N($CH_3$)—$CH_2CH_2$—, —N($CH_3$)—$CH_2CH_2CH_2$—, —N($CH_3$)—$CH_2CH_2CH_2CH_2$—, NH—$CH_2$—O—, —NH—$CH_2CH_2$—O—, —NH—$CH_2CH_2CH_2$—O—, —NH—$CH_2CH_2CH_2CH_2$—O—, —N($CH_3$)—$CH_2$—O—, —N($CH_3$)—$CH_2CH_2$—O—, —N($CH_3$)—$CH_2CH_2CH_2$—O— or —N($CH_3$)—$CH_2CH_2CH_2CH_2$—O—.

In one embodiment, L is —NRx-(3- to 10-membered heterocycloalkylenyl)-(CRxRy)n-, (3- to 10-membered cycloalkylenyl)-(CRxRy)n-, (3- to 10-membered heterocycloalkylenyl)-(CRxRy)n or —O-(3- to 10-membered heterocycloalkylenyl)-(CRxRy)n-; wherein the cycloalkylenyl and heterocycloalkylenyl are substituted with 1 or 2 occurrences of Rd.

In one embodiment, L is —NRx-(3- to 10-membered heterocycloalkylenyl)-$(CRxRy)_{0-3}$. In one embodiment, L is —NH-(3- to 10-membered heterocycloalkylenyl)-$(CRxRy)_{0-3}$. In one embodiment, L is —N($CH_3$)-(3- to 10-membered heterocycloalkylenyl)-$(CRxRy)_{0-3}$; wherein heterocycloalkylenyl is optionally substituted with 1 or 2 occurrences of Rd.

In one embodiment, L is (3- to 10-membered cycloalkylenyl)-$(CRxRy)_{0-3}$; wherein cycloalkylenyl is optionally substituted with 1 or 2 occurrences of Rd.

In one embodiment, L is 3- to 10-membered heterocycloalkylenyl-$(CRxRy)_{0-3}$-; wherein the heterocycloalkylenyl is optionally substituted with 1, 2 or 3 occurrences of Rd.

In one embodiment, L is —O-(3- to 10-membered heterocycloalkylenyl)-$(CRxRy)_{0-3}$-; wherein the heterocyclylenyl is optionally substituted with 1, 2 or 3 occurrences of Rd.

In one embodiment, L is —NRx-(3- to 10-membered heterocycloalkylenyl)-$(CRxRy)_{0-3}$. —NH—(3- to 10-membered heterocycloalkylenyl)-$(CRxRy)_{0-3}$ or —N($CH_3$)-(3- to 10-membered heterocycloalkylenyl)-$(CRxRy)_{0-3}$; wherein the heterocycloalkylenyl is selected from piperidinylenyl, piperazinylenyl, azetidinylenyl, pyrolidinylenyl, tetrahydropyridinylenyl, diazobicyclooctanylenyl, azabicyclooctanylenyl, azaspiroheptanylenyl, tetrahydropyranyl, tetrahydropyridazinylenyl, morpholinylenyl, thiomorpholinylenyl, 1,4-dioxanylenyl, dioxidothiomorpholinylenyl, oxapiperazinylenyl, oxapiperidinylenyl, tetrahydropyranylenyl, dihydropyranylenyl and dihydropyrimidinylenyl, each group is substituted with 1 or 2 occurrences of Rd.

In one embodiment, L is (3- to 10-membered cycloalkylenyl)-$(CRxRy)_{0-3}$, wherein the cycloalkylenyl is selected from cyclopropylenyl, cyclobutylenyl, cyclopentylenyl, cyclohexylenyl and cycloheptylenyl.

In one embodiment, L is

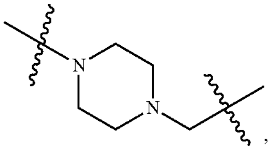,
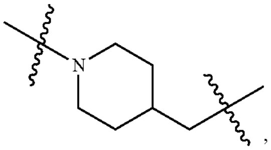,
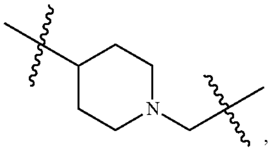,
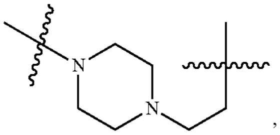,
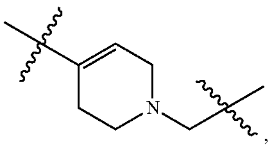,
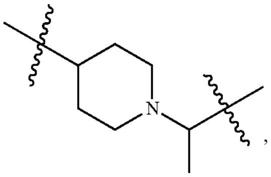,
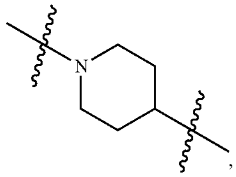,
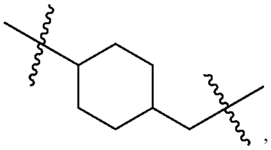,
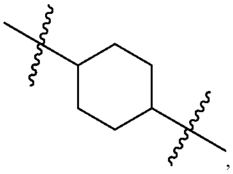,
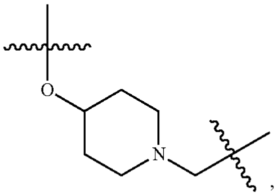,
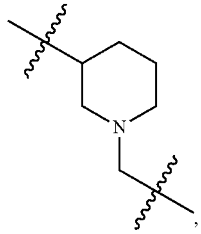,
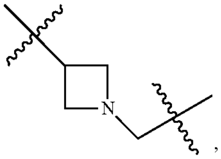,
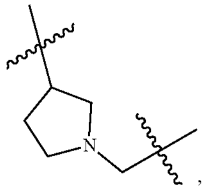,
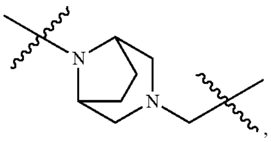,
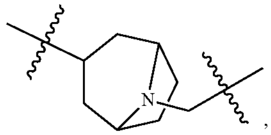,
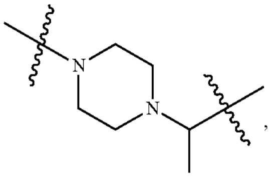,
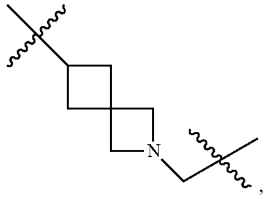, -continued

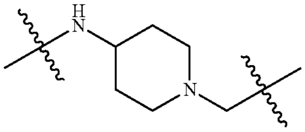

or

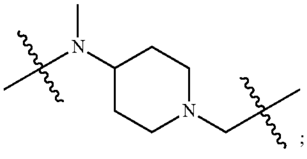

;

wherein each ring is substituted with 1 or 2 occurrences of Rd; wherein each ring is substituted with 1 or 2 occurrences of Rd; and wherein the left side of L is attached with A and right side of the L is attached with M.

In one embodiment, L is —O—$CH_2$—, —O—$CH_2CH_2$—, —O—$CH_2CH_2CH_2$—, —O—$CH_2CH_2CH_2CH_2$—, —O—$CH_2O$—, —O—$CH_2CH_2$—O—, —O—$CH_2CH_2CH_2$—O—, —O—$CH_2CH_2CH_2CH_2$—O—, —NH—$CH_2$—, —NH—$CH_2CH_2$—, —NH—$CH_2CH_2CH_2$—, —NH—$CH_2CH_2CH_2CH_2$—, —N($CH_3$)—$CH_2$—, —N($CH_3$)—$CH_2CH_2$—, —N($CH_3$)—$CH_2CH_2CH_2$—, —N($CH_3$)—$CH_2CH_2CH_2CH_2$—, NH—$CH_2$—O—, —NH—$CH_2CH_2$—O—, —NH—$CH_2CH_2CH_2$—O—, —NH—$CH_2CH_2CH_2CH_2$—O—, —N($CH_3$)—$CH_2$—O—, —N($CH_3$)—$CH_2CH_2$—O—, —N($CH_3$)—$CH_2CH_2CH_2$—O—, —N($CH_3$)—$CH_2CH_2CH_2CH_2$—O—,

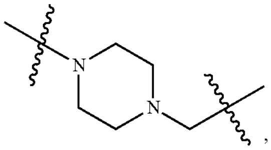

,

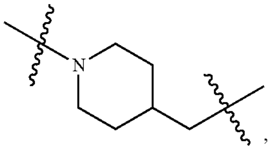

,

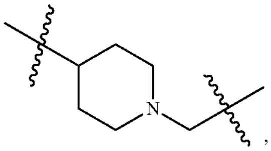

,

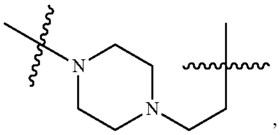

,

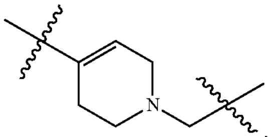

,

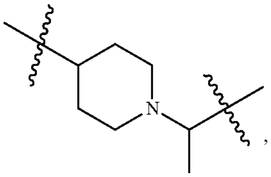

,

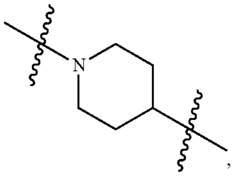

,

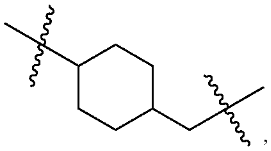

,

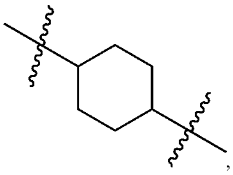

,

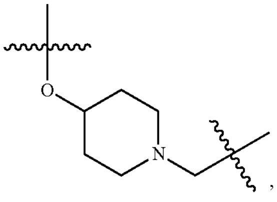

,

-continued

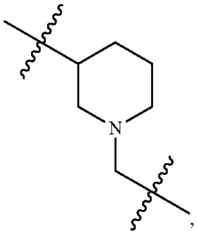

,

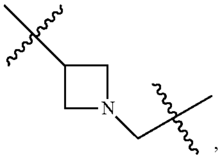

,

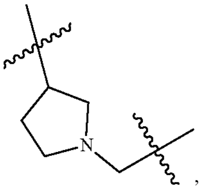

,

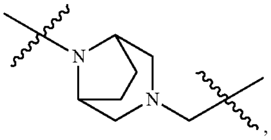

,

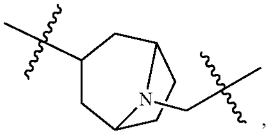

,

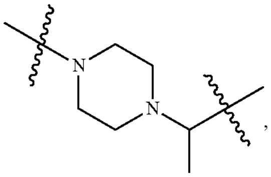

,

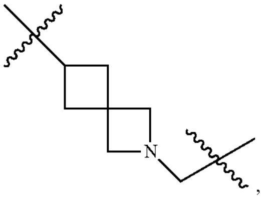

,

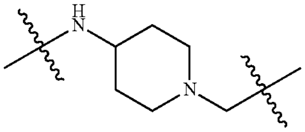

or

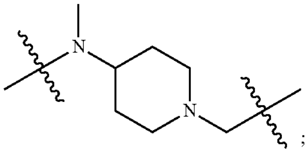

;

wherein each ring is substituted with 1 or 2 occurrences of Rd.

In one embodiment of compound of formula (I),

A represents 5- to 6-membered heteroarylenyl or 6-membered arylenyl; wherein, arylenyl and heteroarylenyl are substituted with 1, 2 or 3 occurrences of Ra;

Ra is hydrogen, hydroxy, hydroxyalkyl, halogen, alkoxy, alkyl, haloalkyl, haloalkoxy, amino, alkylamino or cyano;

$R_1$ is halogen, alkyl, haloalkyl, alkenyl, alkoxy, hydroxy, hydroxyalkyl, —COORb, —CON$(Rb)_2$, 6- to 10-membered aryl or 5- to 10-membered heteroaryl; wherein, the aryl and heteroaryl are optionally substituted with 1, 2 or 3 groups independently selected from oxo, hydroxy, alkoxy, halogen, alkyl, haloalkyl, amino, —ONa, —COORc and —OCORc;

Rb and Rc at each occurrence independently are selected from hydrogen, alkyl or aminoalkyl;

$R_2$ is hydrogen, hydroxy, hydroxyalkyl, halogen, alkoxy, alkyl, haloalkyl or cyano; L is a bond, —O—$(CH_2)$p-, —O—$(CH_2)$p-O—, —C≡C-alkylenyl-, 6-membered heterocycloalkylenyl or 6-membered heterocycloalkylenyl —(CRxRy)n-; wherein the heterocycloalkylenyl is substituted with 1, 2 or 3 occurrences of Rd;

Rd at each occurrence is independently selected from hydrogen, hydroxy, halogen, alkoxy, alkyl, haloalkyl, amino, alkylamino and cyano;

Rx and Ry at each occurrence independently are selected from hydrogen and alkyl;

M is selected from:

M-1

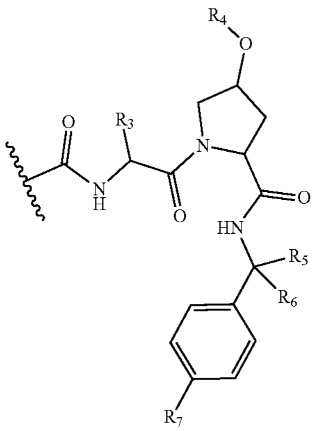

and

M-2

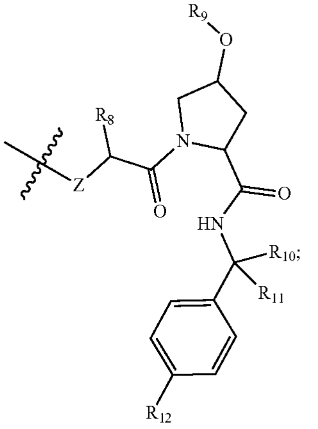

wherein,

Z is 5- to 6-membered heteroarylenyl optionally substituted with 1, 2 or 3 groups independently selected from hydroxy, halogen, alkyl, heteroalkyl, haloalkyl, hydroxyalkyl, aminoalkyl and aminoalkynyl, wherein the aminoalkyl and aminoalkynyl are optionally substituted with 1 or 2 substituents selected from alkyl and —$COCH_3$;

$R_3$ and $R_8$ independently represents alkyl, acyl, heteroalkyl, haloalkyl, hydroxyalkyl or aminoalkyl;

$R_4$ and $R_9$ independently represents hydrogen, alkyl, heteroalkyl, haloalkyl, hydroxyalkyl, aminoalkyl, —CO-aminoalkyl or acyl; wherein the alkyl is optionally substituted with —OCOR' or —$OP(O)(OR")_2$;

R' and R" are independently selected from hydrogen and alkyl;

$R_5$, $R_6$, $R_{10}$ and $R_{11}$ are independently selected from hydrogen, alkyl, halogen, heteroalkyl, haloalkyl, hydroxyalkyl, aminoalkyl, —CONRuRv, acyl, —Na, -alkyl-heterocycloalkyl and -heteroalkyl-heterocycloalkyl; wherein the aminoalkyl and heterocycloalkyl are optionally substituted with 1 or 2 substituents selected from alkyl and —$COCH_3$; or $R_5$ and $R_6$ together combine with the C atom to which they are attached to form 4- to 6-membered heterocycloalkyl optionally substituted with alkyl, or —$COCH_3$; or $R_{10}$ and $R_{11}$ together combine with the C atom to which they are attached to form 4- to 6-membered heterocycloalkyl optionally substituted with alkyl, or —$COCH_3$;

Ru and Rv independently represents hydrogen, alkyl, 4- to 6-membered cycloalkyl, or 6-membered aryl;

$R_7$ and $R_{12}$ are independently thiazolyl substituted with alkyl, hydroxy, amino or haloalkyl;

p is an integer selected from 1 and 2;

n is an integer selected from 1, 2 and 3.

In one embodiment, M is M-1;

M-1

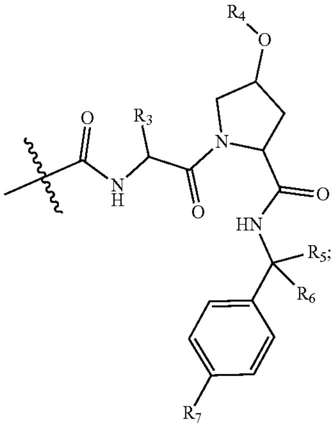

wherein Z is oxazolylenyl or isoxazolylenyl; $R_3$ represents alkyl, haloalkyl or hydroxyalkyl; $R_4$ represents hydrogen, alkyl, heteroalkyl, haloalkyl, hydroxyalkyl or acyl; $R_5$ and $R_6$ independently represents hydrogen, alkyl, halogen, haloalkyl, hydroxyalkyl or (alkyl)aminoalkyl-; and $R_7$ represents thiazolyl substituted with alkyl.

In one embodiment, M is selected from M-1A, M-1B and M-1C:

M-1A

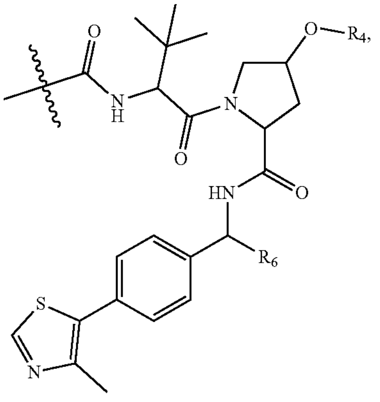

-continued

M-1B

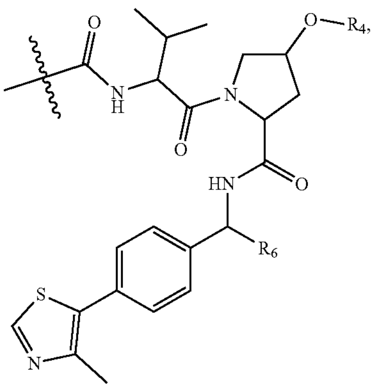

M-1C

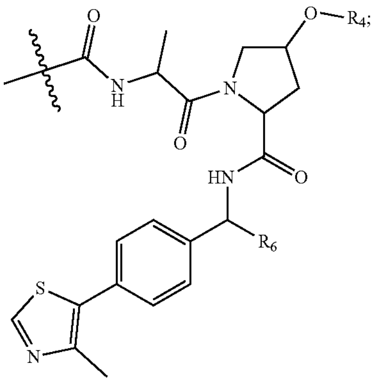

wherein, $R_4$ is hydrogen, alkyl, acyl or —Na; wherein the alkyl is optionally substituted with —OCOR' or —OP(O)(OR")$_2$;

R' and R" are independently selected from hydrogen and alkyl; and $R_6$ is hydrogen, alkyl, hydroxyalkyl, aminoalkyl, or haloalkyl; wherein aminoalkyl optionally substituted with 1 or 2 substituents selected from alkyl and —$COCH_3$.

In one embodiment, M-1A is,

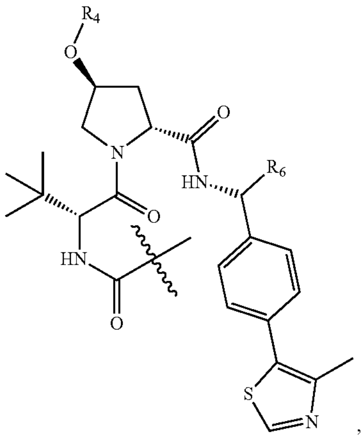

,

-continued

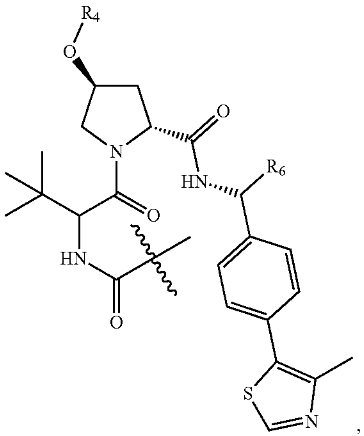

,

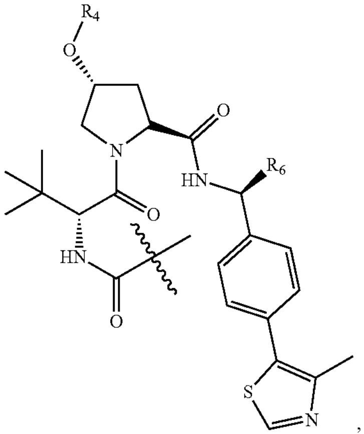

,

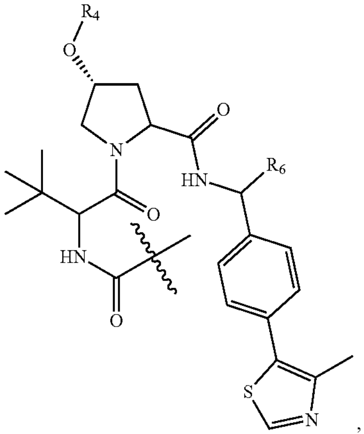

,

-continued
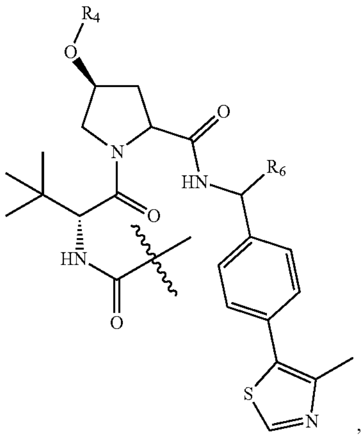
,
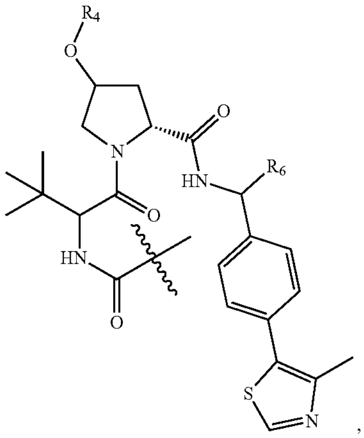
,
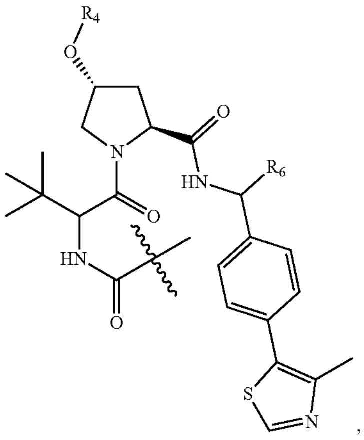
,
-continued
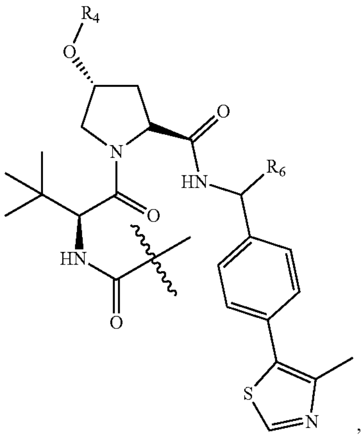
,
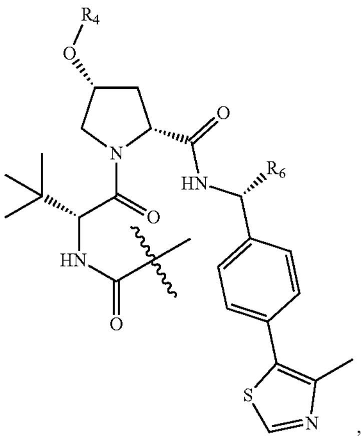
,
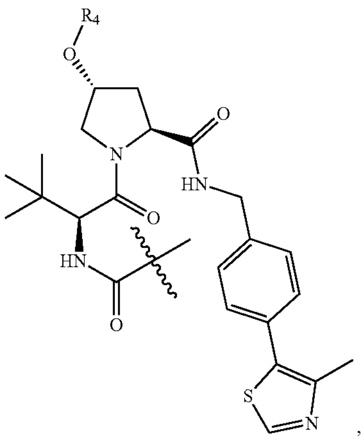
, -continued
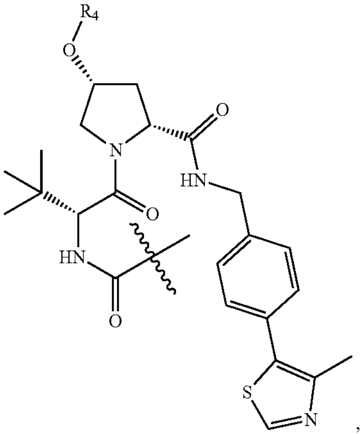
,
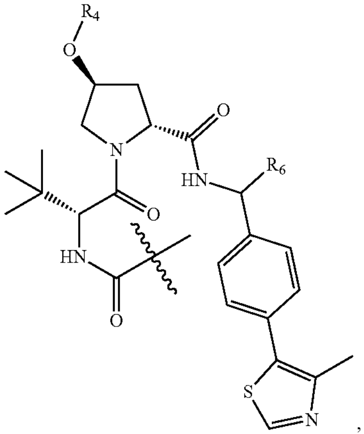
,
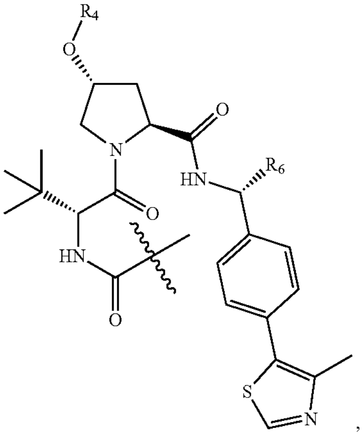
,
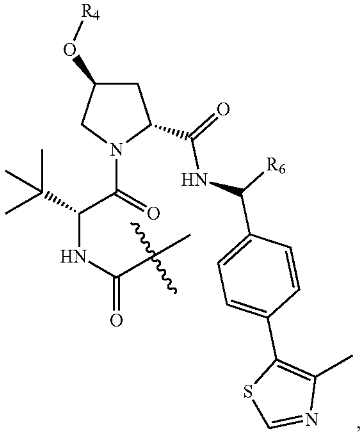
,
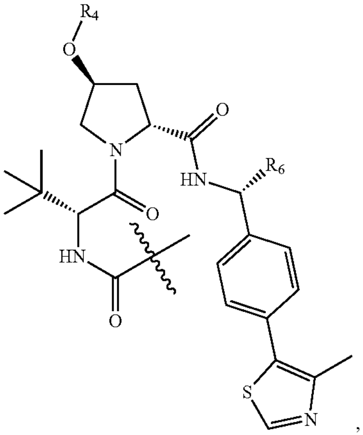
,
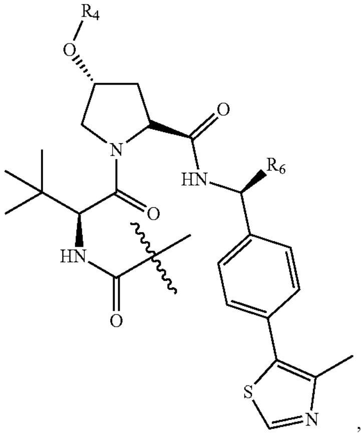
, -continued

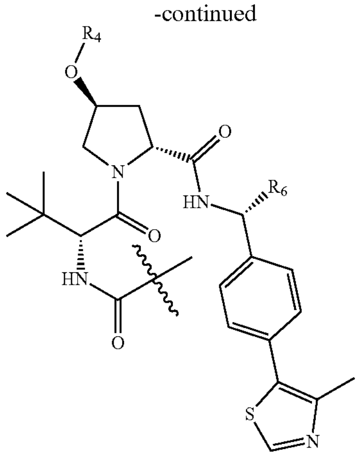

or

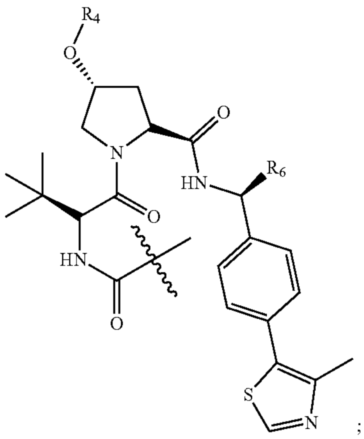

;

wherein, $R_4$ is selected from hydrogen, alkyl, acyl and —Na; wherein the alkyl is optionally substituted with —OCOR' and —OP(O)(OR")$_2$;

R' and R" are independently selected from hydrogen and alkyl; and $R_6$ is selected from hydrogen, alkyl, haloalkyl, hydroxy-alkyl or aminoalkyl; wherein the aminoalkyl optionally substituted with 1 or 2 substituents selected from alkyl and —$COCH_3$.

In one embodiment, M-1B and M-1C is,

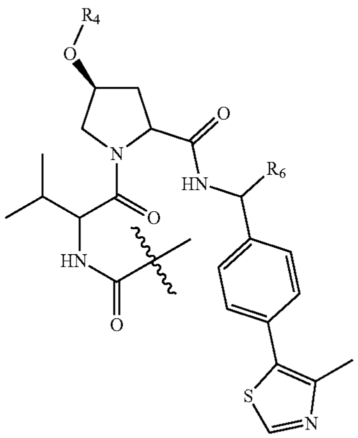

,

-continued

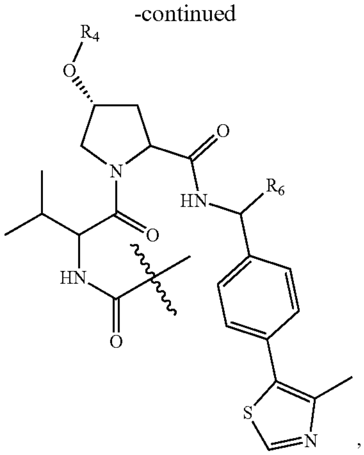

,

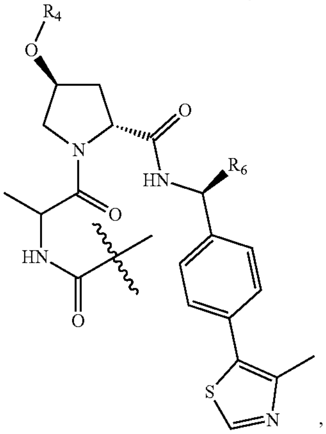

,

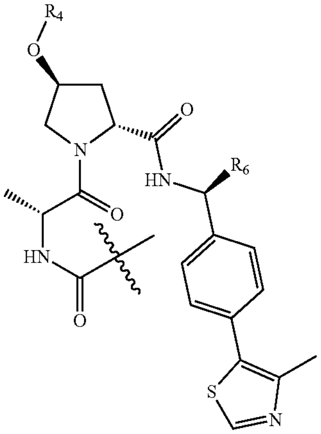

,

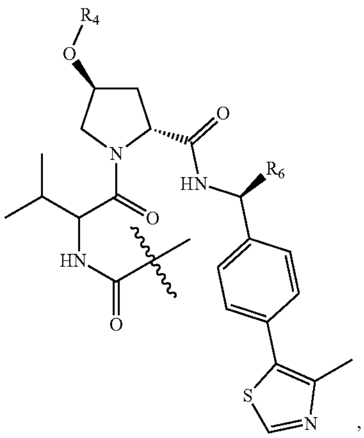

,

-continued

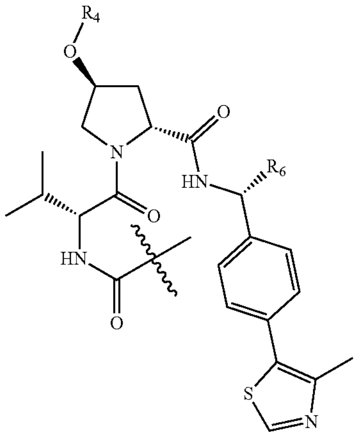

,

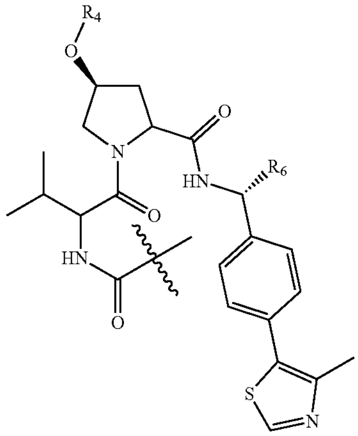

or

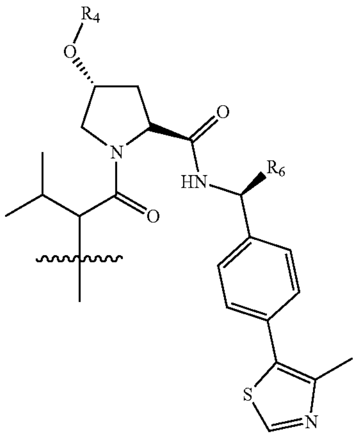

;

wherein, $R_4$ is selected from hydrogen, alkyl, acyl and —Na; wherein the alkyl is optionally substituted with —OCOR' and —OP(O)(OR")$_2$;

R' and R" are independently selected from hydrogen and alkyl; and $R_6$ is selected from hydrogen, alkyl, haloalkyl, hydroxyalkyl and aminoalkyl; wherein the aminoalkyl optionally substituted with 1 or 2 substituents selected from alkyl and —$COCH_3$.

In one embodiment, M-1A is represented by the formula:

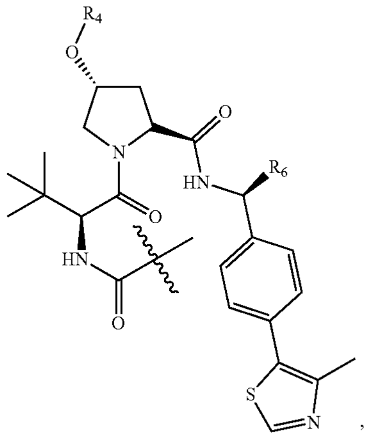

,

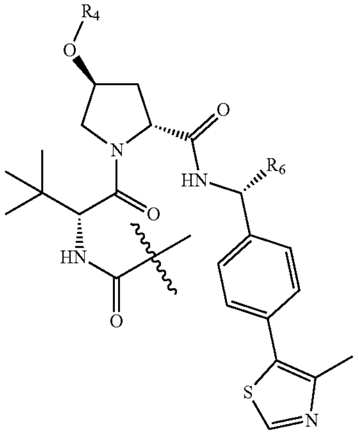

or

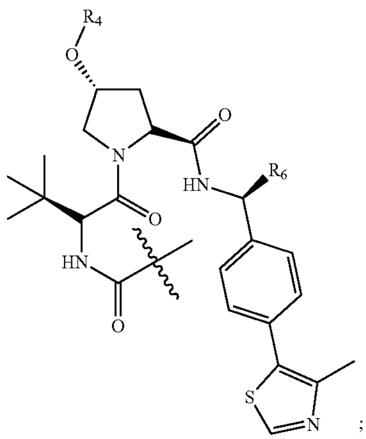

;

wherein, $R_4$ is selected from hydrogen and alkyl; and $R_6$ is selected from hydrogen, hydroxyalkyl, (alkyl)aminoalkyl- or alkyl.

In one embodiment, M-1A is represented by the structure:

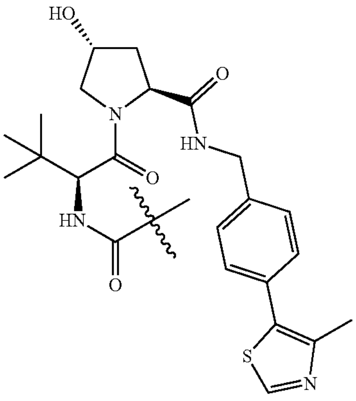

,

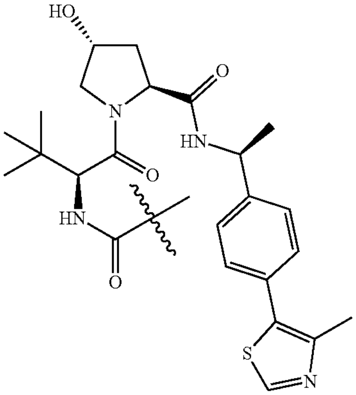

,

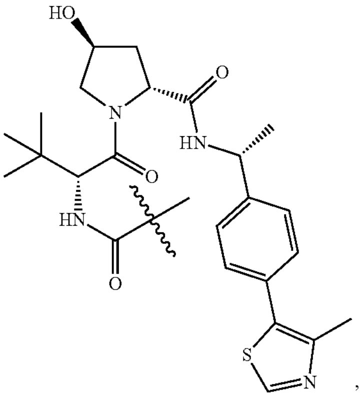

,

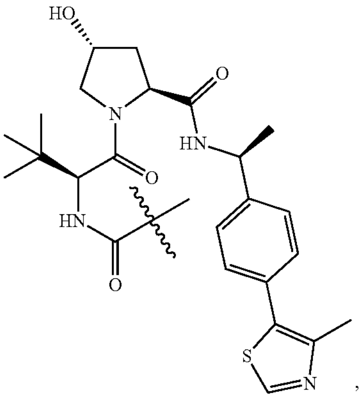

,

-continued

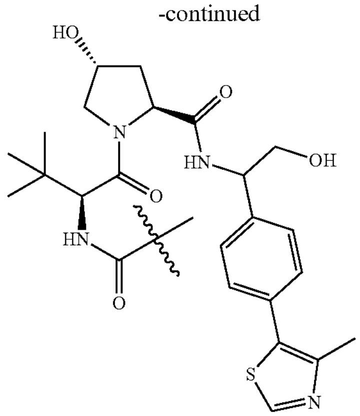

or

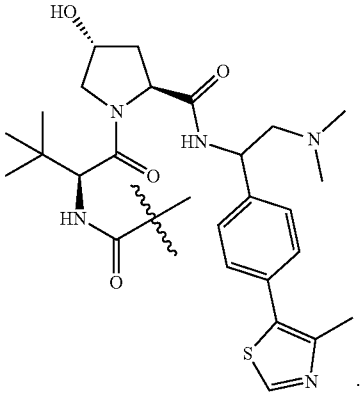

.

In one embodiment, M is M-2:

M-2

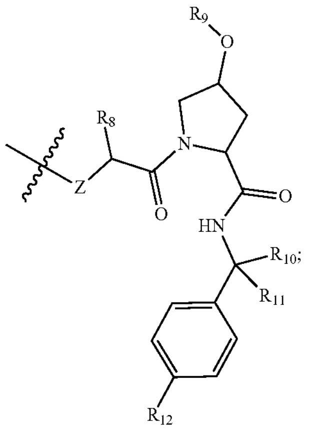

wherein $R_8$, $R_9$, $R_{10}$, $R_{11}$ and $R_{12}$ are as defined in compound of formula (I).

In one embodiment, M is M-2; wherein

Z represents 5- to 6-membered heteroarylenyl optionally substituted with 1, 2 or 3 groups independently selected from hydroxy, halogen, alkyl, heteroalkyl, haloalkyl, hydroxyalkyl, aminoalkyl and aminoalkynyl; wherein the aminoalkyl and aminoalkynyl are optionally substituted with 1 or 2 substituents selected from alkyl and —$COCH_3$;

$R_8$ represents alkyl, acyl, heteroalkyl, haloalkyl, hydroxyalkyl or aminoalkyl;

$R_9$ represents hydrogen, alkyl, acyl or —Na;

$R_{10}$ and $R_{11}$ are independently selected from hydrogen, alkyl, haloalkyl, hydroxyalkyl and aminoalkyl; wherein the aminoalkyl optionally substituted with 1 or 2 substituents selected from alkyl or —$COCH_3$; and $R_{12}$ is 5- to 6-membered heteroaryl substituted with alkyl, hydroxy, amino or haloalkyl.

In one embodiment, M is M-2; wherein Z is oxazolylenyl or isoxazolylenyl; $R_8$ represents alkyl, haloalkyl or hydroxyalkyl; $R_9$ represents hydrogen, alkyl, heteroalkyl, haloalkyl, hydroxyalkyl or acyl; $R_{10}$ and $R_{11}$ independently represents hydrogen, alkyl, halogen, haloalkyl, hydroxyalkyl or (alkyl) aminoalkyl-; and $R_{12}$ represents thiazolyl substituted with alkyl.

In one embodiment, M-2 is selected from M-2A, M-2B and M-2C:

M-2A

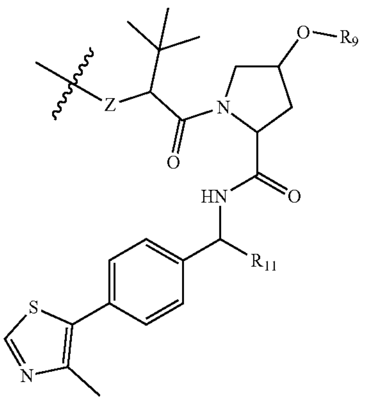

M-2B

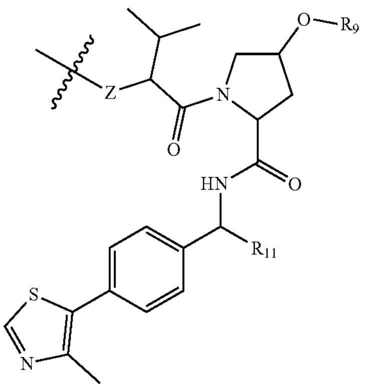

M-2C

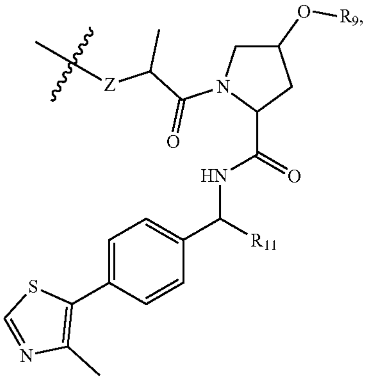

wherein,

Z represents oxazolylenyl optionally substituted with 1, 2 or 3 groups independently selected from hydroxy, halogen, alkyl, heteroalkyl, haloalkyl, hydroxyalkyl, aminoalkyl and aminoalkynyl, wherein the aminoalkyl and aminoalkynyl are optionally substituted with 1 or 2 substituents selected from alkyl and —$COCH_3$;

$R_9$ is hydrogen, alkyl, acyl or —Na; and $R_{11}$ is hydrogen, alkyl, haloalkyl, hydroxyalkyl or aminoalkyl; wherein the aminoalkyl optionally substituted with 1 or 2 substituents selected from alkyl and —$COCH_3$.

In one embodiment, M is selected from M-1A, M-1B, M-1C, M-2A, M-2B and M-2C; wherein, Z represents 5- to 6-membered heteroarylenyl optionally substituted with 1, 2 or 3 groups independently selected from hydroxy, halogen, alkyl, heteroalkyl, haloalkyl, hydroxyalkyl, aminoalkyl and aminoalkynyl; wherein the aminoalkyl and aminoalkynyl are optionally substituted with 1 or 2 substituents selected from alkyl and —$COCH_3$;

$R_4$ and $R_9$ independently is hydrogen, alkyl, acyl or —Na; wherein the alkyl is optionally substituted with —OCOR' or —OP(O)(OR")$_2$;

R' and R" are independently selected from hydrogen and alkyl; and $R_6$ and $R_{11}$ independently is hydrogen, alkyl, haloalkyl, hydroxyalkyl or aminoalkyl; wherein the aminoalkyl optionally substituted with 1 or 2 substituents selected from alkyl and —$COCH_3$.

In one embodiment, Z represents isoxazolylenyl, oxazolylenyl, or pyrrazolylenyl.

In one embodiment, M-2 represented by the structure:

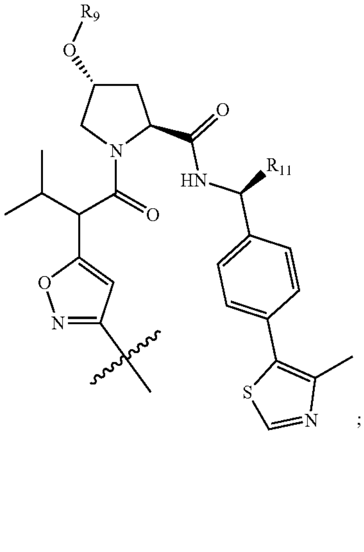

;

wherein $R_9$ represents hydrogen; and $R_{11}$ represents hydrogen or alkyl.

In one embodiment, M is represented by the structure:

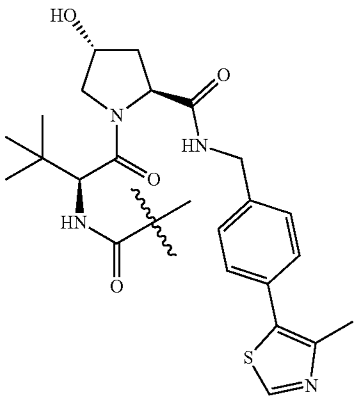

,

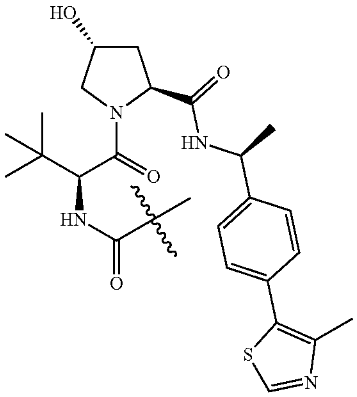

,

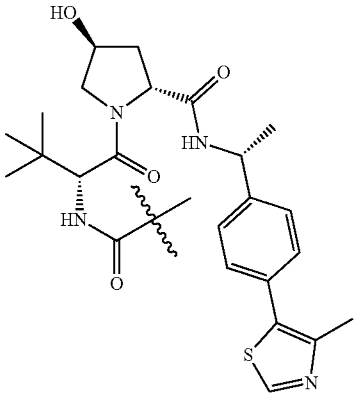

,

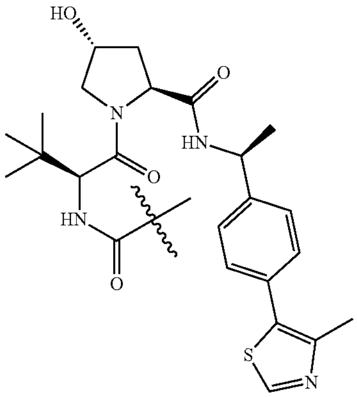

,

-continued

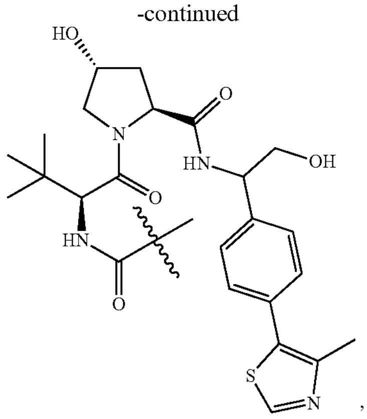

,

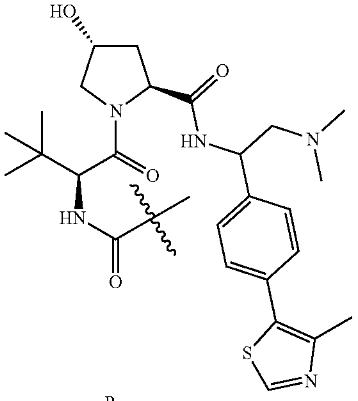

or

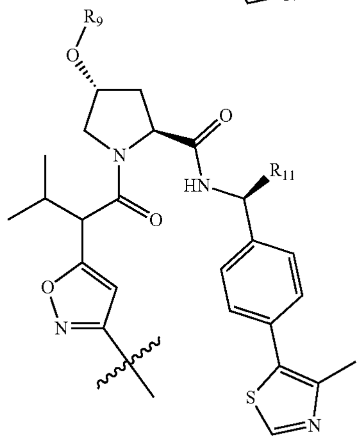

.

In one embodiment, if L is a bond, M is attached to A in compound of formula (I).

In one embodiment, the present invention provides compound of formula (IA) or a pharmaceutically acceptable salt or a stereoisomer or a tautomer or a prodrug thereof:

(IA)

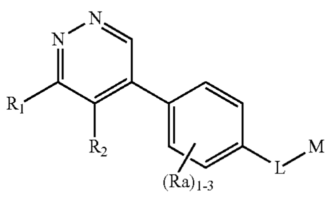

wherein $R_1$, $R_2$, Ra, L and M are as defined in compound of formula (I).

In one embodiment of compound of formula (IA), $R_1$ is halogen, hydroxy, 6- to 10-membered aryl or 5- to 10-membered heteroaryl; wherein the aryl and heteroaryl are optionally substituted with 1, 2 or 3 groups independently selected from alkyl, hydroxy, alkoxy, halogen and haloalkyl.

In one embodiment of compound of formula (IA), $R_1$ is 6- to 10-membered aryl or 5- to 10-membered heteroaryl; wherein the aryl and heteroaryl are optionally substituted with 1, 2 or 3 groups independently selected from alkyl, hydroxy, alkoxy, halogen and haloalkyl.

In one embodiment of compound of formula (IA), $R_1$ is —Cl, —OH,

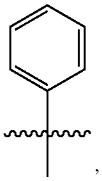, 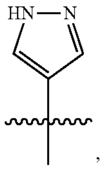, 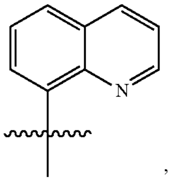, 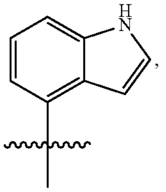, 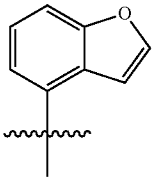 or 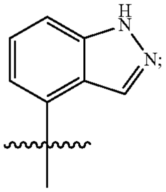;

wherein each ring is optionally substituted with 1, 2 or 3 groups independently selected from alkyl, hydroxy, alkoxy, halogen and haloalkyl.

In one embodiment of compound of formula (IA), $R_2$ is hydrogen, hydroxy, halogen, alkoxy, alkyl or haloalkyl.

In one embodiment of compound of formula (IA), $R_2$ represents hydrogen or halogen.

In one embodiment of compound of formula (IA), Ra is hydrogen, hydroxy, hydroxyalkyl, halogen, alkoxy, alkyl, haloalkyl, haloalkoxy, amino, alkylamino or cyano.

In one embodiment of compound of formula (IA), Ra is hydrogen, hydroxy, hydroxyalkyl, halogen, alkoxy and haloalkyl.

In one embodiment of compound of formula (IA), Ra is hydrogen, halogen, or haloalkyl.

In one embodiment of compound of formula (IA), Ra is hydrogen or halogen.

In one embodiment of compound of formula (IA), L is a bond.

In one embodiment of compound of formula (IA), L is a bond, —O—$(CH_2)$p-, —O—$(CH_2)$p-O—, —NRx-$(CH_2)$p-, —NRx-$(CH_2)$p-O—, —NRx-(3- to 10-membered heterocycloalkylenyl)-(CRxRy)n-, (3- to 10-membered cycloalkylenyl)-(CRxRy)n-, (3- to 10-membered heterocycloalkylenyl)-(CRxRy)n or —O-(3- to 10-membered heterocycloalkylenyl)-(CRxRy)n-.

In one embodiment of compound of formula (IA), L is —O—$CH_2CH_2CH_2CH_2$—, —O—$CH_2$—$CH_2CH_2$—, O—$CH_2CH_2$—O—, —O—$CH_2CH_2CH_2$—O—, —NH—$CH_2CH_2$—O—, —N$(CH_3)$—$CH_2CH_2$—O—, —NH—$CH_2CH_2CH_2CH_2$—, —N$(CH_3)$—$CH_2CH_2CH_2CH_2$—,

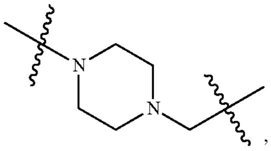, 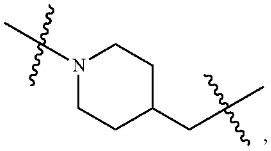,

-continued

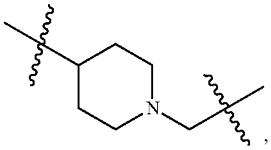, 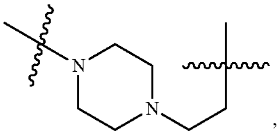, 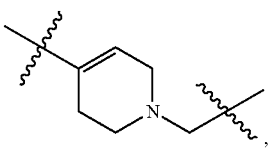, 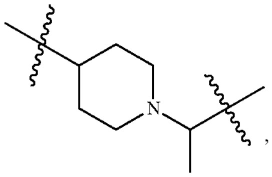, 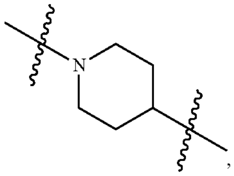, 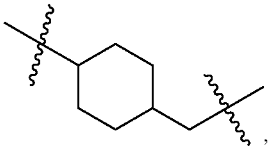, 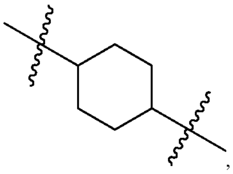, 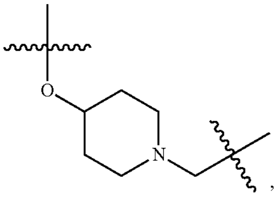, 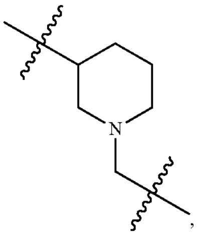, 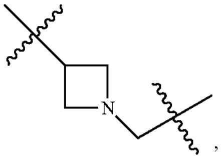, 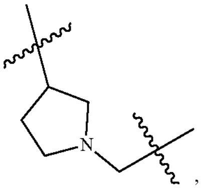, 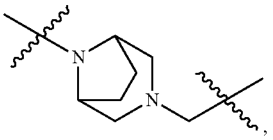, 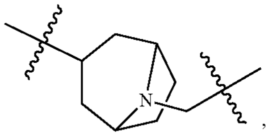, 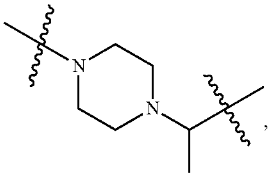, 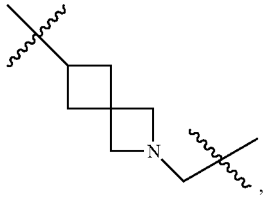, 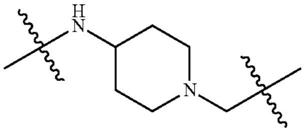 or -continued

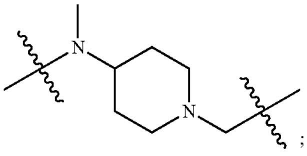

;

wherein each group substituted with 1 or 2 occurrences of Rd.

In one embodiment of compound of formula (IA), M is selected from M-1 and M-2; wherein Z is oxazolylenyl or isoxazolylenyl;

$R_3$ and $R_8$ independently represents alkyl, haloalkyl or hydroxyalkyl;

$R_4$ and $R_9$ independently represents hydrogen, alkyl, heteroalkyl, haloalkyl, hydroxyalkyl or acyl;

$R_5$ and $R_6$ independently represents hydrogen, alkyl, heteroalkyl, haloalkyl, hydroxyalkyl or (alkyl)aminoalkyl-;

$R_{10}$ and $R_{11}$ independently represents hydrogen, alkyl, halogen, haloalkyl, hydroxyalkyl or (alkyl)aminoalkyl-; and $R_7$ and $R_{12}$ represents thiazolyl substituted with alkyl.

In one embodiment of compound of formula (IA), M is represented by the structure:

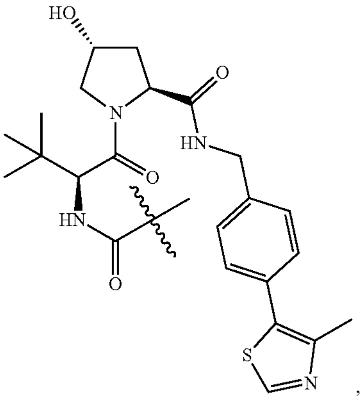

,

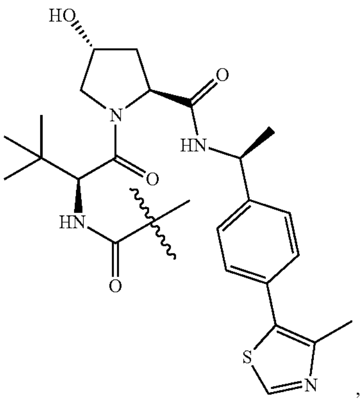

,

-continued

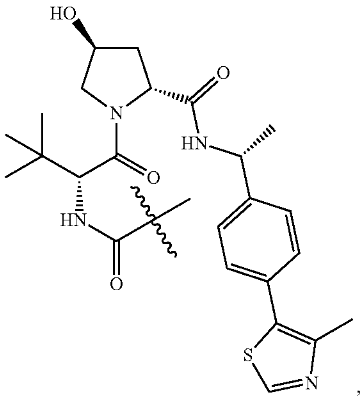

,

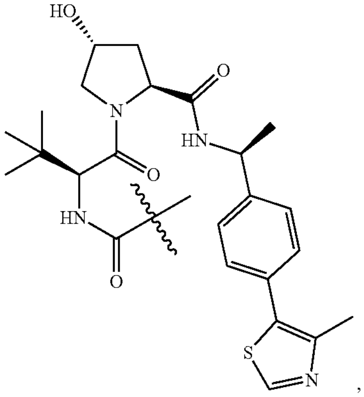

,

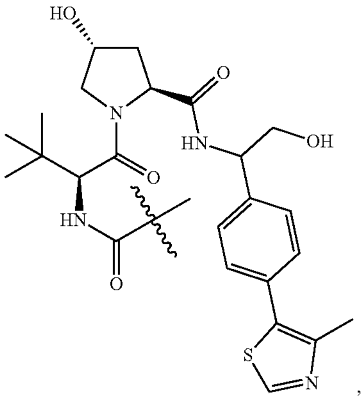

,

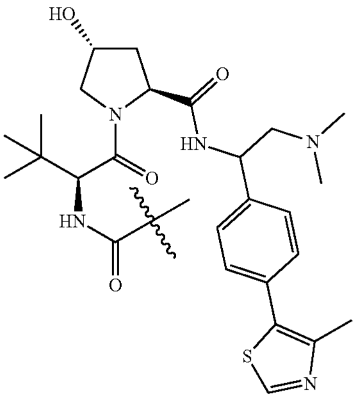

or

-continued

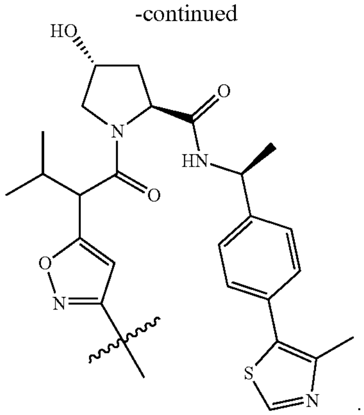

.

In one embodiment of compound of formula (IA), $R_1$ is halogen, hydroxy, 6- to 10-membered aryl or 5- to 10-membered heteroaryl; wherein the aryl and heteroaryl are optionally substituted with 1, 2 or 3 groups independently selected from hydroxy, alkoxy, halogen, alkyl and haloalkyl;

$R_2$ is hydrogen or halogen;

Ra, at each occurrence, independently represents hydrogen, halogen or haloalkyl;

L is a bond, $-O-CH_2CH_2CH_2-$, $-O-CH_2CH_2CH_2CH_2-$, $-O-CH_2CH_2-O-$, $-O-CH_2CH_2CH_2-O-$, $-NH-CH_2CH_2CH_2CH_2-$, $-N(CH_3)-CH_2CH_2-O-$, $-N(CH_3)-CH_2CH_2CH_2CH_2-$, $-NH-CH_2CH_2-O-$,

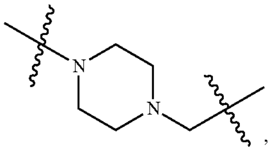

,

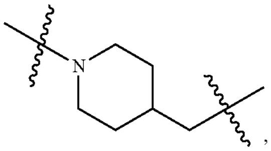

,

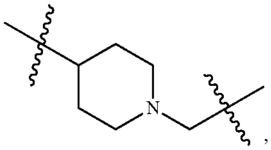

,

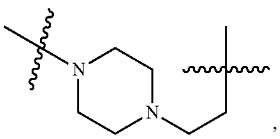

,

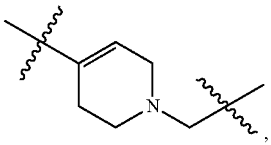

,

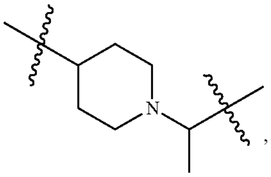

,

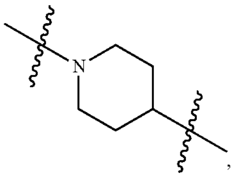

,

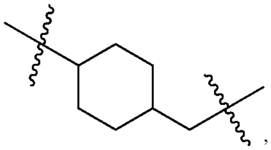

,

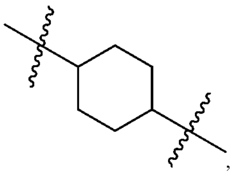

,

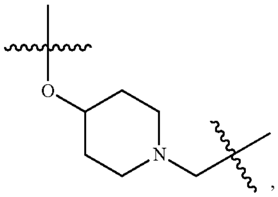

,

-continued

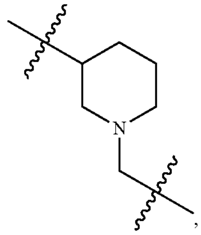

,

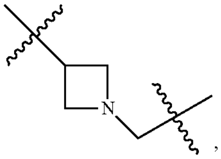

,

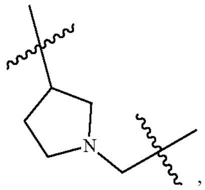

,

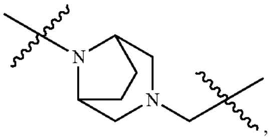

,

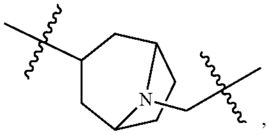

,

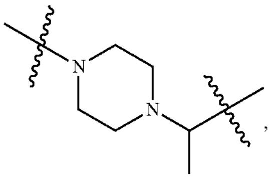

,

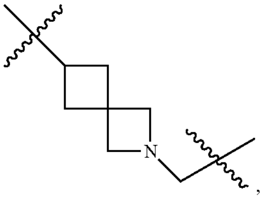

,

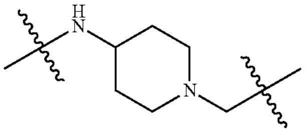

or

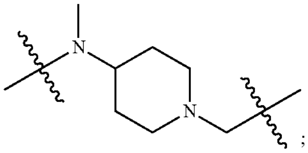

;

wherein each group substituted with 1 or 2 occurrences of Rd;

Z is oxazolylenyl or isoxazolylenyl;

$R_3$ and $R_8$ independently represents alkyl, haloalkyl or hydroxyalkyl;

$R_4$ and $R_9$ independently represents hydrogen, alkyl, heteroalkyl, haloalkyl, hydroxyalkyl or acyl;

$R_5$ and $R_6$ independently represents hydrogen, alkyl, heteroalkyl, haloalkyl, hydroxyalkyl or (alkyl)aminoalkyl-;

$R_{10}$ and $R_{11}$ independently represents hydrogen, alkyl, halogen, haloalkyl, hydroxyalkyl or (alkyl)aminoalkyl-; and $R_7$ and $R_{12}$ represents thiazolyl substituted with alkyl.

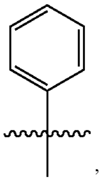

,

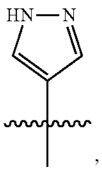

,

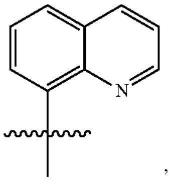

,

-continued

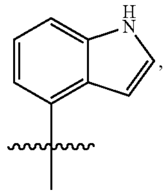,
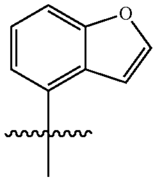 or
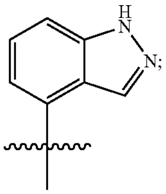;

wherein each ring is optionally substituted with 1, 2 or 3 groups independently selected from alkyl, hydroxy, alkoxy, halogen and haloalkyl;

$R_2$ is hydrogen or halogen;

Ra is hydrogen or halogen;

L is —O—$CH_2CH_2CH_2$—, —O—$CH_2CH_2CH_2CH_2$—, —O—$CH_2CH_2$—O—, —O—$CH_2CH_2CH_2$—O—, —NH—$CH_2CH_2CH_2CH_2$—, —N($CH_3$)—$CH_2CH_2$—O—, —N($CH_3$)—$CH_2CH_2CH_2CH_2$—, —NH—$CH_2CH_2$—O—,

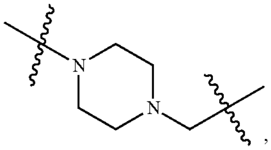,
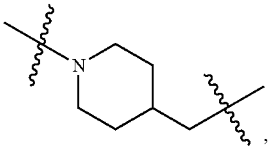,
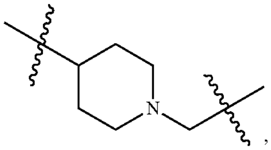,
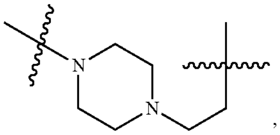,
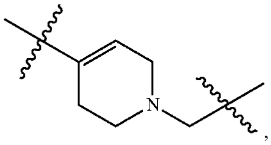,
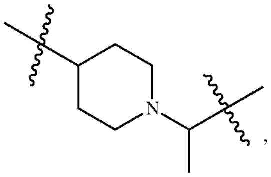,
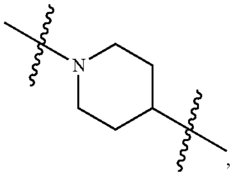,
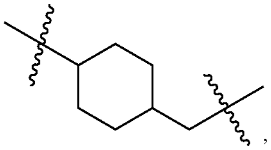,
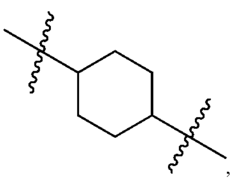,
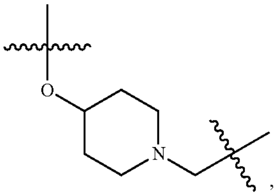,
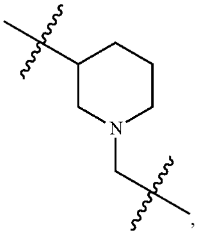,
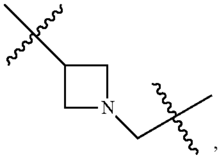, -continued

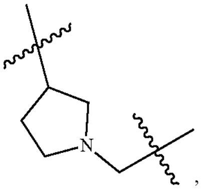,
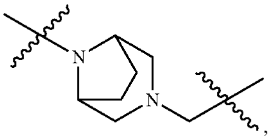,
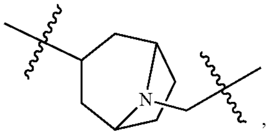,
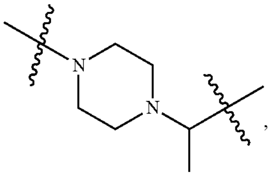,
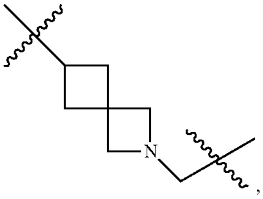,
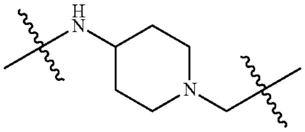 or
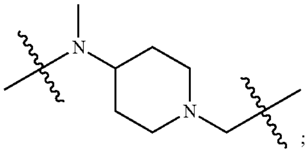;

wherein each ring is substituted with 1 or 2 occurrences of Rd;

M represents

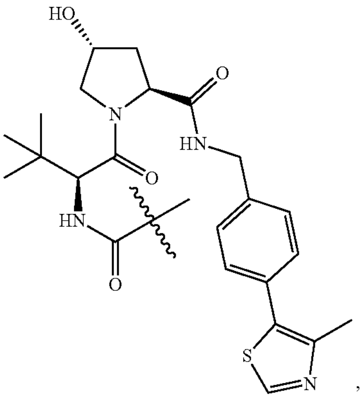,

-continued
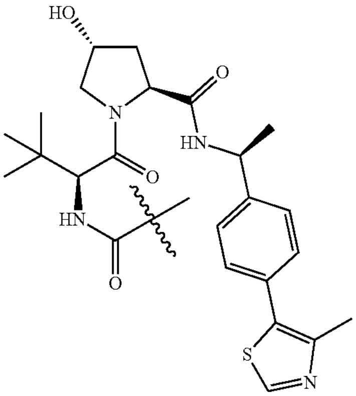
,
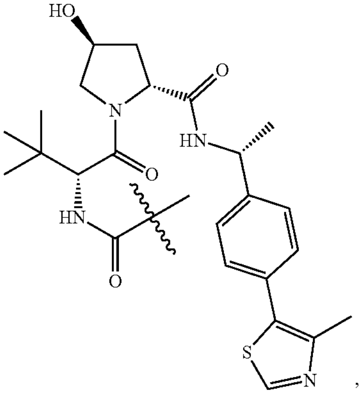
,
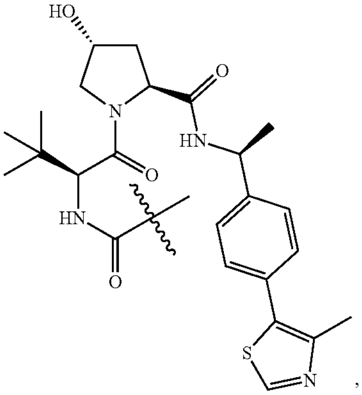
,
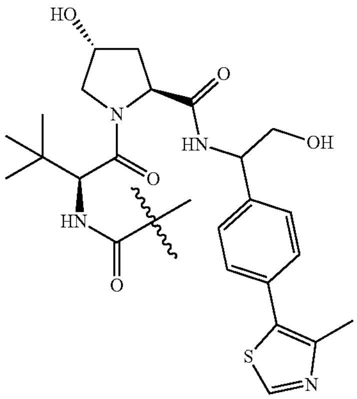
,
-continued
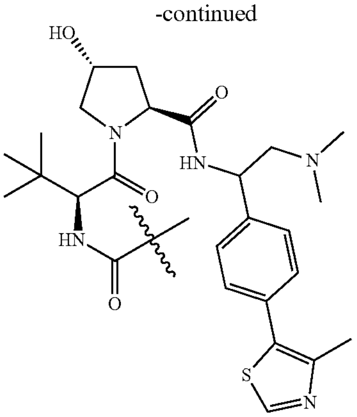
or
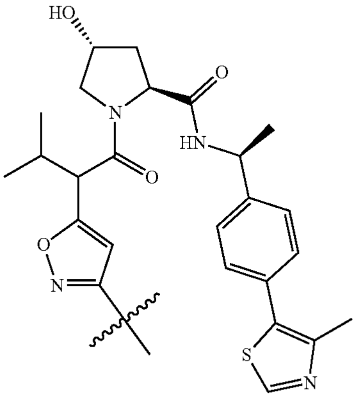
.
In one embodiment, the present invention provides compound of formula (IB) or a pharmaceutically acceptable salt or a stereoisomer or a tautomer or a prodrug thereof:
(IB)
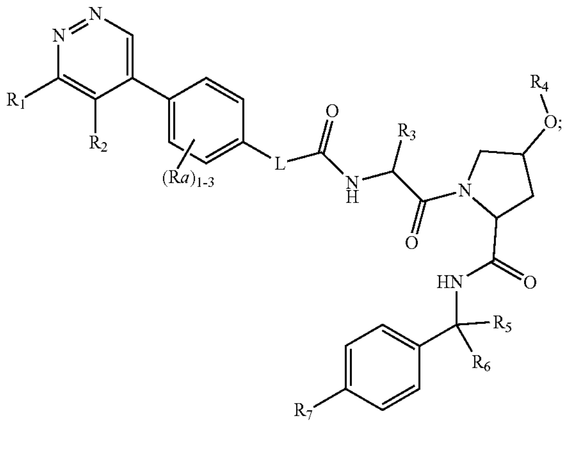
wherein $R_1$, $R_2$, Ra, $R_3$, $R_4$, $R_5$, $R_6$ and $R_7$ are as defined in compound of formula (I).

In one embodiment of compound of formula (IB), $R_1$ represents —Cl, —OH,

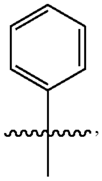, 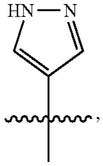, 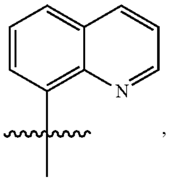, 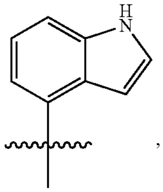,

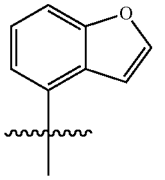 or 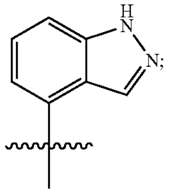;

wherein each ring is optionally substituted with 1 or 2 groups independently selected from alkyl, hydroxy and halogen.

In one embodiment of compound of formula (IB), L is a bond, —O—$(CH_2)$p-, —O—$(CH_2)$p-O—, —NRx-$(CH_2)$p-, —NRx-$(CH_2)$p-O—, —NRx-(3- to 10-membered heterocycloalkylenyl)-(CRxRy)n-, (3- to 10-membered cycloalkylenyl)-(CRxRy)n-, (3- to 10-membered heterocycloalkylenyl)-(CRxRy)n or —O-(3- to 10-membered heterocycloalkylenyl)-(CRxRy)n-.

In one embodiment of compound of formula (IA), L is —O—$CH_2CH_2CH_2$—, —O—$CH_2CH_2CH_2CH_2$—, —O—$CH_2CH_2$—O—, —O—$CH_2CH_2CH_2$—O—, —NH—$CH_2CH_2CH_2CH_2$—, —N$(CH_3)$—$CH_2CH_2$—O—, —N$(CH_3)$—$CH_2CH_2CH_2CH_2$—, —NH—$CH_2CH_2$—O—,

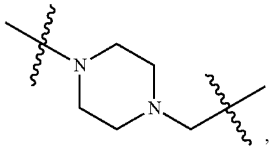, 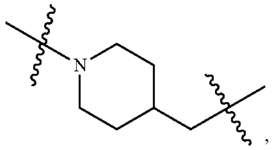,

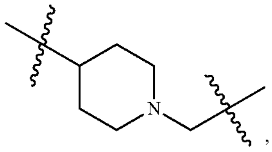, 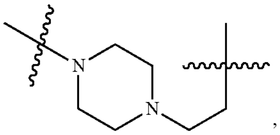,

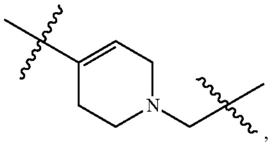, 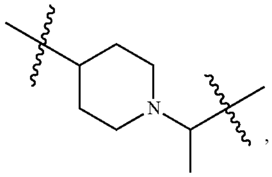,

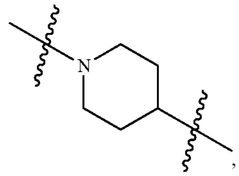, 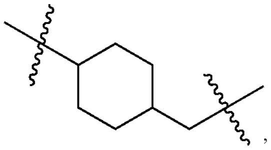,

-continued

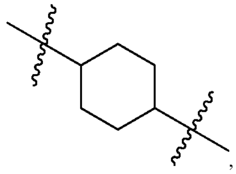, 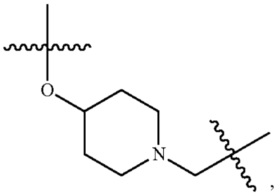,

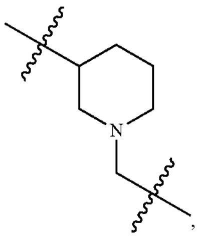, 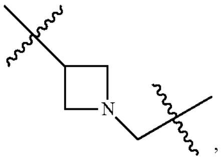,

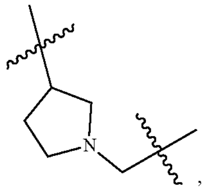, 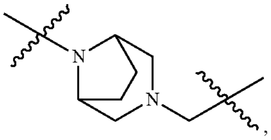,

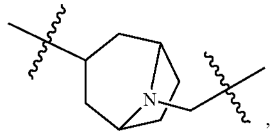, 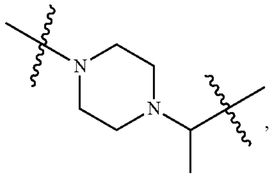,

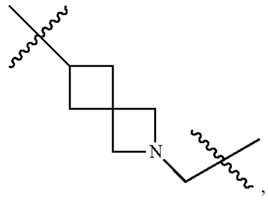,

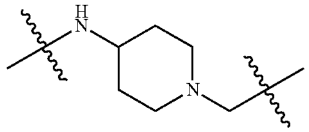 or

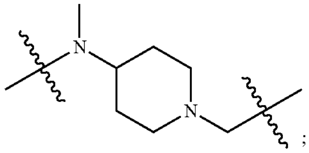;

wherein each ring is substituted with 1 or 2 occurrences of Rd.

In one embodiment of compound of formula (IB), $R_1$ represents —Cl, —OH,

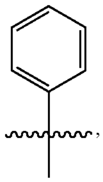, 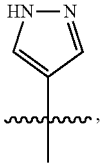, 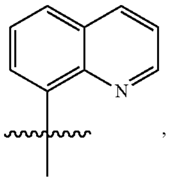, 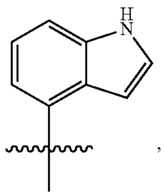,

-continued

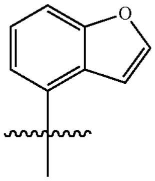

or

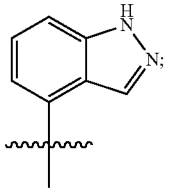

wherein each ring is optionally substituted with 1, 2 or 3 groups independently selected from alkyl, hydroxy and halogen;

$R_2$ is hydrogen or halogen;

Ra is hydrogen or halogen;

L is a bond, —O—$CH_2CH_2CH_2$—, —O—$CH_2CH_2CH_2CH_2$—, —O—$CH_2CH_2$—O—, —O—$CH_2CH_2CH_2$—O—, —NH—$CH_2CH_2CH_2CH_2$—, —N($CH_3$)—$CH_2CH_2$—O—, —N($CH_3$)—$CH_2CH_2CH_2CH_2$—, —NH—$CH_2CH_2$—O—,

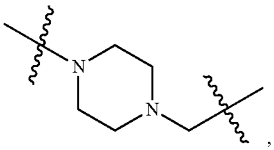
,
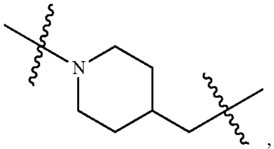
,
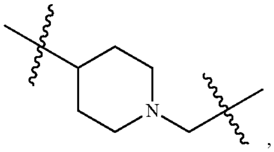
,
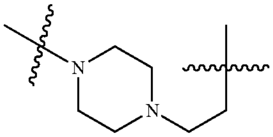
,
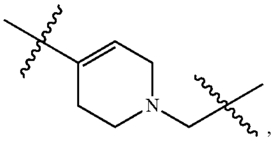
,
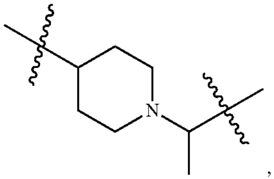
,
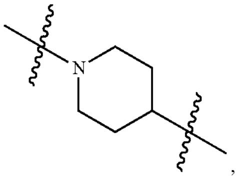
,
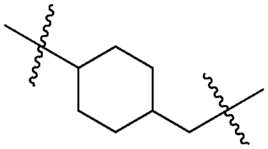
,
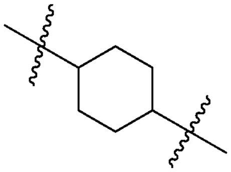
,
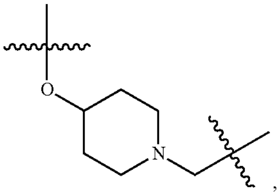
,
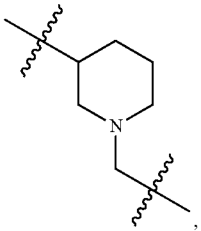
,
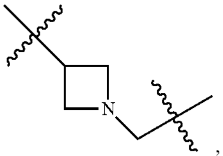
, -continued

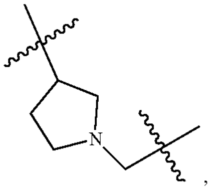
,
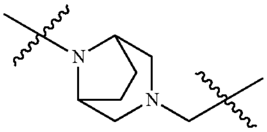
,
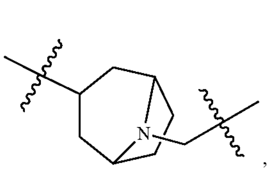
,
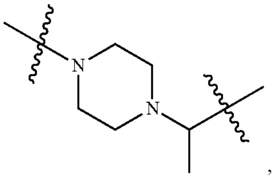
,
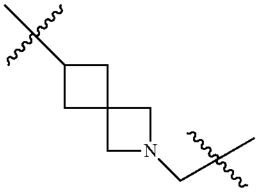
,
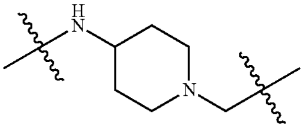

or

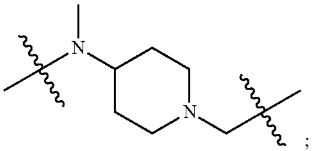
;

wherein each group substituted with 1 or 2 occurrences of Rd;

$R_3$ represents alkyl;

$R_4$ represents hydrogen or alkyl;

$R_5$ represents hydrogen;

$R_6$ represents alkyl, halogen, haloalkyl, hydroxyalkyl or (alkyl)aminoalkyl-; and $R_7$ represents thiazolyl substituted with alkyl.

In one embodiment, the present invention provides compound of formula (IC) or a pharmaceutically acceptable salt or a stereoisomer or a tautomer or a prodrug thereof:

(IC)

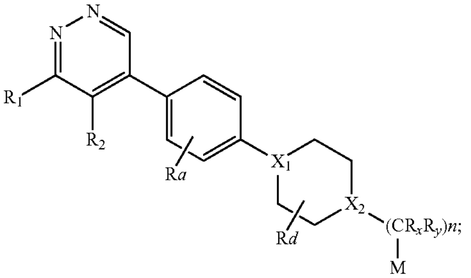

wherein $X_1$ and $X_2$ independently represents N or C; and $R_1$, $R_2$, Ra, Rd, Rx, Ry, $X_1$, $X_2$, n and M are as defined in compound of formula (I).

In one embodiment of compound of formula (IC),
$R_1$ is —Cl, —OH,
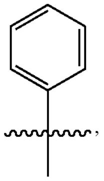,
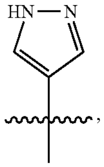,
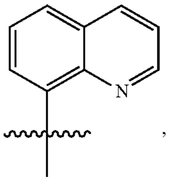,
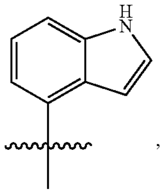,
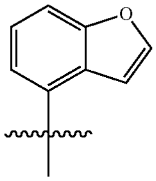
or
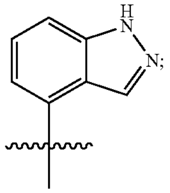
wherein each ring is optionally substituted with 1 or 2 groups independently selected from alkyl, hydroxy and halogen.
In one embodiment of compound of formula (IC), Rx is hydrogen; and Ry is hydrogen or alkyl.
In one embodiment of compound of formula (IC), M represents
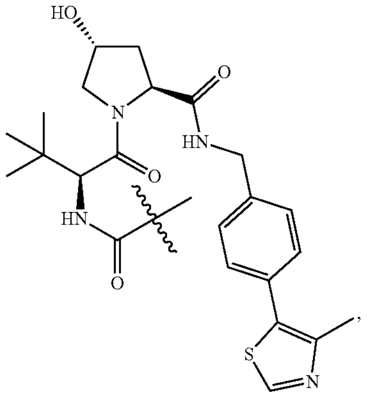
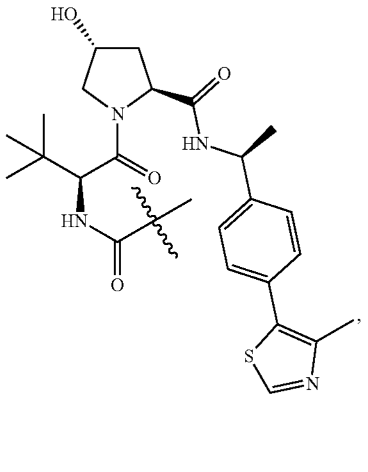
-continued
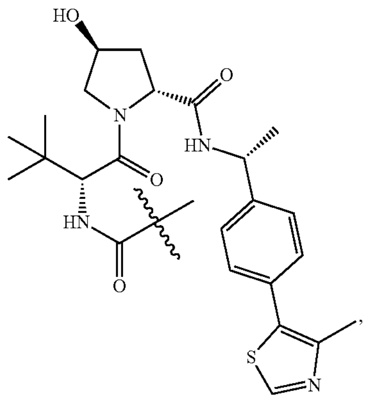
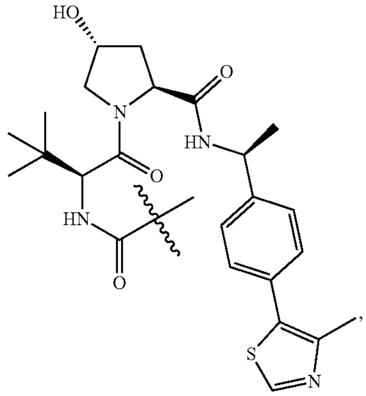
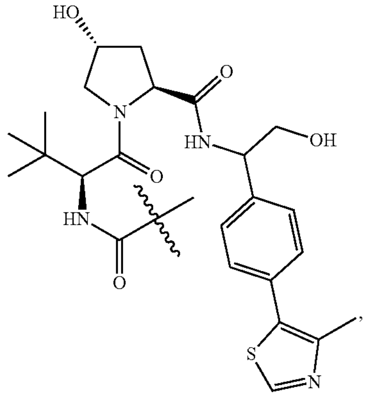
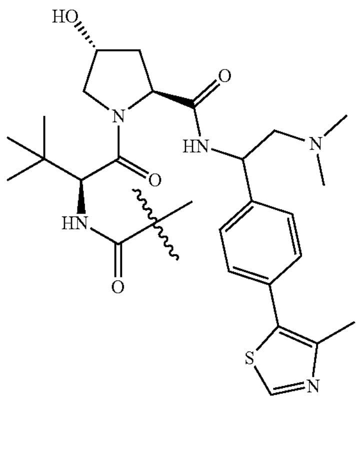
or -continued

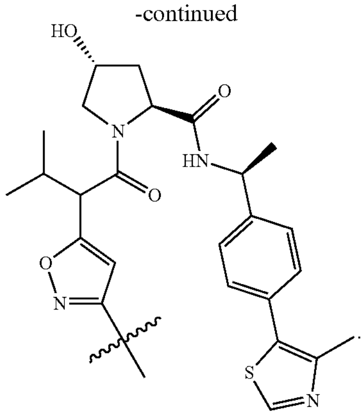
.

In one embodiment of compound of formula (IC), $X_1$ and $X_2$ independently represents N or C;

$R_1$ is —Cl, —OH,

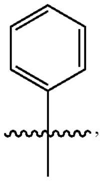
,
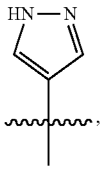
,
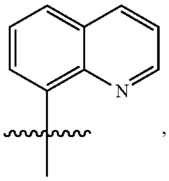
,
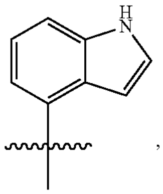
,
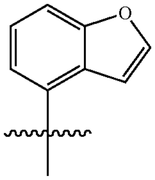
or
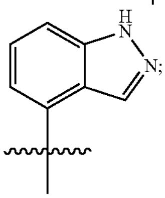
;

wherein each ring is optionally substituted with 1 or 2 groups independently selected from alkyl, hydroxy and halogen;

$R_2$ is hydrogen or halogen;

Ra represents hydrogen or halogen;

Rd is hydrogen or hydroxy;

Rx is hydrogen;

Ry is hydrogen or alkyl;

M represents

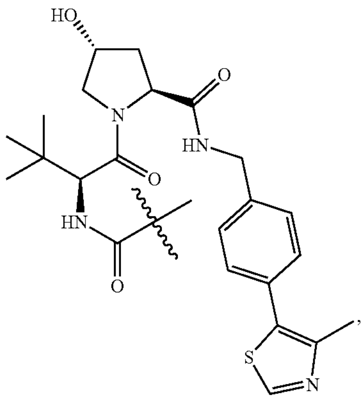
,

-continued

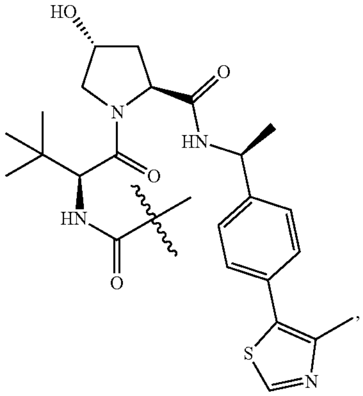
,

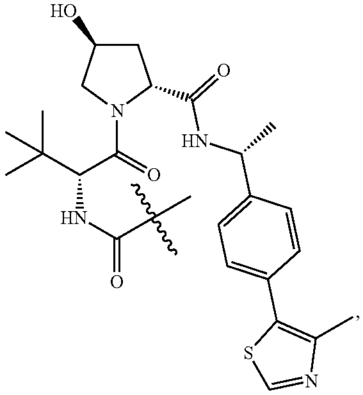
,

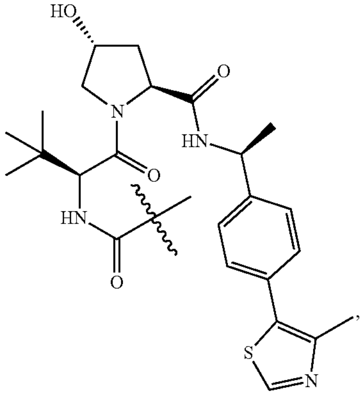
,

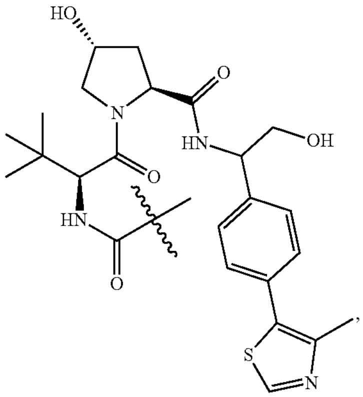
,

-continued

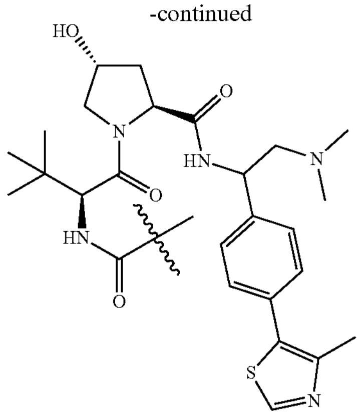

or

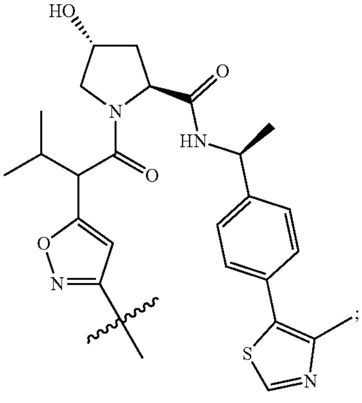

;

n is 0, 1, 2 or 3.

In one embodiment, the present invention provides compound of formula (ID) or a pharmaceutically acceptable salt or a stereoisomer or a tautomer or a prodrug thereof:

(ID)

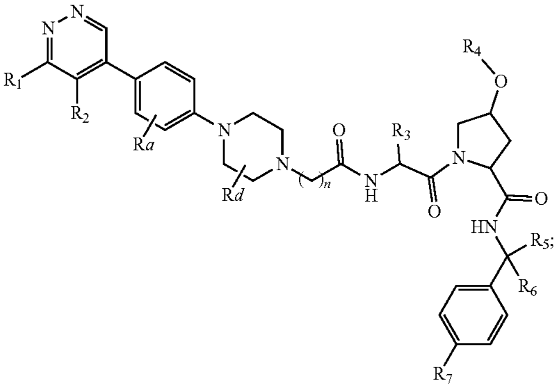

wherein $R_1$, $R_2$, Ra, Rd, $R_3$, $R_4$, $R_5$, $R_6$, $R_7$ and n are as defined in compound of formula (I).

In one embodiment of compound of formula (ID), $R_1$ is halogen, hydroxy, 6- to 10-membered aryl or 5- to 10-membered heteroaryl; wherein, the aryl and heteroaryl are optionally substituted hydroxy, halogen, alkyl and haloalkyl;

$R_2$ is hydrogen or halogen;

Ra represents hydrogen or halogen;

Rd is hydrogen or hydroxy;

$R_3$ represents alkyl, acyl or haloalkyl;

$R_4$ represents hydrogen or alkyl;

$R_5$ represents hydrogen;

$R_6$ represents hydrogen, alkyl, halogen, haloalkyl, hydroxyalkyl or (alkyl)aminoalkyl-;

$R_7$ thiazolyl substituted with alkyl; and n is 0, 1, 2 or 3.

In one embodiment of compound of formula (ID), $R_1$ is halogen, hydroxy, 6- to 10-membered aryl or 5- to 10-membered heteroaryl; wherein, the aryl and heteroaryl are optionally substituted hydroxy, halogen, alkyl and haloalkyl;

$R_2$ is hydrogen or halogen;

Ra represents hydrogen or halogen;

Rd is hydrogen or hydroxy;

$R_3$ represents alkyl, acyl or haloalkyl;

$R_4$ represents hydrogen or alkyl;

$R_5$ represents hydrogen;

$R_6$ represents hydrogen, alkyl, halogen, hydroxyalkyl or (alkyl)aminoalkyl-;

$R_7$ thiazolyl substituted with alkyl; and n is 0, 1, 2 or 3.

In one embodiment, the present invention provides compound of formula (IE) or a pharmaceutically acceptable salt or a stereoisomer or a tautomer or a prodrug thereof:

(IE)

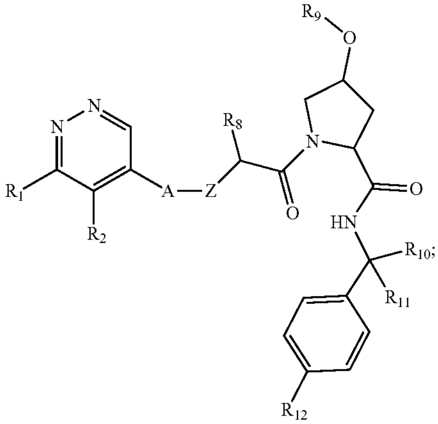

wherein $R_1$, $R_2$, $R_8$, $R_9$, $R_{10}$, $R_{11}$, $R_{12}$, A and Z are as defined in compound of formula (I).

In one embodiment of compound of formula (IE), $R_1$ represents —Cl, —OH,

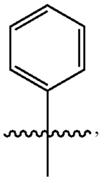

,

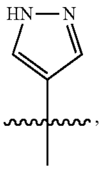

,

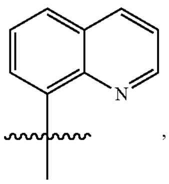

,

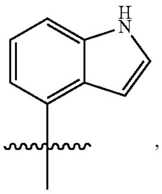

,

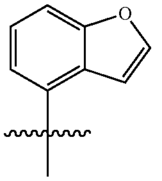

or

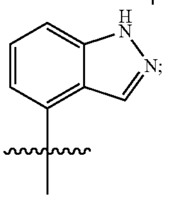

wherein each ring is optionally substituted with 1 or 2 groups independently selected from alkyl, hydroxy and halogen.

$R_2$ is hydrogen or halogen;

A represents

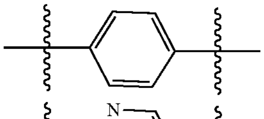, 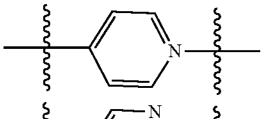,
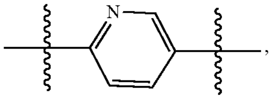, 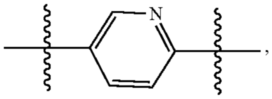,
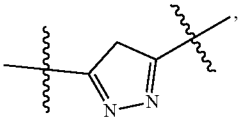, 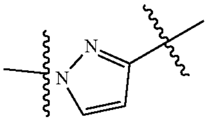 or

-continued

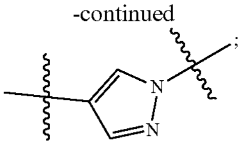;

wherein each ring is substituted with n or 2 occurrences hydrogen or halogen;

Z represents oxazolylenyl or isoxazolylenyl;

$R_8$ represents alkyl;

$R_9$ represents hydrogen;

$R_{10}$ represents hydrogen;

$R_{11}$ represents alkyl; and $R_{12}$ represents thiazolyl substituted with alkyl.

In one embodiment, the present invention provides a compound or a pharmaceutically acceptable salt or a stereoisomer or a tautomer or a prodrug thereof; wherein the compound is selected from:

| Compound | IUPAC |
|---|---|
| 1 | (2S,4R)-4-hydroxy-1-(2-(3-(4-(6-(2-hydroxyphenyl)pyridazin-4-yl)phenyl)isoxazol-5-yl)-3-methylbutanoyl)-N-((S)-1-(4-(4-methylthiazol-5-yl)phenyl)ethyl)pyrrolidine-2-carboxamide; |
| 2 | (2S,4R)-4-hydroxy-1-((S)-2-(2-(4-(4-(6-(2-hydroxyphenyl)pyridazin-4-yl)phenyl)piperazin-1-yl)acetamido)-3,3-dimethylbutanoyl)-N-((S)-1-(4-(4-methylthiazol-5-yl)phenyl)ethyl)pyrrolidine-2-carboxamide; |
| 3 | (2S,4R)-1-((S)-2-(2-(4-(4-(6-chloropyridazin-4-yl)phenyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide; |
| 4 | (2S,4R)-1-((S)-2-(2-(4-(4-(6-(5-fluoro-2-hydroxyphenyl)pyridazin-4-yl)phenyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide; |
| 5 | (2S,4R)-4-hydroxy-1-((S)-2-(2-(4-(5-(6-(2-hydroxyphenyl)pyridazin-4-yl)pyridin-2-yl)piperazin-1-yl)acetamido)-3,3-dimethylbutanoyl)-N-((S)-1-(4-(4-methylthiazol-5-yl)phenyl)ethyl)pyrrolidine-2-carboxamide; |
| 6 | (2S,4R)-4-hydroxy-1-((S)-2-(2-(1-(4-(6-(2-hydroxyphenyl)pyridazin-4-yl)phenyl)piperidin-4-yl)acetamido)-3,3-dimethylbutanoyl)-N-((S)-1-(4-(4-methylthiazol-5-yl)phenyl)ethyl)pyrrolidine-2-carboxamide; |
| 7 | (2S,4R)-1-((S)-2-(2-(4-(4-(6-(2-fluorophenyl)pyridazin-4-yl)phenyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide; |
| 8 | (2S,4R)-4-hydroxy-1-((S)-2-(3-(4-(4-(6-(2-hydroxyphenyl)pyridazin-4-yl)phenyl)piperazin-1-yl)propanamido)-3,3-dimethylbutanoyl)-N-((S)-1-(4-(4-methylthiazol-5-yl)phenyl)ethyl)pyrrolidine-2-carboxamide; |
| 9 | (2S,4R)-1-((S)-3,3-dimethyl-2-(2-(4-(4-(6-(1-methyl-1H-pyrazol-4-yl)pyridazin-4-yl)phenyl)piperazin-1-yl)acetamido)butanoyl)-4-hydroxy-N-((S)-1-(4-(4-methylthiazol-5-yl)phenyl)ethyl)pyrrolidine-2-carboxamide; |
| 10 | (2S,4R)-4-hydroxy-1-((S)-2-(2-(4-(4-(6-(2-hydroxyphenyl)pyridazin-4-yl)phenyl)-3,6-dihydropyridin-1(2H)-yl)acetamido)-3,3-dimethylbutanoyl)-N-((S)-1-(4-(4-methylthiazol-5-yl)phenyl)ethyl)pyrrolidine-2-carboxamide; |
| 11 | (2S,4R)-4-hydroxy-1-((S)-2-(2-(4-(4-(6-(2-hydroxyphenyl)pyridazin-4-yl)phenyl)piperidin-1-yl)acetamido)-3,3-dimethylbutanoyl)-N-((S)-1-(4-(4-methylthiazol-5-yl)phenyl)ethyl)pyrrolidine-2-carboxamide; |
| 12 | (2S,4R)-4-hydroxy-1-((S)-2-(2-(4-(4-(6-(2-hydroxyphenyl)pyridazin-4-yl)phenyl)piperidin-1-yl)acetamido)-3,3-dimethylbutanoyl)-N-(4-(4-methylthiazol-5-yl)benzyl)pyrrolidine-2-carboxamide; |
| 13 | (2S,4R)-1-((S)-2-(2-(4-(4-(6-(5-fluoro-2-hydroxyphenyl)pyridazin-4-yl)phenyl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide; |
| 14 | (2S,4R)-4-hydroxy-1-((2S)-2-(2-(4-(4-(6-(2-hydroxyphenyl)pyridazin-4-yl)phenyl)piperidin-1-yl)propanamido)-3,3-dimethylbutanoyl)-N-((S)-1-(4-(4-methylthiazol-5-yl)phenyl)ethyl)pyrrolidine-2-carboxamide; |
| 15 | (2S,4R)-1-((S)-2-(2-(4-(2-fluoro-4-(6-(2-hydroxyphenyl)pyridazin-4-yl)phenyl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide; |
| 16 | N-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)-1-(4-(6-(2-hydroxyphenyl)pyridazin-4-yl)phenyl)piperidine-4-carboxamide; |
| 17 | (2S,4R)-4-hydroxy-1-((S)-2-(2-(4-(4-(6-(2-hydroxyphenyl)pyridazin-4-yl)phenyl)cyclohexyl)acetamido)-3,3-dimethylbutanoyl)-N-((S)-1-(4-(4-methylthiazol-5-yl)phenyl)ethyl)pyrrolidine-2-carboxamide; |

-continued

| Compound | IUPAC |
|---|---|
| 18 | (2S,4R)-4-hydroxy-1-((S)-2-(4-(4-(6-(2-hydroxyphenyl)pyridazin-4-yl)phenyl)cyclohexane-1-carboxamido)-3,3-dimethylbutanoyl)-N-((S)-1-(4-(4-methylthiazol-5-yl)phenyl)ethyl)pyrrolidine-2-carboxamide; |
| 19 | (2S,4R)-4-hydroxy-1-((S)-2-(2-(4-(4-(6-(2-hydroxyphenyl)pyridazin-4-yl)phenoxy)piperidin-1-yl)acetamido)-3,3-dimethylbutanoyl)-N-((S)-1-(4-(4-methylthiazol-5-yl)phenyl)ethyl)pyrrolidine-2-carboxamide; |
| 20 | (2S,4R)-4-hydroxy-1-((2S)-2-(2-(3-(4-(6-(2-hydroxyphenyl)pyridazin-4-yl)phenyl)piperidin-1-yl)acetamido)-3,3-dimethylbutanoyl)-N-((S)-1-(4-(4-methylthiazol-5-yl)phenyl)ethyl)pyrrolidine-2-carboxamide; |
| 21 | (2S,4R)-4-hydroxy-1-((S)-2-(2-(3-(4-(6-(2-hydroxyphenyl)pyridazin-4-yl)phenyl)azetidin-1-yl)acetamido)-3,3-dimethylbutanoyl)-N-((S)-1-(4-(4-methylthiazol-5-yl)phenyl)ethyl)pyrrolidine-2-carboxamide; |
| 22 | (2S,4R)-4-hydroxy-1-((2S)-2-(2-(3-(4-(6-(2-hydroxyphenyl)pyridazin-4-yl)phenyl)pyrrolidin-1-yl)acetamido)-3,3-dimethylbutanoyl)-N-((S)-1-(4-(4-methylthiazol-5-yl)phenyl)ethyl)pyrrolidine-2-carboxamide; |
| 23 | (2S,4R)-4-hydroxy-1-((S)-2-(2-(4-(3-(6-(2-hydroxyphenyl)pyridazin-4-yl)phenyl)piperidin-1-yl)acetamido)-3,3-dimethylbutanoyl)-N-((S)-1-(4-(4-methylthiazol-5-yl)phenyl)ethyl)pyrrolidine-2-carboxamide; |
| 24 | (2S,4R)-4-hydroxy-1-((2S)-2-(2-(8-(4-(6-(2-hydroxyphenyl)pyridazin-4-yl)phenyl)-3,8-diazabicyclo[3.2.1]octan-3-yl)acetamido)-3,3-dimethylbutanoyl)-N-((S)-1-(4-(4-methylthiazol-5-yl)phenyl)ethyl)pyrrolidine-2-carboxamide; |
| 25 | (2S,4R)-4-hydroxy-1-((2S)-2-(2-(3-(4-(6-(2-hydroxyphenyl)pyridazin-4-yl)phenyl)-8-azabicyclo[3.2.1]octan-8-yl)acetamido)-3,3-dimethylbutanoyl)-N-((S)-1-(4-(4-methylthiazol-5-yl)phenyl)ethyl)pyrrolidine-2-carboxamide; |
| 26 | (2S,4R)-1-((S)-2-(2-(4-(2-fluoro-4-(6-(2-hydroxyphenyl)pyridazin-4-yl)phenyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide; |
| 27 | (2S,4R)-4-hydroxy-1-((S)-2-(2-(4-(5-(6-(2-hydroxyphenyl)pyridazin-4-yl)pyridin-2-yl)piperidin-1-yl)acetamido)-3,3-dimethylbutanoyl)-N-((S)-1-(4-(4-methylthiazol-5-yl)phenyl)ethyl)pyrrolidine-2-carboxamide; |
| 28 | 2S,4R)-4-hydroxy-1-((2S)-2-(2-(4-(4-(6-(2-hydroxyphenyl)pyridazin-4-yl)phenyl)piperazin-1-yl)propanamido)-3,3-dimethylbutanoyl)-N-((S)-1-(4-(4-methylthiazol-5-yl)phenyl)ethyl)pyrrolidine-2-carboxamide; |
| 29 (Isomer-1) | (2S,4R)-4-hydroxy-1-((2S)-2-(2-(4-(4-(6-(2-hydroxyphenyl)pyridazin-4-yl)phenyl)piperazin-1-yl)propanamido)-3,3-dimethylbutanoyl)-N-((S)-1-(4-(4-methylthiazol-5-yl)phenyl)ethyl)pyrrolidine-2-carboxamide; |
| 30 (Isomer-2) | (2S,4R)-4-hydroxy-1-((2S)-2-(2-(4-(4-(6-(2-hydroxyphenyl)pyridazin-4-yl)phenyl)piperazin-1-yl)propanamido)-3,3-dimethylbutanoyl)-N-((S)-1-(4-(4-methylthiazol-5-yl)phenyl)ethyl)pyrrolidine-2-carboxamide; |
| 31 | (2S,4R)-4-hydroxy-1-((S)-2-(2-(6-(4-(6-(2-hydroxyphenyl)pyridazin-4-yl)phenyl)-2-azaspiro[3.3]heptan-2-yl)acetamido)-3,3-dimethylbutanoyl)-N-((S)-1-(4-(4-methylthiazol-5-yl)phenyl)ethyl)pyrrolidine-2-carboxamide; |
| 32 | (2S,4R)-4-hydroxy-1-((S)-2-(2-(4-hydroxy-4-(4-(6-(2-hydroxyphenyl)pyridazin-4-yl)phenyl)piperidin-1-yl)acetamido)-3,3-dimethylbutanoyl)-N-((S)-1-(4-(4-methylthiazol-5-yl)phenyl)ethyl)pyrrolidine-2-carboxamide; |
| 33 | (2S,4R)-4-hydroxy-1-((S)-2-(2-(4-(4-(6-(2-hydroxyphenyl)pyridazin-4-yl)-1H-pyrazol-1-yl)piperidin-1-yl)acetamido)-3,3-dimethylbutanoyl)-N-((S)-1-(4-(4-methylthiazol-5-yl)phenyl)ethyl)pyrrolidine-2-carboxamide; |
| 34 | (2S,4R)-4-hydroxy-1-((S)-2-(5-(4-(6-(2-hydroxyphenyl)pyridazin-4-yl)phenoxy)pentanamido)-3,3-dimethylbutanoyl)-N-((S)-1-(4-(4-methylthiazol-5-yl)phenyl)ethyl)pyrrolidine-2-carboxamide; |
| 35 | (2S,4R)-4-hydroxy-1-((S)-2-(4-(4-(6-(2-hydroxyphenyl)pyridazin-4-yl)phenoxy)butanamido)-3,3-dimethylbutanoyl)-N-((S)-1-(4-(4-methylthiazol-5-yl)phenyl)ethyl)pyrrolidine-2-carboxamide; |
| 36 | (2S,4R)-4-hydroxy-1-((S)-2-(5-((4-(6-(2-hydroxyphenyl)pyridazin-4-yl)phenyl)amino)pentanamido)-3,3-dimethylbutanoyl)-N-((S)-1-(4-(4-methylthiazol-5-yl)phenyl)ethyl)pyrrolidine-2-carboxamide; |
| 37 | (2S,4R)-1-((S)-2-(2-(4-(4-(6-(2-(difluoromethyl)phenyl)pyridazin-4-yl)phenyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide; |
| 38 | (2S,4R)-1-((S)-3,3-dimethyl-2-(2-(4-(4-(6-(quinolin-8-yl)pyridazin-4-yl)phenyl)piperazin-1-yl)acetamido)butanoyl)-4-hydroxy-N-((S)-1-(4-(4-methylthiazol-5-yl)phenyl)ethyl)pyrrolidine-2-carboxamide; |
| 39 | (2S,4R)-1-((S)-2-(2-(4-(4-(6-(1H-indol-7-yl)pyridazin-4-yl)phenyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide; |
| 40 | (2S,4R)-1-((S)-2-(2-(4-(4-(6-(benzofuran-7-yl)pyridazin-4-yl)phenyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide; |
| 41 | (2S,4R)-1-((S)-2-(2-(4-(4-(6-(1H-indazol-7-yl)pyridazin-4-yl)phenyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide; |
| 42 | (2S,4R)-4-hydroxy-1-(2-(3-(2-(4-(6-(2-hydroxyphenyl)pyridazin-4-yl)phenoxy)ethoxy)isoxazol-5-yl)-3-methylbutanoyl)-N-((S)-1-(4-(4-methylthiazol-5-yl)phenyl)ethyl)pyrrolidine-2-carboxamide; |

-continued

| Compound | IUPAC |
|---|---|
| 43 | (2S,4R)-4-hydroxy-1-(2-(3-(3-(4-(6-(2-hydroxyphenyl)pyridazin-4-yl)phenoxy)propoxy)isoxazol-5-yl)-3-methylbutanoyl)-N-((S)-1-(4-(4-methylthiazol-5-yl)phenyl)ethyl)pyrrolidine-2-carboxamide; |
| 44 | (2S,4R)-4-hydroxy-1-(2-(3-(2-((4-(6-(2-hydroxyphenyl)pyridazin-4-yl)phenyl)(methyl)amino)ethoxy)isoxazol-5-yl)-3-methylbutanoyl)-N-((S)-1-(4-(4-methylthiazol-5-yl)phenyl)ethyl)pyrrolidine-2-carboxamide; |
| 45 | (2S,4R)-4-hydroxy-1-((S)-2-(2-(4-((4-(6-(2-hydroxyphenyl)pyridazin-4-yl)phenyl)amino)piperidin-1-yl)acetamido)-3,3-dimethylbutanoyl)-N-((S)-1-(4-(4-methylthiazol-5-yl)phenyl)ethyl)pyrrolidine-2-carboxamide; |
| 46 | (2S,4R)-4-hydroxy-1-((S)-2-(2-(4-((4-(6-(2-hydroxyphenyl)pyridazin-4-yl)phenyl)(methyl)amino)piperidin-1-yl)acetamido)-3,3-dimethylbutanoyl)-N-((S)-1-(4-(4-methylthiazol-5-yl)phenyl)ethyl)pyrrolidine-2-carboxamide; |
| 47 | (2S,4R)-4-hydroxy-1-((S)-2-(2-(4-(4-(6-hydroxypyridazin-4-yl)phenyl)piperazin-1-yl)acetamido)-3,3-dimethylbutanoyl)-N-((S)-1-(4-(4-methylthiazol-5-yl)phenyl)ethyl)pyrrolidine-2-carboxamide; |
| 48 | (2S,4R)-4-hydroxy-N-((R)-2-hydroxy-1-(4-(4-methylthiazol-5-yl)phenyl)ethyl)-1-((S)-2-(2-(4-(4-(6-(2-hydroxyphenyl)pyridazin-4-yl)phenyl)piperazin-1-yl)acetamido)-3,3-dimethylbutanoyl)pyrrolidine-2-carboxamide; |
| 49 | (2S,4R)-N-(2-(dimethylamino)-1-(4-(4-methylthiazol-5-yl)phenyl)ethyl)-4-hydroxy-1-((S)-2-(2-(4-(4-(6-(2-hydroxyphenyl)pyridazin-4-yl)phenyl)piperazin-1-yl)acetamido)-3,3-dimethylbutanoyl)pyrrolidine-2-carboxamide; and |
| 50 | (2S,4R)-4-hydroxy-1-(2-(3-(2-((4-(6-(2-hydroxyphenyl)pyridazin-4-yl)phenyl)amino)ethoxy)isoxazol-5-yl)-3-methylbutanoyl)-N-((S)-1-(4-(4-methylthiazol-5-yl)phenyl)ethyl)pyrrolidine-2-carboxamide; |

or a pharmaceutically acceptable salt or a stereoisomer or a tautomer or a prodrug thereof.

Method of Treatment

In one embodiment, the present invention provides a compound of formula (I) or a pharmaceutically acceptable salt or a stereoisomer or a tautomer or a prodrug thereof for use as a medicament.

In one embodiment, the present invention provides a use of a compound of formula (I) or a pharmaceutical acceptable salt or a stereoisomer or a tautomer or a prodrug thereof, in the manufacture of a medicament for the treatment of diseases or disorders dependent upon SMARCA2 and/or SMARCA4.

In one embodiment, the present invention provides a compound of formula (I) or a pharmaceutical acceptable salt or a stereoisomer or a tautomer or a prodrug thereof, for use in treating a disease or disorder dependent upon SMARCA2 and/or SMARCA4.

In one embodiment, a disease or disorder dependent upon SMARCA2 and/or SMARCA4 is cancer.

In one embodiment, the present invention provides a method of degrading a target protein comprising administering to a subject a therapeutically effective amount of a compound of formula (I) or a pharmaceutically acceptable salt or a stereoisomer or a tautomer or a prodrug thereof, wherein the compound is effective for degrading the target protein.

In one embodiment, the present invention provides a method for treating or delaying progression of a disease or disorder dependent upon SMARCA2 and/or SMARCA4 in a subject comprising administering to the subject, in need thereof, a therapeutically effective amount of a compound of formula (I) or a pharmaceutically acceptable salt or a stereoisomer or a tautomer or a prodrug thereof.

In one embodiment, diseases or disorders that are dependent upon SMARCA2 and/or SMARCA4, include cancer.

In one embodiment, the present invention provides a method for inhibiting tumor growth in a subject afflicted with cancer comprising administering a compound of formula (I) or a pharmaceutically acceptable salt or a stereoisomer or a tautomer or a prodrug thereof to the subject, in need thereof.

In one embodiment, the present invention provides a pharmaceutical composition comprising a compound of formula (I), or a pharmaceutically acceptable salt thereof or a stereoisomer or a tautomer or a prodrug thereof as described herein and at least one pharmaceutically acceptable excipient (such as a pharmaceutically acceptable carrier or diluent).

Preferably, the pharmaceutical composition comprises a therapeutically effective amount of at least one compound described herein or a pharmaceutically acceptable salt or a stereoisomer or a tautomer or a prodrug thereof. The compounds described in the present invention may be associated with a pharmaceutically acceptable excipient (such as a carrier or a diluent) or be diluted by a carrier or enclosed within a carrier which can be in the form of a capsule, sachet, paper or other container.

In one embodiment, the present invention provides a pharmaceutical composition comprising a compound of formula (I), for use in degrading a target protein in a subject wherein the target protein is SMARCA2 and/or SMARCA4.

In one embodiment, the subject is afflicted with a disease or disorder dependent upon SMARCA2 and/or SMARCA4.

In one embodiment, the subject is afflicted with cancer mediated by the target protein, wherein the target protein is SMARCA2 and/or SMARCA4.

In one embodiment, the present invention provides a pharmaceutical composition comprising a compound of formula (I) or a pharmaceutically acceptable salt or a stereoisomer or a tautomer or a prodrug thereof as described herein for use as a medicament.

In one embodiment, the present invention provides a pharmaceutical composition comprising a compound of formula (I), for use in treating or delaying progression of a disease or disorder mediated by SMARCA2 and/or SMARCA4.

In one embodiment, diseases or disorders that are dependent upon SMARCA2 and/or SMARCA4, are cancers selected from hematologic cancers, lung cancer (NSCLC i.e. non-small cell lung cancer), acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, head and neck cancer, hemangioblastoma, hepatoma, hepatocellular cancer, hormone insensitive prostate cancer, leiomyosarcoma, leukemia, liposarcoma, liver cancer, lymphagioendotheliosarcoma, lymphangiosarcoma, lymphoblastic leukemia, lymphoma (Hodgkin's and non-Hodgkin's; Burkitt's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, malignant rhabdoid tumor (MRT), rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

In one embodiment, the cancer dependent upon SMARCA2 and/or SMARCA4 is lung cancer such as NSCLC, i.e., non-small cell lung cancer.

In one embodiment, the cancer dependent upon SMARCA2 and/or SMARCA4 is melanoma.

In one further embodiment, the cancer is a SMARCA2 and/or SMARCA4 dependent cancer.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous, or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing the compounds of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatine capsules using such excipients as lactose or milk sugar as well as high molecular weight polyethylene glycols and the like.

The active compounds can also be in micro-encapsulated form with one or more excipients as noted above. The solid dosage forms of tablets, draggers, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, including but not limited to tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this application.

The ointments, pastes, creams, and gels may contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this application, excipients such as lactose, talc, silicic acid, aluminium hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Administration of the disclosed compounds and pharmaceutical compositions can be accomplished via any mode of administration for therapeutic agents. These modes include systemic or local administration such as oral, nasal, parenteral, intravenous, transdermal, subcutaneous, vaginal, buccal, rectal or topical administration modes.

Depending on the intended mode of administration, the disclosed compounds or pharmaceutical compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatine capsules comprising one or more compounds of the present disclosure and a pharmaceutically acceptable carrier, such as, but not limited to, a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminium silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, alginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, one or more disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

One or more disclosed compounds or compositions can be delivered by parental administration. The parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Definitions

Unless defined otherwise, all technical and scientific terms used herein have the same meaning as is commonly understood by one of skill in art to which the subject matter herein belongs. As used in the specification and the appended claims, unless specified to the contrary, the following terms have the meaning indicated in order to facilitate the understanding of the present invention.

The singular forms "a", "an" and "the" encompass plural references unless the context clearly indicates otherwise.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as the event or circumstance where the alkyl is not substituted.

The term "substituted" refers to moieties having substituents replacing hydrogen on one or more carbons of the backbone. It will be understood that "substitution" or "substituted with" includes an implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For the purposes of this invention, the heteroatoms such as nitrogen may have hydrogen substituents and/or any permissible substituents of organic compounds described herein which satisfy the valences of the heteroatoms. It will be understood by those skilled in the art that substituents can themselves be substituted, if appropriate.

As used herein, the term "alkylenyl" refers to divalent alkyl groups as defined herein. The term "alkyl" refers to saturated aliphatic groups, including but not limited to $C_1$-$C_{10}$ straight-chain alkyl groups or $C_3$-$C_{10}$ branched-chain alkyl groups. Preferably, "alkyl" group refers to $C_1$-$C_6$ straight-chain alkyl groups or $C_3$-$C_6$ branched-chain alkyl groups. Most preferably, the "alkyl" group refers to $C_1$-$C_4$ straight-chain alkyl groups or $C_3$-$C_8$ branched-chain alkyl groups. Examples of "alkyl" include, but are not limited to, methyl, ethyl, 1-propyl, 2-propyl, isopropyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl and 4-octyl. Accordingly, examples of "alkylenyl" include, but are not limited to, $—CH_2—$, $—CH_2CH_2—$, $—CH(CH_3)CH_2—$, $—CH_2CH_2CH_2CH_2—$, $—CH(CH_3)CH_2CH_2CH_2—$ and $—CH_2CH(CH_3)CH_2CH_2—$, The "alkyl" group may be optionally substituted.

As used herein, the term "haloalkyl" refers to alkyl substituted with one or more halogen atoms, wherein the halo and alkyl groups are as defined above. Examples of "haloalkyl" include but are not limited to fluoromethyl, difluoromethyl, chloromethyl, trifluoromethyl and 2,2,2-trifluoroethyl.

As used herein, the term "aminoalkyl" refers to an alkyl group substituted with an amino group, wherein the amino and alkyl groups are as defined above. Examples of "aminoalkyl" include but are not limited to $—CH_3—NH_2$, $—CH_2—CH_2—NH_2$, $—CH_2—CH_2—CH_2—NH_2$, $—CH(CH_3)—CH_2—NH_2$, $—CH_2—CH_2—NH(CH_3)$ and $—CH_2—CH_2—N(CH_3)_2$.

As used herein, the term "alkylamino" refers to an amino group substituted with one or two alkyl group(s), wherein the amino and alkyl groups are as defined above. Examples of "alkylamino" include but are not limited to $—NH(CH_3)$, $—N(CH_3)_2$, $—NH(C_2H_5)$ and $—NH(C_2H_5)_2$.

As used herein, the term "hydroxylalkyl" or "hydroxyalkyl" refers to an alkyl group, as defined above, wherein one or more of the alkyl group's hydrogen atoms have been replaced with hydroxyl group. Examples of hydroxylalkyl moieties include but are not limited to $—CH_2OH$, $—CH_2CH_2OH$, $—CH_2CH_2CH_2OH$, $—CH_2CH(OH)CH_2OH$, $—CH_2CH(OH) CH_3$, $—CH(CH_3)CH_2OH$.

As used herein, the term "cycloalkylenyl" refers to a divalent cycloalkylenyl group as defined herein. The term "cycloalkyl" means $C_3$-$C_{10}$ saturated cyclic hydrocarbon ring. A cycloalkyl may be a single ring, which typically contains from 3 to 7 carbon ring atoms. Examples of single ring cycloalkyls include but are not limited to cyclopropyl, cyclobutyl, cyclopentyl, cyclohexyl and cycloheptyl. A cycloalkyl may alternatively be polycyclic or contain more than one ring. Examples of polycyclic cycloalkyls include bridged, fused and spirocyclic carbocyclyls. Accordingly, examples of 'cycloalkylenyl include, but not limited to, cyclopropylenyl, cyclobutylenyl, cyclopentylenyl, cyclohexylenyl and cycloheptylenyl.

As used herein, the term "heterocycloalkylenyl" refers to a divalent heterocycloalkyl group as defined herein. The term "heterocycloalkyl" refers to a non-aromatic, saturated or partially saturated, bridged bicyclic, spirocyclic, monocyclic or polycyclic ring system of 3 to 15 member, unless the ring size is specifically mentioned, having at least one heteroatom or heterogroup selected from O, N, S, S(O), $S(O)_2$, NH and C(O) with the remaining ring atoms being independently selected from the group consisting of carbon, oxygen, nitrogen, and sulfur. The term "heterocycloalkyl" also refers to the bridged bicyclic ring system having at least one heteroatom or hetero group selected from O, N, S, S(O), $S(O)_2$, NH and C(O). Examples of "heterocycloalkyl" include, but not limited to, azetidinyl, oxetanyl, imidazolidinyl, pyrrolidinyl, oxazolidinyl, thiazolidinyl, pyrazolidinyl, tetrahydrofuranyl, piperidinyl, dihydropyridinyl, piperazinyl, tetrahydropyranyl, morpholinyl, thiomorpholinyl, 1,4-dioxanyl, dioxidothiomorpholinyl, oxapiperazinyl, oxapiperidinyl, tetrahydrofuryl, tetrahydropyranyl, tetrahydrothiophenyl, dihydropyranyl, indolinyl, indolinylmethyl, isoindolinyl, oxoisoindolinyl, dioxoisoindolinyl, aza-bicyclooctanyl, diazabicyclooctanyl, azocinyl, chromanyl, isochromanyl xanthenyl and 2-oxa-6-azaspiro[3.3]heptanyl. Accordingly, examples of 'heterocycloalkylenyl' include, but not limited to, azetidinylenyl, oxetanylenyl, pyrrolidinylenyl, piperidinylenyl, piperazinylenyl, tetrahydropyridinylenyl, diazobicyclooctanylenyl, azabicyclooctanylenyl, azaspiroheptanylenyl, tetrahydropyranyl, tetrahydropyridazinylenyl, morpholinylenyl, thiomorpholinylenyl, 1,4-dioxanylenyl, dioxidothiomorpholinylenyl, oxapiperazinylenyl, oxapiperidinylenyl, tetrahydropyranylenyl, dihydropyranylenyl and dihydropyrimidinylenyl. Attachment of a heterocycloalkyl substituent can occur via either a carbon atom or a heteroatom. A heterocycloalkyl group can be optionally substituted with one or more suitable groups by one or more aforesaid groups. Preferably "heterocycloalkyl" refers to 5- to 6-membered ring (unless the ring size is specifically mentioned) selected from the group consisting of imidazolidinyl, pyrrolidinyl, oxazolidinyl, thiazolidinyl, pyrazolidinyl, tetrahydrofuranyl, piperidinyl, piperazinyl, tetrahydropyranyl, morpholinyl and thiomorpholinyl. All heterocycloalkyl are optionally substituted by one or more aforesaid groups.

As used herein, the term "heteroarylenyl" refers to a divalent heteroaryl group as defined herein. The term "heteroaryl" alone or in combination with other term(s) means a completely unsaturated ring system containing a total of 5 to 14 ring atoms, unless the ring size is specifically mentioned. At least one of the ring atoms is a heteroatom (i.e., O, N, or S), with the remaining ring atoms/groups being independently selected from C, N, O and S. A heteroaryl may be a single-ring (monocyclic) or multiple rings (bicyclic, tricyclic or polycyclic) fused together or linked covalently. Preferably, "heteroaryl" is a 5- to 6-membered ring, unless the ring size is specifically mentioned. The rings may contain from 1 to 4 additional heteroatoms selected from N, O and S, wherein the N atom is optionally quarternized. Any suitable ring position of the heteroaryl moiety may be covalently linked to the defined chemical structure. Examples of "heteroaryl" include, but not limited to, furanyl, thienyl, pyrrolyl, pyrazolyl, imidazolyl, oxazolyl, cinnolinyl, isoxazolyl, thiazolyl, isothiazolyl, 1H-tetrazolyl, oxadiazolyl, triazolyl, pyridyl (pyridinyl), 3-fluoropyridyl, pyrimidinyl, pyrazinyl, pyridazinyl, benzoxazolyl, benzisoxazolyl, benzothiazolyl, benzofuranyl, benzothienyl, benzotriazinyl, phthalazinyl, thianthrene, dibenzofuranyl, dibenzothienyl, benzimidazolyl, indolyl, isoindolyl, indazolyl, quinolinyl, isoquinolinyl, quinazolinyl, quinoxalinyl, purinyl, pteridinyl, 9H-carbazolyl, α-carbolinyl, indolizinyl, benzoisothiazolyl, benzoxazolyl, pyrrolopyridyl, furopyridinyl, purinyl, benzothiadiazolyl, benzooxadiazolyl, benzotriazolyl, benzotriadiazolyl, carbazolyl, dibenzothienyl, acridinyl and the like. Accordingly, examples of heteroarylenyl include, but not limited to, furanylenyl, thienylenyl, pyrrolylenyl, pyrazolylenyl, imidazolylenyl, oxazolylenyl, isoxazolylenyl, thiazolylenyl, isothiazolylenyl, 1H-tetrazolylenyl, oxadiazolylenyl, triazolylenyl, pyridylenyl (pyridinylenyl), pyrimidinylenyl, pyrazinylenyl and pyridazinylenyl. Heteroaryl group may be optionally further substituted.

As used herein, the term "alkenyl" refers to a carbon chain which contains at least one carbon-carbon double bond, and which may be linear or branched or combinations thereof. Examples of "alkenyl" include, but not limited to, vinyl, allyl, isopropenyl, pentenyl, hexenyl, heptenyl, 1-propenyl, 2-butenyl and 2-methyl-2-butenyl.

As used herein, the term "amino" refers to an $—NH_2$ group.

As used herein, the term "halo" or "halogen" alone or in combination with other term(s) means fluorine, chlorine, bromine or iodine.

As used herein, the term "hydroxy" or "hydroxyl" alone or in combination with other term(s) means —OH.

As used herein, the term "oxo" refers to =O group.

As used herein, the term "alkoxy" refers to the group —O-alkyl, where alkyl groups are as defined above. Exemplary $C_1$-$C_{10}$ alkoxy group include, but are not limited to, methoxy, ethoxy, n-propoxy, n-butoxy, t-butoxy or n-pentoxy. An alkoxy group can be optionally substituted with one or more suitable groups. Preferably, the term "alkoxy" refers to $C_1$-$C_4$ alkoxy groups. Few examples of $C_1$-$C_4$ alkoxy include methoxy, ethoxy, n-propoxy, n-butoxy or t-butoxy.

The term "aryl", as employed herein as such or as part of another group, refers to a monocyclic, bicyclic or polycyclic aromatic hydrocarbon ring system of 6 to 14 carbon atoms. Preferably, "aryl" refers to ($C_6$-$C_{10}$)aryl. Examples of aryl groups include, but are not limited to phenyl, naphthyl, biphenyl, anthryl, biphenylenyl and acenaphthyl. Preferred aryl group is phenyl. The term "arylenyl" refers to a divalent aryl group. Accordingly, examples of arylenyl groups include, but are not limited to phenylenyl, naphthylenyl, biphenylenyl and anthrylenyl.

The term "acyl" refers to a group R—CO— or —CO—R wherein R is an optionally substituted alkyl group defined above. Examples of 'acyl' groups are, but not limited to, $CH_3CO$—, $CH_3CH_2CO$—$CH_3CH_2CH_2CO$— or $(CH_3)_2CHCO$—.

The term "heteroatom" as used herein designates a sulfur, nitrogen or oxygen atom.

As used herein, the term 'compound(s)' comprises the compounds disclosed in the present invention.

The term "salt/salts" refers to the salts derived from appropriate bases include alkali metal (e.g., sodium and potassium), alkaline earth metal (e.g., magnesium), ammonium and $N'(C_{1-4}\ alkyl)_4$ salts.

As used herein, the term "comprise" or "comprising" is generally used in the sense of include, that is to say permitting the presence of one or more features or components.

As used herein, the term "or" means "and/or" unless stated otherwise.

As used herein, the term "including" as well as other forms, such as "include", "includes" and "included" is not limiting.

As used herein, the term "composition" is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

As used herein, the term "pharmaceutical composition" refers to a composition(s) containing a therapeutically effective amount of at least one compound of formula (I) or a pharmaceutically acceptable salt or a stereoisomer thereof and a pharmaceutically acceptable carrier.

The pharmaceutical composition(s) usually contain(s) about 1% to 99%, for example, about 5% to 75%, or from about 10% to about 50% or from about 10% to about 30% by weight of the compound of formula (I) or a pharmaceutically acceptable salt or a stereoisomer thereof. The amount of the compound of formula (I) or pharmaceutically acceptable salt or a stereoisomer thereof in the pharmaceutical composition(s) can range from about 1 mg to about 1000 mg, or from about 2.5 mg to about 500 mg, or from about 5 mg to about 250 mg, or in any range falling within the broader range of 1 mg to 1000 mg or higher or lower than the aforementioned range.

As used herein, the expression "pharmaceutically acceptable carrier, diluent or excipient" includes, without limitation, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier that has been approved by the United States Food and Drug Administration as being acceptable for use in humans or domestic animals.

The term "administer," "administering," or "administration" as used in this disclosure refers to either directly administering one or more disclosed compounds or a pharmaceutically acceptable salt or a stereoisomer of one or more disclosed compounds or a composition comprising one or more disclosed compounds to a subject, or administering a prodrug derivative or analog of the compound or a pharmaceutically acceptable salt of the compound or composition to the subject, which can form an equivalent amount of active compound within the subject's body.

The term "carrier" as used in this disclosure, encompasses carriers, excipients and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

As used herein, the term "treat", "treating" and "treatment" refer to a method of alleviating or abrogating a disease and/or its attendant symptoms.

As used herein, the term "subject" refers to an animal, preferably a mammal and most preferably a human.

As used herein, "delaying progression" of a disease means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late-stage cancer, such as development of metastasis, may be delayed.

As used herein, the term, "therapeutically effective amount" refers to an amount of a compound of formula (I) or a pharmaceutically acceptable salt or a stereoisomer or a tautomer or a prodrug thereof; or a composition comprising the compound of formula (I) or a pharmaceutically acceptable salt or a stereoisomer or a tautomer or a prodrug thereof, effective in producing the desired therapeutic response in a particular subject suffering from a disease or disorder, in particular their use in disease or disorder associated with cancer mediated by SMARCA2 and/or SMARCA4. Particularly, the term "therapeutically effective amount" includes the amount of the compound of formula (I) or a pharmaceutically acceptable salt or a stereoisomer or a tautomer or a prodrug thereof, when administered, that induces a positive modification in the disease or disorder to be treated or is sufficient to delay the progression of, or is to prevent development of, or alleviate to some extent, one or more of the symptoms of the disease or disorder being treated in a subject. In respect of the therapeutic amount of the compound, the amount of the compound used for the treatment of a subject is low enough to avoid undue or severe side effects, within the scope of sound medical judgment can also be considered. The therapeutically effective amount of the compound or composition will be varied with the particular condition being treated, the severity of the condition being treated or prevented, the duration of the treatment, the nature of concurrent therapy, the age and physical condition of the subject, the specific compound or composition employed the particular pharmaceutically acceptable carrier utilized.

"Pharmaceutically acceptable" means that, which is useful in preparing a pharmaceutical composition that is generally safe, non-toxic and neither biologically nor otherwise undesirable and includes that which is acceptable for veterinary as well as human pharmaceutical use.

The term "pharmaceutically acceptable salt" refers to a product obtained by reaction of the compound of the present invention with a suitable acid or a base. Pharmaceutically acceptable salts of the compounds of this invention include those derived from suitable inorganic bases such as Li, Na, K, Ca, Mg, Fe, Cu, Al, Zn and Mn salts; Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention (compound of formula (I)) can form pharmaceutically acceptable salts with various organic bases such as lysine, arginine, guanidine, diethanolamine or metformin. Suitable base salts include, but are not limited to, aluminum, calcium, lithium, magnesium, potassium, sodium or zinc salts.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. In one embodiment cancer is SMARCA2 and/or SMARCA4 mediated cancer. Exemplary cancer include but not limited to hematologic cancers, lung cancer (NSCLC i.e. non-small cell lung cancer), acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, head and neck cancer, hemangioblastoma, hepatoma, hepatocellular cancer, hormone insensitive prostate cancer, leiomyosarcoma, leukemia, liposarcoma, liver cancer, lymphagioendotheliosarcoma, lymphangiosarcoma, lymphoblastic leukemia, lymphoma (Hodgkin's and non-Hodgkin's; Burkitt's), malignancies and hyperproliferative disorders of the bladder, breast, colon, lung, ovaries, pancreas, prostate, skin and uterus, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, malignant rhabdoid tumor (MRT), rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

The term "stereoisomers" refers to any enantiomers, diastereomers or geometrical isomers of the compounds of formula (I), wherever they are chiral or when they bear one or more double bonds. When the compounds of the formula (I) and related formulae are chiral, they can exist in racemic or in optically active form. It should be understood that the present invention encompasses all stereochemical isomeric forms, including diastereomeric, enantiomeric and epimeric forms, as well as d-Isomers and -Isomers and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric Isomers. The present invention includes all cis, trans, syn, anti, entgegen (E) and zusammen (Z) Isomers as well as the appropriate mixtures thereof.

The term "enantiomers" refers to a pair of stereoisomers which are non-superimposable mirror images of one another. The term "enantiomer" refers to a single member of this pair of stereoisomers. The term "racemic" refers to a 1:1 mixture of a pair of enantiomers. The disclosure includes enantiomers of the compounds described herein. Each compound herein disclosed includes all the enantiomers that conform to the general structure of the compound. The compounds may be in a racemic or enantiomerically pure form, or any other form in terms of stereochemistry. In some embodiments the compounds are the (S)-enantiomer.

The term "diastereomers" refers to the set of stereoisomers which cannot be made superimposable by rotation around single bonds. For example, cis- and trans-double bonds, endo- and exo-substitution on bicyclic ring systems, and compounds containing multiple stereogenic centers with different relative configurations are considered to be diastereomers. The term "diastereomer" refers to any member of this set of compounds. In some examples presented, the synthetic route may produce a single diastereomer or a mixture of diastereomers. The disclosure includes diastereomers of the compounds described herein.

Pharmaceutical Composition

The compounds of the present invention may be used as single drug or as a pharmaceutical composition in which the compound is mixed with various pharmacologically acceptable materials.

The compounds of the invention are typically administered in the form of a pharmaceutical composition. Such compositions can be prepared using procedures well known in the pharmaceutical art and comprise at least one compound of the invention. The pharmaceutical composition of the present patent application comprises one or more compounds described herein and one or more pharmaceutically acceptable excipients. Typically, the pharmaceutically acceptable excipients are approved by regulatory authorities or are generally regarded as safe for human or animal use. The pharmaceutically acceptable excipients include, but are not limited to, carriers, diluents, glidants and lubricants, preservatives, buffering agents, chelating agents, polymers, gelling agents, viscosifying agents and solvents.

The pharmaceutical composition can be administered by oral, parenteral or inhalation routes. Examples of the parenteral administration include administration by injection, percutaneous, transmucosal, trans nasal and transpulmonary administrations.

Examples of suitable carriers include, but are not limited to, water, salt solutions, alcohols, polyethylene glycols, peanut oil, olive oil, gelatin, lactose, terra alba, sucrose, dextrin, magnesium carbonate, sugar, amylose, magnesium stearate, talc, gelatin, agar, pectin, acacia, stearic acid, lower alkyl ethers of cellulose, silicic acid, fatty acids, fatty acid amines, fatty acid monoglycerides and diglycerides, fatty acid esters and polyoxyethylene.

The pharmaceutical composition may also include one or more pharmaceutically acceptable auxiliary agents, wetting agents, suspending agents, preserving agents, buffers, sweetening agents, flavouring agents, colorants, or any combination of the foregoing.

The pharmaceutical compositions may be in conventional forms, for example, tablets, capsules, solutions, suspensions, injectables or products for topical application. Further, the pharmaceutical composition of the present invention may be formulated so as to provide desired release profile.

Administration of the compounds of the invention, in pure form or in an appropriate pharmaceutical composition, can be carried out using any of the accepted routes of administration of pharmaceutical compositions. The route of administration may be any route which effectively transports the active compound of the patent application to the appropriate or desired site of action.

Suitable routes of administration include, but are not limited to, oral, nasal, buccal, dermal, intradermal, transdermal, parenteral, rectal, subcutaneous, intravenous, intraurethral, intramuscular or topical.

Solid oral formulations include, but are not limited to, tablets, capsules (soft or hard gelatin), dragees (containing the active ingredient in powder or pellet form), troches and lozenges.

Liquid formulations include, but are not limited to, syrups, emulsions, and sterile injectable liquids, such as suspensions or solutions.

Topical dosage forms of the compounds include ointments, pastes, creams, lotions, powders, solutions, eye or ear drops, impregnated dressings, and may contain appropriate conventional additives such as preservatives, solvents to assist drug penetration.

Suitable doses of the compounds for use in treating the diseases or disorders described herein can be determined by those skilled in the relevant art. Therapeutic doses are generally identified through a dose ranging study in humans based on preliminary evidence derived from the animal studies. Doses must be sufficient to result in a desired therapeutic benefit without causing unwanted side effects. Mode of administration, dosage forms, and suitable pharmaceutical excipients can also be well used and adjusted by those skilled in the art. All changes and modifications are envisioned within the scope of the present patent application.

The term, "prodrug" is meant to indicate a compound that may be converted under physiological conditions or by solvolysis to a biologically active compound described herein (e.g., compound of structure (I)). Thus, the term "prodrug" refers to a precursor of a biologically active compound that is pharmaceutically acceptable. In some embodiments, a prodrug is inactive when administered to a subject, but is converted in-vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein. The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound and the like.

In some embodiments, prodrugs include compounds of structure (I) having a phosphate, phosphoalkoxy, ester or boronic ester substituent. Without being bound by theory, it is believed that such substituents are converted to a hydroxyl group under physiological conditions. Accordingly, embodiments include any of the compounds of the present invention, wherein a hydroxyl group has been replaced with a phosphate, phosphoalkoxy, ester or boronic ester group, for example a phosphate or phosphoalkoxy group. For example, in some embodiments a hydroxyl group on $R_4$ or $R_9$ moiety is replaced with a phosphate, phosphoalkoxy, ester or boronic ester group, for example a phosphate or alkoxy phosphate group.

According to one embodiment, the compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms of the compound are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorous, sulfur, fluorine, chlorine and iodine, such as $^{2}H$ ("D"), $^{3}H$, $^{11}C$, $^{13}C$, $^{14}C$, $^{13}N$, $^{15}N$, $^{15}O$, $^{17}O$, $^{18}O$ $^{32}P$, $^{33}P$, $^{35}S$, $^{18}F$, $^{36}Cl$, $^{123}I$ and $^{125}I$. Isotopically labeled compounds of the present inventions can generally be prepared by following procedures analogous to those disclosed in the schemes and/or in the examples herein below, by substituting an isotopically labeled reagent for a non-isotopically labeled reagent.

EXPERIMENTAL

The abbreviations used in the entire specification is summarized below with their meaning. MeOH—Methanol, EtOH—Ethanol, DCM—Dichloromethane, DMF—N,N-Dimethylformamide, EtOAc—Ethyl acetate, ACN—Acetonitrile, THE—Tetrahydrofuran, DMSO—Dimethyl sulfoxide DIPEA—N,N-Diisopropylethylamine, NCS—N-chloro succinimide, HATU (1-[Bis(dimethylamino)-methylene]-1H-1,2,3-triazolo[4,5-b]pyridinium 3-oxid hexafluoro phosphate), KOAc—Potassium acetate, $Na_2SO_4$—Sodium sulphate, $Na_2CO_3$—Sodium carbonate, $K_2CO_3$—Potassium carbonate, $KO^tBu$—Potassium tert-butoxide, TEA—Triethyl amine; $LiOH{\cdot}H_2O$—Lithium hydroxide monohydrate; EDC·HCl—1-(3-Dimethylaminopropyl)-3-ethylcarbodiimide hydrochloride, HOBt—Hydroxybenzotriazole, NaH—Sodium hydride, $NH_4OH$—Ammonium hydroxide, NaOH—Sodium hydroxide, HCl—Hydrochloric acid, $Pd(pph_3)_2Cl_2$. DCM—Bis(triphenylphosphine)palladium (II) dichloride Dichloromethane complex; $Pd(OAc)_2$—Palladium (II) acetate, $Pd_2(dba)_3$—Tris(dibenzylideneacetone) dipalladium(O), mL—Milliliter, TLC—Thin layer chromatography, RT—Room temperature, h—Hour, N—Normality, M—Molarity, $^{1}$HNMR—Proton nuclear magnetic resonance, DMSO-$d_6$—Deuterated Dimethyl sulfoxide, $CDCl_3$—Deuterated chloroform, s—Singlet, d—Doublet, t—Triplet, m—Multiplet, H—Proton, MHz—Mega hertz, Hz—Hertz, Ppm—Parts per million, Bs—Broad singlet, HPLC—High-performance liquid chromatography, LCMS—Liquid chromatography Mass spectroscopy, g—Gram, mmol—Milli mol.

Intermediate 1: 5-Bromo-3-chloropyridazine

Step-a: Synthesis of 5-Bromo-3-chloropyridazine (1a)

To a stirred solution of 4-bromo-6-chloropyridazin-3-amine (10.0 g, 48.30 mmol) in THE (100 mL) was added tert butyl nitrite (9.8 g, 82.12 mmol, 1.7 eq) at RT. The reaction mixture was heated at 80° C. for 3 h in a sealed tube. After completion of the reaction (monitored by TLC), the reaction mixture was diluted with EtOAc. The combined organic layer was washed with water, brine solution, dried over anhydrous sodium sulphate and concentrated under vacuum to give the residue which was purified by combiflash column chromatography using 50-60% ethyl acetate in hexane as eluent to afford the title compound as off-white solid (5.3 g, 57%). $^{1}$H NMR (400 MHz, DMSO-$d_6$): δ 9.50 (d, J=2.0 Hz, 1H), 8.48 (d, J=2.0 Hz, 1H); LC-MS: m/z 192.8 (M+H).

Intermediate 2: Tert-butyl 2-(4-(4-(4,4,5,5-tetramethyl-1,3,2-dioxaborolan-2-yl)phenyl)piperazin-1-yl) acetate

Step a: Synthesis of 1-(4-bromophenyl)piperazine hydrochloride

To a stirred solution of tert-butyl 4-(4-bromophenyl) piperazine-1-carboxylate (5.0 g, 14.7 mmol) in DCM (50 mL) was added 4N dioxane HCl (50 mL) at 0° C. and stirred for 16 h at RT under nitrogen atmosphere. Then the reaction mixture was concentrated under vacuum to get crude product. The crude product was triturated with n-pentane and then dried under vacuum to afford pure title compound as pale-yellow solid (5 g). $^{1}$H NMR (400 MHz, DMSO-$d_6$): δ 9.29 (bs, 1H), 7.38 (d, J=9.2 Hz, 2H), 6.94 (d, J=9.2 Hz, 2H), 5.06 (m, 4H), 3.35 (m, 4H); LC-MS: m/z 354.8 (M+H).

Step-b: Synthesis of Tert-butyl 2-(4-(4-bromophenyl piperazin-1-yl)acetate)

To a stirred solution of 1-(4-bromophenyl)piperazine hydrochloride (5.0 g, 18.1 mmol) in DMF (50 mL) was added DIPEA (4.66 g, 36.2 mmol) at RT and stirred for 15 min then added Tert-butyl 2-bromoacetate (5.3 g, 27.15 mmol) and stirred for 4 h at RT under nitrogen atmosphere. The reaction mixture was quenched with cold water and stirred for 1 h, the solid so formed was filtered and dried under vacuum to afford title compound as off-white solid (4.5 g, 70%).

$^{1}$H NMR (400 MHz, DMSO-$d_6$): δ 7.29 (d, J=8.4 Hz, 2H), 6.84 (d, J=8.4 Hz, 2H), 3.11 (s, 2H), 3.07 (m, 4H), 2.58 (m, 4H), 1.37 (s, 9H); LC-MS: m/z 340.8 (M+H).

Step-c: Synthesis of tert-butyl 2-(4-(4-(4,4,5,5-tetramethyl-1,3,2-dioxaborolan-2-yl)phenyl)piperazin-1-yl)acetate To a stirred solution of tert-butyl 2-(4-(4-bromophenyl piperazin-1-yl)acetate) (4.2 g, 11.8 mmol) in dioxane (80 mL) was added bis pinacolato diboron (4.52 g, 17.8 mmol) and KOAc (2.33 g, 23.7 mmol) at RT and degassed with nitrogen for 5 min then $Pd(dppf)Cl_2{\cdot}DCM$ (0.89 g, 1.18 mmol) was added into the reaction mixture and heated at 100° C. for 4 h. Once the reaction was completed (monitored by TLC), the reaction mixture was diluted with EtOAc. The combined organic layer was washed with water, brine solution, dried over anhydrous sodium sulphate and concentrated under vacuum to afford the title compound as off-white solid (5 g, 100%). $^{1}$H NMR (400 MHz, DMSO-$d_6$): δ 7.50 (d, J=8.0 Hz, 2H), 6.89 (d, J=8.8 Hz, 2H), 3.20 (bs, 4H), 3.15 (s, 2H), 2.62 (d, J=4.4 Hz, 4H), 1.41 (s, 9H), 1.26 (s, 12H); LC-MS: m/z 402.7 (M+H).

Intermediate 3: Ethyl 2-(1-(4-(4,4,5,5-tetramethyl-1,3,2-dioxaborolan-2-yl)phenyl)piperidin-4-yl)acetate

Step a: Synthesis of ethyl 2-(1-(4-bromo-2-nitrophenyl)piperidin-4-yl)acetate To a stirred solution of 4-bromo-1-fluoro-2-nitrobenzene (2.0 g, 9.1 mmol) in DMF (20 mL) were added ethyl 2-(piperidin-4-yl)acetate (1.87 g, 10.9 mmol) and DIPEA (3.7 g, 27.4 mmol) at RT and heated at 100° C. for 4 h. The reaction mixture was quenched with cold water and extracted with EtOAc. The combined organic layer was washed with water, brine solution, dried over anhydrous sodium sulphate and concentrated under vacuum to get crude product. The crude product was purified by combiflash column chromatography using 20-25% ethyl acetate in hexane as eluent to afford the title compound as yellow solid (1.3 g, 38%). $^{1}$H NMR (400 MHz, DMSO-$d_6$): δ 7.99 (d, J=2.4 Hz, 1H), 7.70 (dd, J=2.4, 6.4 Hz, 1H), 7.24 (d, J=8.8 Hz, 1H), 4.05 (q, J=5.4 Hz, 2H), 3.12 (d, J=12.4 Hz, 2H), 2.82-2.76 (m, 2H), 2.26 (d, J=7.2 Hz, 2H), 1.84-1.79 (m, 1H), 1.69 (d, J=12.4 Hz, 2H), 1.32-1.22 (m, 2H), 1.17 (t, J=7.4 Hz, 3H); LC-MS: m/z 371.0 (M+H).

Step b: Synthesis of ethyl 2-(1-(2-amino-4-bromophenyl)piperidin-4-yl)acetate To a stirred solution of ethyl 2-(1-(4-bromo-2-nitrophenyl)piperidin-4-yl)acetate (1.3 g, 3.5 mmol) in methanol (10 mL) and water (3 mL) mixture were added iron (3.1 g, 28 mmol) and $NH_4OH$ (1.5 g, 28 mmol) and stirred at RT for 4 h. After completion of the reaction (monitored by TLC), the reaction mixture was diluted with methanol and filtered. The filtrate was concentrated and diluted with EtOAc washed with water, brine solution, dried over anhydrous sodium sulphate and concentrated under vacuum to afford the title compound as off-white solid (1.2 g, 100%). $^1$H NMR (400 MHz, DMSO-$d_6$): δ 6.80-6.78 (m, 2H), 6.63 (dd, J=2.4 & 6.0 Hz, 1H), 4.91 (s, 2H), 4.06 (q, J=7.0 Hz, 2H), 2.97 (d, J=11.6 Hz, 2H), 2.27 (d, J=6.8 Hz, 2H), 1.73-1.69 (m, 5H), 1.40-1.36 (m, 2H), 1.19 (t, J=7.0 Hz, 3H).

Step c: Synthesis of ethyl 2-(1-(4-bromophenyl)piperidin-4-yl)acetate

To a stirred solution of ethyl 2-(1-(2-amino-4-bromophenyl)piperidin-4-yl)acetate (1.0 g, 2.9 mmol) in THE (10 mL) was added tert butyl nitrite (0.58 g, 5.1 mmol) and stirred at RT for 3 h. After completion of the reaction (monitored by TLC), the reaction mixture was diluted with EtOAc. The combined organic layer was washed with water, brine solution, dried over anhydrous sodium sulphate and concentrated under vacuum to get crude product. The crude product was purified by combiflash column chromatography using 20% ethyl acetate in hexane as eluent to afford the title compound as off-white solid (0.37 g, 34%). $^1$H NMR (400 MHz, DMSO-$d_6$): δ 7.30 (d, J=8.8 Hz, 2H), 6.87 (d, J=9.2 Hz, 2H), 4.06 (q, J=14.4 Hz, 2H), 3.64 (d, J=12.8 Hz, 2H), 2.67-2.62 (m, 2H), 2.25 (d, J=7.2 Hz, 2H), 1.70 (d, J=12.4 Hz, 3H), 1.28-1.25 (m, 2H), 1.17 (t, J=7.2 Hz, 3H). LC-MS: m/z 326.1 (M+H).

Step d: Synthesis of ethyl 2-(1-(4-(4,4,5,5-tetramethyl-1,3,2-dioxaborolan-2-yl)phenyl)piperidin-4-yl) acetate To a stirred solution of ethyl 2-(1-(4-bromophenyl)piperidin-4-yl)acetate (0.37 g, 1.13 mmol) in dioxane (10 mL) was added bis pinacolato diboron (0.45 g, 1.7 mmol) and KOAc (0.22 g, 2.27 mmol) at RT and degassed with nitrogen for 5 min. Then Pd(dppf)$Cl_2$·DCM (0.09 g, 0.11 mmol) was added into the reaction mixture, heated at 100° C. for 6 h. Once the reaction was completed (monitored by TLC), the reaction mixture was diluted with EtOAc. The combined organic layer was washed with water, brine solution, dried over anhydrous sodium sulphate and concentrated under vacuum to get the residue which was purified by combiflash column chromatography using 10-15% ethyl acetate in hexane as eluent to afford the title compound as yellow solid (0.25 g, 58%).

$^1$H NMR (400 MHz, DMSO-$d_6$): δ 7.48 (d, J=8.4 Hz, 2H), 6.87 (d, J=8.4 Hz, 2H), 4.06 (q, J=14.4 Hz, 2H), 3.78 (d, J=12.4 Hz, 2H), 2.75-2.66 (m, 1H), 2.24 (d, J=6.8 Hz, 2H), 1.87 (t, J=7.2 Hz, 1H), 1.72-1.68 (m, 2H), 1.29-1.16 (m, 18H). LC-MS: m/z 373.9 (M+H).

Intermediate 4: Ethyl 3-methyl-2-(3-(4-(4,4,5,5-tetramethyl-1,3,2-dioxaborolan-2-yl)phenyl)isoxazol-5-yl)butanoate

Step a: Synthesis of 4-bromobenzaldehyde oxime

To a solution of 4-bromobenzaldehyde (30 g, 162.16 mmol) and hydroxylamine hydrochloride (14.64 g, 210.8 mmol) in ethanol (300 mL) was added pyridine (19.21 mL, 243.2 mmol) to the reaction mixture and stirred at RT for 6 h. After reaction completion, reaction mixture was quenched with ice-cold water and stirred for 20 min. The obtained solid was further washed with water and dried under vacuum to get crude compound. The crude compound was washed with hexane and dried under vacuum to give title compound as white solid (24 g, 74%). $^1$H NMR (400 MHz, DMSO-$d_6$): δ 11.37 (s, 1H), 8.13 (s, 1H), 7.60 (d, J=10.8 Hz, 2H), 7.54 (d, J=10.4 Hz, 2H); LC-MS: m/z 199.9 (M+H).

Step b: Synthesis of 2-(3-(4-bromophenyl)isoxazol-5-yl)ethan-1-ol

To a solution of 4-bromobenzaldehyde oxime (15 g, 75 mmol) in DCM (300 mL) were added NCS (12.01 g, 90 mmol) and heated at 45° C. for 30 min. The reaction mixture was cooled to RT and but-3-yn-1-ol (6.3 g, 90 mmol) and TEA (10.52 mL, 75 mmol) were dropwise added into the reaction mixture over the period of 15 min. The reaction mixture was again heated at 45° C. for 7 h. After reaction completion, reaction mixture was quenched with ice-cold water and extracted with EtOAc. The combined organic layer was washed with water, brine solution, dried over anhydrous sodium sulphate and concentrated under vacuum to get the residue which was purified by combiflash column chromatography using 10% ethyl acetate in hexane as eluent to afford the title compound as white solid (7.5 g, 37%). $^1$H NMR (400 MHz, DMSO-$d_6$): δ 7.80 (d, J=6.4 Hz, 2H), 7.71 (d, J=6.8 Hz, 2H), 6.86 (s, 1H), 4.92 (t, J=10.8 Hz, 1H), 3.75 (q, J=11.6 Hz, 2H), 2.94 (t, J=12.8 Hz, 2H); LC-MS: m/z 267.90 (M+H).

Step c: Synthesis of 2-(3-(4-bromophenyl)isoxazol-5-yl)acetic acid

To a stirred solution of 2-(3-(4-bromophenyl)isoxazol-5-yl)ethan-1-ol (7.5 g, 27.9 mmol) in acetone (150 mL) at 0° C. was dropwise added Jones reagent (15 mL) and temperature was brought to RT over the period of 2 h. After reaction completion, the reaction mass was diluted with acetone and filtered. The filtrate was concentrated under vacuum to get crude product. The crude product was triturated with hexane and dried under vacuum to afford pure title compound as off-white solid (7 g, 88%). $^1$H NMR (400 MHz, DMSO-$d_6$): δ 7.82 (d, J=8.8 Hz, 2H), 7.71 (d, J=8.4 Hz, 2H), 6.96 (s, 1H), 3.96 (s, 2H); LC-MS: m/z 283.09 (M+H).

Step d: Synthesis of ethyl 2-(3-(4-bromophenyl)isoxazol-5-yl)acetate

To a stirred solution of 2-(3-(4-bromophenyl)isoxazol-5-yl)acetic acid (7 g, 24.9 mmol) in ethanol (140 mL) at 0° C. was dropwise added $H_2SO_4$ (7 mL) and then heated at 80° C. for 2 h. After completion of the reaction (monitored by TLC), the reaction mixture was concentrated and then diluted with EtOAc. The combined organic layer was washed with water, brine solution, dried over anhydrous sodium sulphate and concentrated under vacuum to give the residue which was purified by combiflash column chromatography using 7% ethyl acetate in hexane as eluent to afford the title compound as off-white solid (5.8 g, 76%).

$^1$H NMR (400 MHz, DMSO-$d_6$): δ 7.82 (d, J=8.4 Hz, 2H), 7.72 (d, J=8.4 Hz, 2H), 6.99 (s, 1H), 4.17 (q, J=14.4 Hz, 2H), 4.08 (s, 2H), 1.22 (t, J=14.4 Hz, 3H); LC-MS: m/z 309.9 (M+H).

Step e: Synthesis of ethyl 2-(3-(4-bromophenyl) isoxazol-5-yl)-3-methylbutanoate To a solution of ethyl 2-(3-(4-bromophenyl)isoxazol-5-yl)acetate (5.8 g, 18.77 mmol), in THE (80 mL) was dropwise added KO$^t$Bu 1M solution (28.1 mL, 28.1 mmol) at 0° C. and stirred for 15 min. Then 2-iodo propane (2.25 mL, 22.5 mmol) was added into the reaction mixture and stirred at RT for 16 h. After reaction completion, the reaction mixture was quenched with ice-cold water and extracted with EtOAc. The combined organic layer was washed with water, brine solution, dried over anhydrous sodium sulphate and concentrated under vacuum to give the residue which was purified by combiflash column chromatography using 4-5% ethyl acetate in hexane as eluent to give title compound as colourless liquid (3.8 g, 57%). $^1$H NMR (400 MHz, DMSO-$d_6$): δ 7.84 (d, J=8.8 Hz, 2H), 7.72 (d, J=8.0 Hz, 2H), 7.05 (s, 1H), 4.16 (q, J=7.2 Hz, 2H), 3.85 (d, J=8.0 Hz, 1H), 2.38 (m, 1H), 1.19 (t, J=14.4 Hz, 3H), 0.98 (d, J=6.4 Hz, 3H) 0.89 (d, J=6.8 Hz, 3H); LC-MS: m/z 351.9 (M+H).

Step f: Synthesis of ethyl 3-methyl-2-(3-(4-(4,4,5,5-tetramethyl-1,3,2-dioxaborolan-2-yl)phenyl)isoxazol-5-yl)butanoate To a stirred solution of Ethyl 2-(3-(4-bromophenyl)isoxazol-5-yl)-3-methylbutanoate (3.8 g, 10.82 mmol) in dioxane (50 mL) was added bis-pinacolato diboron (4.12 g, 16.2 mmol) and KOAc (2.12 g, 21.6 mmol) at RT and degassed with nitrogen for 5 min. Pd(dppf)$Cl_2$·DCM (0.88 g, 1.08 mmol) was added into the reaction mixture and heated at 100° C. for 2 h. stirred. Once the reaction was completed (monitored by TLC), the reaction mixture was diluted with EtOAc. The combined organic layer was washed with water, brine solution, dried over anhydrous sodium sulphate and concentrated under vacuum to afford the title compound as colourless liquid (4.1 g, 94%). $^1$H NMR (400 MHz, DMSO-$d_6$): δ 7.90 (d, J=8.0 Hz, 2H), 7.79 (d, J=7.6 Hz, 2H), 7.05 (s, 1H), 4.18 (q, J=11.2 Hz, 2H), 3.85 (d, J=8.0 Hz, 1H), 2.44-2.33 (m, 1H), 1.31 (s, 12H), 1.20 (t, J=7.2 Hz, 3H), 0.98 (d, J=6.8 Hz, 3H), 0.89 (d, J=6.4 Hz, 3H); LC-MS: m/z 400.2 (M+H).

Intermediate 5: 4-(6-Chloropyridazin-4-yl)phenol

Step-a: Synthesis of 4-(6-Chloropyridazin-4-yl)phenol

To a stirred solution of 5-bromo-3-chloropyridazine (5 g, 26.04 mmol), (4-hydroxyphenyl)boronic acid (3.3 g, 23.4 mmol) in 1,4-dioxane (70 mL) and water (15 mL) was added $Na_2CO_3$ (7 g, 65.1 mmol) and degassed with Nitrogen for 15 min. Pd(dppf)$Cl_2$·DCM (1.3 g, 1.56 mmol) was added and the reaction mixture was heated for 16 h at 110° C. in sealed tube. Once the reaction was completed (monitored by TLC), the reaction mixture was diluted with EtOAc. The combined organic layer was washed with water, brine solution, dried over anhydrous sodium sulphate and concentrated under vacuum to give the residue which was purified by combiflash column chromatography using 60% ethyl acetate in hexane as eluent to afford the title compound as off-white solid (0.5 g, 23%). $^1$H NMR (400 MHz, $CDCl_3$): δ 10.19 (s, 1H), 9.61 (d, J=2 Hz, 1H), 8.15 (d, J=2 Hz, 1H), 7.89 (d, J=8.8 Hz, 2H), 6.95 (d, J=8.8 Hz, 2H); LC-MS: m/z 206.9 (M+H).

Intermediate 6: Ethyl 1-(4-(4,4,5,5-tetramethyl-1,3,2-dioxaborolan-2-yl)phenyl)piperidine-4-carboxylate Intermediate-6 was prepared by procedure similar to the one described in Intermediate-3 with appropriate variations in reactants, quantities of reagents, protections and deprotections, solvents and reaction conditions.

1H NMR (400 MHz, DMSO-$d_6$): δ 7.48 (d, J=8.4 Hz, 2H), 6.88 (d, J=8.4 Hz, 2H), 4.05 (q, J=7.2 Hz, 2H) 3.73 (d, J=13.2 Hz, 2H), 2.83 (td, J=13.2, 2.4 Hz, 2H), 2.54 (m, 1H), 1.86 (m, 2H), 1.60 (m, 2H), 1.24 (s, 12H), 1.17 (t, J=7.2 Hz, 3H).

Intermediate 7: Tert-butyl 2-(4-(4-(4,4,5,5-tetramethyl-1,3,2-dioxaborolan-2-yl)phenyl)-3,6-dihydropyridin-1(2H)-yl)acetate Step-a: Synthesis of tert-butyl 4-(4-bromophenyl)-3,6-dihydropyridine-1(2H)-carboxylate To a stirred solution of 1-bromo-4-iodobenzene (1 g, 3.53 mmol), tert-butyl 4-(4,4,5,5-tetramethyl-1,3,2-dioxaborolan-2-yl)-3,6-dihydropyridine-1(2H)-carboxylate (0.87 g, 2.82 mmol) in 1,4-dioxane (10 mL) and water (2.5 mL) was added $K_2CO_3$ (1.22 g, 8.83 mmol) and degassed with nitrogen for 15 min. Pd(dppf)$Cl_2$·DCM (0.3 g, 0.35 mmol) was added and the reaction mixture was heated for 16 h at 100° C. in sealed tube. Once the reaction was completed (monitored by TLC), the reaction mixture was diluted with EtOAc. The combined organic layer was washed with water, brine solution, dried over anhydrous sodium sulphate and concentrated under vacuum to give the residue which was purified by combiflash column chromatography using 50% ethyl acetate in hexane as eluent to afford the title compound as off-white solid (1.3 g, 83%). $^1$H NMR (400 MHz, DMSO-$d_6$): δ 7.53 (d, J=8 Hz, 2H), 7.39 (d, J=8 Hz, 2H), 6.20 (s, 1H), 3.98 (bs, 2H), 3.52 (t, J=5.2 Hz, 2H), 2.43 (bs, 2H), 1.42 (s, 9H); LC-MS: m/z 338.0 (M+H).

Step-b: Synthesis of 4-(4-bromophenyl)-1,2,3,6-tetrahydropyridine hydrochloride

To a stirred solution of tert-butyl 4-(4-bromophenyl)-3,6-dihydropyridine-1(2H)-carboxylate (1 g, 2.95 mmol) in DCM (15 mL) at 0° C. was added 4M HCl in 1,4-dioxane (5 mL). The reaction mixture was stirred at room temperature for 2 h. After completion of the reaction (monitored by TLC) the reaction mixture was concentrated under reduced pressure and washed with diethyl ether to afford the title compound (0.8 g, 98%). %).

$^1$H NMR (400 MHz, DMSO-$d_6$): δ 9.35 (bs, 1H), 7.57 (d, J=8 Hz, 2H), 7.43 (d, J=8 Hz, 2H), 6.24 (s, 1H), 3.72 (bs, 2H), 3.28 (bs, 2H), 2.66 (bs, 2H). LC-MS: m/z 238 (M+1).

Step-c: Synthesis of tert-butyl 2-(4-(4-bromophenyl)-3,6-dihydropyridin-1(2H)-yl)acetate To a stirred solution of 4-(4-bromophenyl)-1,2,3,6-tetrahydropyridine hydrochloride (0.8 g, 2.91 mmol) in DMF (10 mL) was added DIPEA (1.12 g, 8.73 mmol) at RT and stirred for 15 min then added tert-butyl 2-bromoacetate (0.56 g, 2.91 mmol) and stirred for 4 h at RT under nitrogen atmosphere. The reaction mixture was quenched with cold water and stirred for 1 h, the solid so formed was filtered and dried under vacuum to afford title compound as yellow solid (1.3 g, 97%).

$^1$H NMR (400 MHz, DMSO-$d_6$): δ 7.51 (d, J=8 Hz, 2H), 7.38 (d, J=8 Hz, 2H), 6.19 (s, 1H), 3.22 (s, 2H), 3.20 (m, 2H), 2.74 (m, 2H), 2.44 (bs, 2H), 1.42 (s, 9H): LC-MS: m/z 352.2 (M+H).

Step-d: Synthesis of tert-butyl 2-(4-(4-(4,4,5,5-tetramethyl-1,3,2-dioxaborolan-2-yl)phenyl)-3,6-dihydropyridin-1(2H)-yl)acetate To a stirred solution of tert-butyl 2-(4-(4-bromophenyl)-3,6-dihydropyridin-1(2H)-yl)acetate (0.5 g, 1.41 mmol) in dioxane (20 mL) was added bis pinacolato diboron (0.43 g, 1.70 mmol) and KOAc (0.28 g, 2.83 mmol) at RT and degassed with nitrogen for 5 min then Pd(dppf)$Cl_2$·DCM (0.11 g, 0.14 mmol) was added into the reaction mixture and heated at 100° C. for 4 h. Once the reaction was completed (monitored by TLC), the reaction mixture was diluted with EtOAc. The combined organic layer was washed with water, brine solution, dried over anhydrous sodium sulphate and concentrated under vacuum to afford the title compound as off-white solid (0.5 g, 88%). $^1$H NMR (400 MHz, DMSO-$d_6$): δ 7.63 (d, J=10.8 Hz, 2H), 7.43 (d, J=10.8 Hz, 2H), 6.22 (s, 1H), 3.22 (bs, 4H), 2.73 (m, 2H), 2.46 (bs, 2H), 1.42 (s, 9H), 1.28 (s, 12H): LC-MS: m/z 400.4 (M+H).

The compounds listed in Table-1 were prepared by procedure similar to the one described in Intermediate-7 with appropriate variations in reactants, quantities of reagents, protections and deprotections, solvents and reaction conditions. The characterization data of the compounds are summarized herein the below table.

| Intermediate | Structure | Characterization Data $^1$H NMR (400 MHz, DMSO-$d_6$) |
|---|---|---|
| Tert-butyl 2-(4-(2-fluoro-4-(4,4,5,5-tetramethyl-1,3,2-dioxaborolan-2-yl)phenyl)-3,6-dihydropyridin-1(2H)-yl)acetate | 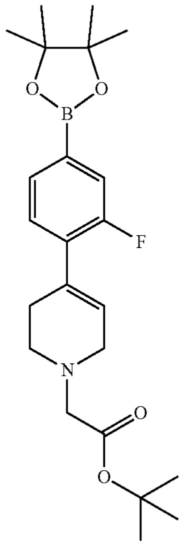 [SMILES: CC(C)(C)OC(=O)CN1CC=C(c2ccc(B3OC(C)(C)C(C)(C)O3)cc2F)CC1] | 1H NMR (400 MHz, DMSO-d6): 7.41(m, 1H), 7.25-7.36 (m, 2H), 5.98 (bs, 1H), 3.90 (bs, 1H), 3.19 (bs, 3H), 2.70 (t, J = 5.6 Hz, 2H), 2.40 (bs, 2H), 1.38 (s, 9H), 1.28 (s, 12H); LC-MS: m/z 418.15 (M + H). |
| Tert-butyl 2-(3-(4-(4,4,5,5-tetramethyl-1,3,2-dioxaborolan-2-yl)phenyl)pyrrolidin-1-yl)acetate | 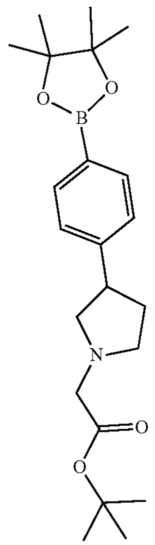 [SMILES: CC(C)(C)OC(=O)CN1CCC(c2ccc(B3OC(C)(C)C(C)(C)O3)cc2)C1] | 1H NMR (400 MHz, DMSO-d6): δ 7.63 (d, J = 8 Hz, 2H), 7.34 (d, J = 8 Hz, 2H), 3.22 (m, 2H), 2.98 (m, 1H), 2,82 (m, 2H), 2.66 (m, 2H), 2.25 (m, 1H), 1.76 (m, 1H), 1.45 (s, 9H), 1.32 (s, 12H): LC-MS: m/z 388.3 (M + H). |

-continued

| Intermediate | Structure | Characterization Data $^1H$ NMR (400 MHz, DMSO-$d_6$) |
| --- | --- | --- |
| Tert-butyl 2-(4-(3-(4,4,5,5-tetramethyl-1,3,2-dioxaborolan-2-yl)phenyl)-3,6-dihydropyridin-1(2H)-yl)acetate | 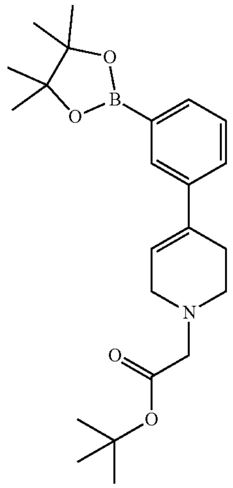 [SMILES: CC(C)(C)OC(=O)CN1CC=C(c2cccc(B3OC(C)(C)C(C)(C)O3)c2)CC1] | LC-MS: m/z 400.3 (M + H). |
| Tert-butyl 2-(5-(4-(4,4,5,5-tetramethyl-1,3,2-dioxaborolan-2-yl)phenyl)-3,6-dihydropyridin-1(2H)-yl)acetate | 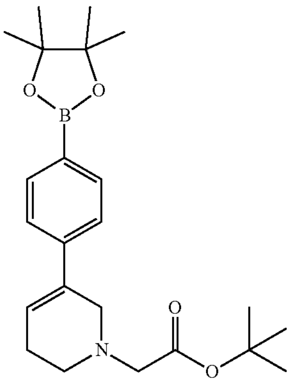 [SMILES: CC(C)(C)OC(=O)CN1CCC=C(c2ccc(B3OC(C)(C)C(C)(C)O3)cc2)C1] | 1H NMR (400 MHz, DMSO-d6): δ 7.61 (d, J = 8 Hz, 2H), 7.35 (d, J = 8 Hz, 2H), 6.25 (bs, 1H), 3.40 (bs, 2H), 3.29 (s, 2H), 2.65 (m, 2H), 2.25 (m, 2H), 1.41 (s, 9H), 1.27 (s, 12H):LC-MS: m/z 400.1 (M + H). |
| Tert-butyl 2-(4-(4-(4,4,5,5-tetramethyl-1,3,2-dioxaborolan-2-yl)phenoxy)piperidin-1-yl)acetate | 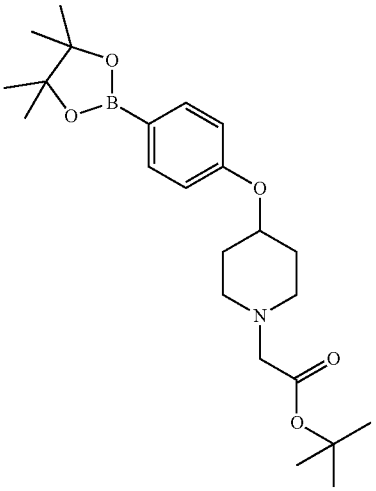 [SMILES: CC(C)(C)OC(=O)CN1CCC(Oc2ccc(B3OC(C)(C)C(C)(C)O3)cc2)CC1] | $^1H$ NMR (400 MHz, DMSO-d6): δ 7.59 (d, J = 8 Hz, 2H), 6.93 (d, J = 8 Hz, 2H), 4.42 (m, 1H), 3.11 (s, 2H), 2.75 (m, 2H), 2.44 (m, 2H), 1.90 (m, 2H), 1.62 (m, 2H), 1.41 (s, 9H), 1.26 (s, 12H):LC-MS: m/z 418.3 (M + H). |

Intermediate 8: Tert-butyl 4-(2-fluoro-4-(4,4,5,5-tetramethyl-1,3,2-dioxaborolan-2-yl)phenyl)piperazine-1-carboxylate Step-i: Synthesis of tert-butyl 4-(4-bromo-2-fluorophenyl)piperazine-1-carboxylate To a stirred solution of 4-bromo-2-fluoro-1-iodobenzene (1 g, 3.23 mmol), N-Boc piperazine (0.63 g, 3.39 mmol) in toluene (20 mL) was added NaO$^t$Bu (0.93 g, 9.63 mmol) and degassed with nitrogen for 15 min followed by $Pd_2(dba)_3$ (0.146 g, 0.16 mmol) and Xantphos (0.09 g, 0.16 mmol) was added and the reaction mixture was heated for 6 h at 120° C. in sealed tube. Once the reaction was completed (monitored by TLC), the reaction mixture was diluted with EtOAc. The combined organic layer was washed with water, brine solution, dried over anhydrous sodium sulphate and concentrated under vacuum to give the residue which was purified by combiflash column chromatography using 60% ethyl acetate in hexane as eluent to afford the title compound as off-white solid (0.65 g, 54%).

$^1$H NMR (400 MHz, $CDCl_3$): δ 7.44 (d, J=11.6 Hz 1H), 7.30 (d, J=8.8 Hz, 1H), 7.00 (t, J=8.8 Hz, 1H), 3.45 (m, 4H), 2.94 (m, 4H), 1.44 (s, 9H); LC-MS: m/z 358.9 (M+H).

Step-ii: Synthesis of tert-butyl 4-(2-fluoro-4-(4,4,5,5-tetramethyl-1,3,2-dioxaborolan-2-yl)phenyl)piperazine-1-carboxylate To a stirred solution of tert-butyl 4-(4-bromo-2-fluorophenyl)piperazine-1-carboxylate (0.65 g, 1.81 mmol) in dioxane (10 mL) was added bis pinacolato diboron (0.55 g, 2.17 mmol) and KOAc (0.53 g, 5.43 mmol) at RT and degassed with nitrogen for 5 min then $Pd(dppf)Cl_2{\cdot}DCM$ (0.15 g, 0.18 mmol) was added into the reaction mixture and heated at 90° C. for 16 h. Once the reaction was completed (monitored by TLC), the reaction mixture was diluted with EtOAc. The combined organic layer was washed with water, brine solution, dried over anhydrous sodium sulphate and concentrated under vacuum to afford the title compound as off-white solid (0.65 g, 88%). $^1$H NMR (400 MHz, DMSO-$d_6$): δ 7.43 (dd, J=8.0, 1.2 Hz, 1H), 7.37 (dd, J=8.0, 1.2 Hz, 1H), 6.82 (t, J=8.8 Hz, 1H), 3.52 (m, 4H), 3.00 (m, 4H), 1.41 (s, 9H), 1.25 (s, 12H); LC-MS: m/z 407.1 (M+H).

Intermediate 9: Ethyl 2-(4-(4-(4,4,5,5-tetramethyl-1,3,2-dioxaborolan-2-yl)phenyl)-3,6-dihydropyridin-1(2H)-yl)propanoate Step-a: Synthesis of ethyl 2-(4-(4-bromophenyl)-3,6-dihydropyridin-1(2H)-yl)propanoate To a stirred solution of 4-(4-bromophenyl)-1,2,3,6-tetrahydropyridine hydrochloride (1 g, 3.64 mmol) in DMF (10 mL) was added DIPEA (2.35 g, 18.2 mmol) at RT and stirred for 15 min then added ethyl 2-bromopropanoate (0.79 g, 4.37 mmol) and stirred for 4 h at RT under nitrogen atmosphere. The reaction mixture was quenched with cold water and stirred for 1 h, the solid so formed was filtered and dried under vacuum to afford title compound as off-white solid (0.8 g, 56%). $^1$H NMR (400 MHz, DMSO-$d_6$): δ 7.46 (d, J=8 Hz, 2H), 7.33 (d, J=8 Hz, 2H), 6.15 (s, 1H), 4.07 (m, 2H), 3.39 (q, J=6.8 Hz, 1H), 3.22 (bs, 2H), 2.78 (m, 2H), 2.67 (m, 1H), 2.38 (bs, 2H), 1.18 (m, 6H): LC-MS: m/z 338 (M+H).

Step-b: Synthesis of ethyl 2-(4-(4-(4,4,5,5-tetramethyl-1,3,2-dioxaborolan-2-yl)phenyl)-3,6-dihydropyridin-1(2H)-yl)propanoate To a stirred solution of ethyl 2-(4-(4-bromophenyl)-3,6-dihydropyridin-1(2H)-yl)propanoate (0.8 g, 2.36 mmol) in dioxane (15 mL) was added bis pinacolato diboron (0.9 g, 3.54 mmol) and KOAc (0.69 g, 7.09 mmol) at RT and degassed with nitrogen for 5 min then $Pd(dppf)Cl_2{\cdot}DCM$ (0.19 g, 0.23 mmol) was added into the reaction mixture and heated at 80° C. for 16 h. Once the reaction was completed (monitored by TLC), the reaction mixture was diluted with EtOAc. The combined organic layer was washed with water, brine solution, dried over anhydrous sodium sulphate and concentrated under vacuum to afford the title compound as off-white solid (0.9 g, 98%).

$^1$H NMR (400 MHz, DMSO-$d_6$): δ 7.62 (d, J=10.8 Hz, 2H), 7.42 (d, J=10.8 Hz, 2H), 6.22 (s, 1H), 4.11 (m, 2H), 3.43 (q, J=6.8 Hz, 1H), 3.28 (bs, 2H), 2.84 (m, 2H), 2.45 (bs, 2H), 1.28 (s, 12H), 1.21 (m 6H): LC-MS: m/z 386.3 (M+H).

Intermediate 10: Ethyl 2-(4-(4-(4,4,5,5-tetramethyl-1,3,2-dioxaborolan-2-yl)phenyl)piperazin-1-yl)propanoate Intermediate-10 was prepared by procedure similar to the one described in Intermediate-9 with appropriate variations in reactants, quantities of reagents, protections and deprotections, solvents and reaction conditions. LC-MS: m/z 389.3 (M+H).

Intermediate 11: Ethyl 2-(4'-(4,4,5,5-tetramethyl-1,3,2-dioxaborolan-2-yl)-2,3,4,5-tetrahydro-[1,1'-biphenyl]-4-yl)acetate Step-a: Synthesis of ethyl 2-(4'-bromo-2,3,4,5-tetrahydro-[1,1'-biphenyl]-4-yl)acetate To a stirred solution of 1-bromo-4-iodobenzene (0.8 g, 2.82 mmol), ethyl 2-(4-(4,4,5,5-tetramethyl-1,3,2-dioxaborolan-2-yl)cyclohex-3-en-1-yl)acetate (0.99 g, 3.39 mmol) in 1,4-dioxane (8 mL) and water (1 mL) was added $K_2CO_3$ (0.97 g, 7.07 mmol) and degassed with nitrogen for 15 min. $Pd(dppf)Cl_2{\cdot}DCM$ (0.23 g, 0.28 mmol) was added and the reaction mixture was heated for 6 h at 100° C. in sealed tube. Once the reaction was completed (monitored by TLC), the reaction mixture was diluted with EtOAc. The combined organic layer was washed with water, brine solution, dried over anhydrous sodium sulphate and concentrated under vacuum to give the residue which was purified by combiflash column chromatography using 50% ethyl acetate in hexane as eluent to afford the title compound as colourless liquid (0.48 g, 52%). $^1$H NMR (400 MHz, DMSO-$d_6$): δ 7.49 (d, J=8.4 Hz, 2H), 7.36 (d, J=8.4 Hz, 2H), 6.16 (d, J=2 Hz, 1H), 4.08 (q, J=6.8 Hz, 2H), 2.39 (bs, 2H), 2.31 (d, J=7.2 Hz, 2H), 2.28 (m, 1H), 1.83-2.05 (m, 3H), 1.38 (m, 1H), 1.19 (t, J=6.8 Hz, 3H).

Step-b: Synthesis of ethyl 2-(4'-(4,4,5,5-tetramethyl-1,3,2-dioxaborolan-2-yl)-2,3,4,5-tetrahydro-[1,1'-biphenyl]-4-yl)acetate To a stirred solution of ethyl 2-(4'-bromo-2,3,4,5-tetrahydro-[1,1'-biphenyl]-4-yl)acetate (0.5 g, 1.54 mmol) in dioxane (5 mL) was added bis pinacolato diboron (0.58 g, 2.32 mmol) and KOAc (0.38 g, 3.86 mmol) at RT and degassed with nitrogen for 5 min then $Pd(dppf)Cl_2{\cdot}DCM$ (0.12 g, 0.15 mmol) was added into the reaction mixture and heated at 100° C. for 3 h. Once the reaction was completed (monitored by TLC), the reaction mixture was diluted with EtOAc. The combined organic layer was washed with water, brine solution, dried over anhydrous sodium sulphate and concentrated under vacuum to afford the title compound as colourless sticky solid (0.48 g, 83%).

$^1$H NMR (400 MHz, DMSO-$d_6$): δ 7.61 (d, J=8 Hz, 2H), 7.41 (d, J=8 Hz, 2H), 6.19 (bs, 1H), 4.07 (q, J=6.8 Hz, 2H), 2.41 (bs, 2H), 2.31 (m, 3H), 1.85-2.04 (m, 3H), 1.40 (m, 1H), 1.28 (s, 12H), 1.22 (t, J=6.8 Hz, 3H).

Intermediate 12: Ethyl 4'-(4,4,5,5-tetramethyl-1,3,2-dioxaborolan-2-yl)-2,3,4,5-tetrahydro-[1,1'-biphenyl]-4-carboxylate Intermediate-12 was prepared by procedure similar to the one described in Intermediate-11 with appropriate variations in reactants, quantities of reagents, protections and deprotections, solvents and reaction conditions. $^1$H NMR (400 MHz, DMSO-$d_6$): δ 7.61 (d, J=8 Hz, 2H), 7.41 (d, J=8 Hz, 2H), 6.22 (bs, 1H), 4.09 (q, J=6.8 Hz, 2H), 2.57 (m, 1H), 2.30-2.50 (m, 4H), 2.08 (m, 1H), 1.71 (m, 1H), 1.28 (s, 12H), 1.20 (t, J=6.8 Hz, 3H); LC-MS: m/z 357.3 (M+H).

Intermediate 13: Tert-butyl 3-(4-(4,4,5,5-tetramethyl-1,3,2-dioxaborolan-2-yl)phenyl)-8-azabicyclo[3.2.1]oct-2-ene-8-carboxylate Intermediate-13 was prepared by procedure similar to the one described in Intermediate-11 with appropriate variations in reactants, quantities of reagents, protections and deprotections, solvents and reaction conditions. $^1$H NMR (400 MHz, DMSO-$d_6$): δ 7.62 (d, J=7.6 Hz, 2H), 7.41 (d, J=7.6 Hz, 2H), 6.61 (d, J=5.2 Hz, 1H), 4.38 (m, 2H), 2.95 (m, 1H), 2.05-2.33 (m, 2H), 1.85 (m, 2H), 1.63 (m, 1H), 1.37 (s, 9H), 1.28 (s, 12H); LC-MS: m/z 312.3 (M+H).

Intermediate 14: Tert-butyl (1R,5S)-8-(4-(4,4,5,5-tetramethyl-1,3,2-dioxaborolan-2-yl)phenyl)-3,8-diazabicyclo[3.2.1]octane-3-carboxylate

Step-a: Synthesis of tert-butyl (1R,5S)-8-(4-bromophenyl)-3,8-diazabicyclo[3.2.1]octane-3-carboxylate To a stirred solution of 1-bromo-4-iodobenzene (1.6 g, 5.65 mmol), tert-butyl 3,8-diazabicyclo[3.2.1]octane-3-carboxylate (1.43 g, 6.78 mmol) in toluene (30 mL) was added KOtBu (1.55 g, 13.89 mmol) and degassed with nitrogen for 15 min followed by $Pd_2(dba)_3$, 0.25 g, 0.28 mmol) Xantphos (0.16 g, 0.28 mmol) was added and the reaction mixture was heated for 16 h at 110° C. in sealed tube. Once the reaction was completed (monitored by TLC), the reaction mixture was diluted with EtOAc. The combined organic layer was washed with water, brine solution, dried over anhydrous sodium sulphate and concentrated under vacuum to give the residue which was purified by combiflash column chromatography using 50% ethyl acetate in hexane as eluent to afford the title compound as off-white solid (1.1 g, 53%). $^1$H NMR (400 MHz, DMSO-$d_6$): δ 7.24 (d, J=8 Hz, 2H), 6.59 (d, J=8 Hz, 2H), 4.08 (m, 2H), 3.65 (d, J=12.8 Hz, 1H), 3.51 (d, J=12.8 Hz, 1H), 3.08-3.25 (m, 2H), 1.95 (m, 2H), 1.77 (m, 2H), 1.35 (s, 9H); LC-MS: m/z 367 (M+H).

Step-b: Synthesis of tert-butyl (1R,5S)-8-(4-(4,4,5,5-tetramethyl-1,3,2-dioxaborolan-2-yl)phenyl)-3,8-diazabicyclo[3.2.1]octane-3-carboxylate To a stirred solution of tert-butyl (1R,5S)-8-(4-bromophenyl)-3,8-diazabicyclo[3.2.1]octane-3-carboxylate (1.1 g, 2.99 mmol) in dioxane (5 mL) was added bis pinacolato diboron (1.14 g, 4.49 mmol) and KOAc (0.88 g, 8.9 mmol) at RT and degassed with nitrogen for 5 min then Pd(dppf)$Cl_2$·DCM (0.24 g, 0.29 mmol) was added into the reaction mixture and heated at 100° C. for 4 h. Once the reaction was completed (monitored by TLC), the reaction mixture was diluted with EtOAc. The combined organic layer was washed with water, brine solution, dried over anhydrous sodium sulphate and concentrated under vacuum to afford the title compound as pale-yellow solid (0.5 g, 40%). $^1$H NMR (400 MHz, DMSO-$d_6$): δ 7.49 (d, J=8 Hz, 2H), 6.83 (d, J=8 Hz, 2H), 4.34 (m, 2H), 3.42-3.58 (m, 2H), 3.12 (m, 1H), 2.98 (m, 1H), 1.91 (m, 2H), 1.69 (m, 2H), 1.38 (s, 9H), 1.25 (s, 12H); LC-MS: m/z 415.2 (M+H).

Intermediate 15: (1'-(Tert-butoxycarbonyl)-1',2',3',6'-tetrahydro-[2,4'-bipyridin]-5-yl)boronic acid Intermediate-15 was prepared by procedure similar to the one described in Intermediate-11 with appropriate variations in reactants, quantities of reagents, protections and deprotections, solvents and reaction conditions. $^1$H NMR (400 MHz, DMSO-$d_6$): δ 8.72 (s, 1H), 7.96 (m, 2H), 7.55 (d, J=8 Hz, 1H), 6.78 (bs, 1H), 4.05 (m, 2H), 3.53 (m, 2H), 2.55 (m, 2H), 1.32 (s, 9H); LC-MS: m/z 305.1 (M+H).

Intermediate 16: Methyl 5-((4-(4,4,5,5-tetramethyl-1,3,2-dioxaborolan-2-yl)phenyl)amino)pentanoate

Step-a: Synthesis of methyl 5-((4-bromophenyl)amino)pentanoate

To a stirred solution of 4-bromo aniline (0.5 g, 2.90 mmol) in DMF (5 mL) was added $K_2CO_3$ (0.14 g, 2.90 mmol) at RT and stirred for 15 min then added methyl-2-bromopropanoate (1.13 g, 5.81 mmol) and stirred for 24 h at 60° C. under nitrogen atmosphere. Once the reaction was completed (monitored by TLC), the reaction mixture was diluted with ice cold water and extracted with EtOAc. The combined organic layer was washed with water, brine solution, dried over anhydrous sodium sulphate and concentrated under vacuum to give the residue which was purified by combiflash column chromatography using 10% ethyl acetate in hexane as eluent to afford the title compound as off-white solid (0.28 g, 33%). $^1$H NMR (400 MHz, DMSO-$d_6$): δ 7.22 (dd, J=8.8, 1.6 Hz, 2H), 6.53 (dd, J=8.8, 1.6 Hz, 2H), 3.61 (s, 3H), 3.00 (m, 2H), 2.37 (t, J=7.6 Hz, 2H), 1.52-1.68 (m, 4H): LC-MS: m/z 288.0 (M+H).

Step-b: Synthesis of methyl 5-((4-(4,4,5,5-tetramethyl-1,3,2-dioxaborolan-2-yl)phenyl)amino)pentanoate To a stirred solution of methyl 5-((4-bromophenyl)amino)pentanoate (0.28 g, 0.97 mmol) in dioxane (5 mL) was added bis pinacolato diboron (0.32 g, 1.26 mmol) and KOAc (0.29 g, 2.93 mmol) at RT and degassed with nitrogen for 5 min then Pd(dppf)$Cl_2$·DCM (0.08 g, 0.09 mmol) was added into the reaction mixture and heated at 80° C. for 16 h. Once the reaction was completed (monitored by TLC), the reaction mixture was filtered through celite and washed with EtOAc. The combined organic layer was concentrated under vacuum to give the residue which was purified by combiflash column chromatography using 10% ethyl acetate in hexane as eluent to afford the title compound as yellow solid (0.15 g, 46%).

$^1$H NMR (400 MHz, DMSO-$d_6$): δ 7.41 (d, J=8 Hz, 2H), 6.54 (d, J=8 Hz, 2H), 6.04 (m, 1H), 3.61 (s, 3H), 3.05 (m, 2H), 2.37 (t, J=7.6 Hz, 2H), 1.56-1.68 (m, 4H): 1.28 (s, 12H); LC-MS: m/z 334.05 (M+H).

Intermediate 17: Tert-butyl 2-(3-(4-(4,4,5,5-tetramethyl-1,3,2-dioxaborolan-2-yl)phenyl)azetidin-1-yl) acetate Step-a: Synthesis of Tert-butyl 3-(2-((4-methoxyphenyl)sulfonyl)hydrazineylidene)azetidine-1-carboxylate To a stirred solution of 4-methoxybenzenesulfonohydrazide (2 g, 11.68 mmol), Tert-butyl 3-oxoazetidine-1-carboxylate (2.36 g, 11.68 mmol) in toluene (40 mL) and the reaction mixture was heated for 16 h at 50° C. in sealed tube. Once the reaction was completed (monitored by TLC), reaction mass was concentrated under vacuum to give the residue which was purified by combiflash column chromatography using 40% ethyl acetate in hexane as eluent to afford the title compound as white solid (1.75 g, 42%).

$^1$H NMR (400 MHz, DMSO-$d_6$): δ 10.81 (bs, 1H), 7.78 (dd, J=6.8, 2 Hz, 2H), 7.16 (dd, J=6.8, 2 Hz, 2H), 4.50 (bs, 4H), 3.88 (s, 3H), 1.41 (s, 9H); LC-MS: m/z 353.9 (M−H).

Step-b: Synthesis of tert-butyl 3-(4-bromophenyl)azetidine-1-carboxylate

To a stirred solution of tert-butyl 3-(2-((4-methoxyphenyl)sulfonyl) hydrazineylidene)azetidine-1-carboxylate (1.2 g, 3.37 mmol), (4-bromophenyl)boronic acid (1.01 g, 5.06 mmol) in dioxane (35 mL) was added $Cs_2CO_3$ (1.65 g, 5.06 mmol) and degassed with nitrogen for 30 min. Then the reaction mixture was heated for 16 h at 110° C. in sealed tube. Once the reaction was completed (monitored by TLC), the reaction mixture was diluted with EtOAc and filtered. Filtrate was concentrated under vacuum to give the residue which was purified by combiflash column chromatography using 20% ethyl acetate in hexane as eluent to afford the title compound as colourless liquid (0.36 g, 34%). $^1$H NMR (400 MHz, $CDCl_3$): δ 7.47 (d, J=8.4 Hz, 2H), 7.19 (d, J=8.8 Hz, 2H), 4.32 (m, 2H), 3.92 (m, 2H), 3.67 (m, 1H), 1.46 (s, 9H); LC-MS: m/z 212 (M-100).

Step-c: Synthesis of 3-(4-bromophenyl)azetidine

To a stirred solution of tert-butyl 3-(4-bromophenyl) azetidine-1-carboxylate (0.36 g, 1.15 mmol) in DCM (3 mL) was added trifluoro acetic acid (0.3 mL) at 0° C. and then slowly brought to RT and stirred at RT for 1 h. The reaction mixture was evaporated under reduced pressure, the resultant residue was washed with diethyl ether and dried under vacuum to afford the title compound off-white solid (0.28 g, 97.7%). $^1$H NMR (400 MHz, $CDCl_3$): δ 9.85 (bs, 1H), 7.53 (d, J=7.6 Hz, 2H), 7.25 (d, J=7.6 Hz, 2H), 4.35 (m, 2H), 4.20 (m, 3H); LC-MS: m/z 212 (M+H).

Step-d: Synthesis of tert-butyl 2-(3-(4-bromophenyl)azetidin-1-yl)acetate

To a stirred solution of 3-(4-bromophenyl)azetidine (0.28 g, 1.12 mmol) in DMF (5 mL) was added DIPEA (0.72 g, 5.63 mmol) at RT and stirred for 15 min then added Tert-butyl 2-bromoacetate (0.24 g, 1.24 mmol) and stirred for 2 h at RT under nitrogen atmosphere. The reaction mixture was quenched with cold water and stirred for 1 h, the solid so formed was filtered and dried under vacuum to afford title compound as pale-yellow sticky solid (0.28 g, 76%). $^1$H NMR (400 MHz, $CDCl_3$): δ 7.40 (d, J=7.6 Hz, 2H), 7.14 (d, J=7.6 Hz, 2H), 3.85 (m, 2H), 3.70 (m, 1H), 3.22 (m, 4H), 1.44 (s, 9H); LC-MS: m/z 326.1 (M+H).

Step-e: Synthesis of tert-butyl 2-(3-(4-(4,4,5,5-tetramethyl-1,3,2-dioxaborolan-2-yl)phenyl)azetidin-1-yl)acetate To a stirred solution of tert-butyl 2-(3-(4-bromophenyl) azetidin-1-yl)acetate (0.28 g, 0.85 mmol) in dioxane (5 mL) was added bis pinacolato diboron (0.32 g, 1.28 mmol) and KOAc (0.21 g, 2.14 mmol) at RT and degassed with nitrogen for 5 min then Pd(dppf)$Cl_2$·DCM (0.07 g, 0.08 mmol) was added into the reaction mixture and heated at 110° C. for 16 h. Once the reaction was completed (monitored by TLC), the reaction mixture was diluted with EtOAc. The combined organic layer was washed with water, brine solution, dried over anhydrous sodium sulphate and concentrated under vacuum to afford the title compound as white sticky solid (0.3 g, 93%).

$^1$H NMR (400 MHz, $CDCl_3$): δ 7.76 (d, J=8 Hz, 2H), 7.28 (d, J=8 Hz, 2H), 3.93 (m, 2H), 3.83 (m, 1H), 3.28 (m, 2H), 3.24 (s, 2H), 1.33 (s, 9H), 1.25 (s, 12H); LC-MS: m/z 374.4 (M+H).

Intermediate 18: Tert-butyl 6-(4-(4,4,5,5-tetramethyl-1,3,2-dioxaborolan-2-yl)phenyl)-2-azaspiro [3.3]heptane-2-carboxylate Step-a: Synthesis of tert-butyl 6-(2-((4-methoxyphenyl)sulfonyl)hydrazineylidene)-2-azaspiro[3.3]heptane-2-carboxylate To a stirred solution of 4-methoxybenzenesulfonohydrazide (1.5 g, 7.41 mmol), Tert-butyl 6-oxo-2-azaspiro[3.3] heptane-2-carboxylate (1.56 g, 7.41 mmol) in toluene (30 mL) and the reaction mixture was heated for 16 h at 50° C. in sealed tube. Once the reaction was completed (monitored by TLC), reaction mass was concentrated under vacuum to give the residue which was purified by combiflash column chromatography using 35% ethyl acetate in hexane as eluent to afford the title compound as white solid (2.8 g, 95%). $^1$H NMR (400 MHz, DMSO-$d_6$): δ 10.21 (bs, 1H), 7.68 (d, J=8.4 Hz, 2H), 7.05 (d, J=8.4 Hz, 2H), 3.82 (bs, 4H), 3.78 (s, 3H), 2.95 (m, 4H), 1.31 (s, 9H); LC-MS: m/z 394.1 (M−H).

Step-b: Synthesis of tert-butyl 6-(4-bromophenyl)-2-azaspiro[3.3]heptane-2-carboxylate To a stirred solution of Tert-butyl 6-(2-((4-methoxyphenyl)sulfonyl)hydrazineylidene)-2-azaspiro[3.3]heptane-2-carboxylate (2.8 g, 7.08 mmol), (4-bromophenyl)boronic acid (2.13 g, 10.6 mmol) in dioxane (60 mL) was added $Cs_2CO_3$ (4.6 g, 14.16 mmol) and degassed with nitrogen for 30 min. Then the reaction mixture was heated for 16 h at 110° C. in sealed tube. Once the reaction was completed (monitored by TLC), the reaction mixture was diluted with EtOAc and filtered.

Filtrate was concentrated under vacuum to give the residue which was purified by combiflash column chromatography using 20% ethyl acetate in hexane as eluent to afford the title compound as colourless liquid (1.3 g, 52%). $^1$H NMR (400 MHz, DMSO-$d_6$): δ 7.38 (d, J=8.4 Hz, 2H), 7.01

(d, J=8.4 Hz, 2H), 4.02 (s, 2H), 3.81 (s, 2H), 3.18 (m, 1H), 2.54 (m, 2H), 2.21 (m, 2H), 1.42 (s, 9H).

Step-c: Synthesis of tert-butyl 6-(4-(4,4,5,5-tetramethyl-1,3,2-dioxaborolan-2-yl)phenyl)-2-azaspiro[3.3]heptane-2-carboxylate To a stirred solution of tert-butyl 6-(4-bromophenyl)-2-azaspiro[3.3]heptane-2-carboxylate (1.3 g, 3.69 mmol) in dioxane (35 mL) was added bis pinacolato diboron (1.4 g, 5.53 mmol) and KOAc (0.90 g, 9.22 mmol) at RT and degassed with nitrogen for 5 min then Pd(dppf)$Cl_2$·DCM (0.30 g, 0.36 mmol) was added into the reaction mixture and heated at 110° C. for 16 h. Once the reaction was completed (monitored by TLC), the reaction mixture was diluted with EtOAc. The combined organic layer was washed with water, brine solution, dried over anhydrous sodium sulphate and concentrated under vacuum to afford the title compound as creamy sticky solid (0.3 g, 93%). $^1$H NMR (400 MHz, DMSO-$d_6$): δ 7.74 (d, J=8 Hz, 2H), 7.16 (d, J=8 Hz, 2H), 4.05 (s, 2H), 3.83 (s, 2H), 3.38 (m, 1H), 2.56 (m, 2H), 2.58 (m, 2H), 1.33 (s, 9H), 1.25 (s, 12H). LC-MS: m/z 374.05 (M+H).

Intermediate 19: (2S,4R)-1-((S)-2-Amino-3,3-dimethylbutanoyl)-4-hydroxy-N-(2-hydroxy-1-(4-(4-methylthiazol-5-yl)phenyl)ethyl)pyrrolidine-2-carboxamide hydrochloride Step-a: Synthesis of tert-butyl (2-hydroxy-1-(4-(4-methylthiazol-5-yl)phenyl)ethyl)carbamate To a stirred solution of tert-butyl (1-(4-bromophenyl)-2-hydroxyethyl)carbamate (2.4 g, 7.59 mmol) and 4-methylthiazole (0.9 g, 9.11 mmol) in DMF (12 mL) was added KOAc (1.49 g, 15.89 mmol) and Pd$(OAC)_2$ (0.34 g, 1.51 mmol). The reaction mixture was heated at 90° C. for 3 h. After completion of the reaction (monitored by TLC) the reaction mixture was allowed to cool to RT and poured into ice cold water. The resulting mixture was extracted with ethyl acetate (2×50 mL). The combined organic layer was washed with water (50 mL), brine (50 mL), dried over anhydrous sodium sulphate and concentrated under vacuum to give the residue which was purified by combiflash column chromatography using 50% ethyl acetate in hexane as eluent to afford the title compound (0.5 g, 30%). $^1$H NMR (400 MHz, DMSO-$d_6$): δ 8.98 (s, 1H), 7.44 (d, J=7.6 Hz, 2H), 7.38 (d, J=7.6 Hz, 2H), 7.30 (d, J=8.4 Hz, 1H), 4.83 (t, J=6 Hz, 1H), 4.56 (m, 1H), 3.51 (t, J=6 Hz, 2H), 2.45 (s, 3H), 1.37 (s, 9H), LC-MS: m/z 335.0 (M+1).

Step-b: Synthesis of 2-amino-2-(4-(4-methylthiazol-5-yl)phenyl)ethan-1-ol hydrochloride To a stirred solution of tert-butyl (2-hydroxy-1-(4-(4-methylthiazol-5-yl)phenyl)ethyl)carbamate (0.3 g, 0.89 mmol) in DCM (2 mL) at 0° C. was added 4M HCl in 1,4-dioxane (1.5 mL). The reaction mixture was stirred at room temperature for 2 h. After completion of the reaction (monitored by TLC) the reaction mixture was concentrated under reduced pressure and washed with diethyl ether to afford the title compound (0.2 g, 95%).

$^1$H NMR (400 MHz, DMSO-$d_6$): δ 9.04 (s, 1H), 8.48 (bs, 2H), 7.57 (m, 4H), 4.34 (m, 1H), 3.72 (m, 2H), 2.46 (s, 3H), LC-MS: m/z 335.0 (M+1).

Step-c: Synthesis of tert-butyl ((2S)-1-((2S,4R)-4-hydroxy-2-((2-hydroxy-1-(4-(4-methylthiazol-5-yl)phenyl)ethyl)carbamoyl)pyrrolidin-1-yl)-3,3-dimethyl-1-oxobutan-2-yl)carbamate To a solution of 2-amino-2-(4-(4-methylthiazol-5-yl)phenyl)ethan-1-ol hydrochloride (0.2 g, 0.85 mmol) and (2S,4R)-1-((S)-2-((tert-butoxycarbonyl)amino)-3,3-dimethylbutanoyl)-4-hydroxypyrrolidine-2-carboxylic acid (0.35 g, 1.02 mmol) in DMF (3 mL) at 0° C. was added HATU (0.48 g, 1.28 mmol) followed by dropwise addition of DIPEA (0.5 ml, 2.56 mmol) and stirred for 2 h at RT. After completion of the reaction (monitored by TLC) the reaction mixture was allowed to cool to RT and poured into ice cold water. The resulting mixture was extracted with EtOAc (2×50 mL). The combined organic layer was washed with water (20 mL), brine (20 mL), dried over anhydrous sodium sulphate and concentrated under vacuum to give the crude product which was purified by combiflash column chromatography using 5% MeOH in DCM as eluent to afford the title compound (0.17 g, 53%). LC-MS: m/z 561.2 (M+1).

Step-d: Synthesis of (2S,4R)-1-((S)-2-amino-3,3-dimethylbutanoyl)-4-hydroxy-N-(2-hydroxy-1-(4-(4-methylthiazol-5-yl)phenyl)ethyl)pyrrolidine-2-carboxamide hydrochloride To a stirred solution of tert-butyl ((2S)-1-((2S,4R)-4-hydroxy-2-((2-hydroxy-1-(4-(4-methylthiazol-5-yl)phenyl)ethyl)carbamoyl)pyrrolidin-1-yl)-3,3-dimethyl-1-oxobutan-2-yl)carbamate (0.17 g, 0.30 mmol) in DCM (2 mL) at 0° C. was added 4M HCl in 1,4-dioxane (1.5 mL). The reaction mixture was stirred at room temperature for 16 h. The solvents were evaporated under reduced pressure and the residue was washed with diethyl ether to afford the title compound (0.16 g, 100%) which was used in the next step without further purification. LC-MS: m/z 461.1 (M+1).

Intermediate 20: (2S,4R)-1-((S)-2-Amino-3,3-dimethylbutanoyl)-N-(2-(dimethylamino)-1-(4-(4-methylthiazol-5-yl)phenyl)ethyl)-4-hydroxypyrrolidine-2-carboxamide hydrochloride Step-a: Synthesis of 2-((tert-butoxycarbonyl)amino)-2-(4-(4-methylthiazol-5-yl)phenyl)ethyl methanesulfonate To a stirred solution of tert-butyl (2-hydroxy-1-(4-(4-methylthiazol-5-yl)phenyl)ethyl)carbamate (0.6 g, 1.79 mmol) in DCM (10 mL) at 0° C. were added methane sulphonic chloride (0.2 mL, 2.69 mmol) and followed by TEA (0.64 mL, 4.49 mmol) and the reaction mixture was stirred at room temperature for 2 h. After completion of the reaction (monitored by TLC) the reaction mixture was allowed to cool to RT and poured into ice cold water. The resulting mixture was extracted with EtOAc (2×50 mL). The combined organic layer was washed with water (30 mL), brine (30 mL), dried over anhydrous sodium sulphate and concentrated under vacuum to give the crude product which was purified by combiflash column chromatography using 2% MeOH in DCM as eluent to afford the title compound (0.48 g, 64%). $^1$H NMR (400 MHz, DMSO-$d_6$): δ 9.01 (d, J=2 Hz, 1H), 7.75 (d, J=8.8 Hz, 1H), 7.50 (m, 4H), 4.94 (m, 1H), 4.24-4.33 (m, 2H), 3.18 (s, 3H), 2.46 (s, 3H), 1.39 (s, 9H): LC-MS: m/z 413.0 (M+1).

Step-b: Synthesis of tert-butyl (2-(dimethylamino)-1-(4-(4-methylthiazol-5-yl)phenyl)ethyl)carbamate To a stirred solution of 2-((tert-butoxycarbonyl)amino)-2-(4-(4-methylthiazol-5-yl)phenyl)ethyl methanesulfonate (0.480 g, 0.89 mmol) in acetonitrile (2 mL) was added DIPEA (0.6 mL) and cooled to 0° C. then N,N dimethyl amine gas was passed through reaction mass for 15 mins and the reaction mixture was stirred for 16 h. After completion of the reaction (monitored by TLC) the reaction mixture was concentrated under reduced pressure and extracted with EtOAc (2×50 mL). The combined organic layer was washed with water and brine dried over anhydrous sodium sulphate and concentrated under vacuum to afford the crude title compound as a brown liquid (0.300 g crude). $^1$H NMR (400 MHz, DMSO-$d_6$): δ 8.98 (d, J=2 Hz, 1H), 7.30-7.45 (m, 5H), 4.68 (m, 1H), 3.46 (m, 2H), 2.46 (s, 3H), 2.17 (s, 3H), 2.09 (s, 3H), 1.30 (s, 9H): LC-MS: m/z 362.1 (M+1).

Step-c: Synthesis of N1,N1-dimethyl-2-(4-(4-methylthiazol-5-yl)phenyl)ethane-1,2-diamine hydrochloride N1,N1-Dimethyl-2-(4-(4-methylthiazol-5-yl)phenyl)ethane-1,2-diamine hydrochloride was prepared by procedure similar to the one described in step-b of Intermediate 19. LC-MS: m/z 262.0 (M+1).

Step-d: Synthesis of tert-butyl ((2S)-1-((2S,4R)-2-((2-(dimethylamino)-1-(4-(4-methylthiazol-5-yl)phenyl)ethyl)carbamoyl)-4-hydroxypyrrolidin-1-yl)-3,3-dimethyl-1-oxobutan-2-yl)carbamate Tert-butyl ((2S)-1-((2S,4R)-2-((2-(dimethylamino)-1-(4-(4-methylthiazol-5-yl)phenyl)ethyl)carbamoyl)-4-hydroxypyrrolidin-1-yl)-3,3-dimethyl-1-oxobutan-2-yl)carbamate was prepared by procedure similar to the one described in step-c of Intermediate 19. LC-MS: m/z 588.3 (M+1).

Step-e: Synthesis of (2S,4R)-1-((S)-2-amino-3,3-dimethylbutanoyl)-N-(2-(dimethylamino)-1-(4-(4-methylthiazol-5-yl)phenyl)ethyl)-4-hydroxypyrrolidine-2-carboxamide hydrochloride (2S,4R)-1-((S)-2-Amino-3,3-dimethylbutanoyl)-N-(2-(dimethylamino)-1-(4-(4-methylthiazol-5-yl)phenyl)ethyl)-4-hydroxypyrrolidine-2-carboxamide hydrochloride was prepared by procedure similar to the one described in step-d of Intermediate 19. LC-MS: m/z 488.2 (M+1).

Example-1: (2S,4R)-4-Hydroxy-1-(2-(3-(4-(6-(2-hydroxyphenyl)pyridazin-4-yl)phenyl) isoxazol-5-yl)-3-methylbutanoyl)-N—((S)-1-(4-(4-methylthiazol-5-yl)phenyl)ethyl) pyrrolidine-2-carboxamide (Compound 1, Racemic)

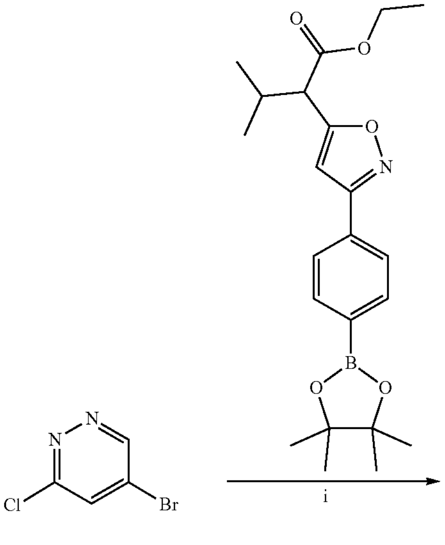

-continued

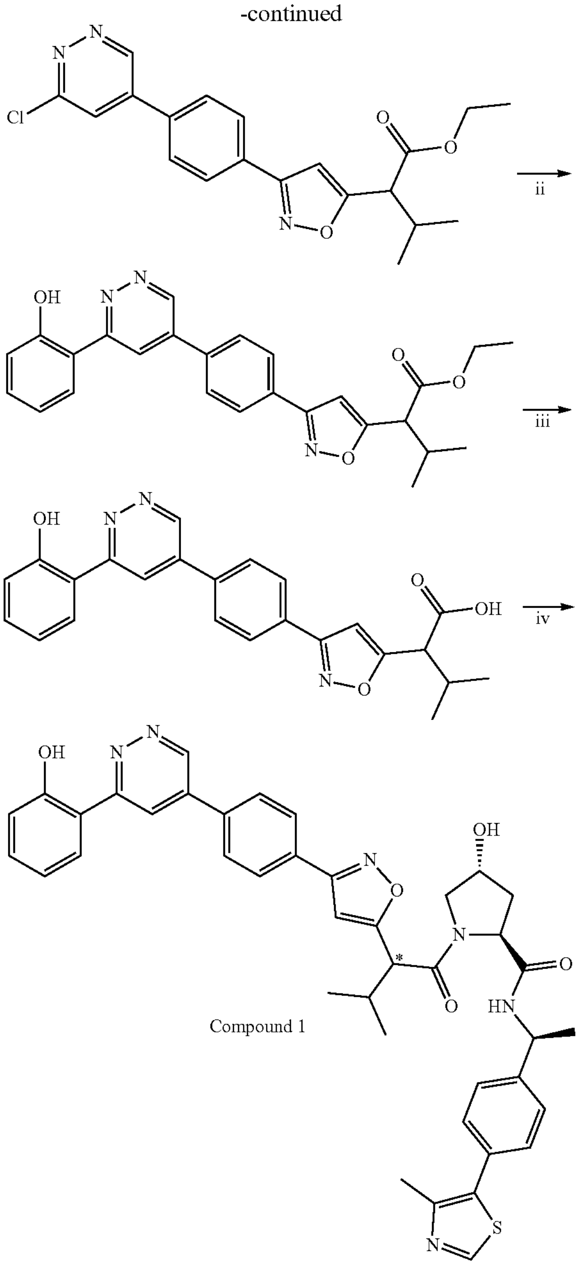

Compound 1

Step-i: Synthesis of Ethyl 2-(3-(4-(6-chloropyridazin-4-yl)phenyl)isoxazol-5-yl)-3-methylbutanoate A mixture of 1,4-dioxane (13 mL) and water (2 mL) was taken in microwave vial and degassed with nitrogen for 5 min. To this, 5-bromo-3-chloropyridazine (0.91 g, 4.72 mmol) and ethyl 3-methyl-2-(3-(4-(4,4,5,5-tetramethyl-1,3,2-dioxaborolan-2-yl)phenyl)isoxazol-5-yl)butanoate (1.42 g, 3.63 mmol) were added followed by the addition of $K_2CO_3$ (1 g, 7.26 mmol) and Pd(dppf)$Cl_2$·DCM (0.29 g, 0.36 mmol). The reaction mixture was heated for 1 h at 110° C. in microwave. Once the reaction was completed (monitored by TLC), the reaction mixture was diluted with EtOAc. The combined organic layer was washed with water, brine solution, dried over anhydrous sodium sulphate and concentrated under vacuum to give the residue which was purified by combiflash column chromatography using 50-60% ethyl acetate in hexane as eluent to afford the title compound as off-white solid (1 g, 71%).

$^1$H NMR (400 MHz, DMSO-$d_6$): δ 9.76 (d, J=2.0 Hz, 1H), 8.38 (d, J=2.0 Hz, 1H), 8.17 (d, J=8.4 Hz, 2H), 8.09 (d, J=8.4 Hz, 2H), 7.18 (s, 1H), 4.17 (d, J=2.8 Hz, 2H), 3.88 (d, J=8.4 Hz, 1H), 2.45-2.38 (m, 1H), 1.22 (t, J=7.2 Hz, 3H), 1.00 (d, J=6.8 Hz, 3H), 0.91 (d, J=6.8 Hz, 3H); LC-MS: m/z 386.1 (M+H).

Step-ii: Synthesis of Ethyl 2-(3-(4-(6-(2-hydroxyphenyl)pyridazin-4-yl)phenyl)isoxazol-5-yl)-3-methylbutanoate A mixture of 1,4-dioxane (15 mL) and water (3 mL) were taken in microwave vial and degassed with nitrogen for 5 min. To this, ethyl 2-(3-(4-(6-chloropyridazin-4-yl)phenyl)isoxazol-5-yl)-3-methylbutanoate (0.95 g, 2.46 mmol) and (2-hydroxyphenyl) boronic acid (0.68 g, 4.9 mmol) were added followed by the addition of $K_2CO_3$ (0.85 g, 6.1 mmol) and Pd(dppf)$Cl_2$·DCM (0.2 g, 0.24 mmol). The reaction mixture was heated for 1 h at 120° C. in microwave. Once the reaction was completed (monitored by TLC), the reaction mixture was diluted with EtOAc. The combined organic layer was washed with water, brine solution, dried over anhydrous sodium sulphate and concentrated under vacuum to give the residue which was purified by combiflash column chromatography using 50-60% ethyl acetate in hexane as eluent to afford the title compound as yellow solid (0.75 g, 69%).

$^1$H NMR (400 MHz, DMSO-$d_6$): δ 13.05 (s, 1H), 9.69 (d, J=2.0 Hz, 1H), 8.79 (d, J=2.0 Hz, 1H), 8.24 (d, J=8.4 Hz, 3H), 8.12 (d, J=8.4 Hz, 2H), 7.44-7.40 (m, 1H), 7.19 (s, 1H), 7.03 (d, J=7.2 Hz, 2H), 4.19-4.16 (m, 2H), 3.34 (d, J=8.4 Hz, 1H), 2.46-2.41 (m, 1H), 1.20 (t, J=14 Hz, 3H), 1.01 (d, J=6.8 Hz, 3H), 0.92 (d, J=6.4 Hz, 3H); LC-MS: m/z 444.1 (M+H).

Step-iii: Synthesis of 2-(3-(4-(6-(2-Hydroxyphenyl)pyridazin-4-yl)phenyl)isoxazol-5-yl)-3-methylbutanoic acid To a stirred solution of ethyl 2-(3-(4-(6-(2-Hydroxyphenyl)pyridazin-4-yl)phenyl)isoxazol-5-yl)-3-methylbutanoate (0.75 g, 1.69 mmol) in THE (5 mL) and $H_2O$ (5 mL) mixture was added LiOH·$H_2O$ (0.21 g, 5.07 mmol) at 0° C. The reaction mixture was stirred for 3 h at RT. Then the reaction mixture was evaporated under reduced pressure and the resultant residue was diluted with methanol and acidified to pH 6 using amberlite IT120 (acidic rasin) and filtered and filtrate was concentrated under vacuum to afford the title compound as a dark brown solid (0.65 g, 93%).

$^1$H NMR (400 MHz, DMSO-$d_6$): δ 9.66 (s, 1H), 8.78 (s, 1H), 8.23 (s, 1H), 8.20 (d, J=8.4 Hz, 2H), 8.06 (d, J=8.4 Hz, 2H), 7.39 (t, J=14.4 Hz, 1H), 7.00 (t, J=15.2 Hz, 2H), 6.82 (s, 1H), 3.17 (d, J=8.8 Hz, 1H), 2.32-2.27 (m, 1H), 0.98 (d, J=6.4 Hz, 3H), 0.80 (d, J=6.8 Hz, 3H); LC-MS: m/z 416.1 (M+H).

Step-iv: Synthesis of ((2S,4R)-4-Hydroxy-1-(2-(3-(4-(6-(2-hydroxyphenyl)pyridazin-4-yl)phenyl)isoxazol-5-yl)-3-methylbutanoyl)-N—((S)-1-(4-(4-methylthiazol-5-yl)phenyl)ethyl)pyrrolidine-2-carboxamide To a solution of 2-(3-(4-(6-(2-hydroxyphenyl)pyridazin-4-yl)phenyl)isoxazol-5-yl)-3-methylbutanoic acid (0.1 g, 0.24 mmol), (2S,4R)-4-hydroxy-N—((S)-1-(4-(4-methylthiazol-5-yl)phenyl)ethyl)pyrrolidine-2-carboxamide hydrochloride (0.11 g, 0.28 mmol) and HATU (0.14 g, 0.36 mmol) in DMF (5 mL) was added DIPEA (0.21 mL, 1.2 mmol) dropwise at 0° C. and slowly brought to RT and the reaction mixture was stirred for 1 h at RT. Then the reaction mixture was poured into ice cold water and extracted with ethyl acetate. The combined organic layer was washed with water, brine solution, dried over anhydrous sodium sulphate and concentrated under vacuum to give the crude product which was purified by preparative HPLC to afford the title compound as off-white solid (0.025 g, 14%).

$^1$H NMR (400 MHz, DMSO-$d_6$): δ 13.12 (bs, 1H), 9.69 (d, J=2.4 Hz, 1H), 8.99 (t, J=8 Hz, 1H), 8.90 (s, 1H), 8.79 (d, J=2 Hz, 1H), 8.19-8.26 (m, 3H), 8.06-8.11 (m, 2H), 7.46-7.37 (m, 5H), 7.10-7.01 (m, 3H), 5.12 (m, 1H), 4.95-4.92 (m, 1H), 4.46-4.38 (m, 1H), 4.31 (bs, 1H), 3.89-4.04 (m, 1H), 3.55-3.76 (m, 2H), 2.47 (s, 2H), 2.37 (s, 1H), 2.06 (d, J=12 Hz, 1H), 1.82-1.76 (m, 1H), 1.50 (d, J=4.4 Hz, 1H), 1.39 (d, J=4.4 Hz, 3H), 1.03 (d, J=6.4 Hz, 3H), 0.90 (d, J=3.2 Hz, 3H); LC-MS: m/z 729.3 (M+H).

Example-2: (2S,4R)-4-Hydroxy-1-((S)-2-(2-(4-(4-(6-(2-hydroxyphenyl)pyridazin-4-yl)phenyl)piperazin-1-yl)acetamido)-3,3-dimethylbutanoyl)-N—((S)-1-(4-(4-methylthiazol-5-yl)phenyl)ethyl)pyrrolidine-2-carboxamide (Compound 2)

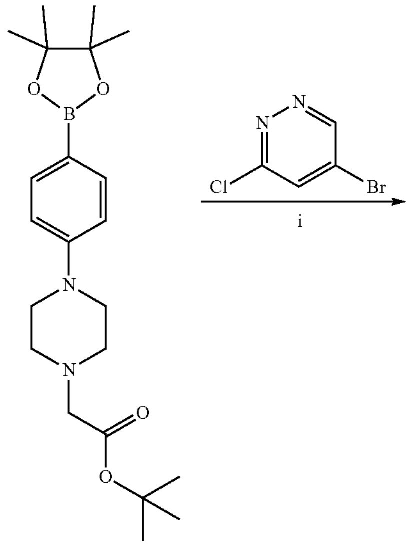

-continued
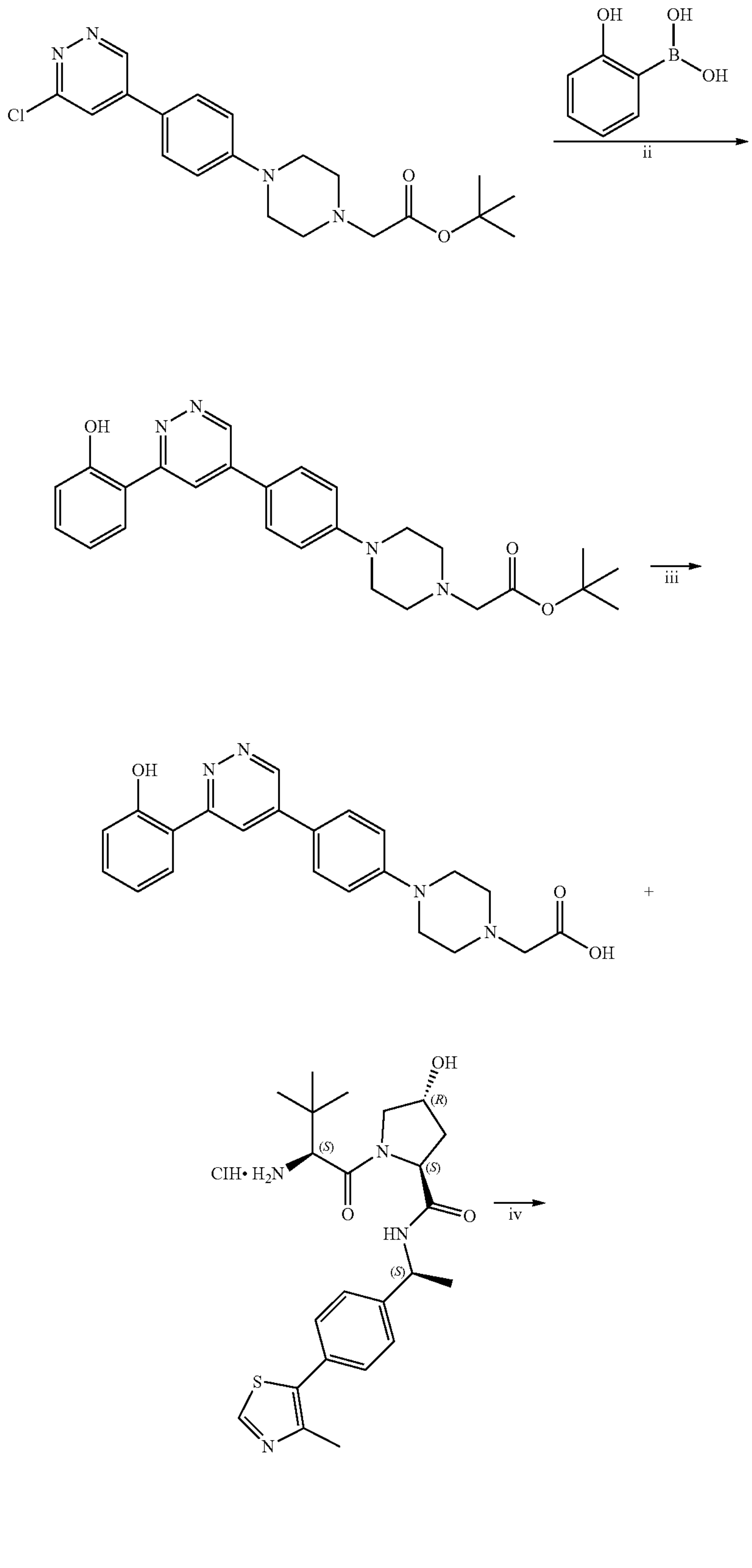

-continued

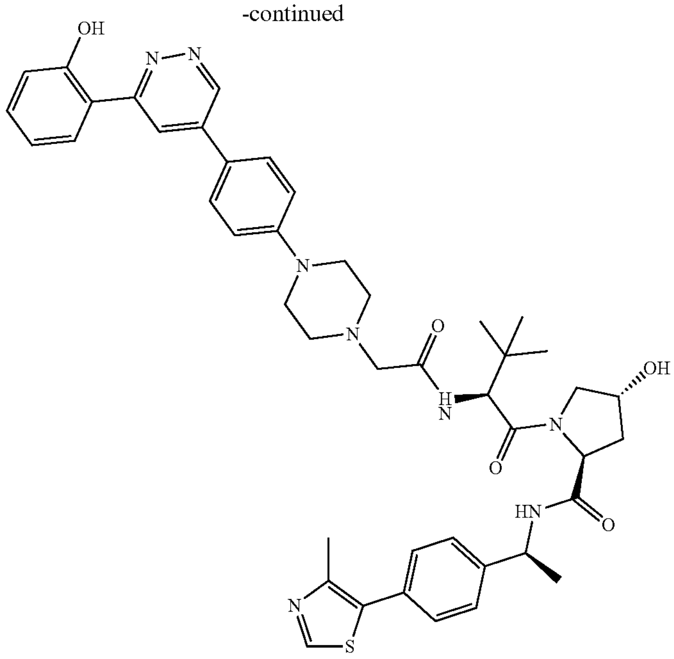

Compound 2

Step-i: Synthesis of Tert-butyl 2-(4-(4-(6-chloro-pyridazin-4-yl)phenyl)piperazin-1-yl)acetate To a stirred solution of 5-bromo-3-chloropyridazine (1.6 g, 8.3 mmol), Tert-butyl 2-(4-(4-(4,4,5,5-tetramethyl-1,3,2-dioxaborolan-2-yl)phenyl)piperazin-1-yl)acetate (2.78 g, 6.9 mmol) in 1,4-dioxane (30 mL) and water (3 mL) was added $K_2CO_3$ (1.77 g, 16.7 mmol) and degassed with nitrogen for 5 min. Pd(dppf)$Cl_2$·DCM (0.68 g, 0.83 mmol) was added and the reaction mixture was heated for 4 h at 120° C. in sealed tube. Once the reaction was completed (monitored by TLC), the reaction mixture was diluted with EtOAc. The combined organic layer was washed with water, brine solution, dried over anhydrous sodium sulphate and concentrated under vacuum to give the residue which was purified by combiflash column chromatography using 40-80% ethyl acetate in hexane as eluent to afford the title compound as sticky material (1.7 g, 63%).

$^1$H NMR (400 MHz, DMSO-$d_6$): 9.62 (d, J=1.6 Hz, 1H), 8.15 (d, J=2.0 Hz, 1H), 7.91 (d, J=8.8 Hz, 2H), 7.07 (d, J=8.8 Hz, 2H), 3.34 (s, 2H), 3.31 (bs, 4H), 2.64 (d, J=4.4 Hz, 4H), 1.42 (s, 9H); LC-MS: m/z 389.0 (M+H).

Step-ii: Synthesis of Tert-butyl 2-(4-(4-(6-(2-hydroxyphenyl)pyridazin-4-yl)phenyl)piperazin-1-yl) acetate To a stirred solution of tert-butyl 2-(4-(4-(6-chloro-pyridazin-4-yl)phenyl)piperazin-1-yl)acetate (0.5 g, 1.28 mmol), (2-hydroxyphenyl)boronic acid (0.27 g, 1.93 mmol) in 1,4-dioxane (10 mL) and water (3 mL) were added $Na_2CO_3$ (0.54 g, 5.18 mmol) and degassed with nitrogen for 5 min. Pd(dppf)$Cl_2$·DCM (0.1 g, 0.13 mmol) was added and the reaction mixture was heated for 3 h at 130° C. in sealed tube. Once the reaction was completed (monitored by TLC), the reaction mixture was diluted with EtOAc. The combined organic layer was washed with water, brine solution, dried over anhydrous sodium sulphate and concentrated under vacuum to give the residue which was purified by combi-flash column chromatography using 60% ethyl acetate in hexane as eluent to afford the title compound as sticky material (0.35 g, 60%).

$^1$H NMR (400 MHz, DMSO-$d_6$): 13.53 (s, 1H), 9.57 (d, J=2.0 Hz, 1H), 8.62 (d, J=2.0 Hz, 1H), 8.25 (d, J=7.2 Hz, 1H), 8.01 (d, J=8.8 Hz, 2H), 7.40 (t, J=6.8 Hz, 1H), 7.11 (d, J=8.8 Hz, 2H), 7.01 (d, J=6.0 Hz, 2H), 3.18 (s, 2H), 2.66 (d, J=4.4 Hz, 4H), 2.50 (d, J=4.4 Hz, 4H), 1.43 (s, 9H). LC-MS: m/z 447.15 (M+H).

Step-iii: Synthesis of 2-(4-(4-(6-(2-hydroxyphenyl) pyridazin-4-yl)phenyl)piperazin-1-yl)acetic acid To a stirred solution of tert-butyl 2-(4-(4-(6-(2-Hydroxy-phenyl)pyridazin-4-yl)phenyl)piperazin-1-yl)acetate (0.7 g, 1.56 mmol) in DCM (10 mL), was added 4 N dioxane hydrochloride (7 mL) at 0° C. and then slowly brought to RT and stirred for 6 h. The reaction mixture was evaporated under reduced pressure, the resultant residue was washed with diethyl ether and dried under vacuum to afford the title compound as orange solid (0.5 g, 74%). $^1$H NMR (400 MHz, DMSO-$d_6$): 10.6 (bs, 1H), 9.67 (d, J=2.0 Hz, 1H), 8.70 (s, 1H), 8.15 (d, J=8.0 Hz, 1H), 8.10 (d, J=8.8 Hz, 2H), 7.46-7.45 (m, 1H), 7.20 (d, J=9.2 Hz, 2H), 7.07-7.01 (m, 2H), 4.24 (s, 2H), 3.64-3.57 (m, 8H); LC-MS: m/z 391.1 (M+H).

Step-iv: Synthesis of (2S,4R)-4-Hydroxy-1-((S)-2-(2-(4-(4-(6-(2-hydroxyphenyl)pyridazin-4-yl)phenyl) piperazin-1-yl)acetamido)-3,3-dimethylbutanoyl)-N—((S)-1-(4-(4-methylthiazol-5-yl)phenyl)ethyl) pyrrolidine-2-carboxamide To a solution of 2-(4-(4-(6-(2-hydroxyphenyl)pyridazin-4-yl)phenyl)piperazin-1-yl)acetic acid (0.5 g, 1.28 mmol) and (2S,4R)-1-((S)-2-amino-3,3-dimethylbutanoyl)-4-hydroxy-N—((S)-1-(4-(4-methylthiazol-5-yl)phenyl)ethyl)

pyrrolidine-2-carboxamide hydrochloride (0.62 g, 1.28 eq.) in DMF (3 mL) at 0° C. was added HATU (0.73 g, 1.92 mmol) followed by the dropwise addition of DIPEA (0.7 mL, 3.84 mmol) and the reaction mixture was stirred for 4 h at RT. Then the reaction mixture was poured into ice cold water and extracted with ethyl acetate. The combined organic layer was washed with water, brine solution, dried over anhydrous sodium sulphate and concentrated under vacuum to get the crude product which was purified by combiflash column chromatography using 5% methanol in DCM as eluent to afford the title compound as yellow solid (0.11 g, 11%).

$^1$H NMR (400 MHz, DMSO-$d_6$): 13.53 (s, 1H), 9.58 (d, J=2.0 Hz, 1H), 8.98 (s, 1H), 8.62 (d, J=2.0 Hz, 1H), 8.45 (d, J=8.0 Hz, 1H), 8.26 (d, J=6.8 Hz, 1H), 8.03 (d, J=8.8 Hz, 2H), 7.79 (d, J=9.2 Hz, 1H), 7.44-7.35 (m, 5H), 7.15 (d, J=9.2 Hz, 2H), 7.00 (t, J=8.0 Hz, 2H), 5.14 (d, J=3.2 Hz, 1H), 4.88 (t, J=7.2 Hz, 1H), 4.53 (d, J=9.6 Hz, 1H), 4.44 (t, J=8.4 Hz, 1H), 4.29 (bs, 1H), 3.59 (s, 2H), 3.38 (s, 4H), 3.16 (d, J=16.0 Hz, 1H), 3.03 (d, J=16.0 Hz, 1H), 2.67-2.66 (m, 4H), 2.45 (s, 3H), 2.32 (t, J=2.0 Hz, 1H), 1.76-1.70 (m, 1H), 1.36 (d, J=6.8 Hz, 3H), 0.96 (s, 9H); LC-MS: m/z 817.45 (M+H).

Example-3: (2S,4R)-1-((S)-2-(2-(4-(4-(6-chloropyridazin-4-yl)phenyl)piperazin-1-yl) acetamido)-3,3-dimethylbutanoyl)-4-hydroxy-N—((S)-1-(4-(4-methylthiazol-5-yl)phenyl) ethyl)pyrrolidine-2-carboxamide (Compound 3)

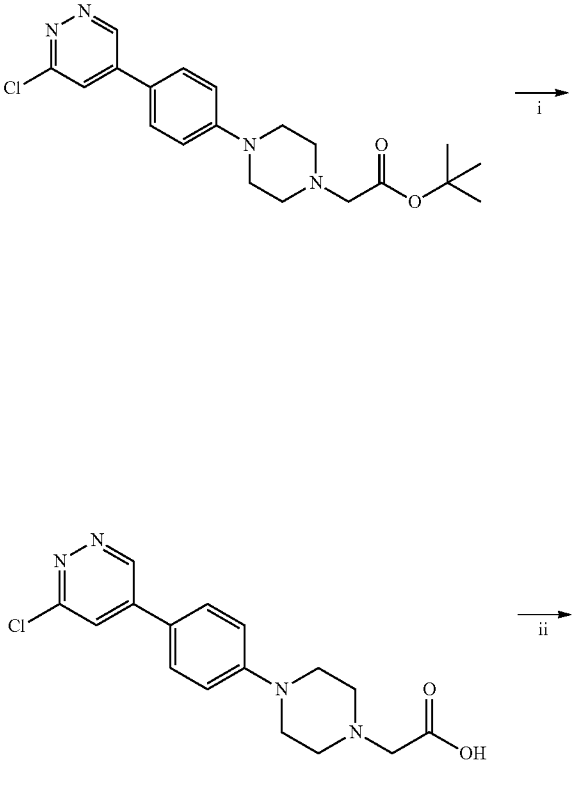

-continued

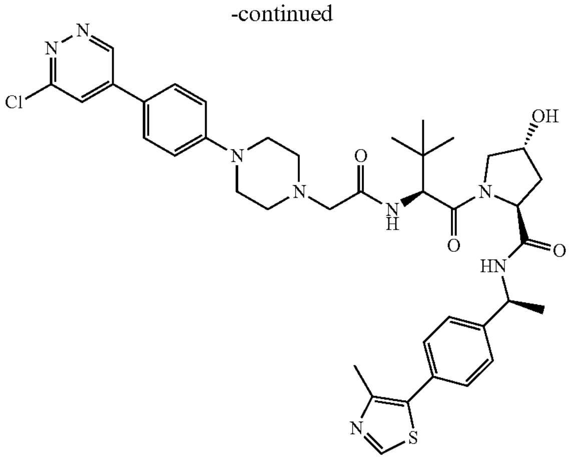

Compound 3

Step-i: Synthesis of 2-(4-(4-(6-chloropyridazin-4-yl) phenyl)piperazin-1-yl)acetic acid To a stirred solution of tert-butyl 2-(4-(4-(6-chloropyridazin-4-yl)phenyl)piperazin-1-yl)acetate (0.07 g, 0.179 mmol) in DCM (5 mL) was added 4N-dioxane hydrochloride (2 mL) at 0° C. and then slowly brought to RT and stirred for 16 h. The reaction mixture was evaporated under reduced pressure, the resultant residue was washed with diethyl ether and dried under vacuum to afford the title compound as orange solid (0.065 g, 99%). LC-MS: m/z 333.1 (M+H).

Step-ii: Synthesis of (2S,4R)-1-((S)-2-(2-(4-(4-(6-Chloropyridazin-4-yl)phenyl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide To a solution of 2-(4-(4-(6-chloropyridazin-4-yl)phenyl) piperazin-1-yl)acetic acid (0.07 g, 0.20 mmol) and (2S,4R)-1-((S)-2-Amino-3,3-dimethylbutanoyl)-4-hydroxy-N—((S)-1-(4-(4-methylthiazol-5-yl)phenyl)ethyl)pyrrolidine-2-carboxamide hydrochloride (0.09 g, 0.20 eq.) in DMF (2 mL) at 0° C. was added HATU (0.09 g, 0.24 mmol) followed by the dropwise addition of DIPEA (0.06 mL, 0.4 mmol) and the reaction mixture was stirred for 4 h at RT. Then the reaction mixture was poured into ice cold water and extracted with ethyl acetate. The combined organic layer was washed with water, brine solution, dried over anhydrous sodium sulphate and concentrated under vacuum to get the crude product which was purified by preparative HPLC to afford the title compound as yellow solid (0.014 g, 8%).

$^1$H NMR (400 MHz, DMSO-$d_6$): 9.60 (d, J=1.2 Hz, 1H), 8.94 (s, 1H), 8.38 (d, J=7.6 Hz, 1H), 8.12 (d, J=2.0 Hz, 1H), 7.89 (d, J=8.8 Hz, 2H), 7.74 (d, J=9.6 Hz, 1H), 7.40 (d, J=8.0 Hz, 2H), 7.33 (d, J=8.4 Hz, 2H), 7.07 (d, J=8.8 Hz, 2H), 5.09 (d, J=3.2 Hz, 1H), 4.86 (t, J=14.0 Hz, 1H), 4.49 (d, J=9.2 Hz, 1H), 4.42 (t, J=4.2 Hz, 1H), 4.26 (s, 1H), 3.56 (s, 1H), 3.18-3.06 (m, 2H), 2.64-2.58 (m, 6H), 2.42 (s, 4H), 2.30 (s, 2H), 1.88 (s, 1H), 1.74 (s, 1H), 1.34 (d, J=6.8 Hz, 3H), 0.93 (s, 9H). LC-MS: m/z 759.35 (M+H).

Example-4: (2S,4R)-1-((S)-2-(2-(4-(4-(6-(5-Fluoro-2-hydroxyphenyl)pyridazin-4-yl) phenyl)piperazin-1-yl)acetamido)-3,3-dimethylbutanoyl)-4-hydroxy-N—((S)-1-(4-(4-methylthiazol-5-yl)phenyl)ethyl) pyrrolidine-2-carboxamide (Compound 4)

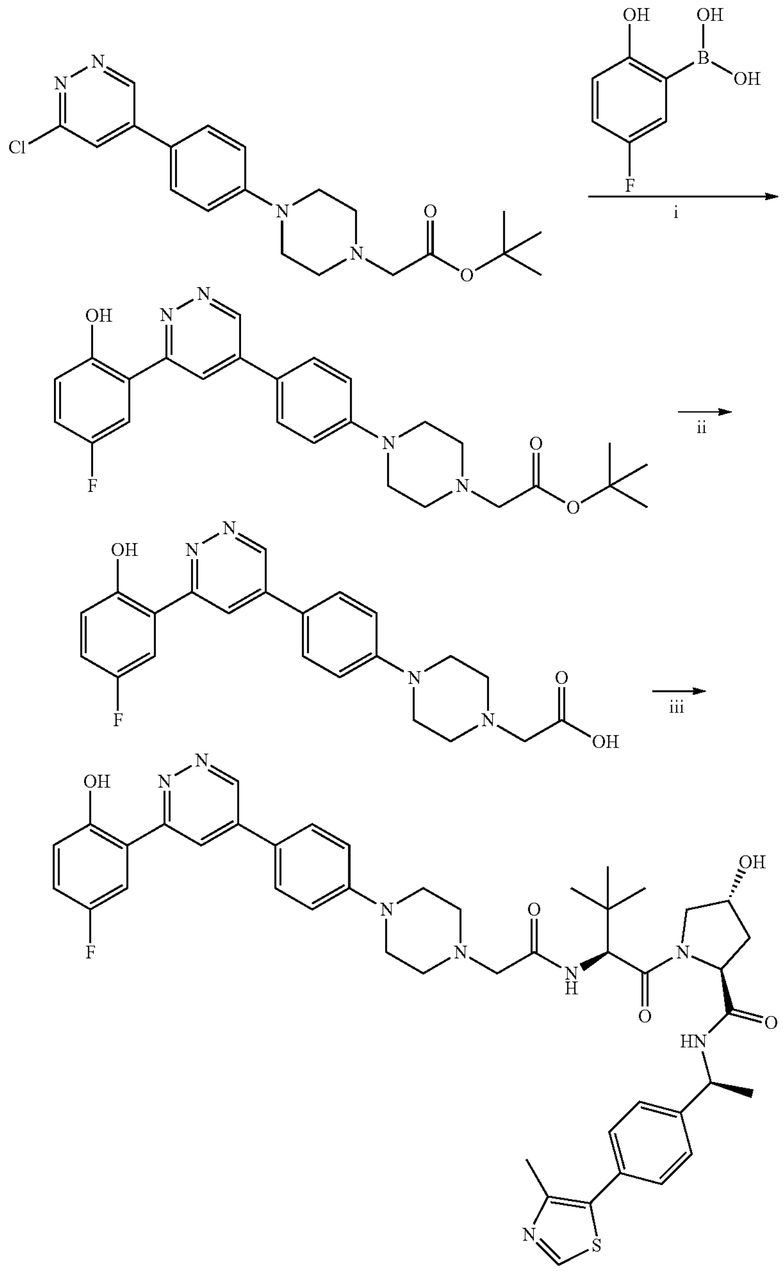

Compound 4

Step-i: Synthesis of Tert-butyl 2-(4-(4-(6-(5-fluoro-2-hydroxyphenyl)pyridazin-4-yl)phenyl)piperazin-1-yl)acetate To a stirred solution of Tert-butyl 2-(4-(4-(6-chloropyridazin-4-yl)phenyl)piperazin-1-yl)acetate (0.1 g, 0.26 mmol), (4-fluoro-2-hydroxyphenyl)boronic acid (0.06 g, 0.38 mmol) in 1,4-dioxane (1.6 mL) and water (0.4 mL) was added $Na_2CO_3$ (0.08 g, 0.77 mmol) and degassed with nitrogen for 15 min. Pd(dppf)$Cl_2$·DCM (0.02 g, 0.026 mmol) was added and the reaction mixture was heated for 1.2 h at 130° C. in microwave. Once the reaction was completed (monitored by TLC), the reaction mixture was diluted with EtOAc. The combined organic layer was washed with water, brine solution, dried over anhydrous sodium sulphate and concentrated under vacuum to give the residue which was purified by combiflash column chromatography using 60% ethyl acetate in hexane as eluent to afford the title compound as pale-yellow solid (0.06 g, 50%).

$^1$H NMR (400 MHz, DMSO-$d_6$): 13.30 (s, 1H), 9.60 (d, J=1.2 Hz, 1H), 8.64 (d, J=1.2 Hz, 1H), 8.16 (dd, J=2.8 & 10.0 Hz, 1H), 8.03 (d, J=8.8 Hz, 2H), 7.25 (t, J=4.0 Hz, 1H), 7.11 (d, J=8.8 Hz, 2H), 7.04-7.00 (m, 1H), 3.18 (s, 2H), 2.66 (bs, 4H), 2.40 (bs, 4H), 1.43 (s, 9H). LC-MS: m/z 465.2 (M+H).

Step-ii: Synthesis of 2-(4-(4-(6-(5-Fluoro-2-hydroxyphenyl)pyridazin-4-yl)phenyl)piperazin-1-yl) acetic acid To a stirred solution of Tert-butyl 2-(4-(4-(6-(5-fluoro-2-hydroxyphenyl)pyridazin-4-yl)phenyl)piperazin-1-yl)acetate (0.16 g, 0.34 mmol) in DCM (4 mL) was added 4 N dioxane hydrochloride (1.2 mL) at 0° C. and then slowly brought to RT and stirred at RT for 6 h. The reaction mixture was evaporated under reduced pressure, the resultant residue was washed with diethyl ether and dried under vacuum to afford the title compound as orange solid (0.15 g, 98%). LC-MS: m/z 407.1 (M−H).

Step-iii: Synthesis of (2S,4R)-1-((S)-2-(2-(4-(4-(6-(5-Fluoro-2-hydroxyphenyl)pyridazin-4-yl)phenyl) piperazin-1-yl)acetamido)-3,3-dimethylbutanoyl)-4-hydroxy-N—((S)-1-(4-(4-methylthiazol-5-yl)phenyl) ethyl)pyrrolidine-2-carboxamide To a solution of 2-(4-(4-(6-(5-Fluoro-2-hydroxyphenyl) pyridazin-4-yl)phenyl)piperazin-1-yl)acetic acid (0.07 g, 0.16 mmol) and (2S,4R)-1-((S)-2-Amino-3,3-dimethylbutanoyl)-4-hydroxy-N—((S)-1-(4-(4-methylthiazol-5-yl)phenyl)ethyl) pyrrolidine-2-carboxamide hydrochloride compound (0.08, 0.16 eq.) in DMF (2 mL) at 0° C. was added HATU (0.07 g, 0.19 mmol) followed by dropwise addition of DIPEA (0.05 mL, 0.31 mmol). The reaction mixture was stirred for 3 h at RT. Then the reaction mixture was poured into ice cold water and extracted with ethyl acetate. The combined organic layer was washed with water, brine solution, dried over anhydrous sodium sulphate and concentrated under vacuum to get the crude product which was purified by preparative HPLC to afford the title compound as yellow solid (0.014 g, 10%).

$^1$H NMR (400 MHz, DMSO-$d_6$): 13.30 (s, 1H), 9.61 (s, 1H), 8.97 (s, 1H), 8.65 (s, 1H), 8.49 (d, J=7.6 Hz, 1H), 8.16 (t, J=10.0 Hz, 1H), 8.04 (d, J=8.8 Hz, 2H), 7.78 (d, J=9.6 Hz, 1H), 7.43 (d, J=8.0 Hz, 2H), 7.36 (d, J=7.6 Hz, 2H), 7.26 (t, J=7.2 Hz, 1H), 7.14 (d, J=4.4 Hz, 2H), 7.04-7.00 (m, 1H), 5.12 (s, 1H), 4.89 (t, J=7.4 Hz, 1H), 4.53 (d, J=10.0 Hz, 1H), 4.45 (t, J=8.0 Hz, 1H), 4.29 (s, 1H), 3.60 (s, 2H), 3.38-3.05 (m, 2H), 2.66-2.60 (m, 6H), 2.55-2.45 (m, 4H), 2.06 (t, J=9.8 Hz, 1H), 1.78 (s, 2H), 1.36 (d, J=6.8 Hz, 3H), 0.96 (s, 9H). LC-MS: m/z 835.3 (M+H).

Example-5: (2S,4R)-4-hydroxy-1-((S)-2-(2-(4-(5-(6-(2-hydroxyphenyl)pyridazin-4-yl) pyridin-2-yl)piperazin-1-yl)acetamido)-3,3-dimethylbutanoyl)-N—((S)-1-(4-(4-methylthiazol-5-yl)phenyl)ethyl) pyrrolidine-2-carboxamide (Compound 5)

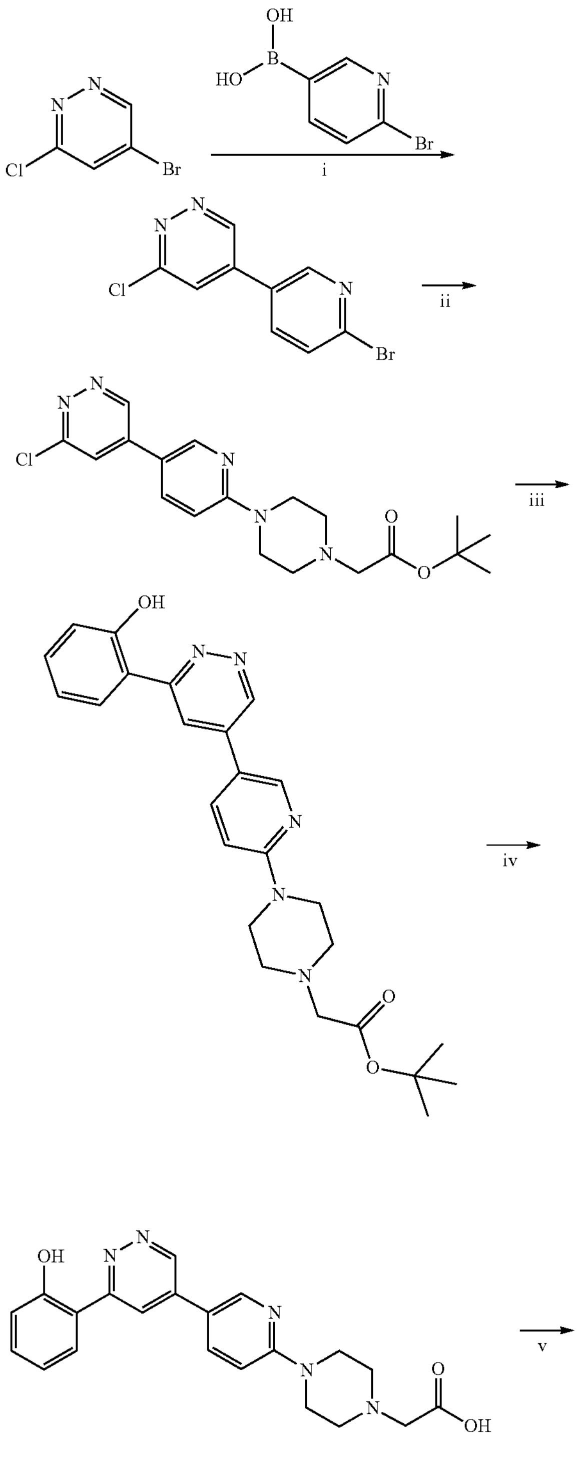

-continued

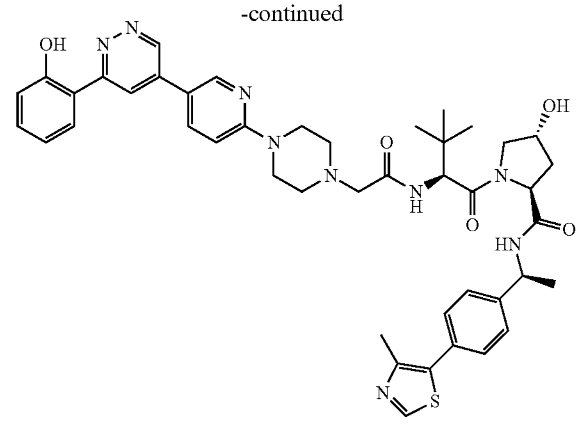

Compound 5

Step-i: Synthesis of 5-(6-Bromopyridin-3-yl)-3-chloropyridazine

To a stirred solution of 5-bromo-3-chloropyridazine (0.5 g, 2.48 mmol), (6-bromopyridin-3-yl) boronic acid (0.47 g, 2.48 mmol) in 1,4-dioxane (15 mL) was added 2M $Na_2CO_3$ (1 g, 9.9 mmol) 4 mL solution and degassed with nitrogen for 15 min. Pd(dppf)$Cl_2$·DCM (0.04 g, 0.05 mmol) was added and the reaction mixture was heated for 1 h at 80° C. in microwave. Once the reaction was completed (monitored by TLC), the reaction mixture was diluted with EtOAc. The combined organic layer was washed with water, brine solution, dried over anhydrous sodium sulphate and concentrated under vacuum to give the residue which was purified by combiflash column chromatography using 60% ethyl acetate in hexane as eluent to afford the title compound as yellow solid (0.45 g, 64%).

$^1$H NMR (400 MHz, DMSO-$d_6$): δ 9.75 (d, J=2.0 Hz, 1H), 9.01 (d, J=2.4 Hz, 1H), 8.43 (d, J=2.0 Hz, 1H), 8.36 (dd, J=2.8 Hz, 2.4 Hz 1H), 7.90 (d, J=8.4 Hz, 1H); LC-MS: m/z 272 (M+H).

Step-ii: Synthesis of Tert-butyl 2-(4-(5-(6-chloropyridazin-4-yl)pyridin-2-yl)piperazin-1-yl)acetate To a stirred solution of 5-(6-bromopyridin-3-yl)-3-chloropyridazine (0.32 g, 1.18 mmol) in DMSO (10 mL) were added Tert-butyl 2-(piperazin-1-yl)acetate (0.35 g, 1.78 mmol) and DIPEA (0.85 g, 4.72 mmol) at RT and heated at 120° C. for 16 h. Then the reaction mixture was quenched with cold water and extracted with EtOAc. The combined organic layer was washed with water, brine solution, dried over anhydrous sodium sulphate and concentrated under vacuum to give the residue which was purified by combiflash column chromatography using 45-50% ethyl acetate in hexane as eluent to afford the title compound as yellow solid (0.2 g, 40%).

$^1$H NMR (400 MHz, DMSO-$d_6$): δ 9.31 (d, J=2.0 Hz, 1H), 8.54 (d, J=2.4 Hz, 1H), 7.76 (dd, J=2.8 Hz, 2.4 Hz, 1H), 7.58 (d, J=2.0 Hz, 1H), 6.74 (d, J=9.2 Hz, 1H), 3.74 (t, J=4.8 Hz, 4H), 3.19 (s, 2H), 2.70 (t, J=4.8 Hz, 4H), 1.47 (s, 9H); LC-MS: m/z 390.2 (M+H).

Step-iii: Synthesis of Tert-butyl 2-(4-(5-(6-(2-hydroxyphenyl)pyridazin-4-yl)pyridin-2-yl)piperazin-1-yl)acetate To a stirred solution of tert-butyl 2-(4-(5-(6-chloropyridazin-4-yl)pyridin-2-yl)piperazin-1-yl)acetate (0.25 g, 0.64 mmol), (2-hydroxyphenyl)boronic acid (0.13 g, 0.96 mmol) in 1,4-dioxane (10 mL) was added 2M $Na_2CO_3$ (0.27 g, 2.56 mmol) 1.2 mL solution and degassed with nitrogen for 15 min. Pd(dppf)$Cl_2$·DCM (0.05 g, 0.06 mmol) was added and the reaction mixture was heated for 2 h at 120° C. in microwave. Once the reaction was completed (monitored by TLC), the reaction mixture was diluted with EtOAc. The combined organic layer was washed with water, brine solution, dried over anhydrous sodium sulphate and concentrated under vacuum to get the residue which was purified by combiflash column chromatography using 60% ethyl acetate in hexane as eluent to afford the title compound as yellow solid (0.18 g, 62%).

$^1$H NMR (400 MHz, DMSO-$d_6$): δ 13.78 (s, 1H), 9.26 (d, J=2.0 Hz, 1H), 8.62 (d, J=2.8 Hz, 1H), 8.11 (d, J=2.4 Hz, 1H), 7.85-7.80 (m, 2H), 7.40-7.39 (m, 1H), 7.13-7.11 (m, 1H), 7.01 (t, J=8.0 Hz, 1H), 6.78 (d, J=8.8 Hz, 1H), 3.76 (t, J=4.8 Hz, 4H), 3.2 (s, 2H), 2.72 (t, J=4.8 Hz, 4H), 1.47 (s, 9H); LC-MS: m/z 448.25 (M+H).

Step-iv: Synthesis of 2-(4-(5-(6-(2-Hydroxyphenyl)pyridazin-4-yl)pyridin-2-yl)piperazin-1-yl)acetic acid To a stirred solution of tert-butyl 2-(4-(5-(6-(2-Hydroxyphenyl)pyridazin-4-yl)pyridin-2-yl)piperazin-1-yl)acetate (0.15 g, 0.33 mmol) in DCM (10 mL) was added 4 N dioxane hydrochloride (5 mL) at 0° C. and then slowly brought to RT and stirred at RT for 2 h. The reaction mixture was evaporated under reduced pressure, the resultant residue was washed with diethyl ether and dried under vacuum to afford the title compound as orange solid (0.1 g, 63%). LC-MS: m/z 392.1 (M+H).

Step-v: Synthesis of (2S,4R)-4-Hydroxy-1-((S)-2-(2-(4-(5-(6-(2-hydroxyphenyl)pyridazin-4-yl)pyridin-2-yl)piperazin-1-yl)acetamido)-3,3-dimethylbutanoyl)-N—((S)-1-(4-(4-methylthiazol-5-yl)phenyl)ethyl)pyrrolidine-2-carboxamide To a solution of 2-(4-(5-(6-(2-Hydroxyphenyl)pyridazin-4-yl)pyridin-2-yl)piperazin-1-yl)acetic acid (0.1 g, 0.25 mmol) and (2S,4R)-1-((S)-2-Amino-3,3-dimethylbutanoyl)-4-hydroxy-N—((S)-1-(4-(4-methylthiazol-5-yl)phenyl)ethyl) pyrrolidine-2-carboxamide hydrochloride (0.13, 0.28 eq.) in DMF (3 mL) at 0° C. was added HATU (0.14 g, 0.37 mmol) followed by the dropwise addition of DIPEA (0.18 mL, 1 mmol) and the reaction mixture was stirred for 4 h at RT. Then the reaction mixture was poured into ice cold water and extracted with ethyl acetate. The combined organic layer was washed with water, brine solution, dried over anhydrous sodium sulphate and concentrated under vacuum to give the crude product which was purified by preparative HPLC to afford the title compound as yellow solid (0.03 g, 16%).

$^1$H NMR (400 MHz, DMSO-$d_6$): δ 13.5 (bs, 1H), 9.61 (s, 1H), 8.97 (s, 1H), 8.90 (s, 1H), 8.66 (s, 1H), 8.42 (d, J=8.0 Hz, 1H), 8.31 (d, J=8.8 Hz, 1H), 8.25 (d, J=8.0 Hz, 1H), 7.79 (d, J=9.6 Hz, 1H), 7.44-7.35 (m, 5H), 7.07-6.99 (m, 3H), 5.12 (bs, 1H), 4.89 (t, J=6.8 Hz, 1H), 4.53 (d, J=9.6 Hz, 1H), 4.45 (t, J=7.6 Hz, 1H), 4.29 (bs, 1H), 3.71-3.60 (m, 5H), 3.16-3.02 (m, 2H), 2.61 (bs, 4H), 2.45 (m, 3H), 2.08-2.03 (m, 1H), 1.84 (s, 1H), 1.77-1.75 (m, 1H), 1.37 (d, J=6.8 Hz, 3H), 096 (s, 9H); LC-MS: m/z 818.2 (M+H).

Example-6: (2S,4R)-4-Hydroxy-1-((S)-2-(2-(1-(4-(6-(2-hydroxyphenyl)pyridazin-4-yl)phenyl)piperidin-4-yl)acetamido)-3,3-dimethylbutanoyl)-N—((S)-1-(4-(4-methylthiazol-5-yl)phenyl)ethyl)pyrrolidine-2-carboxamide (Compound 6)

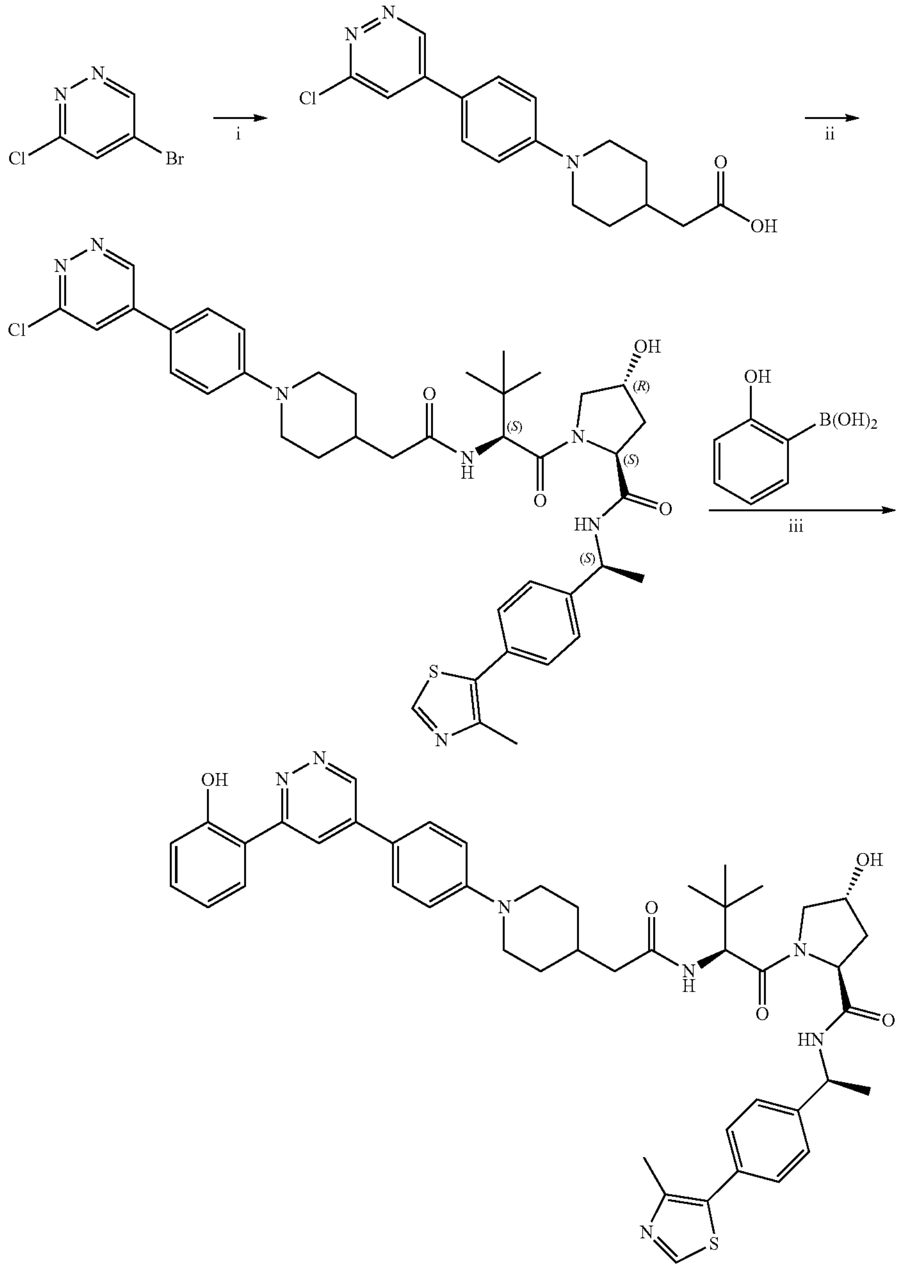

Compound 6

Step-i: Synthesis of 2-(1-(4-(6-Chloropyridazin-4-yl)phenyl)piperidin-4-yl)acetic acid To a stirred solution of 5-Bromo-3-chloropyridazine (0.13 g, 0.67 mmol), ethyl 2-(1-(4-(4,4,5,5-tetramethyl-1,3,2-dioxaborolan-2-yl)phenyl)piperidin-4-yl)acetate (0.25 g, 0.67 mmol) and $Na_2CO_3$ (0.28 g, 2.68 mmol) in 1,4-dioxane (5 mL) and water (2 mL) and degassed with nitrogen for 15 min. $Pd(dppf)Cl_2 \cdot DCM$ (0.055 g, 0.0067 mmol) was added and the reaction mixture was microwaved at 120° C. for 6 h in sealed tube. Once the reaction was completed (monitored by TLC), the reaction mixture was diluted with EtOAc. The combined organic layer was washed with water, brine solution, dried over anhydrous sodium sulphate and concentrated under vacuum to give the residue which was purified by combiflash column chromatography using 8-12% methanol in DCM as eluent to afford the title compound as sticky material (0.09 g, 40%).

$^1$H NMR (400 MHz, DMSO-$d_6$): δ 12.11 (s, 1H), 9.61 (d, J=2.0 Hz, 1H), 8.14 (d, J=2.0 Hz, 1H), 7.89 (d, J=8.8 Hz, 2H), 7.05 (d, J=9.2 Hz, 2H), 3.95-3.89 (m, 2H), 2.83 (t, J=6.0 Hz, 2H), 2.18 (d, J=6.8 Hz, 2H), 1.91-1.86 (m, 1H), 1.76-1.73 (m, 1H), 1.29-1.20 (m, 2H). LC-MS: m/z 331.9 (M−H).

Step-ii: Synthesis of (2S,4R)-1-((S)-2-(2-(1-(4-(6-Chloropyridazin-4-yl)phenyl)piperidin-4-yl)acetamido)-3,3-dimethylbutanoyl)-4-hydroxy-N—((S)-1-(4-(4-methylthiazol-5-yl)phenyl)ethyl)pyrrolidine-2-carboxamide To a solution of 2-(1-(4-(6-Chloropyridazin-4-yl)phenyl)piperidin-4-yl)acetic acid (0.09 g, 0.27 mmol) and (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (0.13 g, 0.27 eq.) in DMF (2 mL) at 0° C. was added HATU (0.155 g, 0.40 mmol) followed by the dropwise addition of DIPEA (0.14 mL, 0.81 mmol) and the reaction mixture was stirred for 4 h at RT. Then the reaction mixture was poured into ice cold water and extracted with ethyl acetate. The combined organic layer was washed with water, brine solution, dried over anhydrous sodium sulphate and concentrated under vacuum to give the crude product which was purified by combiflash column chromatography using 5% methanol in DCM as eluent to afford the title compound as off-white solid (0.125 g, 61%).

$^1$H NMR (400 MHz, DMSO-$d_6$): δ 9.61 (d, J=2.0 Hz, 1H), 8.99 (s, 1H), 8.40 (d, J=7.6 Hz, 1H), 8.13 (d, J=1.6 Hz, 1H), 7.90-7.85 (m, 3H), 7.48-7.36 (m, 4H), 7.05 (d, J=9.2 Hz, 2H), 5.12 (d, J=3.6 Hz, 1H), 4.92 (t, J=7.2 Hz, 1H), 4.54-4.28 (m, 2H), 4.21 (s, 1H), 3.93-3.89 (m, 2H), 3.61 (s, 2H), 2.95-2.79 (m, 2H), 2.45 (s, 3H), 2.24-2.21 (m, 1H), 2.13-2.12 (m, 1H), 2.01-1.67 (m, 5H), 1.37 (d, J=7.2 Hz, 3H), 1.23-1.21 (m, 2H), 0.95 (s, 9H). LC-MS: m/z 756.3 (M−H).

Step-iii: Synthesis of (2S,4R)-4-Hydroxy-1-((S)-2-(2-(1-(4-(6-(2-hydroxyphenyl)pyridazin-4-yl)phenyl)piperidin-4-yl)acetamido)-3,3-dimethylbutanoyl)-N—((S)-1-(4-(4-methylthiazol-5-yl)phenyl)ethyl)pyrrolidine-2-carboxamide To a stirred solution of (2S,4R)-1-((S)-2-(2-(1-(4-(6-Chloropyridazin-4-yl)phenyl)piperidin-4-yl)acetamido)-3,3-dimethylbutanoyl)-4-hydroxy-N—((S)-1-(4-(4-methylthiazol-5-yl)phenyl)ethyl)pyrrolidine-2-carboxamide (0.12 g, 0.15 mmol), (2-Hydroxyphenyl)boronic acid (0.033 g, 0.23 mmol) and $K_2CO_3$ (0.07 g, 0.48 mmol) in 1,4-dioxane (4 mL) and water (1 mL) and degassed with nitrogen for 5 min. Pd(dppf)$Cl_2$·DCM (0.013 g, 0.016 mmol) was added and the reaction mixture was microwaved at 120° C. for 1 h in microwave. Once the reaction was completed (monitored by TLC), the reaction mixture was diluted with EtOAc. The combined organic layer was washed with water, brine solution, dried over anhydrous sodium sulphate and concentrated under vacuum to give the residue which was purified by combiflash column chromatography using 8-12% methanol in DCM as eluent to afford the title compound as pale-yellow solid (0.015 g, 11%).

$^1$H NMR (400 MHz, DMSO-$d_6$): 13.58 (s, 1H), 9.56 (d, J=2.0 Hz, 1H), 8.99 (s, 1H), 8.60 (d, J=2.0 Hz, 1H), 8.40 (d, J=7.6 Hz, 1H), 8.25 (d, J=7.2 Hz, 1H), 7.99 (d, J=8.8 Hz, 2H), 7.87 (d, J=9.2 Hz, 1H), 7.45-7.37 (m, 5H), 7.09 (d, J=8.8 Hz, 2H), 6.99 (d, J=8.0 Hz, 2H), 5.12 (d, J=3.6 Hz, 1H), 4.91-4.89 (m, 1H), 4.53 (d, J=9.2 Hz, 1H), 4.43-4.42 (m, 1H), 4.28 (d, J=2.4 Hz, 1H), 3.90 (d, J=6.4 Hz, 2H), 3.62 (d, J=1.6 Hz, 2H), 2.83 (t, J=12.4 Hz, 2H), 2.45 (s, 3H), 2.14-2.13 (m, 1H), 2.13-2.12 (m, 1H), 2.11-1.78 (m, 2H), 1.77-1.69 (m, 3H), 1.37 (d, J=7.2 Hz, 3H), 1.26-1.21 (m, 2H), 0.95 (s, 9H). LC-MS: m/z 816.4 (M+H).

Example-7: (2S,4R)-1-((S)-2-(2-(4-(4-(6-(2-Fluorophenyl)pyridazin-4-yl)phenyl) piperazin-1-yl)acetamido)-3,3-dimethylbutanoyl)-4-hydroxy-N—((S)-1-(4-(4-methyl thiazol-5-yl)phenyl)ethyl) pyrrolidine-2-carboxamide (Compound 7)

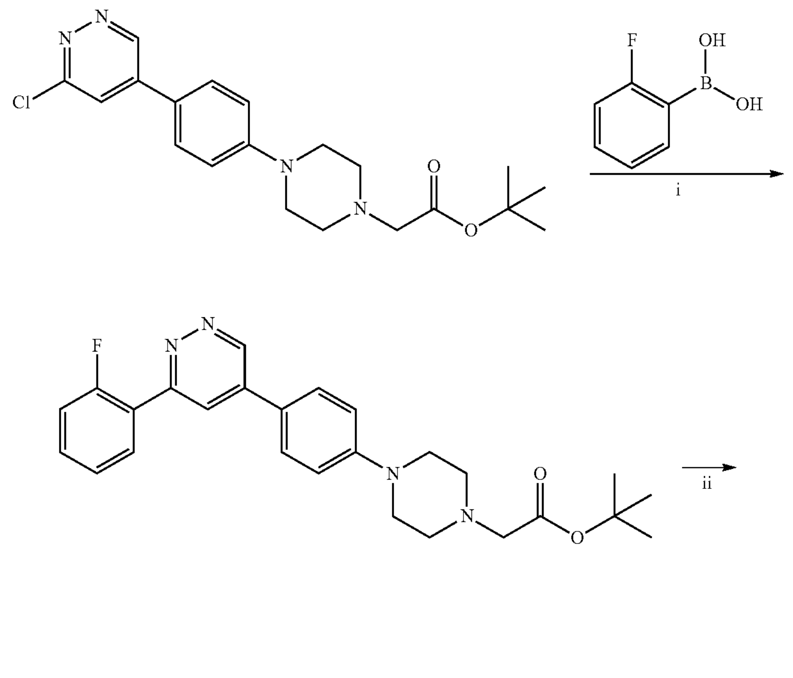

-continued

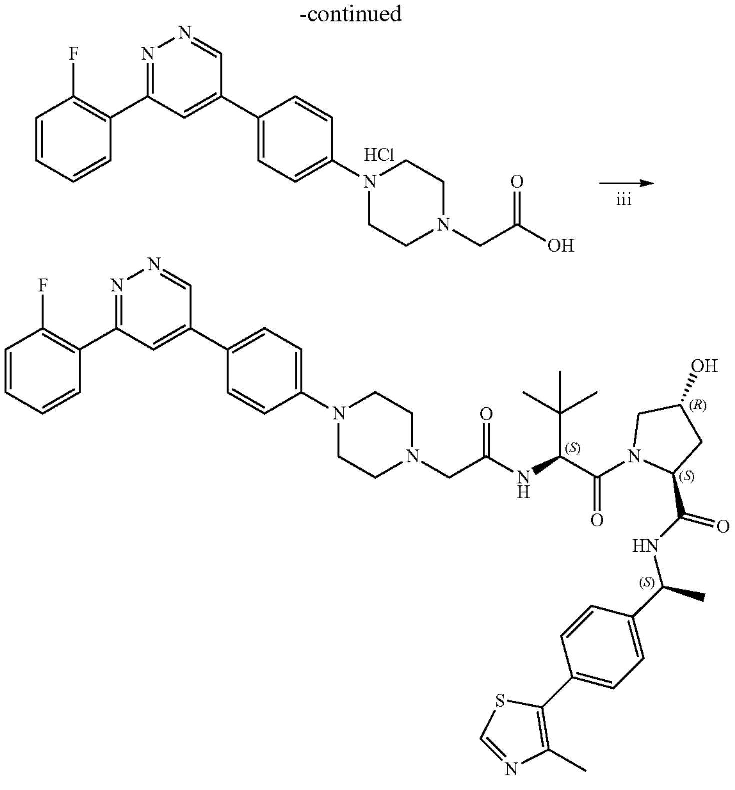

Compound 7

Step-i: Synthesis of Tert-butyl 2-(4-(4-(6-(2-fluorophenyl)pyridazin-4-yl)phenyl)piperazin-1-yl)acetate To a stirred solution of tert-butyl 2-(4-(6-chloropyridazin-4-yl)phenyl)piperazin-1-yl)acetate (0.25 g, 0.64 mmol), 2-fluorophenyl)boronic acid (0.13 g, 0.96 mmol) in 1,4-dioxane (10 mL) and water (1 mL) was added $K_2CO_3$ (0.35 g, 2.57 mmol) and degassed with nitrogen for 5 min. Pd(dppf)$Cl_2$·DCM (0.05 g, 0.064 mmol) was added and the reaction mixture was heated for 4 h at 130° C. in sealed tube. Once the reaction was completed (monitored by TLC), the reaction mixture was diluted with EtOAc. The combined organic layer was washed with water, brine solution, dried over anhydrous sodium sulphate and concentrated under vacuum to give the residue which was purified by combi-flash column chromatography using 50-60% ethyl acetate in hexane as eluent to afford the title compound as sticky material (0.22 g, 76%).

$^1$H NMR (400 MHz, DMSO-$d_6$): 9.39 (d, J=2.0 Hz, 1H), 8.18 (ddd, J=8.0 Hz, 1H), 8.05 (t, J=4.4 Hz, 1H), 7.67 (d, J=8.0 Hz, 2H), 7.47-7.46 (m, 1H), 7.36 (ddd, J=7.6 Hz, 1H), 7.23 (d, J=12.0 Hz, 1H), 7.03 (d, J=9.2 Hz, 2H), 3.38 (t, J=4.8 Hz, 4H), 3.20 (s, 2H), 2.76 (t, J=5.2 Hz, 4H), 1.48 (s, 9H). LC-MS: m/z 449.45 (M+H).

Step-ii: Synthesis of 2-(4-(4-(6-(2-Fluorophenyl) pyridazin-4-yl)phenyl)piperazin-1-yl)acetic acid hydrochloride To a stirred solution of tert-butyl 2-(4-(4-(6-(2-fluorophenyl)pyridazin-4-yl)phenyl)piperazin-1-yl)acetate (0.22 g, 0.48 mmol) in DCM (5 mL) was added 4 N dioxane hydrochloride (2 mL) at 0° C. and then slowly bring to RT and stirred at RT for 6 h. The reaction mixture was evaporated under reduced pressure, the resultant residue was washed with diethyl ether and dried under vacuum to afford the title compound as orange solid (0.2 g, 87%). LC-MS: m/z 393.1 (M+H).

Step-iii: Synthesis of (2S,4R)-1-((S)-2-(2-(4-(4-(6-(2-Fluorophenyl)pyridazin-4-yl)phenyl)piperazin-1-yl)acetamido)-3,3-dimethylbutanoyl)-4-hydroxy-N—((S)-1-(4-(4-methylthiazol-5-yl)phenyl)ethyl) pyrrolidine-2-carboxamide To a solution of 2-(4-(4-(6-(2-fluorophenyl)pyridazin-4-yl)phenyl)piperazin-1-yl)acetic acid hydrochloride (0.1 g, 0.24 mmol) and (2S,4R)-1-((S)-2-amino-3,3-dimethylbutanoyl)-4-hydroxy-N—((S)-1-(4-(4-methylthiazol-5-yl)phenyl)ethyl) pyrrolidine-2-carboxamide hydrochloride (0.115, 0.24 eq.) in DMF (3 mL) at 0° C. was added HATU (0.13 g, 0.36 mmol) followed by the dropwise addition of DIPEA (0.12 mL, 0.72 mmol) and the reaction mixture was stirred for 4 h at RT. Then the reaction mixture was poured into ice cold water and extracted with ethyl acetate. The combined organic layer was washed with water, brine solution, dried over anhydrous sodium sulphate and concentrated under vacuum to give the crude product which was purified by combiflash column chromatography using 5% methanol in DCM as eluent to afford the title compound as pale-yellow solid (0.07 g, 37%).

$^1$H NMR (400 MHz, DMSO-$d_6$): 9.61 (d, J=2.4 Hz, 1H), 8.96 (s, 1H), 8.44 (d, J=7.6 Hz, 1H), 8.18 (d, J=2.0 Hz, 1H), 7.96-7.95 (m, 2H), 7.90 (d, J=8.8 Hz, 1H), 7.77 (d, J=10.0 Hz, 1H), 7.59-7.57 (m, 1H), 7.44-7.34 (m, 6H), 7.12 (d, J=8.8 Hz, 2H), 5.13 (d, J=3.2 Hz, 1H), 4.87 (t, J=7.2 Hz,

1H), 4.53-4.43 (m, 2H), 4.27 (s, 1H), 3.58-3.55 (m, 2H), 3.14 (d, J=16.0 Hz, 1H), 3.01 (d, J=16.0 Hz, 1H), 2.66-2.64 (m, 4H), 2.45 (t, J=1.6 Hz, 4H), 2.07-2.02 (m, 1H), 1.77-1.75 (m, 1H), 1.46 (d, J=6.8 Hz, 1H), 1.35 (d, J=7.2 Hz, 3H), 1.20 (s, 2H), 0.94 (s, 9H). LC-MS: m/z 819.4 (M+H).

Example-8: (2S,4R)-4-Hydroxy-1-((S)-2-(3-(4-(4-(6-(2-hydroxyphenyl)pyridazin-4-yl)phenyl)piperazin-1-yl)propanamido)-3,3-dimethylbutanoyl)-N—((S)-1-(4-(4-methylthiazol-5-yl)phenyl)ethyl)pyrrolidine-2-carboxamide (Compound 8)

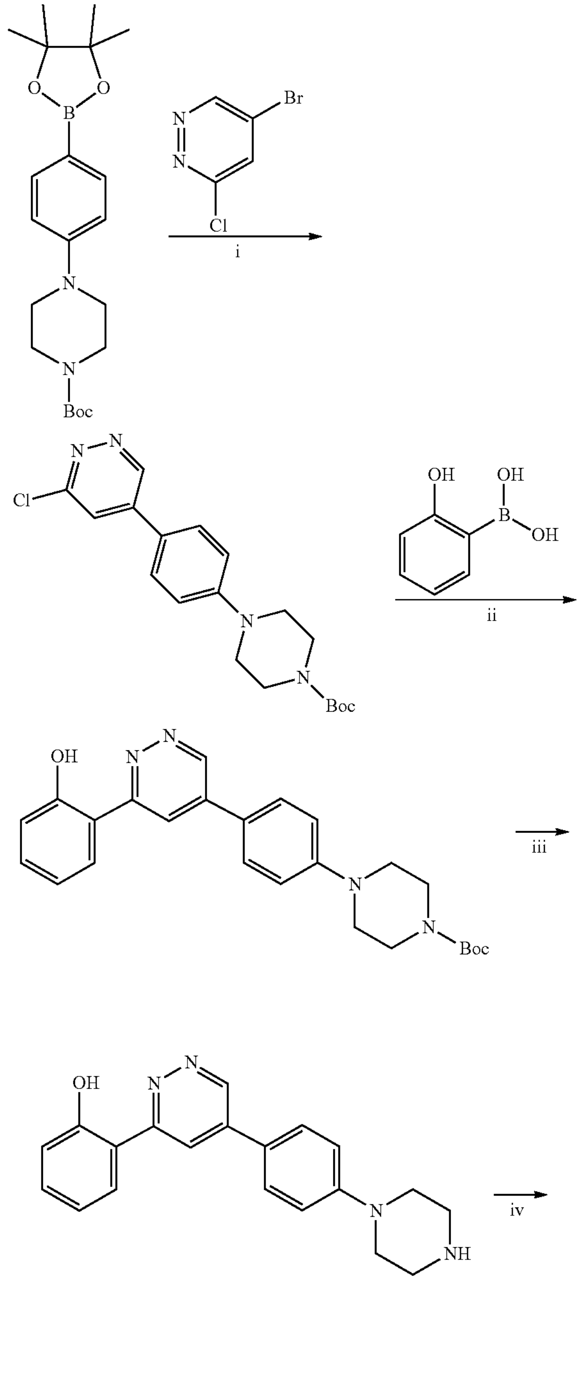

-continued

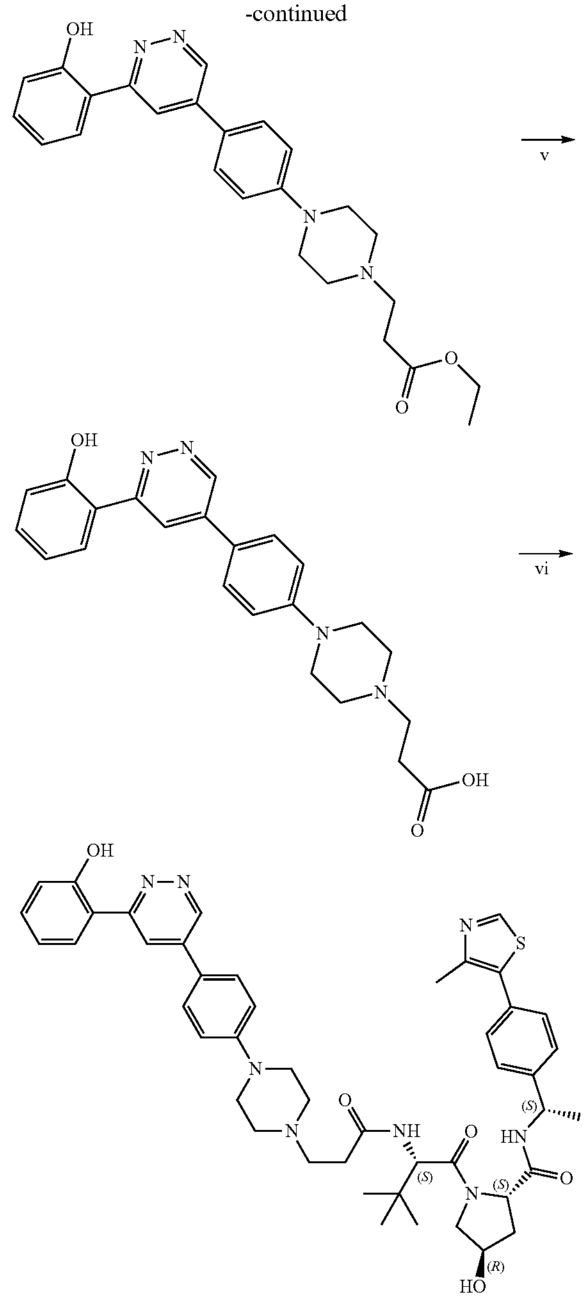

Compound 8

Step-i: Synthesis of Tert-butyl 4-(4-(6-chloropyridazin-4-yl)phenyl)piperazine-1-carboxylate To a stirred solution of 5-bromo-3-chloropyridazine (0.72 g, 3.8 mmol), tert-butyl 4-(4-(4,4,5,5-tetramethyl-1,3,2-dioxaborolan-2-yl)phenyl)piperazine-1-carboxylate (1 g, 2.57 mmol) in 1,4-dioxane (20 mL) and water (4 mL) was added $Na_2CO_3$ (0.82 g, 7.73 mmol) and degassed with nitrogen for 15 min. Pd(dppf)$Cl_2$·DCM (0.31 g, 0.38 mmol) was added and the reaction mixture was heated for 16 h at 130° C. in sealed tube. Once the reaction was completed (monitored by TLC), the reaction mixture was diluted with EtOAc. The combined organic layer was washed with water, brine solution, dried over anhydrous sodium sulphate and concentrated under vacuum to give the residue which was purified by combiflash column chromatography using 60% ethyl acetate in hexane as eluent to afford the title compound as pale-yellow solid (0.5 g, 72%).

$^1$H NMR (400 MHz, $CDCl_3$): δ 9.32 (d, J=1.6 Hz, 1H), 7.61 (d, J=8.8 Hz, 2H), 7.25 (s, 1H), 7.0 (d, J=8.8 Hz, 2H), 3.60 (m, 4H), 3.30 (m 4H), 1.49 (s, 9H); LC-MS: m/z 375.0 (M+H).

Step-ii: Synthesis of Tert-butyl 4-(4-(6-(2-hydroxyphenyl)pyridazin-4-yl)phenyl)piperazine-1-carboxylate To a stirred solution of tert-butyl 4-(4-(6-chloropyridazin-4-yl)phenyl)piperazine-1-carboxylate (0.5 g, 1.33 mmol), (2-hydroxyphenyl)boronic acid (0.22 g, 1.60 mmol) in 1,4-dioxane (10 mL) and water (2 mL) was added $Na_2CO_3$ (0.42 g, 4.01 mmol) and degassed with nitrogen for 5 min. Pd(dppf)$Cl_2$·DCM (0.11 g, 0.13 mmol) was added and the reaction mixture was heated for 6 h at 130° C. in sealed tube. Once the reaction was completed (monitored by TLC), the reaction mixture was diluted with EtOAc. The combined organic layer was washed with water, brine solution, dried over anhydrous sodium sulphate and concentrated under vacuum to give the residue which was purified by combiflash column chromatography using 50-60% ethyl acetate in hexane as eluent to afford the title compound as off-white solid (0.25 g, 43%).

$^1$H NMR (400 MHz, DMSO-$d_6$): δ 13.45 (s, 1H), 9.58 (d, J=2.4 Hz, 1H), 8.62 (d, J=2.0 Hz, 1H), 8.25 (d, J=8.4 Hz, 1H), 8.03 (d, J=9.2 Hz, 2H), 7.40 (m, 1H), 7.12 (d, J=8.8 Hz, 2H), 7.0 (t, J=8.4 Hz, 2H), 3.48 (m, 4H), 3.31 (m, 4H), 1.43 (s, 9H); LC-MS: m/z 433.10 (M+H).

Step-iii: Synthesis of 2-(5-(4-(Piperazin-1-yl)phenyl)pyridazin-3-yl)phenol

To a stirred solution of tert-butyl 4-(4-(6-(2-Hydroxyphenyl)pyridazin-4-yl)phenyl)piperazine-1-carboxylate (0.25 g, 0.66 mmol) in DCM (5 mL) was added 4 N dioxane hydrochloride (0.8 mL) at 0° C. and then slowly brought to RT and stirred at RT for 6 h. The reaction mixture was evaporated under reduced pressure, the resultant residue was washed with diethyl ether and dried under vacuum to afford the title compound as orange solid (0.21 g, 98%).

$^1$H NMR (400 MHz, DMSO-$d_6$): δ 9.78 (s, 1H), 9.60 (bs, 1H), 8.80 (s, 1H), 8.15 (d, J=8.8 Hz, 2H), 7.94 (d, 1H), 7.47 (t, J=15.2 Hz 1H), 7.18-7.45 (m, 3H), 7.05 (t, J=14.8 Hz 1H), 3.56 (bs, 4H), 3.20 (bs, 4H); LC-MS: m/z 333.0 (M+H).

Step-iv: Synthesis of Ethyl 3-(4-(4-(6-(2-Hydroxyphenyl)pyridazin-4-yl)phenyl)piperazin-1-yl)propanoate To a stirred solution of 2-(5-(4-(Piperazin-1-yl)phenyl)pyridazin-3-yl)phenol (0.2 g, 0.54 mmol) in DMF (40 mL) were added Ethyl 3-bromopropanoate (0.12 g, 0.65 mmol) and DIPEA (0.3 g, 1.63 mmol) at RT and stirred at RT for 16 h. Then the reaction mixture was quenched with cold water and extracted with EtOAc. The combined organic layer was washed with water, brine solution, dried over anhydrous sodium sulphate and concentrated under vacuum to give the residue which was purified by combiflash column chromatography using 3-5% methanol in DCM as eluent to afford the title compound as sticky solid (0.09 g, 38%). LC-MS: m/z 433.15 (M+H).

Step-v: Synthesis of 3-(4-(4-(6-(2-Hydroxyphenyl)pyridazin-4-yl)phenyl)piperazin-1-yl)propanoic acid To a stirred solution of compound ethyl 3-(4-(4-(6-(2-hydroxyphenyl)pyridazin-4-yl)phenyl)piperazin-1-yl)propanoate (0.09 g, 0.20 mmol) in methanol:THF:$H_2O$ (2 mL:4 mL:1 mL) mixture was added LiOH·$H_2O$ (0.02 g, 0.41 mmol) at 0° C. The reaction mixture was stirred for 16 h at RT. The reaction mixture was then evaporated under reduced pressure and the resultant residue was diluted with methanol and acidified to pH 6 using Amberlite© IT120 and filtered and filtrate was concentrated under vacuum to afford the title compound as a sticky solid (0.05 g, 59%). LC-MS: m/z 405.1 (M+H).

Step-vi: (2S,4R)-4-Hydroxy-1-((S)-2-(3-(4-(4-(6-(2-hydroxyphenyl)pyridazin-4-yl)phenyl)piperazin-1-yl)propanamido)-3,3-dimethylbutanoyl)-N—((S)-1-(4-(4-methylthiazol-5-yl)phenyl)ethyl)pyrrolidine-2-carboxamide To a solution of 3-(4-(4-(6-(2-Hydroxyphenyl)pyridazin-4-yl)phenyl)piperazin-1-yl)propanoic acid (0.05 g, 0.12 mmol) and (2S,4R)-1-((S)-2-amino-3,3-dimethylbutanoyl)-4-hydroxy-N—((S)-1-(4-(4-methylthiazol-5-yl)phenyl)ethyl) pyrrolidine-2-carboxamide hydrochloride (0.09 g, 0.18 eq.) in DMF (2 mL) at 0° C. was added HATU (0.14 g, 0.37 mmol) followed by the dropwise addition of DIPEA (0.07 mL, 0.37 mmol) and the reaction mixture was stirred for 3 h at RT. Then the reaction mixture was poured into ice cold water and extracted with ethyl acetate. The combined organic layer was washed with water, brine solution, dried over anhydrous sodium sulphate and concentrated under vacuum to get the crude product which was purified by combiflash column chromatography using 8-10% methanol in DCM as eluent to afford the title compound pale-yellow solid (0.015 g, 15%).

$^1$H NMR (400 MHz, DMSO-$d_6$): δ 13.51 (s, 1H), 9.57 (s, 1H), 8.96 (s, 1H), 8.61 (s, 1H), 8.42-8.36 (m, 2H), 8.24 (d, J=8.0 Hz, 1H), 8.01 (d, J=8.4 Hz, 2H), 7.42-7.34 (m, 5H), 7.12 (d, J=8.4 Hz, 2H), 7.01 (d, J=7.6 Hz, 2H), 5.12 (d, J=3.2 Hz 1H), 4.91-4.80 (m, 1H), 4.54 (d, J=9.6 Hz, 1H), 4.42 (t, 1H), 4.28 (bs, 1H), 3.64-3.48 (m, 4H), 2.3-2.7 (m, 9H), 2.08 (m, 2H), 1.78 (m, 1H), 1.45 (m, 1H), 1.34 (m, 4H); 1.23 (bs, 1H), 0.95 (s, 9H); LC-MS: m/z 831.40 (M+H).

Example-9: (2S,4R)-1-((S)-3,3-Dimethyl-2-(2-(4-(4-(6-(1-methyl-1H-pyrazol-4-yl) pyridazin-4-yl)phenyl)piperazin-1-yl)acetamido)butanoyl)-4-hydroxy-N—((S)-1-(4-(4-methylthiazol-5-yl)phenyl)ethyl) pyrrolidine-2-carboxamide (Compound 9)

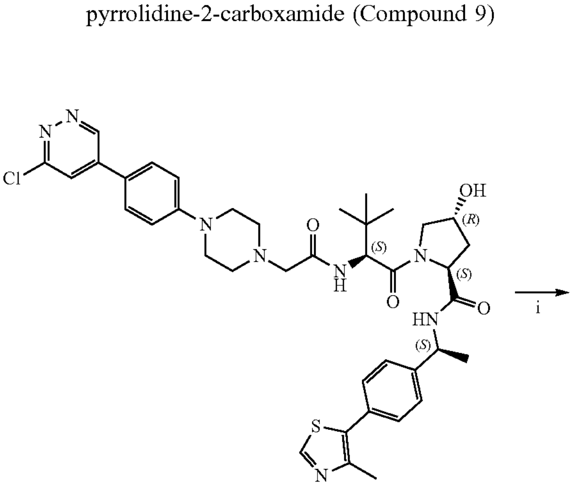

-continued

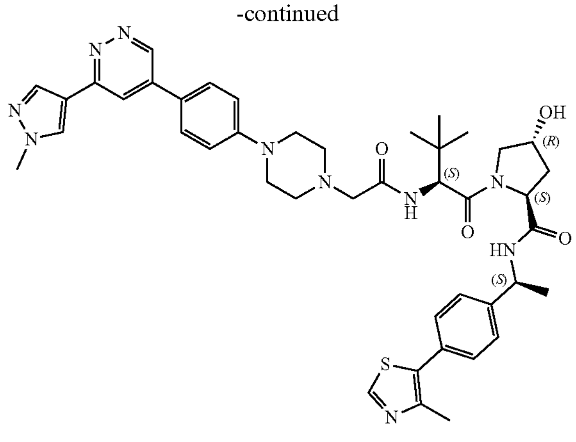

Compound 9

Step-i: Synthesis of (2S,4R)-1-((S)-3,3-Dimethyl-2-(2-(4-(4-(6-(1-methyl-1H-pyrazol-4-yl)pyridazin-4-yl)phenyl)piperazin-1-yl)acetamido)butanoyl)-4-hydroxy-N—((S)-1-(4-(4-methylthiazol-5-yl)phenyl)ethyl)pyrrolidine-2-carboxamide To a stirred solution of (2S,4R)-1-((S)-2-(2-(4-(4-(6-Chloropyridazin-4-yl)phenyl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide (0.3 g, 0.39 mmol), 1-Methyl-1H-pyrazol-4-yl-4-boronic acid (0.123 g, 0.58 mmol) in 1,4-dioxane (10 mL) and water (1 mL) was added $K_2CO_3$ (0.22 g, 1.59 mmol) and degassed with nitrogen for 5 min. Pd(dppf)$Cl_2$·DCM (0.03 g, 0.034 mmol) was added and the reaction mixture was heated for 6 h at 130° C. in sealed tube. Once the reaction was completed (monitored by TLC), the reaction mixture was diluted with EtOAc. The combined organic layer was washed with water, brine solution, dried over anhydrous sodium sulphate and concentrated under vacuum to give the residue which was purified by preparative HPLC to afford the title compound as pale yellow solid (6 mg, 2%)

$^1$H NMR (400 MHz, DMSO-$d_6$): 9.40 (s, 1H), 8.98 (s, 1H), 8.53 (s, 1H), 8.45 (d, J=7.2 Hz, 1H), 8.24 (s, 1H), 8.16 (d, J=2.0 Hz, 1H), 7.92 (d, J=8.0 Hz, 2H), 7.79-7.77 (m, 1H), 7.43 (d, J=8.0 Hz, 2H), 7.36 (d, J=8.0 Hz, 2H), 7.13 (d, J=8.8 Hz, 2H), 5.14 (d, J=2.8 Hz, 1H), 4.95-4.85 (m, 1H), 4.44-4.42 (m, 2H), 4.29-4.28 (m, 1H), 3.94 (bs, 3H), 3.59 (m, 2H), 3.14 (bs, 1H), 3.05 (bs, 1H), 2.67-2.66 (m, 5H), 2.45 (bs, 6H), 2.08-2.01 (m, 1H), 1.80-1.70 (m, 1H), 1.36 (d, J=6.8 Hz, 3H), 0.96 (s, 9H). LC-MS: m/z 805.4 (M+H).

The compounds listed in below Table-2 were prepared by procedure similar to the one described in Example-2 with appropriate variations in reactants, quantities of reagents, protections and deprotections, solvents and reaction conditions. The characterization data of the compounds are summarized herein the below table.

| Structure | Characterization Data |
| --- | --- |
| 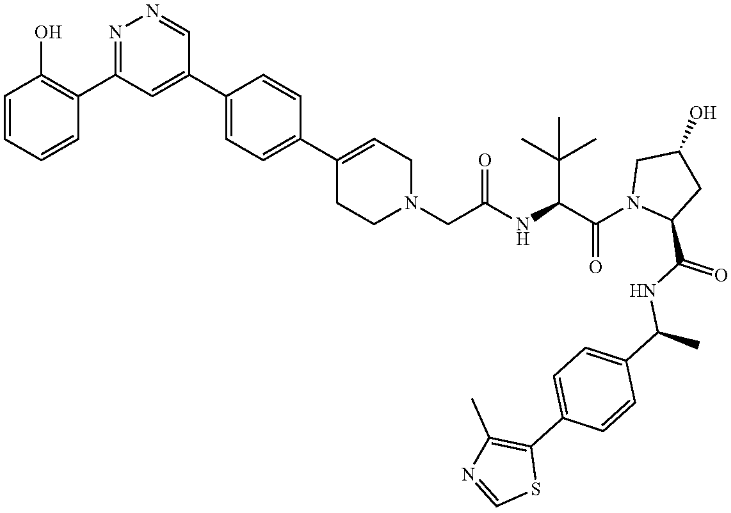<br>Compound 10 | 1H NMR (400 MHz, DMSO-d6): δ 13.12 (s, 1H), 9.60 (d, J = 2.0 Hz, 1H), 8.94 (s, 1H), 8.67 (d, J = 1.6 Hz, 1H), 8.40 (d, J = 4.0 Hz, 1H), 8.20 (d, J = 4.0 Hz, 1H), 8.06 (d, J = 8.0 Hz, 2H), 7.68 (d, J = 8 Hz, 2H), 7.66 (d, J = 8.0 Hz, 2H), 7.38-7.40 (m, 2H), 7.30-7.33 (m, 2H), 7.01-6.98 (m, 2H), 6.40 (bs, 1H), 5.20 (m, 1H), 4.85-4.82 (m, 1H), 4.55(m, 1H), 4.40-4.34 (m, 1H), 4.25-4.21 (m, 1H), 3.58-3.56 (m, 2H), 3.25-3.23 (m, 2H), 3.22-3.20 (m, 1H), 3.08-3.01 (m, 1H), 2.78-2.75 (m, 1H), 2.68-2.60 (m, 2H), 2.58-2.54 (m, 1H), 2.40 (S, 3H), 2.01 (S, 1H), 1.70-1.68 (m, 1H), 1.31 (d, J = 8 Hz, 3H), 0.92(s, 9H). LCMS: 814.25 (M + H). |

-continued
| Structure | Characterization Data |
|---|---|
| 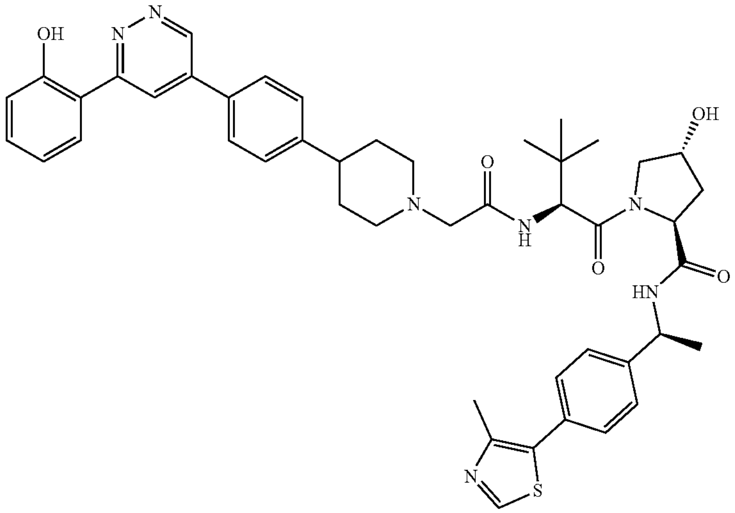 Compound 11 | 1H NMR (400 MHz, DMSO-d6): δ 13.10 (s, 1H), 9.56 (d, J = 2 Hz, 1H), 8.94 (s, 1H), 8.65 (d, J = 2.8 Hz, 1H), 8.52 (d, J = 6.0 Hz, 1H), 8.20 (d, J = 6.0 Hz, 1H), 7.99 (d, J = 7.6 Hz, 2H), 7.74 (d, J = 8.0 Hz, 2H), 7.47 (d, J = 8.0 Hz, 2H), 7.32-7.40 (m, 5H), 7.00 (d, J = 8.4 Hz, 2H), 5.11 (d, J = 2.0 Hz, 1H), 4.84-4.82 (m, 1H), 4.50 (d, J = 9.2 Hz, 1H), 4.41 (t, J = 8.0 Hz, 1H), 4.25 (bs, 1H), 3.55 (bs, 2H), 3.09-3.01 (m, 2H), 2.95-2.90 (m, 4H), 2.41 (s, 3H), 2.03-2.01 (m, 1H), 1.87-1.65 (m, 5H), 1.34 (d, J = 6.8 Hz, 3H), 0.92(s, 9H). LCMS; m/z 816.6 (M + H). |
| 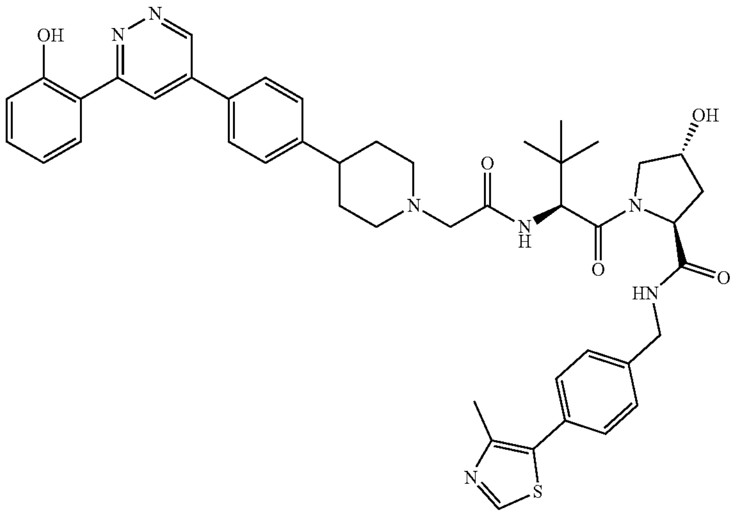 Compound 12 | 1H NMR (400 MHz, DMSO-d6): δ 13.08 (bs, 1H), 9.56 (d, J = 2.0 Hz, 1H), 8.90 (s, 1H), 8.66-8.60 (m, 2H), 8.22 (d, J = 8.0 Hz, 1H), 7.95 (d, J = 8.0 Hz, 2H), 7.84 (d, J = 8.0 Hz, 1H), 7.48 (d, J = 8.0 Hz, 2H), 7.43-7.37 (m, 5H), 7.04-7.00 (m, 2H), 5.16 (bs, 1H), 4.53 (d, J = 8.0 Hz, 1H), 4.46-4.24 (m, 4H), 3.69-3.60 (m, 2H), 3.48-3.40 (m, 2H), 3.13-3.09 (m, 1H), 3.00-2.99 (m, 3H), 2.65-2.62 (m, 1H), 2.39 (s, 3H), 2.35-2.24 (m, 2H), 2.08-2.03 (m, 1H), 2.03-1.98 (m, 3H), 1.77-1.70 (m, 2H), 0.96(s, 9H); LC-MS: m/z 802.6 (M + H) |

-continued
| Structure | Characterization Data |
|---|---|
| 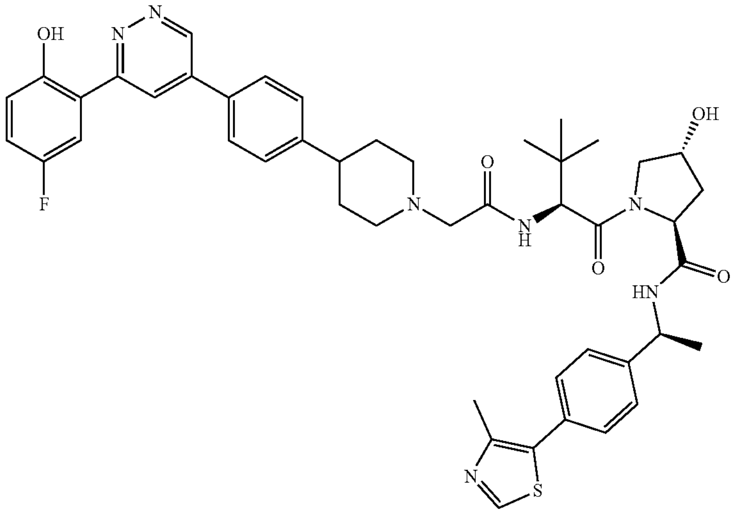 Compound 13 | 1H NMR (400 MHz, DMSO-d6): δ 12.95 (s, 1H), 9.63 (d, J = 2.0 Hz, 1H), 8.97 (s, 1H), 8.72 (d, J = 1.6 Hz, 1H), 8.45 (d, J = 7.6 Hz, 1H), 8.14-8.11 (m, 1H), 8.04 (d, J = 8.4 Hz, 2H), 7.80 (s, 1H), 7.51 (d, J = 8.0 Hz, 2H), 7.43 (d, J = 8.4 Hz, 2H), 7.36 (d, J = 8.0 Hz, 2H), 7.27 (d, J = 3.2 Hz, 1H), 7.06-7.02 (m, 1H), 5.12 (d, J = 6.3 Hz, 1H), 4.89 (s, 1H), 4.53 (d, J = 10.0 Hz, 1H), 4.44 (s, 1H), 4.28 (s, 1H), 3.59 (s, 2H), 2.96 (d, J = 14.8 Hz, 4H), 2.57 (s, 1H), 2.52-2.47 (m, 3H), 2.45 (s, 3H), 2.20-2.09 (m, 1H), 1.86-1.72 (m, 2H), 1.37 (s, 3H), 1.25-1.22 (m, 2H), 0.96 (s, 9H). LCMS: m/z 834.4 (M + H). |
| 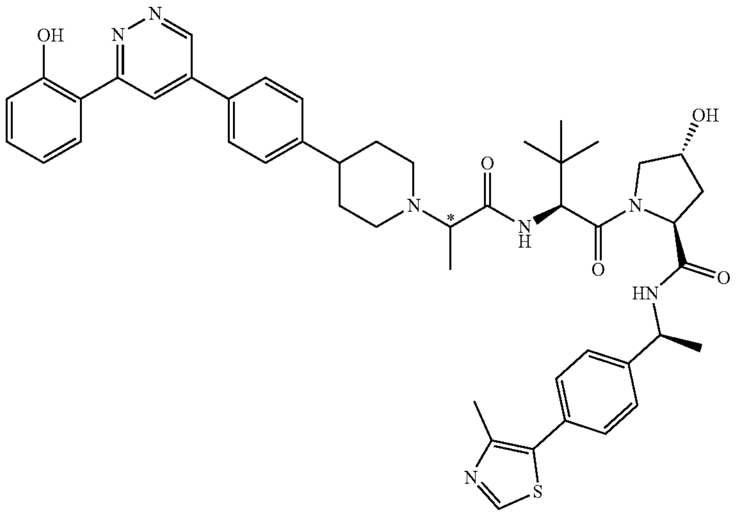 Compound 14, Racemic | 1H NMR (400 MHz, DMSO-d6): δ 13.12 (s, 1H), 9.59 (bs, 1H), 8.97 (bs, 1H), 8.68 (s, 1H), 8.42-8.40 (m, 1H), 8.22 (d, J = 8.0 Hz, 2H), 8.02 (d, J = 8.0 Hz, 2H), 7.89 (m, 1H), 7.49 (d, J = 8.0 Hz, 2H), 7.43-7.39 (m, 2H), 7.37-7.34 (m, 2H), 7.04-7.00 (m, 2H), 5.12 (bs, 1H), 4.89 (bs, 1H), 4.47-4.45 (m, 2H), 4.28 (bs, 1H), 3.60 (bs, 2H), 3.25-3.24 (m, 2H), 2.93 (bs, 2H), 2.80 (bs, 2H), 2.44 (s, 3H), 2.10-1.90 (m, 1H), 1.89-1.86 (m, 2H), 1.76-1.70 (m, 3H), 1.38-1.35 (m, 3H), 1.16-1.10 (m, 3H), 0.96 (s, 9H); LC-MS: m/z 831.6 |

-continued

| Structure | Characterization Data |
|---|---|
| 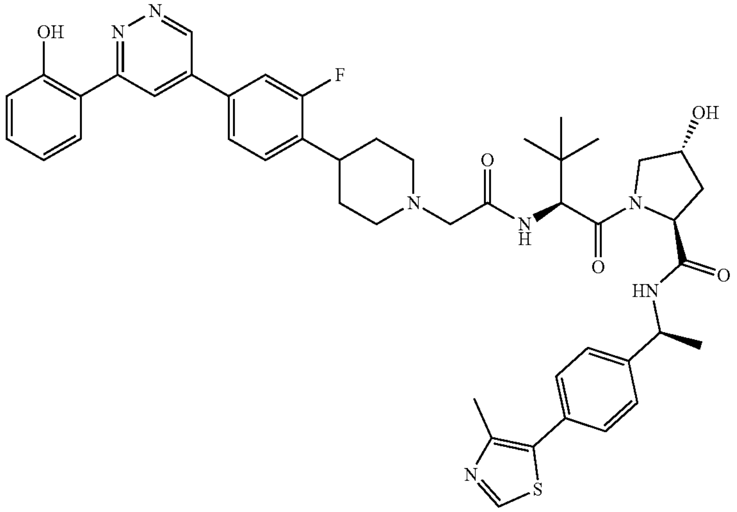 Compound 15 | 1H NMR (400 MHz, DMSO-d6): δ 13.09 (s, 1H), 9.64 (d, J = 2.4 Hz, 1H), 8.98 (s, 1H), 8.73 (d, J = 2.0 Hz, 1H), 8.46 (d, J = 7.6 Hz, 1H), 8.24 (d, J = 8.0 Hz, 1H), 8.00 (d, J = 11.6 Hz, 1H), 7.90 (s, 1H), 7.80 (s, 1H), 7.61 (s, 2H), 7.43 (d, J = 8.0 Hz, 2H), 7.36 (d, J = 8.0 Hz, 2H), 7.04 (d, J = 8.0 Hz, 2H), 5.14 (d, J = 3.6 Hz, 1H), 4.92 (s, 1H), 4.53 (d, J = 9.6 Hz, 1H), 4.48 (s, 1H), 4.32 (s, 1H), 3.59 (s, 2H), 3.11 (s, 1H), 2.97 (d, J = 1.6 Hz, 4H), 2.92 (s, 1H), 2.45 (s, 3H), 2.32 (s, 2H), 2.02 (s, 1H), 1.82-1.76 (m, 4H), 1.38 (d, J = 7.2 Hz, 3H), 0.96 (s, 9H). LCMS; m/z 835.4 (M + H). |
| 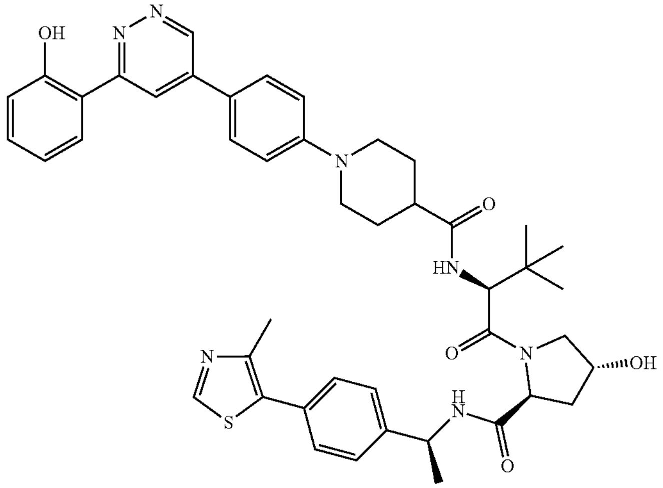 Compound 16 | 1H NMR (400 MHz, DMSO-d6): δ 13.09 (s, 1H), 9.51 (d, J = 2.0 Hz, 1H), 9.51 (d, J = 2.0 Hz, 1H), 8.95 (s, 1H), 8.61 (s, 1H), 8.36 (d, J = 7.6 Hz, 1H), 8.20 (d, J = 8.0 Hz, 1H), 7.95 (d, J = 8.8 Hz, 2H), 7.83 (d, J = 8.8 Hz, 1H), 7.41 (s, 2H), 7.37-7.22 (m, 3H), 7.07 (d, J = 8.4 Hz, 2H), 6.97-6.91 (m, 2H), 5.08 (s, 1H), 4.92-4.85 (m, 1H), 4.48 (d, J = 9.2 Hz, 1H), 4.43 (d, J = 8.4 Hz, 1H), 4.42 (s, 1H), 3.93 (d, J = 12.4 Hz, 2H), 3.60-3.41 (m, 1H), 2.83 (t, J = 12.0 Hz, 2H), 2.63-2.60 (m, 1H), 2.29 (s, 3H), 1.99 (d, J = 12.4 Hz, 1H), 1.78-1.72 (m, 2H), 1.65-1.52 (m, 3H), 1.34 (d, J = 8.2 Hz, 3H), 0.89 (s, 9H). LCMS 802.2 (M + H). |
| 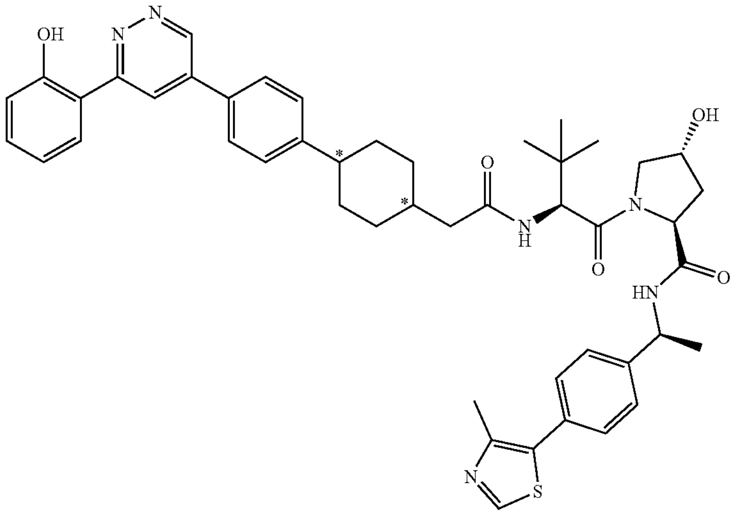 Compound 17, Racemic | 1H NMR (400 MHz, DMSO-d6): δ 13.18 (s, 1H), 9.60 (d, J = 7.2 Hz, 1H), 8.98 (s, 1H), 8.69 (s, 1H), 8.38 (d, J = 7.6 Hz, 1H), 8.23 (d, J = 8.0 Hz, 1H), 8.03-7.97 (m, 2H), 7.82 (d, J = 9.6 Hz, 1H), 7.54 (d, J = 8.4 Hz, 1H), 7.47-7.27 (m, 6H), 7.03 (d, J = 8.0 Hz, 2H), 5.10 (s, 1H), 4.93 (t, J = 7.2 Hz, 1H), 4.56 (t, J = 12.0 Hz, 1H), 4.44 (t, J = 8.4 Hz, 1H), 4.28 (s, 1H), 3.62 (s, 2H), 2.32 (s, 3H), 2.17 (s, 3H), 2.00 (s, 1H), 1.80 (d, J = 8.3 Hz, 4H), 1.57 (d, J = 8.0 Hz, 4H), 1.37 (d, J = 6.8 Hz, 3H), 1.27-1.23 (m, 2H), 0.95 (s, 9H). LCMS; m/z 815.6 (M + H). |

-continued
| Structure | Characterization Data |
| --- | --- |
| 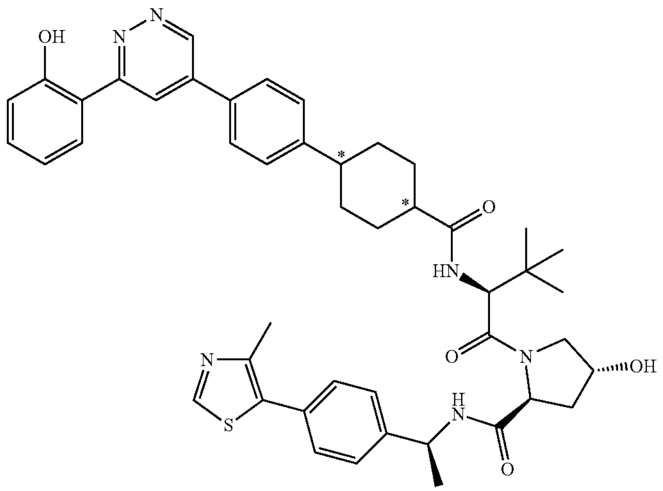 Compound 18, Racemic | 1H NMR (400 MHz, DMSO-d6): δ 13.32 (s, 2H), 9.58 (s, 1H), 8.98 (s, 1H), 8.69 (s, 1H), 8.40 (d, J = 8.0 Hz, 1H), 8.22 (d, J = 8.0 Hz, 1H), 8.00 (d, J = 7.6 Hz, 2H), 7.47-7.37 (m, 6H), 7.04-6.99 (m, 3H), 5.14 (s, 1H), 4.93-490 (m, 1H), 4.58 (d, J = 9.6 Hz, 1H), 4.45-4.41 (m, 3H), 4.29 (s, 2H), 3.62 (s, 2H), 2.67 (d, J = 8.4 Hz, 1H), 2.45 (s, 3H), 2.01 (d, J = 9.2 Hz, 2H), 1.88 (s, 2H), 1.82-1.79 (m, 2H), 1.67 (s, 2H), 1.58 (s, 1H), 1.54-1.50 (m, 1H), 1.37 (d, J = 7.2 Hz, 1H), 0.96 (s, 9H). LCMS: m/z 801.5 (M + H). |
| 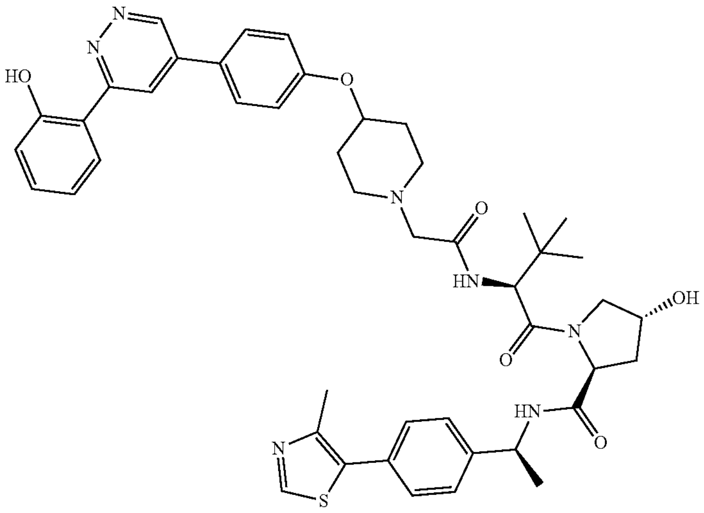 Compound 19 | 1H NMR (400 MHz, DMSO-d6): δ 13.31 (s, 1H), 9.59 (s, 1H), 8.98 (s, 1H), 8.65 (s, 1H), 8.45-8.32 (m, 2H), 8.32-8.15 (m, 1H), 8.06 (d, J = 7.6 Hz, 2H), 7.87-7.72 (m, 1H), 7.44-7.35 (m, 4H), 7.19 (d, J = 7.6 Hz, 2H), 7.02 (d, J = 7.6 Hz, 2H), 5.13 (s, 1H), 4.64 (s, 1H), 4.52 (s, 1H), 4.50 (s, 1H), 4.49 (s, 1H), 3.59 (d, J = 12.8 Hz, 2H), 3.13 (t, J = 6.8 Hz, 2H), 2.98 (s, 1H), 2.63 (s, 2H), 2.45 (s, 3H), 2.03 (s, 2H), 1.82 (s, 2H), 1.38 (d, J = 6.8 Hz, 2H), 1.27-1.24 (m, 3H), 1.16 (s, 2H), 0.94 (s, 9H). LCMS; m/z 832.3 (M + H). |

-continued

| Structure | Characterization Data |
| --- | --- |
| 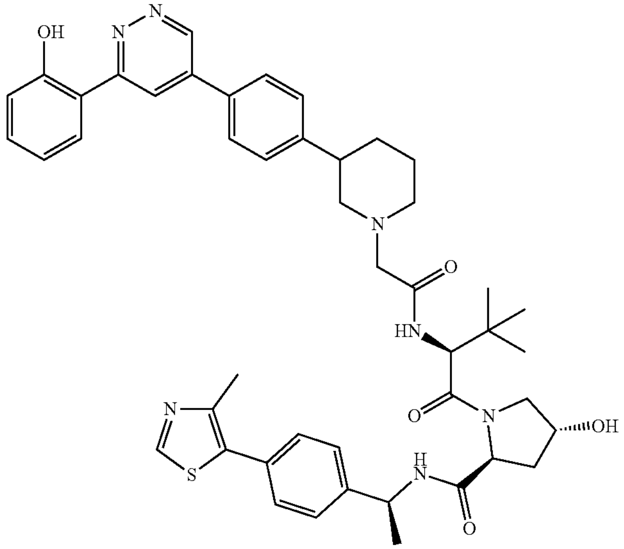<br>Compound 20 | 1H NMR (400 MHz, DMSO-d6): δ 9.53 (d, J = 6.4 Hz, 1H), 9.54 (s, 1H), 9.44 (s, 1H), 8.64 (s, 1H), 8.42 (d, J = 7.6 Hz, 1H), 8.15 (d, J = 8.0 Hz, 1H), 7.97-7.91 (m, 2H), 7.76 (d, J = 9.2 Hz, 1H), 7.50 (d, J = 7.6 Hz, 2H), 7.40 (s, 2H), 7.36-7.28 (m, 2H), 7.01 (s, 1H), 6.98-6.92 (m, 1H), 4.89-4.81 (m, 1H), 6.72 (d, J = 9.2 Hz, 1H), 4.42 (d, J = 8.0 Hz, 1H), 4.24 (s, 1H), 3.52 (d, J = 12.0 Hz, 2H), 3.48-3.40 (m, 2H), 3.06 (d, J = 16.0 Hz, 2H), 2.94-2.84 (m, 1H), 2.28 (s, 3H), 2.26-2.20 (m, 1H), 2.15-2.10 (m, 1H), 2.05-2.00 (m, 1H), 1.86 (d, J = 12.0 Hz, 1H), 1.79-1.70 (m, 3H), 1.60 (s, 2H), 1.34 (d, J = 8.0 Hz, 3H), 0.92 (s, 9H). LCMS 816.6 (M + H). |
| 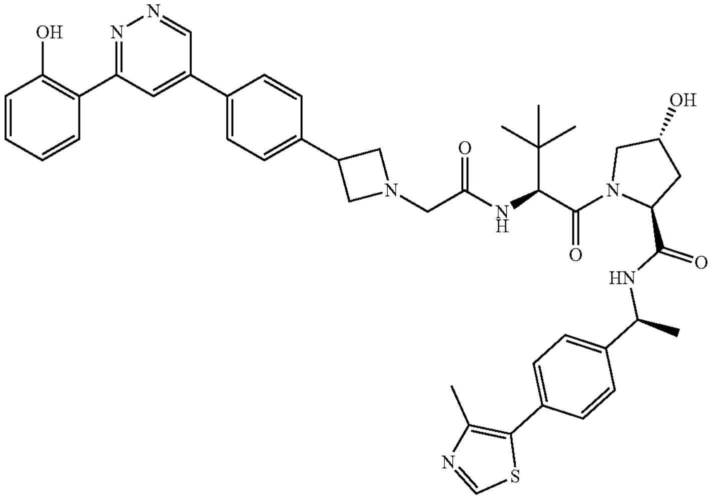<br>Compound 21 | 1H NMR (400 MHz, DMSO-d6): δ 13.18 (s, 1H), 9.65 (s, 1H), 9.02 (s, 1H), 8.75 (s, 1H), 8.50 (d, J = 8.0 Hz, 1H), 8.28 (d, J = 8.0 Hz, 1H), 8.10 (d, J = 8.4 Hz, 2H), 7.70 (d, J = 8.0 Hz, 1H), 7.65 (d, J = 8.0 Hz, 2H), 7.49-7.42 (m, 3H), 7.41-7.38 (m, 2H), 7.10-7.02 (m, 2H), 5.20 (d, J = 7.6 Hz, 1H), 5.00-4.95 (m, 1H), 4.60-4.55 (m, 1H), 4.49-4.45 (m, 1H), 4.32 (s, 1H), 3.90-3.80 (m, 3H), 3.65-3.60 (m, 2H), 3.40-3.30 (m, 2H), 3.25 (s, 1H), 2.49 (s, 3H), 2.12 (s, 2H), 1.41 (d, J = 7.2 Hz, 3H), 1.27 (s, 1H), 0,99 (s, 9H). |
| 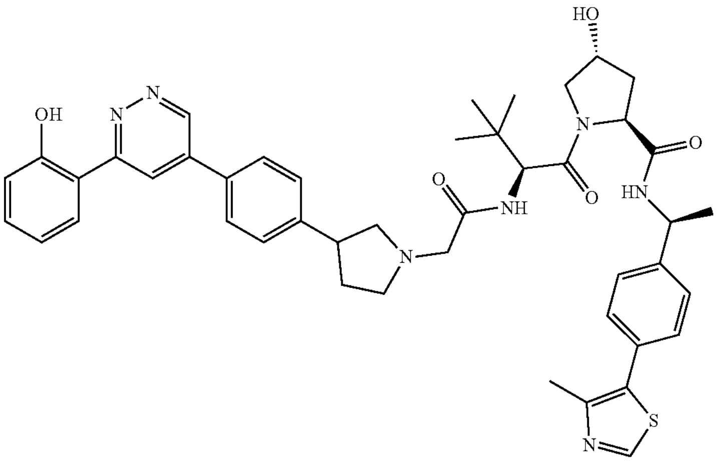<br>Compound 22 | 1H NMR (400 MHz, DMSO-d6): δ 13.15 (s, 1H), 9.64-9.61 (m, 1H), 9.02 (s, 1H), 8.73-8.71 (m, 1H), 8.52-8.45 (m, 1H), 8.25 (d, J = 7.2 Hz, 1H), 8.06-8.03 (m, 2H), 7.32-7.22 (m, 2H), 7.60 (d, J = 8.4 Hz, 2H), 7.48-7.43 (m, 2H), 7.40-7.37 (m, 2H), 7.08-7.04 (m, 2H), 5.17 (s, 1H), 4.94-4.93 (m, 1H), 4.59-4.56 (m, 1H), 4.48 (d, J = 6.4 Hz, 1H), 4.32 (s, 1H), 3.63 (s, 1H), 3.56-3.50 (m, 1H), 3.19-3.08 (m, 2H), 3.00-2.90 (m, 2H), 2.80-2.71 (m, 2H), 2.49 (s, 3H), 2.40-2.38 (m, '1H), 2.10-2.02 (m, 1H), 1.92-1.88 (m, 1H), 1.85-1.75 (m, 1H), 1.55-1.50 (m, 1H), 1.41-1.38 (m, 3H), 1.00-0.94 (m, 9H). LCMS m/z 802.6 (M + H). |

-continued

| Structure | Characterization Data |
| --- | --- |
| 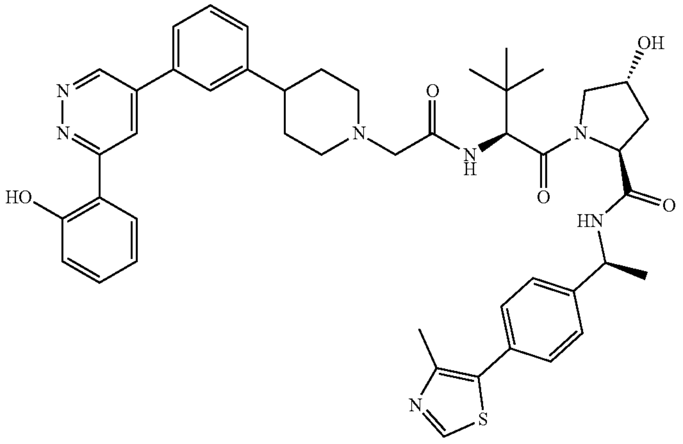<br>Compound 23 | 1H NMR (400 MHz, DMSO-d6): δ 13.51 (s, 1H), 9.56 (s, 1H), 8.96 (s, 1H), 8.79 (s, 1H), 8.20 (d, J = 6.8 Hz, 1H), 8.20 (d, J = 6.8 Hz, 1H), 7.92 (s, 1H), 7.85 (d, J = 6.8 Hz, 1H), 7.75 (d, J = 9.6 Hz, 1H), 7.54-7.50 (m, 2H), 7.48-7.42 (m, 2H), 7.40-7.33 (m, 3H), 6.97 (s, 2H), 4.88 (t, J = 6.8 Hz, 1H), 4.52 (d, J = 9.6 Hz, 1H), 4.45 (t, J = 8.4 Hz, 1H), 4.27 (s, 1H), 3.60-3.54 (m, 2H), 3.31 (s, 1H), 3.13-3.09 (m, 1H), 2.98-2.94 (m, 3H), 2.65 (s, 1H), 2.31 (s, 3H), 2.29-2.22 (m, 2H), 2.07-2.02 (m, 1H), 1.91-1.72 (m, 5H), 1.34 (d, J = 6.8 Hz, 3H), 0.94 (s, 9H). LCMS; m/z 817.3 (M + H). |

The compounds listed in below Table-3 were prepared by procedure similar to the one described in Example-B with appropriate variations in reactants, quantities of reagents, protections and deprotections, solvents and reaction conditions. The characterization data of the compounds are summarized herein the below table.

| Structure | Characterization Data |
| --- | --- |
| 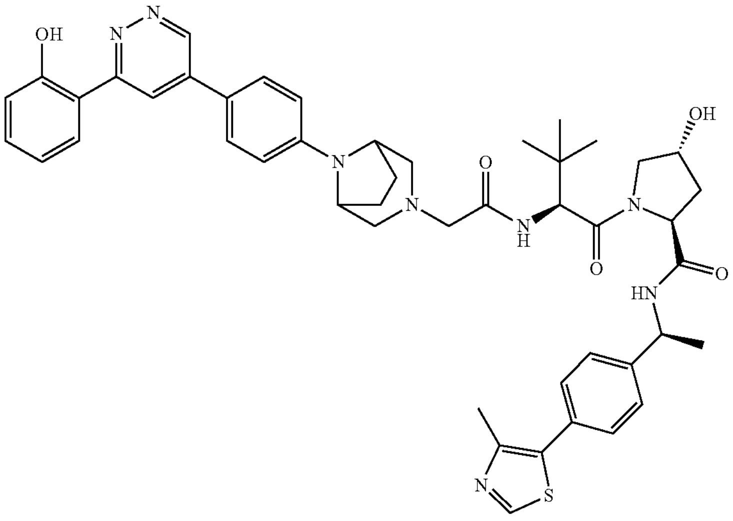<br>Compound 24 | 1H NMR (400 MHz, DMSO-d6): δ 13.45 (s, 1H), 9.57 (d, J = 1.6 Hz, 1H), 8.99 (s, 1H), 8.61 (s, 1H), 8.50 (d, J = 7.6 Hz, 1H), 8.26 (d, J = 7.6 Hz, 1H), 8.00 (d, J = 8.8 Hz, 2H), 7.82 (d, J = 9.2 Hz, 1H), 7.45-7.34 (m, 5H), 7.04-6.99 (m, 4H), 5.14 (d, J = 2.8 Hz, 1H), 4.91 (t, J = 6.8 Hz, 1H), 4.53-4.46 (m, 4H), 4.27 (s, 1H), 3.57 (m, 2H), 2.89 (bs, 2H), 2.67-2.51 (m, 4H), 2.46 (s, 3H), 2.18 (m, 1H), 2.11-1.95 (m, 4H), 1.75 (m, 1H), 1.44 (d, J = 6.8 Hz, 3H), 0.97 (s, 9H). LCMS: m/z 843.8 (M + H). |

-continued
| Structure | Characterization Data |
| --- | --- |
| 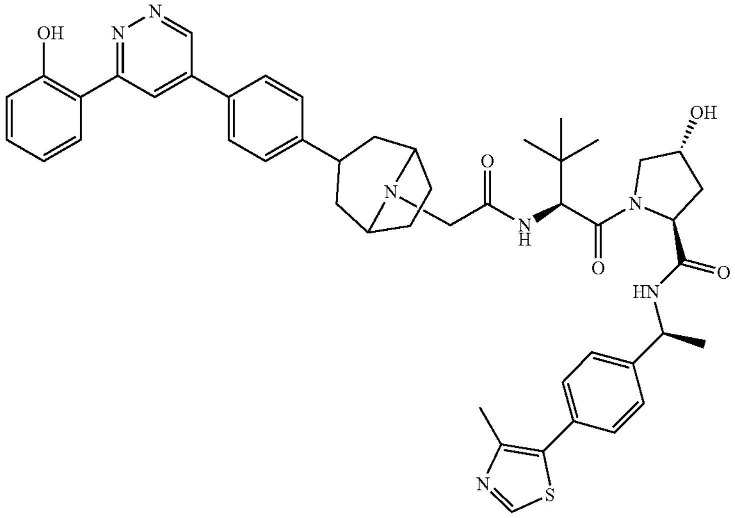<br>Compound 25 | 1H NMR (400 MHz, DMSO-d6): δ 13.13(bs, 1H), 9.58(bs, 1H), 8.96(bs, 1H), 8.67(s, 1H), 8.45(bs, 1H), 8.18-8.22(m, 2H), 7.98-8.03(m, 2H), 7.34-7.55(m, 7H), 7.02(d, J = 8 Hz, 2H), 5.13(bs, 1H), 8.89(bs, 1H), 4.45-4.53(m, 2H), 4.28(bs, 1H), 3.59(bs, 2H), 3.12-3.24(m, 2H), 3.00(bs, 1H), 2.91(bs, 1H), 2.38-2.43(m, 4H), 1.97-2.03(m, 1H), 1.85-1.96(m, 2H), 1.75-1.77(m, 2H), 1.46-1.49(m, 2H), 1.32-1.40(m, 2H), 1.22-1.25(m, 4H), 0.99(bs, 9H). LCMS: m/z 843.3 (M + H). |
| 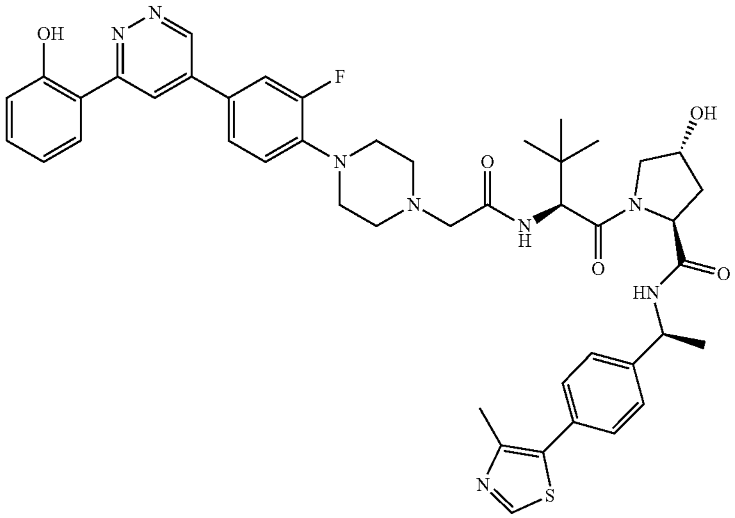<br>Compound 26 | 1H NMR (400 MHz, DMSO-d6): δ 13.32 (bs, 1H), 9.63 (d, J = 2 Hz, 1H), 8.98 (s, 1H), 8.69 (d, J = 2 Hz, 1H), 8.44 (d, J = 7.6 Hz, 1H), 8.26 (d, J = 7.2 Hz, 1H), 8.05 (d, J = 8.8 Hz, 1H), 7.93 (d, J = 8.8 Hz, 1H), 7.78 (d, J = 9.6 Hz, 1H), 7.35-7.44 (m, 5H), 7.25 (t, J = 8.8 Hz, 1H), 7.03 (d, J = 8 Hz, 2H), 5.13 (d, J = 2.8 Hz, 1H), 4.89 (t, J = 8.4 Hz, 1H), 4.53 (d, J = 10 Hz, 1H), 4.43 (t, J = 7.6 Hz, 1H), 4.29 (bs, 1H), 3.62 (m, 2H), 3.22 (m, 4H), 3.06-3.18 (m, 2H), 2.69 (m, 4H), 2.45 (s, 3H), 2.05 (m, 1H), 1.76 (m, 1H), 1.37 (d, J = 6.8 Hz, 3H), 0.96 (s, 9H). LCMS; m/z 835.4 (M + H). |

-continued
| Structure | Characterization Data |
|---|---|
| 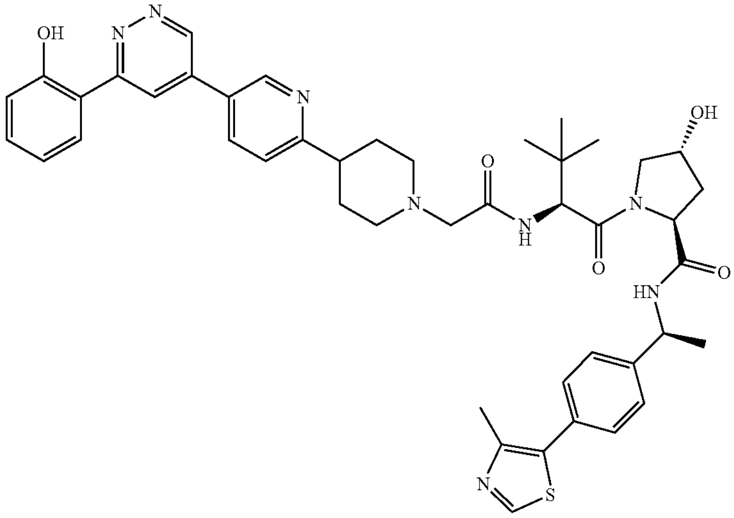 Compound 27 | 1H NMR (400 MHz, DMSO-d6): δ 13.07 (s, 1H), 9.66 (s, 1H), 9.20 (s, 1H), 8.98 (s, 1H), 8.78 (s, 1H), 8.47-8.41 (m, 2H), 8.22 (d, J = 8.0 Hz, 1H), 7.81 (d, J = 9.6 Hz, 1H), 7.56 (d, J = 7.6 Hz, 1H), 7.44-7.40 (m, 3H), 7.36 (d, J = 8.0 Hz, 2H), 7.04 (d, J = 8.0 Hz, 2H), 5.14 (d, J = 3.2 Hz, 1H), 4.89 (s, 1H), 4.53 (d, J = 9.6 Hz, 1H), 4.45 (s, 1H), 4.28 (s, 1H), 3.59 (s, 2H), 3.09 (s, 1H), 2.98 (s, 2H), 2.94 (s, 1H), 2.45 (s, 3H), 2.32 (s, 2H), 1.92 (s, 1H), 1.90 (s, 4H), 1.57 (s, 2H), 1.38 (d, J = 7.2 Hz, 3H), 0.96 (s, 9H). LCMS: m/z 818.3 (M + H). |
| 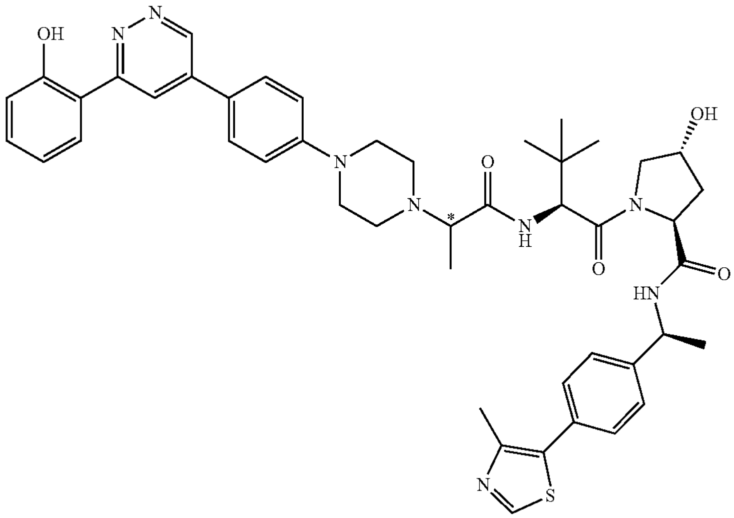 Compound 28, Racemic | 1H NMR (400 MHz, DMSO-d6): δ 13.51 (s, 1H), 9.58 (d, J = 1.6 Hz, 1H), 8.97 (s, 1H), 8.62 (s, 1H), 8.49-8.38 (m, 1H), 8.25 (d, J = 8.0 Hz, 1H), 8.02 (d, J = 8.4 Hz, 2H), 7.92-7.72 (m, 1H), 7.43-7.37 (m, 3H), 7.36-7.34 (m, 2H), 7.13 (d, J = 7.2 Hz, 2H), 7.01 (d, J = 8.0 Hz, 2H), 5.12 (s, 1H), 4.98-4.80 (m, 1H), 4.48-4.32 (m, 2H), 4.30-4.09 (m, 1H), 3.60 (s, 2H), 3.29 (s, 3H), 2.66-2.49 (m, 6H), 2.39 (s, 3H), 2.12-2.01 (m, 1H), 1.80-1.42 (m, 1H), 1.36 (d, J = 6.8 Hz, 3H), 1.61-1.12 (m, 3H), 0.93 (s, 9H). LCMS: m/z 831.6 (M + H). |

-continued
| Structure | Characterization Data |
| --- | --- |
| 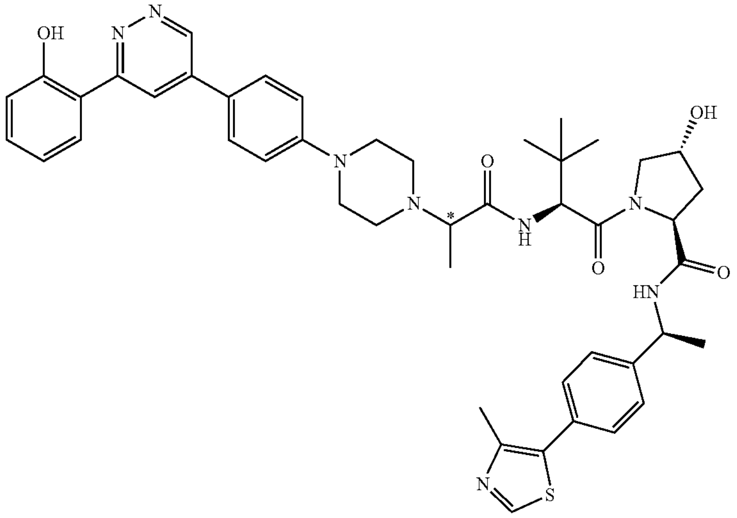 Compound 29, Isomer-1 | 1H NMR (400 MHz, DMSO-d6): δ 13.50 (s, 1H), 9.56 (d, J = 1.6 Hz, 1H), 9.56 (d, J = 1.6 Hz, 1H), 8.96 (s, 1H), 8.61 (d, J = 2.4 Hz, 1H), 8.41 (d, J = 7.6 Hz, 1H), 8.24 (d, J = 8.4 Hz, 1H), 8.11 (d, J = 8.8 Hz, 2H), 7.85 (d, J = 9.6 Hz, 1H), 7.42-7.38 (m, 2H), 7.35-7.25 (m, 2H), 7.13-7.11 (m, 2H), 7.01-6.97 (m, 2H), 5.10 (d, J = 3.2 Hz, 1H), 4.86 (t, J = 7.2 Hz, 1H), 4.47-4.43 (m, 2H), 4.27 (s, 1H), 3.59 (s, 2H), 3.34-3.26 (m, 3H), 2.69-2.59 (m, 4H), 2.49-2.31 (m, 3H), 2.06-2.01 (m, 2H), 1.78-1.74 (m, 2H), 1.35 (d, J = 7.2 Hz, 3H), 1.13 (d, J = 5.2 Hz, 3H), 0.94 (s, 9H). LCMS: m/z 831.6 (M + H). |
| 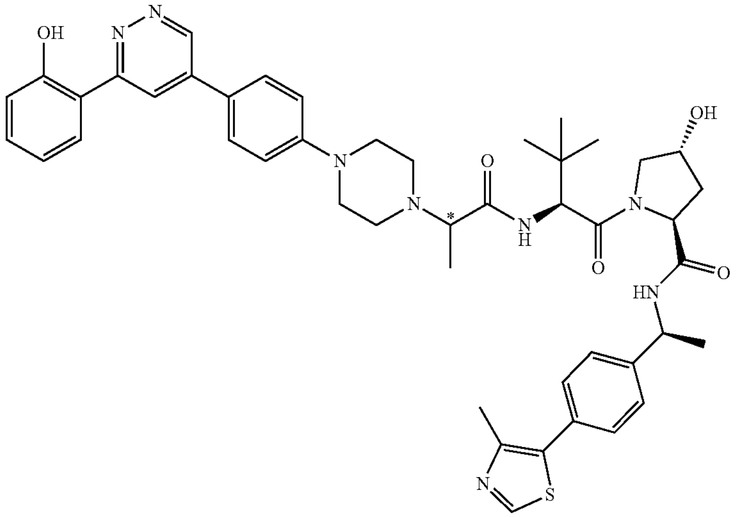 Compound 30, Isomer-2 | 1H NMR (400 MHz, DMSO-d6): δ 13.50 (s, 1H), 9.55 (d, J = 1.2 Hz, 1H), 8.96 (s, 1H), 8.63 (s, 1H), 8.41 (d, J = 8.0 Hz, 1H), 8.23 (d, J = 7.6 Hz, 1H), 8.00 (d, J = 8.8 Hz, 2H), 7.87 (d, J = 9.2 Hz, 1H), 7.45-7.40 (m, 3H), 7.37-7.33 (m, 2H), 7.12 (d, J = 8.8 Hz, 2H), 7.00-6.96 (m, 2H), 5.12 (s, 1H), 4.91-4.85 (m, 2H), 4.49-4.41 (m, 2H), 4.27 (s, 1H), 3.62-3.55 (m, 2H), 3.28 (s, 3H), 2.67-2.62 (m, 4H), 2.48-2.43 (m, 3H), 2.06-2.01 (m, 2H), 1.78-1.72 (m, 1H), 1.34 (d, J = 7.2 Hz, 3H), 1.14 (d, J = 6.8 Hz, 3H), 0.93 (s, 9H). LCMS: m/z 831.6 (M + H). |

-continued

| Structure | Characterization Data |
| --- | --- |
| 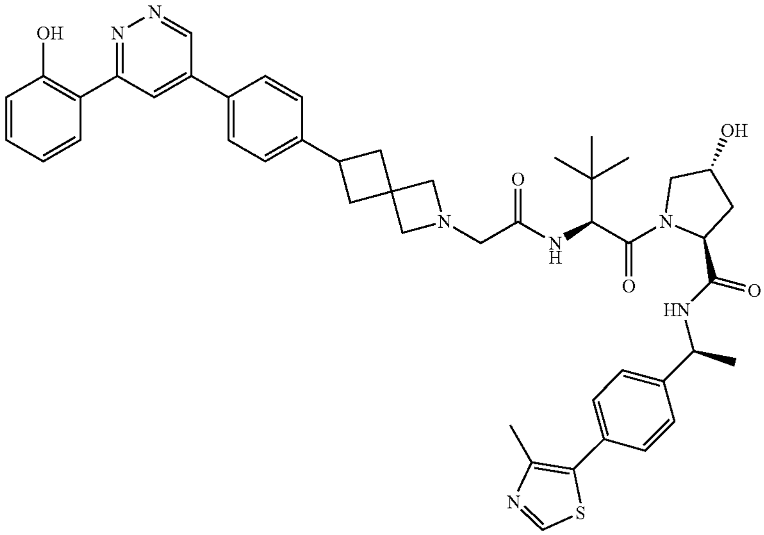 Compound 31 | 1H NMR (400 MHz, DMSO-d6): δ 13.18 (s, 1H), 9.63 (s, 1H), 9.02 (s, 1H), 8.71 (d, J = 2.0 Hz, 1H), 8.51 (d, J = 2.0 Hz, 1H), 8.25 (d, J = 2.0 Hz, 1H), 8.05 (d, J = 8.4 Hz, 2H), 7.60 (d, J = 8.0 Hz, 2H), 7.46-7.50 (m, 4H), 7.40 (d, J = 7.6 Hz, 2H), 7.07 (d, J = 8.4 Hz, 2H), 5.08 (d, J = 8.0 Hz, 1H), 5.00-4.90 (m, 1H), 4.58-4.55 (m, 1H), 4.52-4.48 (m, 1H), 4.30-4.28 (m, 1H), 3.68-3.60 (m, 2H), 3.58-3.45 (m, 3H), 3.35-3.25 (m, 2H), 3.21-3.10 (m, 2H), 2.54 (s, 1H), 2.49 (s, 3H), 2.38-2.28 (m, 2H), 2.15-2.05 (m, 1H), 1.85-1.75 (m, 2H), 1.41 (d, J = 7.2 Hz, 3H), 0.98 (s, 9H). LCMS m/z 828.6 (M + H). |
| 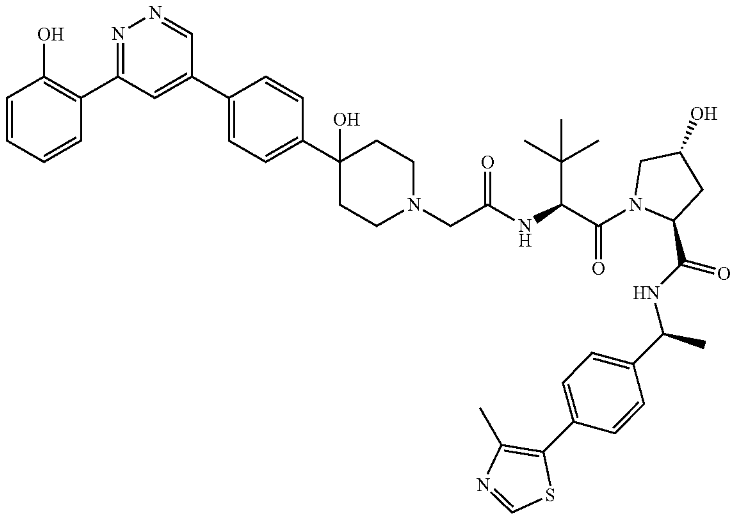 Compound 32 | 1H NMR (400 MHz, DMSO-d6): δ 13.16 (s, 1H), 9.65 (d, J = 2.0 Hz, 1H), 9.01 (s, 1H), 8.73 (d, J = 2.0 Hz, 1H), 8.48 (d, J = 2.0 Hz, 1H), 8.26 (d, J = 7.2 Hz, 1H), 8.09 (d, J = 8.4 Hz, 2H), 7.88 (d, J = 8.0 Hz, 1H), 7.76 (d, J = 8.0 Hz, 3H), 7.47 (d, J = 8.0 Hz, 2H), 7.40 (d, J = 8.0 Hz, 2H), 7.07 (d, J = 8.0 Hz, 2H), 5.17 (d, J = 4.0 Hz, 1H), 5.15 (s, 1H), 4.95 (s, 1H), 4.58 (d, J = 4.0 Hz, 1H), 4.48 (t, J = 8.0 Hz, 1H), 4.32 (bs, 1H), 3.63 (bs, 2H), 3.42-3.40 (m, 1H), 3.15 (d, J = 8.0 Hz, 1H), 3.05 (d, J = 8.0 Hz, 1H), 2.73-2.71 (m, 3H), 2.48 (s, 3H), 2.10 (s, 3H), 1.75 (s, 3H), 1.41 (d, J = 4.0 Hz, 3H), 0.98 (s, 9H). LCMS 832.6 (M + H). |
| 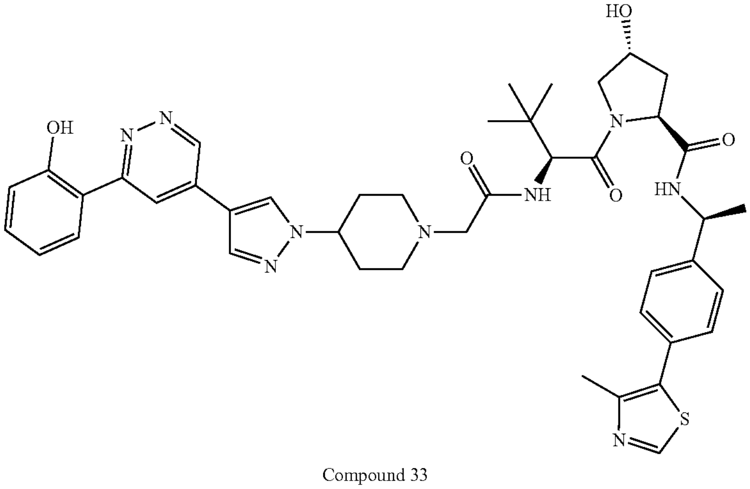 [SMILES: Cc1ncsc1-c1ccc([C@H](C)NC(=O)[C@@H]2C[C@@H](O)CN2C(=O)[C@@H](NC(=O)CN2CCC(n3cc(-c4cnnc(-c5ccccc5O)c4)cn3)CC2)C(C)(C)C)cc1] Compound 33 | 1H NMR (400 MHz, CD3OD): δ 9.36 (s, 1H), 8.86 (s, 1H), 8.66 (s, 1H), 8.52 (s, 1H), 8.28 (s, 1H), 8.06 (d, J = 7.2 Hz, 1H), 7.45-7.32 (m, 5H), 7.00 (d, J = 7.6 Hz, 2H), 5.00 (s, 1H), 4.66 (s, 1H), 4.61-4.56 (m, 2H), 4.47 (s, 1H), 4.42-4.38 (m, 1H), 4.87 (d, J = 11.2 Hz, 1H), 3.75 (d, J = 10.0 Hz, 1H), 3.64 (s, 1H), 3.54 (d, J = 10.4 Hz, 1H), 3.15 (s, 1H), 3.09-3.01 (m, 2H), 2.45 (s, 3H), 2.22 (s, 4H), 2.10-1.90 (m, 1H), 1.58 (d, J = 5.2 Hz, 1H), 1.50 (d, J = 5.6 Hz, 3H), 1.07 (s, 9H). |

Example-10: (2S4R)-4-Hydroxy-1(S)-2-(5-(4-(6-(2-hydroxyphenyl)pyridazin-4-yl)phenoxy)pentanamido)-3,3-dimethylbutanoyl)-N—((S)-1-(4-(4-methylthiazol-5-yl)phenyl)ethyl)pyrrolidine-2-carboxamide (Compound 34)

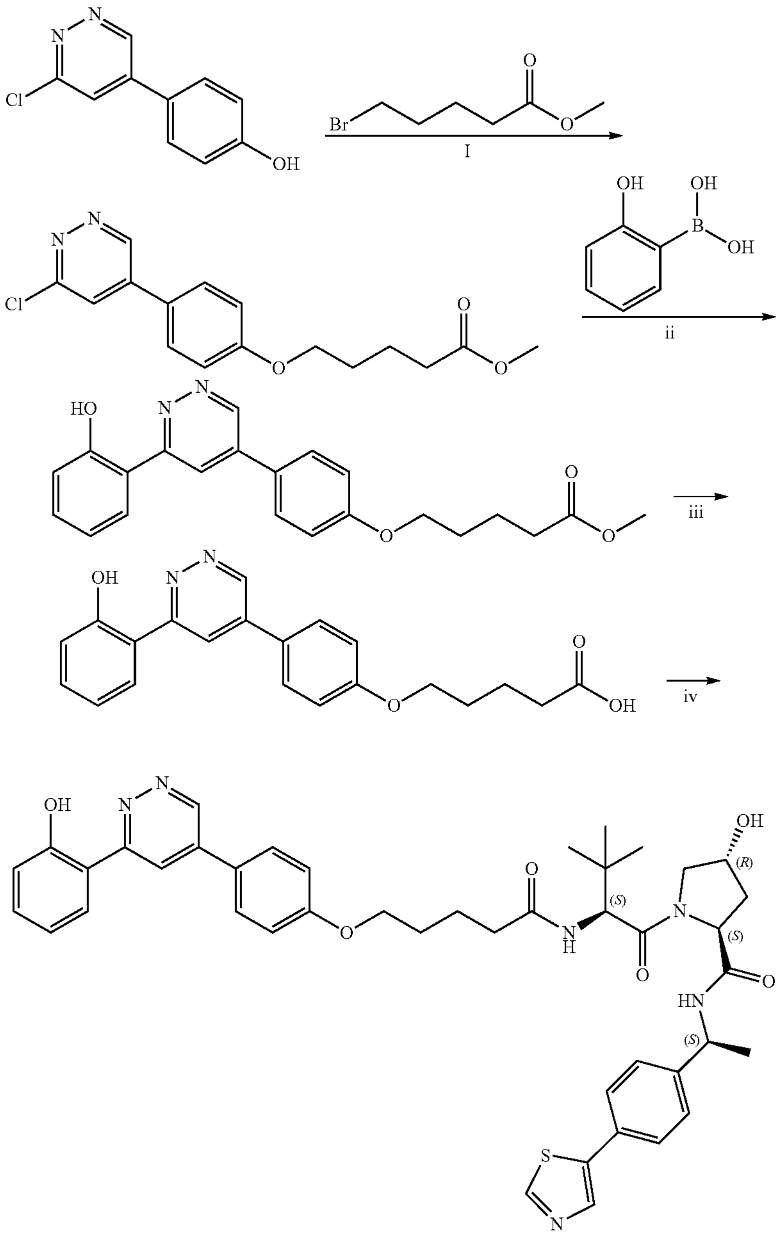

Compound 34

Step-i: Synthesis of Methyl 5-(4-(6-chloropyridazin-4-yl)phenoxy)pentanoate

To a stirred solution of compound 4-(6-chloropyridazin-4-yl)phenol (0.5 g, 2.42 mmol) in acetone (10 mL) were added methyl 5-Bromopentanoate (0.52 mL, 3.64 mmol), $K_2CO_3$ (1 g, 7.28 mmol) and sodium iodide (0.05 g, 0.24 mmol) at RT and the reaction mixture was heated at 90° C. temp in a sealed for 16 h. Once the reaction was completed (monitored by TLC), the reaction mixture was concentrated and then diluted with EtOAc. The combined organic layer was washed with water, brine solution, dried over anhydrous sodium sulphate and concentrated under vacuum to give the residue which was purified by preparative HPLC to afford the title compound as pale-yellow solid (0.5 g, 64%).

$^1$H NMR (400 MHz, $CDCl_3$): δ 9.65 (d, J=2 Hz, 1H), 8.21 (d, J=2 Hz, 1H), 7.98 (d, J=8.8 Hz, 2H), 7.10 (d, J=8.8 Hz, 2H), 4.07 (t, J=6 Hz, 2H), 3.58 (s, 3H), 2.39 (t, J=6.8 Hz, 2H), 1.66-1.77 (m, 4H); LC-MS: m/z 320.9 (M+H).

Step-ii: Synthesis of methyl 5-(4-(6-(2-hydroxyphenyl)pyridazin-4-yl)phenoxy)pentanoate To a stirred solution of methyl 5-(4-(6-chloropyridazin-4-yl)phenoxy)pentanoate (0.5 g, 1.56 mmol), (2-Hydroxyphenyl)boronic acid (0.43 g, 3.12 mmol) in 1,4-dioxane (10 mL) and water (3 mL) was added $Na_2CO_3$ (0.50 g, 4.68 mmol) and degassed with nitrogen for 5 min. Pd(dppf) $Cl_2$·DCM (0.13 g, 0.15 mmol) was added and the reaction mixture was heated for 6 h at 130° C. in sealed tube. Once the reaction was completed (monitored by TLC), the reaction mixture was diluted with EtOAc. The combined organic layer was washed with water, brine solution, dried over anhydrous sodium sulphate and concentrated under vacuum to give the residue which was purified by combiflash column chromatography using 50-60% ethyl acetate in hexane as eluent to afford the title compound as off-white solid (0.19 g, 32%).

$^1$H NMR (400 MHz, $CDCl_3$): δ 13.18 (bs, 1H), 9.29 (d, J=2.4 Hz, 1H), 8.16 (d, J=2 Hz, 1H), 7.83 (dd, J=8, 1.2 Hz, 1H), 7.70 (d, J=8.8 Hz, 2H), 7.38 (t, J=7.2 Hz, 1H), 7.14 (dd, J=8.4, 0.8 Hz, 1H), 7.07 (d, J=8.8 Hz, 2H), 6.99 (t, J=8.4 Hz, 1H), 4.07 (t, J=5.6 Hz, 2H), 3.69 (s, 3H), 2.43 (t, J=6.8 Hz, 2H), 1.85-1.88 (m, 4H); LC-MS: m/z 379.05 (M+H).

Step-iii: Synthesis of 5-(4-(6-(2-Hydroxyphenyl)pyridazin-4-yl)phenoxy)pentanoic acid To a stirred solution of compound methyl 5-(4-(6-(2-hydroxyphenyl)pyridazin-4-yl)phenoxy)pentanoate (0.19 g, 0.50 mmol) in methanol:THF:$H_2O$ (3 mL:4 mL:3 mL) mixture was added LiOH·$H_2O$ (0.03 g, 1.51 mmol) at 0° C. The reaction mixture was stirred for 16 h at RT. The reaction mixture was then evaporated under reduced pressure and the resultant residue was diluted with methanol and acidified to pH 6 using Amberlite© IT120 and filtered and filtrate was concentrated under vacuum to afford the title compound as a sticky solid (0.17 g, 92.8%). LC-MS: m/z 365.0 (M+H).

Step-iv: Synthesis of (2S,4R)-4-Hydroxy-1-((S)-2-(5-(4-(6-(2-hydroxyphenyl)pyridazin-4-yl)phenoxy)pentanamido)-3,3-dimethylbutanoyl)-N—((S)-1-(4-(4-methylthiazol-5-yl)phenyl)ethyl)pyrrolidine-2-carboxamide To a solution of 5-(4-(6-(2-Hydroxyphenyl)pyridazin-4-yl)phenoxy)pentanoic acid (0.17 g, 0.467 mmol) and (2S, 4R)-1-((S)-2-amino-3,3-dimethylbutanoyl)-4-hydroxy-N—((S)-1-(4-(4-methylthiazol-5-yl)phenyl)ethyl) pyrrolidine-2-carboxamide hydrochloride (0.27 g, 0.56 eq.) in DMF (3 mL) at 0° C. was added HATU (0.27 g, 0.70 mmol) followed by the dropwise addition of DIPEA (0.25 mL, 1.4 mmol) and the reaction mixture was stirred for 3 h at RT. Then the reaction mixture was poured into ice cold water and extracted with ethyl acetate. The combined organic layer was washed with water, brine solution, dried over anhydrous sodium sulphate and concentrated under vacuum to get the crude product which was purified by combiflash column chromatography using 8-10% methanol in DCM as eluent to afford the title compound pale-yellow solid (0.09 g, 24%).

$^1$H NMR (400 MHz, DMSO-$d_6$): δ 13.33 (s, 1H), 9.60 (d, J=1.6 Hz, 1H), 8.98 (s, 1H), 8.66 (d, J=2 Hz, 1H), 8.38 (d, J=8 Hz, 1H), 8.25 (d, J=7.6 Hz, 1H), 8.08 (d, J=8.8 Hz, 2H), 7.87 (d, J=9.2 Hz, 1H), 7.36-7.44 (m, 5H), 7.15 (d, J=9.2 Hz, 2H), 7.02 (d, J=8 Hz, 2H), 5.11 (d, J=3.6 Hz, 1H), 4.90 (t, J=7.2 Hz, 1H), 4.54 (d, J=8.8 Hz, 1H), 4.43 (t, J=7.2 Hz, 1H), 4.28 (bs, 1H), 4.09 (d, J=6 Hz, 2H), 3.61 (bs, 2H), 2.45 (s, 3H), 2.23 (m, 1H), 2.17-2.23 (m, 1H), 1.97-2.07 (m, 1H), 1.62-1.83 (m, 5H), 1.47 (d, J=7.2 Hz, 3H), 0.95 (s, 9H); LC-MS: m/z 791.35 (M+H).

Example-11: (2S,4R)-4-Hydroxy-1-((S)-2-(4-(4-(6-(2-hydroxyphenyl)pyridazin-4-yl) phenoxy)butanamido)-3,3-dimethylbutanoyl)-N—((S)-1-(4-(4-methylthiazol-5-yl)phenyl) ethyl)pyrrolidine-2-carboxamide (Compound 35)

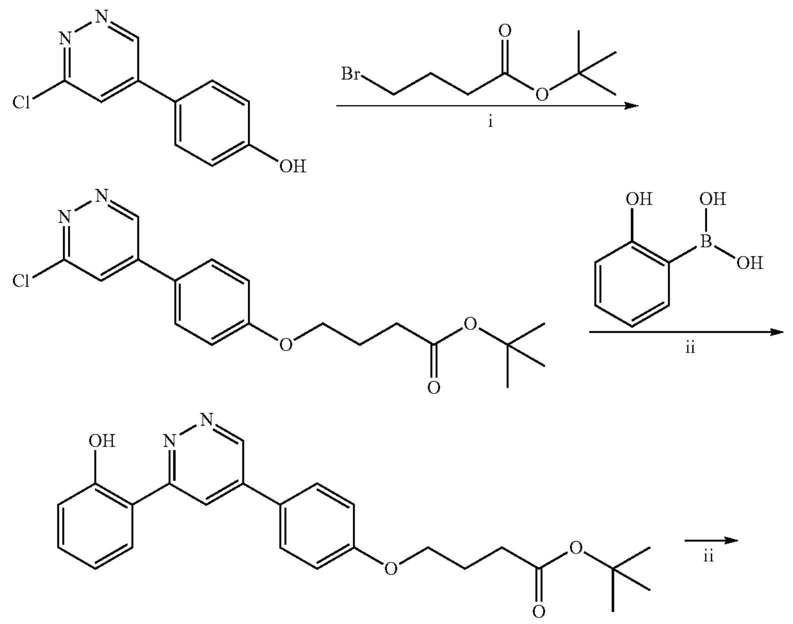

-continued

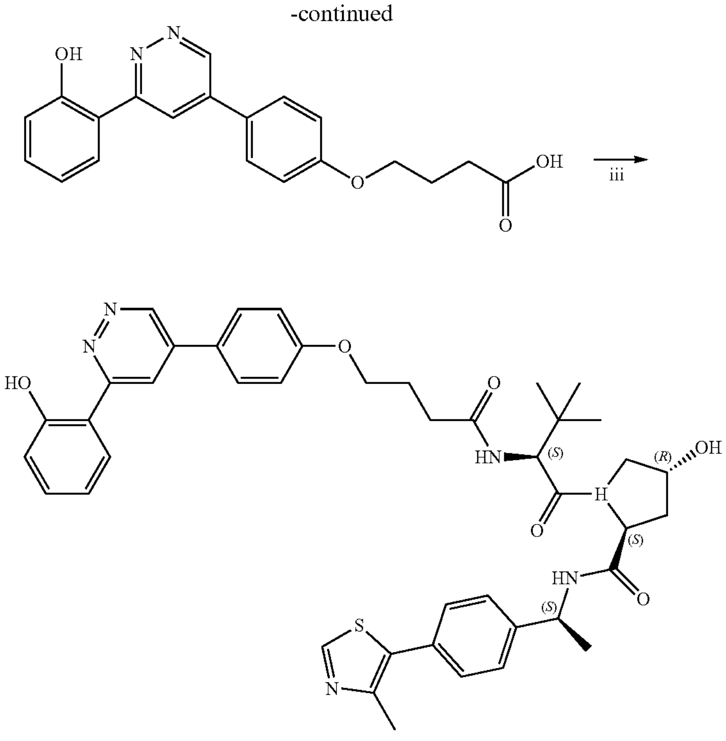

Compound 35

The Compound 35 was prepared by procedure similar to the one described in Example-10 with appropriate variations in reactants, quantities of reagents, protections and deprotections, solvents and reaction conditions.

$^1$H NMR (400 MHz, DMSO-$d_6$): δ 13.35 (s, 1H), 9.60 (s, 1H), 8.98 (s, 1H), 8.67 (s, 1H), 8.39 (d, J=8 Hz, 1H), 8.25 (d, J=8 Hz, 1H), 8.08 (d, J=8 Hz, 2H), 7.96 (d, J=8 Hz, 1H), 7.36-7.44 (m, 5H), 7.14 (d, J=12 Hz, 2H), 7.02 (d, J=8 Hz, 2H), 5.13 (s, 1H), 4.89-4.93 (m, 1H), 4.54 (d, J=8.8 Hz, 1H), 4.41-4.45 (m, 1H), 4.28 (bs, 1H), 4.08 (bs, 2H), 3.62 (s, 2H), 2.45 (s, 3H), 2.38-2.42 (m, 2H), 2.04-1.97 (m, 3H), 1.87-1.79 (m, 1H), 1.45 (d, J=8 Hz, 3H), 0.94 (s, 9H); LC-MS: m/z 776.8 (M+H).

Example-12: (2S,4R)-4-Hydroxy-1-((S)-2-(5-((4-(6-(2-hydroxyphenyl)pyridazin-4-yl) phenyl)amino) pentanamido)-3,3-dimethylbutanoyl)-N—((S)-1-(4-(4-methylthiazol-5-yl) phenyl)ethyl)pyrrolidine-2-carboxamide (Compound 36)

Compound 36

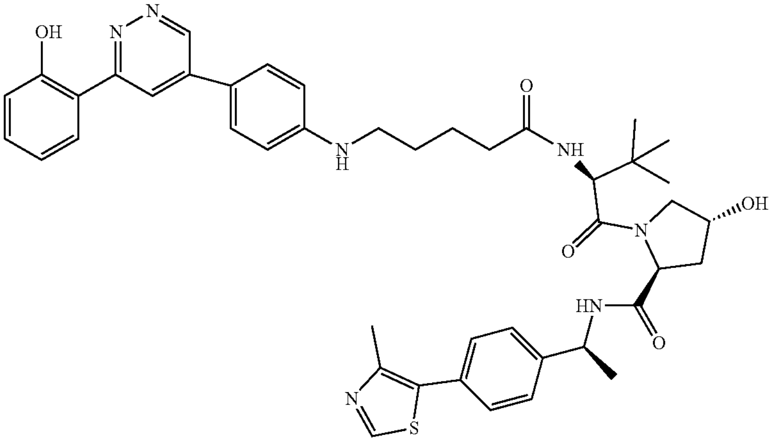

The Compound 36 was prepared by procedure similar to the one described in Example-10 with appropriate variations in reactants, quantities of reagents, protections and deprotections, solvents and reaction conditions.

$^1$H NMR (400 MHz, DMSO-$d_6$): δ 13.72 (bs, 9H), 9.51 (d, J=2.4 Hz, 1H), 8.98 (s, 1H), 8.53 (d, J=2 Hz, 1H), 8.38 (d, J=7.2 Hz, 1H), 8.24 (d, J=6.8 Hz, 1H), 7.92 (d, J=8.8 Hz, 2H), 7.84 (d, J=9.6 Hz, 1H), 7.36-7.44 (m, 5H), 6.99 (d, J=8.8 Hz, 2H), 6.73 (d, J=8.8 Hz, 2H), 6.38 (t, J=5.6 Hz, 1H), 5.11 (d, J=3.6 Hz, 1H), 4.91 (t, J=7.2 Hz, 2H), 4.53 (d, J=9.2 Hz, 1H), 4.42 (t, J=8.4 Hz, H), 4.28 (bs, 14H), 3.60 (bs, 2H), 3.11 (d, J=6.0 Hz, 2H), 2.45 (s, 3H), 2.33 (m, 9H), 2.18 (m, 1H), 2.00 (m, 1H), 1.81 (m, 1H), 1.57 (m, 3H), 1.37 (d, J=6.8 Hz, 3H), 0.94 (s, 9H). LCMS m/z 790.6 (M+H).

The compounds listed in below Table-4 were prepared by procedure similar to the one described in Example-7 with appropriate variations in reactants, quantities of reagents, protections and deprotections, solvents and reaction conditions. The characterization data of the compounds are summarized herein the below table.

| Structure | Characterization Data |
|---|---|
| 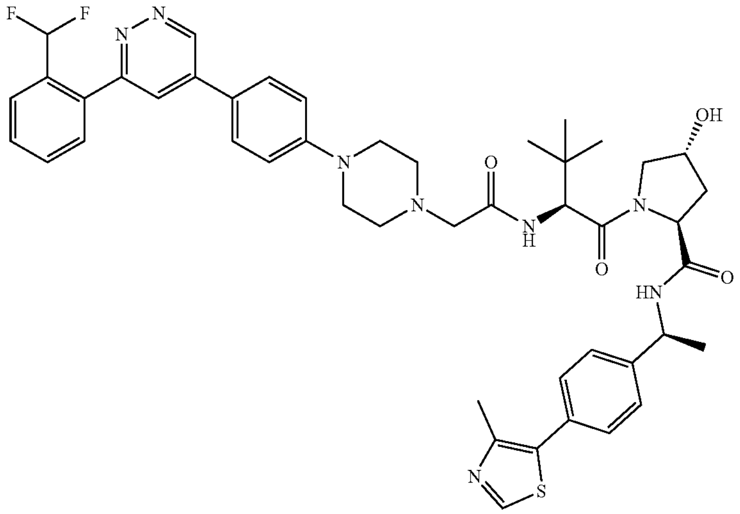 Compound 37 | 1H NMR (400 MHz, DMSO-d6): δ 9.65 (d, J = 2 Hz, 1H), 8.98 (s, 1H), 8.44 (d, J = 8 Hz, 1H), 8.15 (d, J = 4 Hz, 1H), 7.96 (d, J = 8 Hz, 2H), 7.84-7.72 (m, 5H), 7.46-7.42 (m, 2H), 7.37-7.32 (m, 3H), 7.13 (d, J = 8 Hz, 2H), 5.14 (m, 1H), 4.88 (q, J = 12 Hz, 1H), 4.52 (d, J = 12 Hz, 1H), 4.44 (m, 2H), 4.29 (bs, 1H), 3.60-3.59 (m, 2H), 3.39-3.36 (m, 2H), 3.15 (d, J = 16 hz, 1H), 3.03 (d, J = 16 hz, 1H), 2.68-2.65 (m, 4H), 2.45 (s, 3H), 2.08-2.03 (m, 1H), 1.77-1.75 (m, 1H), 1.36 (d, J = 7.2 Hz, 3H), 0.96 (s, 9H); LC-MS: m/z 851.35 (M + H). |
| 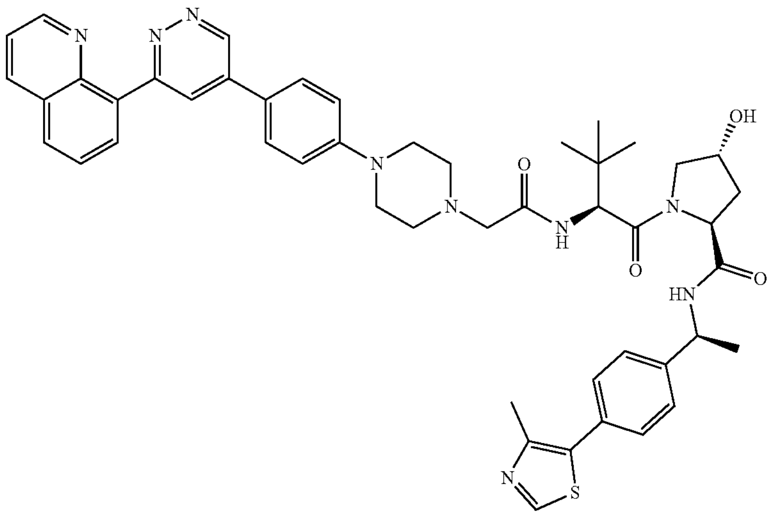 Compound 38 | 1H NMR (400 MHz, DMSO-d6): δ 9.62 (d, J = 2.4 Hz, 1H), 8.98 (s, 1H), 8.95 (m, 1H), 8.53 (dd, J = 8, 2 Hz, 1H), 8.42 (m, 2H), 8.21-8.18 (m, 2H), 7.89-7.77 (m, 4H), 7.64 (m, 1H), 7.43 (d, J = 8 Hz, 2H), 7.36 (d, J = 8 Hz, 2H), 7.13 (d, J = 9.2 Hz, 2H), 5.13 (d, J = 3.2 Hz, 1H), 4.90-4.86 (m, 1H), 4.52 (d, J = 5.6 Hz, 1H), 4.44 (m, 1H), 4.28 (bs, 1H), 3.59 (m, 2H), 3.35 (m, 4H), 3.14 (d, J = 16 hz, 1H), 3.04 (d, J = 16 hz, 1H), 2.65-2.67 (m, 4H), 2.45 (s, 3H), 2.01-2.1 (m, 1H), 1.76-1.77 (m, 1H), 1.36 (d, J = 7.2 Hz, 3H), 0.95 (s, 9H); LC-MS: m/z 852.3 (M + H) |

-continued
| Structure | Characterization Data |
|---|---|
| 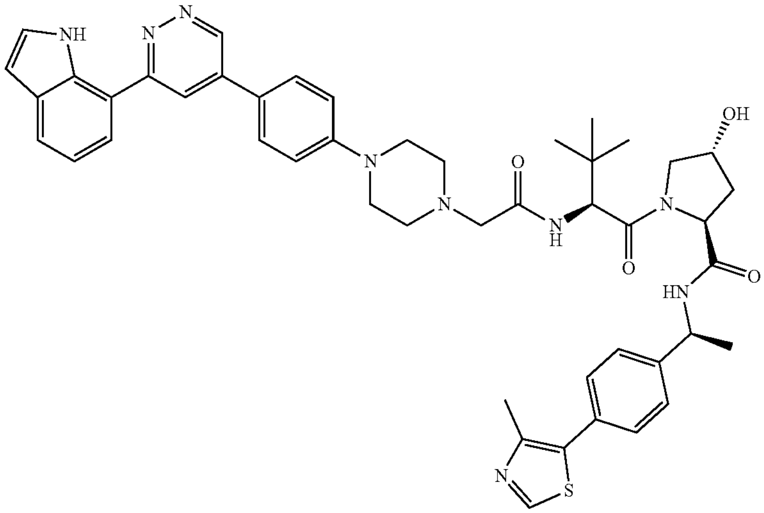 Compound 39 | 1H NMR (400 MHz, DMSO-d6): δ 11.56 (s, 1H), 9.59 (d, J = 4 Hz, 1H), 8.98 (s, 1H), 8.57 (d, J = 2 Hz, 1H), 8.45 (d, J = 8 Hz, 1H), 8.08-8.03 (m, 3H), 7.80-7.75 (m, 2H), 7.42-7.47 (m, 3H), 7.36 (d, J = 8 Hz, 2H), 7.23 (d, J = 8 Hz, 1H), 7.15 (d, J = 8 Hz, 2H), 6.57-6.58 (m, 1H), 5.14 (d, J = 3.2 Hz, 1H), 4.87-4.90 (m, 1H), 4.64-4.68 (m, 1H), 4.52-4.54 (m, 1H), 4.29 (bs, 1H), 3.59-3.62 (m, 2H), 3.36-3.37 (m, 4H), 3.14-3.18 (m, 1H), 3.01-3.05 (m, 1H), 2.65-2.67 (m, 4H), 2.45 (s, 3H), 2.01-2.18 (m, 1H), 1.76-1.77 (m, 1H), 1.35-1.37 (m, 3H), 0.96 (s, 9H); LC-MS: m/z 840.4 (M + H) |
| 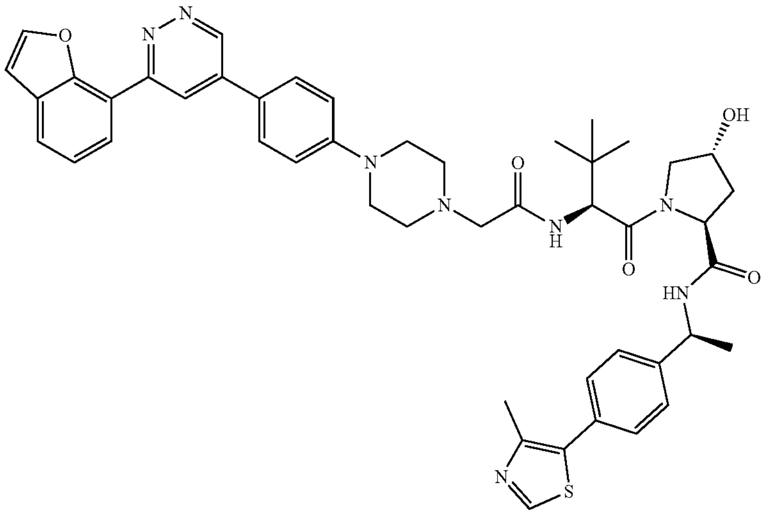 Compound 40 | 1H NMR (400 MHz, DMSO-d6): δ 9.62 (d, J = 2.4 Hz, 1H), 8.98 (s, 1H), 8.56 (d, J = 2.4 Hz, 1H), 8.44 (d, J = 7.6 Hz, 1H), 8.13-8.17 (m, 2H), 7.93 (d, J = 8.8 Hz, 2H), 7.86 (d, J = 7.6 Hz, 1H), 7.78 (d, J = 9.6 Hz, 1H), 7.35-7.49 (m, 5H), 7.12-7.17 (m, 3H), 5.13 (d, J = 3.2 Hz, 1H), 4.88 (t, J = 7.2 Hz, 1H), 4.52 (d, J = 9.6 Hz, 1H), 4.46 (t, J = 8 Hz, 1H), 4.29 (bs, 1H), 3.59 (bs, 2H), 3.36 (m, 4H), 3.16 (d, J = 16 hz, 1H), 3.03 (d, J = 16 hz, 1H), 2.66 (m, 4H) 2.45(s, 3H), 2.06 (m, 1H), 1.76 (m, 1H), 1.36 (d, J = 7.2 Hz, 3H), 0.96 (s, 9H); LC-MS: m/z 840.7 (M + H). |

-continued
| Structure | Characterization Data |
| --- | --- |
| 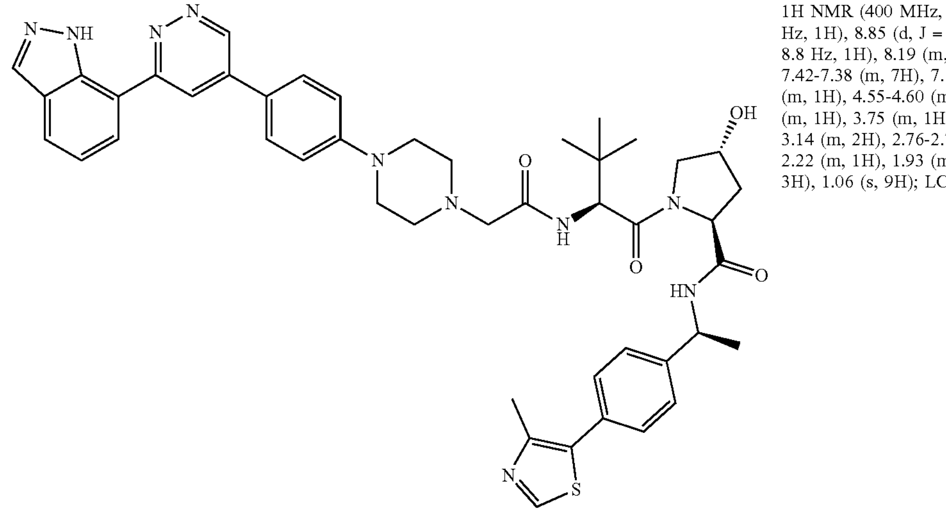 Compound 41 | 1H NMR (400 MHz, CD3OD): δ 9.47 (d, J = 2 Hz, 1H), 8.85 (d, J = 2 Hz, 1H), 8.26 (d, J = 8.8 Hz, 1H), 8.19 (m, 1H), 7.98-7.92 (m, 3H), 7.42-7.38 (m, 7H), 7.17 (d, J = 8 Hz, 1H), 4.95 (m, 1H), 4.55-4.60 (m, 2H), 4.44 (m, 1H), 3.85 (m, 1H), 3.75 (m, 1H), 3.44-3.41 (m, 4H), 3.15-3.14 (m, 2H), 2.76-2.74 (m, 4H), 2.46 (s, 3H), 2.22 (m, 1H), 1.93 (m, 1H), 1.49 (d, J = 8 Hz, 3H), 1.06 (s, 9H); LC-MS: m/z 840.7 (M + H). |
Example-13: (2S,4R)-4-Hydroxy-1-(2-(3-(2-(4-(6-(2-hydroxyphenyl)pyridazin-4-yl) phenoxy)ethoxy) isoxazol-5-yl)-3-methylbutanoyl)-N—((S)-1-(4-(4-methylthiazol-5-yl) phenyl)ethyl)pyrrolidine-2-carboxamide (Compound 42, Racemic)
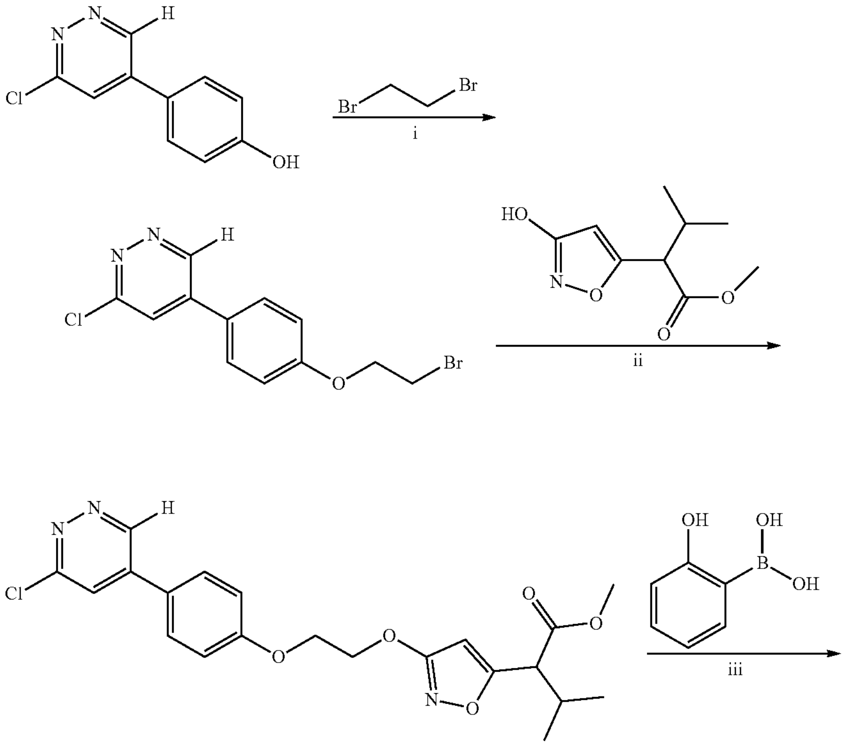

-continued
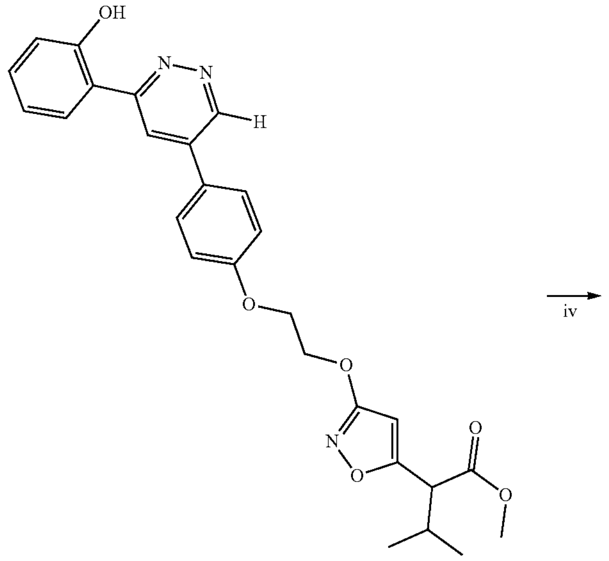
7
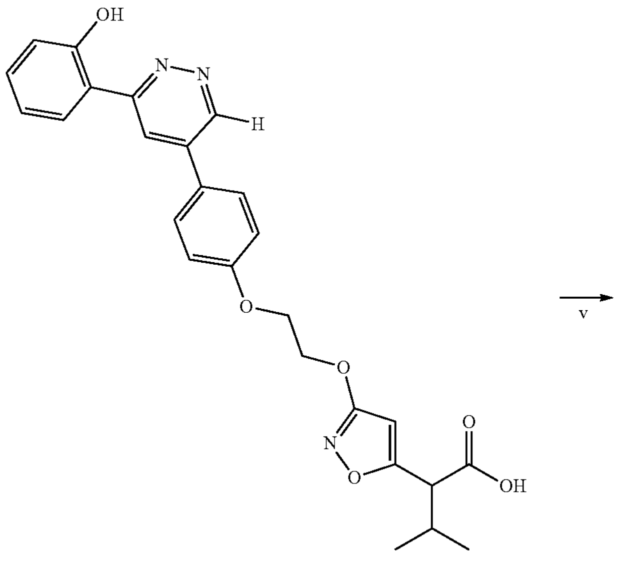

-continued

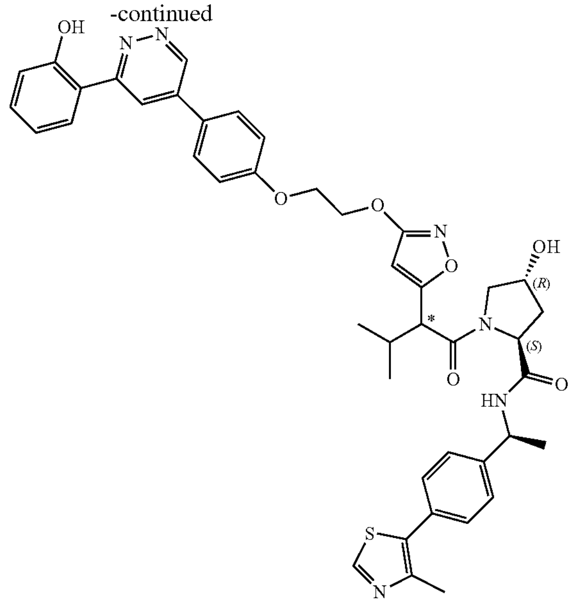

Compound 42

Step-i: Synthesis of 5-(4-(2-Bromoethoxy)phenyl)-3-chloropyridazine

To a stirred solution of compound 4-(6-chloropyridazin-4-yl)phenol (0.5 g, 2.42 mmol) in ethanol (10 mL) were added 1,2-Dibromoethane (0.82 g mL, 9.7 mmol) and $K_2CO_3$ (1.4 g, 9.7 mmol) at RT and the reaction mixture was heated at 100° C. temp in a sealed for 16 h. Once the reaction was completed (monitored by TLC), the reaction mixture was diluted with water and extracted with EtOAc. The combined organic layer was washed with water, brine solution, dried over anhydrous sodium sulphate and concentrated under vacuum to give the residue which was purified by combiflash column chromatography using 40% ethyl acetate in hexane as eluent to afford the title compound as brownish solid. (0.4 g, 52.4%).

$^1$H NMR (400 MHz, $CDCl_3$): δ 9.34 (bs, 1H), 7.66 (s, 1H), 7.65 (d, J=8.8 Hz, 2H), 7.08 (d, J=8.8 Hz, 2H), 4.37 (t, J=6 Hz, 2H), 3.68 (t, J=6.8 Hz, 2H); LC-MS: m/z 314.8 (M+H).

Step-ii: Synthesis of Methyl 2-(3-(2-(4-(6-chloropyridazin-4-yl)phenoxy)ethoxy)isoxazol-5-yl)-3-methylbutanoate To a stirred solution of compound methyl 2-(3-hydroxyisoxazol-5-yl)-3-methylbutanoate (0.2 g, 1 mmol) and 5-(4-(2-Bromoethoxy)phenyl)-3-chloropyridazine (0.38 g, 1.2 mmol) in DMF (5 mL) was added Methyl 2-(3-hydroxyisoxazol-5-yl)-3-methylbutanoate (0.2 g, 1 mmol), $K_2CO_3$ (0.30 g, 2.2 mmol) (0.2 g, mmol) at RT and the reaction mixture was heated at 70° C. temp in a sealed for 12 h. Once the reaction was completed (monitored by TLC), the reaction mixture was diluted with water and extracted with EtOAc. The combined organic layer was washed with water, brine solution, dried over anhydrous sodium sulphate and concentrated under vacuum to give the residue which was purified by combiflash column chromatography using 60% ethyl acetate in hexane as eluent to afford the title compound as brownish solid (0.16 g, 37%).

$^1$H NMR (400 MHz, $CDCl_3$): δ 9.34 (d, J=2 Hz, 1H), 7.65 (m, 3H), 7.10 (d, J=8.8 Hz, 2H), 5.95 (s, 1H), 4.63 (t, J=4.4 Hz, 2H), 4.39 (t, J=4.4 Hz, 2H), 3.73 (s, 3H), 3.51 (d, J=8.8 Hz, 1H), 2.35 (m, 1H), 1.01 (d, J=8.6 Hz, 3H), 0.93 (d, J=8.6 Hz, 3H); LC-MS: m/z 432.05 (M+H).

Step-iii: Synthesis of Methyl 2-(3-(2-(4-(6-(2-hydroxyphenyl)pyridazin-4-yl)phenoxy)ethoxy)isoxazol-5-yl)-3-methylbutanoate To a stirred solution of Methyl 2-(3-(2-(4-(6-chloropyridazin-4-yl)phenoxy)ethoxy)isoxazol-5-yl)-3-methylbutanoate (0.16 g, 0.37 mmol), (2-Hydroxyphenyl)boronic acid (0.1 g, 0.74 mmol) in 1,4-dioxane (3 mL) and water (1 mL) was added $K_2CO_3$ (0.15 g, 1.11 mmol) and degassed with nitrogen for 5 min. Pd(dppf)$Cl_2$·DCM (0.03 g, 0.03 mmol) was added and the reaction mixture was microwave for 1 h at 130° C. in microwave. Once the reaction was completed (monitored by TLC), the reaction mixture was diluted with water and extracted with EtOAc. The combined organic layer was washed with water, brine solution, dried over anhydrous sodium sulphate and concentrated under vacuum to give the residue which was purified by combiflash column chromatography using 50% ethyl acetate in hexane as eluent to afford the title compound as off white solid (0.08 g, 43.9%).

$^1$H NMR (400 MHz, DMSO-$d_6$): δ 13.32 (bs, 1H), 9.61 (d, J=2 Hz, 1H), 8.68 (d, J=2 Hz, 1H), 8.25 (d, J=7.6 Hz, 1H), 8.10 (d, J=8.4 Hz, 2H), 7.40 (t, J=8 Hz, 1H), 7.21 (d, J=8.8 Hz, 2H), 7.02 (d, J=8.4 Hz, 2H), 6.29 (s, 1H), 4.53 (t, J=3.2 Hz, 2H), 4.44 (t, J=3.2 Hz, 2H), 3.71 (d, J=8.4 Hz, 1H), 3.66 (s, 3H), 2.32 (m, 1H), 0.92 (d, J=6.8 Hz, 3H), 0.86 (d, J=6.8 Hz, 3H): LC-MS: m/z 490.1 (M+H).

Step-iv: Synthesis of 2-(3-(2-(4-(6-(2-Hydroxyphenyl)pyridazin-4-yl)phenoxy)ethoxy)isoxazol-5-yl)-3-methylbutanoic acid To a stirred solution of methyl 2-(3-(2-(4-(6-(2-hydroxyphenyl)pyridazin-4-yl)phenoxy)ethoxy)isoxazol-5-yl)-3-methylbutanoate (0.08 g, 0.16 mmol) in methanol:THF:$H_2O$ (1 mL:1 mL:1 mL) mixture was added LiOH·$H_2O$ (0.022 g, 0.49 mmol) at 0° C. The reaction mixture was stirred for 16 h at RT. The reaction mixture was then evaporated under reduced pressure and the resultant residue was diluted with methanol and acidified to pH 6 using Amberlite© IT120 and filtered and filtrate was concentrated under vacuum to afford the title compound as a sticky solid (0.06 g, 77%). $^1$H NMR (400 MHz, DMSO-$d_6$): δ 13.19 (bs, 1H), 12.95 (bs, 1H), 9.61 (d, J=2 Hz, 1H), 8.68 (d, J=2 Hz, 1H), 8.25 (d, J=7.6 Hz, 1H), 8.10 (d, J=8.4 Hz, 2H), 7.40 (t, J=8 Hz, 1H), 7.21 (d, J=8.8 Hz, 2H), 7.02 (d, J=8.4 Hz, 2H), 6.24 (s, 1H), 4.53 (t, J=3.2 Hz, 2H), 4.44 (t, J=3.2 Hz, 2H), 3.53 (d, J=8.8 Hz, 1H), 2.37 (m, 1H), 0.95 (d, J=6.8 Hz, 3H), 0.85 (d, J=6.8 Hz, 3H); LC-MS: m/z 476.1 (M+H).

Step-v: Synthesis of (2S,4R)-4-Hydroxy-1-(2-(3-(2-(4-(6-(2-hydroxyphenyl)pyridazin-4-yl)phenoxy)ethoxy)isoxazol-5-yl)-3-methylbutanoyl)-N—((S)-1-(4-(4-methylthiazol-5-yl)phenyl)ethyl)pyrrolidine-2-carboxamide To a solution of 2-(3-(2-(4-(6-(2-hydroxyphenyl)pyridazin-4-yl)phenoxy)ethoxy)isoxazol-5-yl)-3-methylbutanoic acid (0.015 g, 0.031 mmol) and (2S,4R)-4-Hydroxy-N—((S)-1-(4-(4-methylthiazol-5-yl)phenyl)ethyl)pyrrolidine-2-carboxamide hydrochloride (0.014 g, 0.037 mmol) in DMF (3 mL) at 0° C. was added HATU (0.018 g, 0.047 mmol) followed by the dropwise addition of DIPEA (0.017 mL, 0.094 mmol) and the reaction mixture was stirred for 3 h at RT. Then the reaction mixture was poured into ice cold water and extracted with ethyl acetate. The combined organic layer was washed with water, brine solution, dried over anhydrous sodium sulphate and concentrated under vacuum to get the crude product which was purified by combiflash column chromatography using 8-10% methanol in DCM as eluent to afford the title compound pale yellow solid (0.005 g, 20%).

$^1$H NMR (400 MHz, DMSO-$d_6$): δ 13.33 (s, 1H), 9.61 (d, J=2 Hz, 1H), 8.97 (s, 1H), 8.68 (bs, 1H), 8.25 (d, J=7.6 Hz, 1H), 8.11 (d, J=8.8 Hz, 2H), 7.30-7.44 (m, 6H), 7.21 (d, J=8.8 Hz, 2H), 7.03 (d, J=7.6 Hz, 2H), 6.16 (d, J=9.2 Hz, 1H), 5.11 (bs, 1H), 4.91 (m, 1H), 4.38-4.58 (m, 5H), 4.27 (m, 1H), 3.55-3.78 (m, 2H), 3.47 (m, 1H), 2.45 (s, 3H), 2.22-2.30 (m, 1H), 2.01-2.09 (m, 1H), 1.71-1.79 (m, 1H), 1.33-1.40 (m, 3H), 0.97 (m, 3H), 0.83 (m, 3H); LC-MS: 789.3.

Example-14: (2S,4R)-4-hydroxy-1-(2-(3-(3-(4-(6-(2-hydroxyphenyl)pyridazin-4-yl) phenoxy)propoxy) isoxazol-5-yl)-3-methylbutanoyl)-N—((S)-1-(4-(4-methylthiazol-5-yl) phenyl)ethyl)pyrrolidine-2-carboxamide (Compound 43, Racemic)

Compound 43

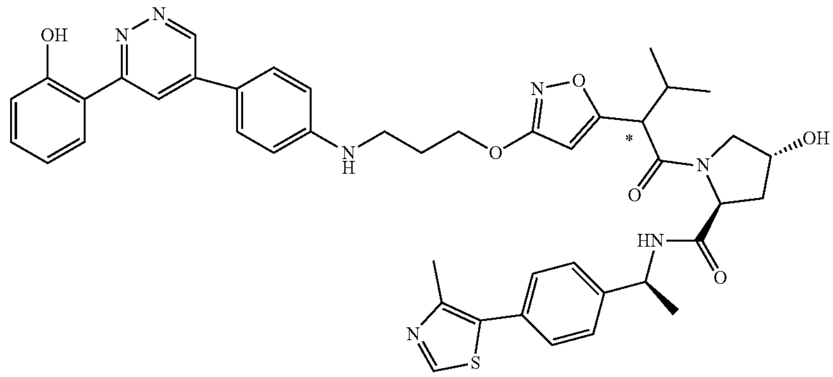

The Compound 43 was prepared by procedure similar to the one described in Example-13 with appropriate variations in reactants, quantities of reagents, protections and deprotections, solvents and reaction conditions.

$^1$H NMR (400 MHz, DMSO-$d_6$): δ 13.33 (s, 1H), 9.59 (m, 1H), 8.97 (m, 1H), 8.67 (bs, 1H), 8.24 (d, J=8 Hz, 1H), 8.06-8.10 (m, 2H), 7.30-7.44 (m, 6H), 7.15-7.19 (m, 2H), 6.99-7.03 (m, 2H), 6.10 (d, J=4 Hz, 1H), 5.12 (bs, 1H), 4.90 (m, 1H), 4.32-4.36 (m, 3H), 4.20-4.24 (m, 3H), 3.64 (m, 2H), 3.44-3.50 (m, 1H), 2.45 (m, 3H), 2.22 (m, 3H), 2.01 (m, 1H), 1.75 (m, 1H), 1.35-1.38 (m, 3H), 0.95-096 (m, 3H), 0.78-0.84 (m, 3H): LC-MS: m/z 803.7 (M+H).

Example-15: (2S,4R)-4-hydroxy-1-(2-(3-(2-((4-(6-(2-hydroxyphenyl)pyridazin-4-yl) phenyl)(methyl) amino)ethoxy)isoxazol-5-yl)-3-methylbutanoyl)-N—((S)-1-(4-(4-methyl thiazol-5-yl)phenyl)ethyl) pyrrolidine-2-carboxamide (Compound 44, Racemic)

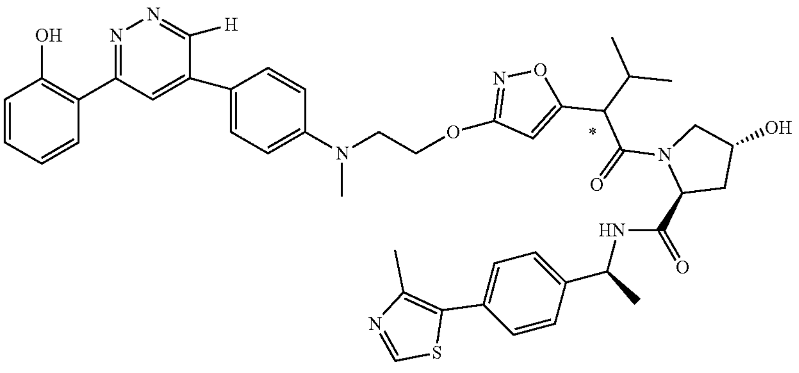

Compound 44

The Compound 44 was prepared by procedure similar to the one described in Example-13 with appropriate variations in reactants, quantities of reagents, protections and deprotections, solvents and reaction conditions.

$^1$H NMR (400 MHz, DMSO-$d_6$): δ 13.66 (d, J=4.8 Hz, 1H), 9.56 (dd, J=5.6 Hz, 2.0 Hz, 1H), 8.98 (d, J=5.6 Hz, 1H), 8.58 (brs, 1H), 8.26-8.17 (m, 3H), 8.01-7.97 (m, 2H), 7.43-7.28 (m, 4H), 7.02-6.90 (m, 2H), 6.07 (d, J=3.2 Hz, 1H), 5.10-5.08 (m, 1H), 5.80-5.74 (m, 1H), 4.37-4.33 (m, 2H), 3.86-3.84 (m, 2H), 3.65-3.59 (m, 3H), 3.32-3.10 (m, 2H), 2.45 (s, 3H), 2.26-2.21 (m, 1H), 2.04-2.00 (m, 1H), 1.78-1.74 (m, 1H), 1.43-1.31 (m, 4H), 0.95-0.93 (m, 2H), 0.81-0.77 (m, 3H). LC-MS: m/z 802.4 (M+H).

Example-16: (2S,4R)-4-hydroxy-1-((S)-2-(2-(4-((4-(6-(2-hydroxyphenyl)pyridazin-4-yl) phenyl)amino) piperidin-1-yl)acetamido)-3,3-dimethylbutanoyl)-N—((S)-1-(4-(4-methyl thiazol-5-yl)phenyl)ethyl) pyrrolidine-2-carboxamide (Compound 45)

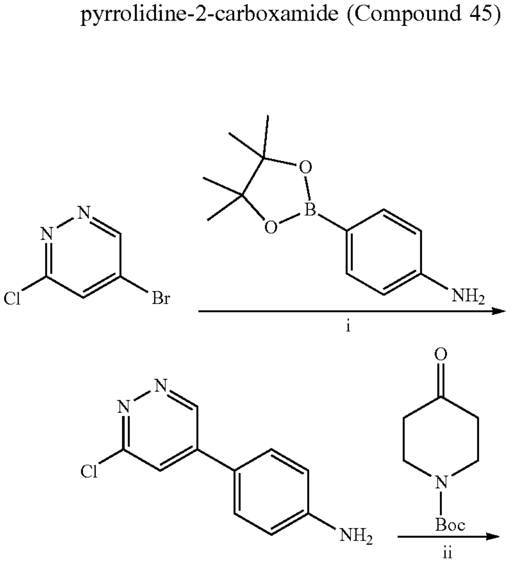

-continued

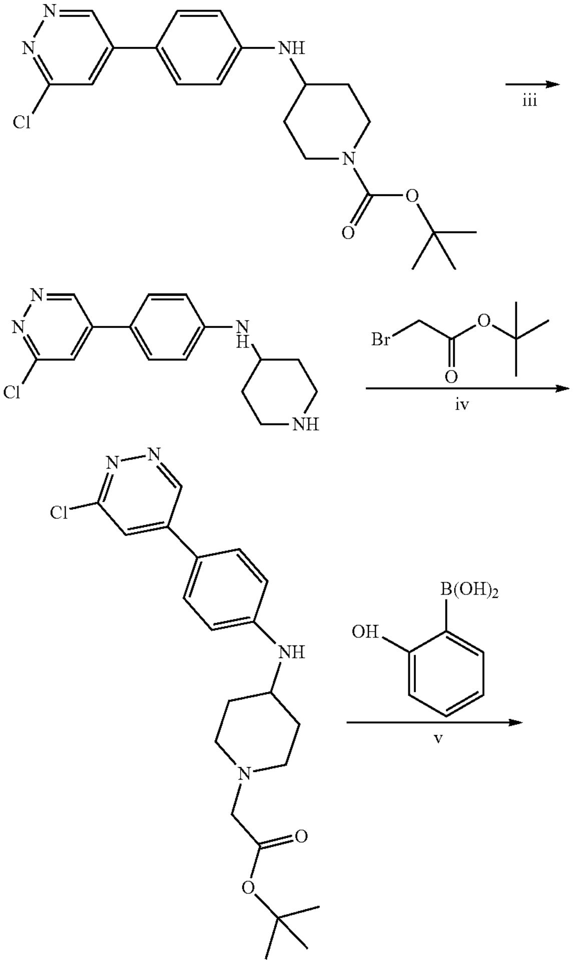

-continued

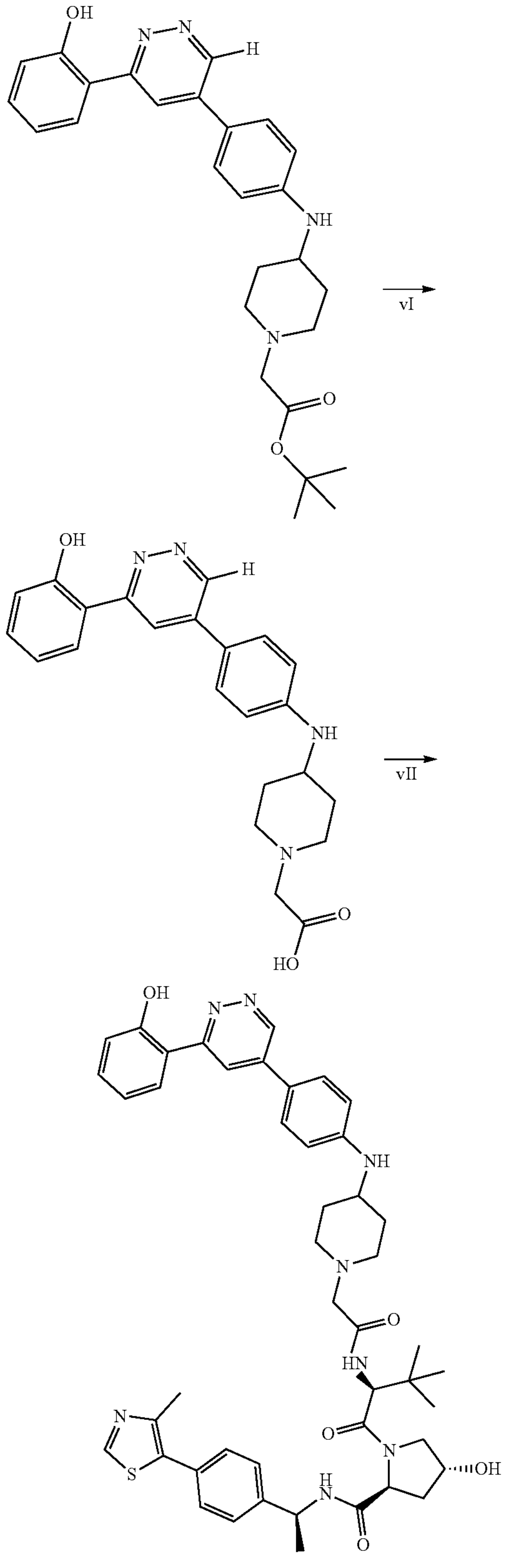

Compound 45

Step-i: Synthesis of 4-(6-Chloropyridazin-4-yl)aniline

To a stirred solution of 5-Bromo-3-chloropyridazine (2 g, 10.3 mmol), 4-(4,4,5,5-Tetramethyl-1,3,2-dioxaborolan-2-yl)aniline (2.49 g, 11.3 mmol) in 1,4-dioxane (40 mL) and water (4 mL) was added $K_2CO_3$ (4.28 g, 31.02 mmol) and degassed with nitrogen for 15 min. Pd(dppf)$Cl_2$·DCM (0.84 g, 1.03 mmol) was added and the reaction mixture was heated for 16 h at 100° C. in sealed tube. Once the reaction was completed (monitored by TLC), the reaction mixture was diluted with EtOAc. The combined organic layer was washed with water, brine solution, dried over anhydrous sodium sulphate and concentrated under vacuum to give the residue which was purified by combiflash column chromatography using 40% ethyl acetate in hexane as eluent to afford the title compound as pale brown solid (0.7 g, 33%). $^1$H NMR (400 MHz, $CDCl_3$): δ 9.57 (d, J=2 Hz, 1H), 8.06 (d, J=2 Hz, 1H), 7.79 (d, J=8.8 Hz, 2H), 6.71 (d, J=8.8 Hz, 2H), 5.92 (bs, 2H); LC-MS: m/z 206.1 (M+H).

Step-ii: Synthesis of Tert-butyl 4-((4-(6-chloropyridazin-4-yl)phenyl)amino)piperidine-1-carboxylate To a stirred solution of 4-(6-Chloropyridazin-4-yl)aniline (0.5 g, 2.43 mmol), Tert-butyl 4-oxopiperidine-1-carboxylate (0.96 g, 4.86 mmol) in ethanol (10 mL) was added acetic acid (0.05 mL) and stirred at RT for 2 hrs. Then sodium cyanoborohydride (0.96 g, 4.86 mmol) was added into the reaction mixture and stirred at RT for 12 hrs. New spot formed on TLC). The reaction mixture concentrated under reduced pressure was diluted with EtOAc. The combined organic layer was washed with water, brine solution, dried over anhydrous sodium sulphate and concentrated under vacuum to give the residue which was purified by combiflash column chromatography using 40% ethyl acetate in hexane as eluent to afford the title compound as yellow solid (0.2 g, 21%).

$^1$H NMR (400 MHz, $CDCl_3$): δ 9.59 (d, J=2 Hz, 1H), 8.07 (d, J=2 Hz, 1H), 7.84 (d, J=8.8 Hz, 2H), 6.76 (d, J=8.8 Hz, 2H), 6.37 (d, J=8.8 Hz, 1H), 3.93 (m, 2H), 3.58 (m, 1H), 2.97 (bs, 2H), 1.94 (m, 2H), 1.44 (s, 9H), 1.30 (m, 2H); LC-MS: m/z 389.2 (M+H).

Step-iii: Synthesis of N-(4-(6-chloropyridazin-4-yl)phenyl)piperidin-4-amine hydrochloride To a stirred solution of Tert-butyl 4-((4-(6-chloropyridazin-4-yl)phenyl)amino)piperidine-1-carboxylate (0.1 g, 0.25 mmol) in DCM (1 mL) was added dioxane HCl (1 mL) at 0° C. and then slowly brought to RT and stirred at RT for 1 h. The reaction mixture was evaporated under reduced pressure, the resultant residue was washed with diethyl ether and dried under vacuum to afford the title compound reddish solid (0.08 g, 95%). $^1$H NMR (400 MHz, $CDCl_3$): δ 9.61 (d, J=2 Hz, 1H), 8.84 (bs, 1H), 8.76 (bs, 1H), 8.01 (d, J=2 Hz, 1H), 7.86 (d, J=8.8 Hz, 2H), 6.79 (d, J=8.8 Hz, 2H), 3.72 (m, 1H), 3.32 (m, 2H), 3.03 (m, 2H), 2.09 (m, 2H), 1.65 (m, 2H); LC-MS: m/z 289.1 (M+H).

Step-iv: Synthesis of Tert-butyl 2-(4-((4-(6-chloropyridazin-4-yl)phenyl)amino)piperidin-1-yl)acetate To a stirred solution of N-(4-(6-Chloropyridazin-4-yl)phenyl)piperidin-4-amine hydrochloride (0.08 g, 0.24 mmol) in DMF (2 mL) was added DIPEA (0.16 g, 1.23 mmol) at RT and stirred for 15 min then added tert-butyl 2-bromoacetate (0.06 g, 0.295 mmol) and stirred for 2 h at RT under nitrogen atmosphere. The reaction mixture was quenched with cold water and stirred for 1 h, the solid so formed was filtered and dried under vacuum to afford title compound as brown solid (0.08 g, 80%).

$^1$H NMR (400 MHz, $CDCl_3$): δ 9.58 (d, J=2 Hz, 1H), 8.06 (d, J=2 Hz, 1H), 7.83 (d, J=8.8 Hz, 2H), 6.74 (d, J=8.8 Hz, 2H), 6.36 (d, J=8.8 Hz, 1H), 4.59 (m, 1H), 3.95 (m, 1H), 3.74 (m, 1H), 3.14 (s, 2H), 2.85 (m, 2H), 2.36 (m, 2H), 1.93 (m, 2H), 1.47 (s, 9H); LC-MS: m/z 403.3 (M+H).

Step-v: Synthesis of Tert-butyl 2-(4-((4-(6-(2-hydroxyphenyl)pyridazin-4-yl)phenyl)amino)piperidin-1-yl)acetate To a stirred solution of Tert-butyl 2-(4-((4-(6-chloropyridazin-4-yl)phenyl)amino)piperidin-1-yl)acetate (0.08 g, 0.199 mmol), 2-hydroxyphenyl boronic acid (0.04 g, 0.298 mmol) in 1,4-dioxane (2 mL) and water (0.2 mL) was added $K_2CO_3$ (0.08 g, 0.59 mmol) and degassed with nitrogen for 10 min. Pd(dppf)$Cl_2$·DCM (0.016 g, 0.02 mmol) was added and the reaction mixture was heated for 16 h at 110° C. in sealed tube. Once the reaction was completed (monitored by TLC), the reaction mixture was diluted with EtOAc. The combined organic layer was washed with water, brine solution, dried over anhydrous sodium sulphate and concentrated under vacuum to give the residue which was purified by combiflash column chromatography using 40% ethyl acetate in hexane as eluent to afford the title compound as pale-yellow solid (0.04 g, 43%).

$^1$H NMR (400 MHz, DMSO-$d_6$): δ 13.73 (s, 1H), 9.54 (d, J=2 Hz, 1H), 8.57 (d, J=2 Hz, 1H), 8.27 (d, J=8.8 Hz, 1H), 7.94 (d, J=8.8 Hz, 2H), 7.42 (m, 1H), 7.04 (m, 2H), 6.78 (d, J=8.8 Hz, 2H), 6.31 (d, J=8.8 Hz, 1H), 3.3 (m, 1H), 3.15 (s, 2H), 2.86 (m, 2H), 2.50 (m, 2H), 2.36 (m, 2H), 1.94 (m, 2H), 1.46 (s, 9H); LC-MS: m/z 461.3 (M+H).

Step-vi: Synthesis of 2-(4-((4-(6-(2-Hydroxyphenyl)pyridazin-4-yl)phenyl)amino)piperidin-1-yl)acetic acid hydrochloride To a stirred solution of Tert-butyl 2-(4-((4-(6-(2-hydroxyphenyl)pyridazin-4-yl)phenyl)amino)piperidin-1-yl)acetate (0.04 g, 0.48 mmol) in DCM (1 mL) was added 4 N dioxane hydrochloride (0.4 mL) at 0° C. and then slowly bring to RT and stirred at RT for 16 h. The reaction mixture was evaporated under reduced pressure, the resultant residue was washed with diethyl ether and dried under vacuum to afford the title compound as orange solid (0.04 g, crude).

$^1$H NMR (400 MHz, DMSO-$d_6$): δ 10.28 (s, 1H), 9.68 (d, J=2 Hz, 1H), 8.66 (d, J=2 Hz, 1H), 8.06 (d, J=8.4 Hz, 2H), 7.49 (m, 1H), 7.05-7.15 (m, 2H), 6.91 (m, 2H), 4.18 (bs, 2H), 3.65 (m, 2H), 3.15 (s, 2H), 3.25 (m, 2H), 2.17 (m, 2H), 1.95 (m, 2H); LC-MS: m/z 405.2 (M+H).

Step-vii: Synthesis of (2S,4R)-4-hydroxy-1-((S)-2-(2-(4-((4-(6-(2-hydroxyphenyl)pyridazin-4-yl)phenyl)amino)piperidin-1-yl)acetamido)-3,3-dimethylbutanoyl)-N—((S)-1-(4-(4-methylthiazol-5-yl)phenyl)ethyl)pyrrolidine-2-carboxamide To a solution of 2-(4-((4-(6-(2-hydroxyphenyl)pyridazin-4-yl)phenyl)amino)piperidin-1-yl)acetic acid hydrochloride (0.03 g, 0.074 mmol) and ((2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide hydrochloride (0.04 g, 0.089 mmol) in DMF (2 mL) at 0° C. was added HATU (0.04 g, 0.11 mmol) followed by the dropwise addition of DIPEA (0.05 mL, 0.37 mmol) and the reaction mixture was stirred for 3 h at RT. Then the reaction mixture was poured into ice cold water and extracted with ethyl acetate. The combined organic layer was washed with water, brine solution, dried over anhydrous sodium sulphate and concentrated under vacuum to get the crude product which was purified by combiflash column chromatography using 8-10% methanol in DCM as eluent to afford the title compound pale yellow solid (0.018 g, 29%).

$^1$H NMR (400 MHz, DMSO-$d_6$): δ 13.72 (s, 1H), 9.55 (d, J=2.0 Hz, 1H), 9.02 (s, 1H), 8.56 (d, J=2.0 Hz, 1H), 8.45 (d, J=2.0 Hz, 1H), 8.34 (s, 1H), 7.95 (d, J=8.8 Hz, 2H), 7.96 (s, 1H), 7.48-7.39 (m, 5H), 7.05-7.02 (m, 2H), 6.80 (d, J=8.8 Hz, 2H), 6.40 (d, J=12.0 Hz, 1H), 5.17 (d, J=3.6 Hz, 1H), 4.98-4.81 (m, 1H), 4.79-4.70 (m, 1H), 4.59-4.43 (m, 1H), 4.32-4.21 (m, 1H), 3.72-3.61 (m, 2H), 3.36 (s, 1H), 3.26-3.09 (m, 2H), 3.01-2.81 (m, 2H), 2.49 (s, 3H), 2.46-2.22 (m, 2H), 2.19-1.92 (m, 3H), 1.85-1.72 (m, 1H), 1.61-1.50 (m, 2H), 1.42 (d, J=6.8 Hz, 3H), 0.99 (s, 9H). LC-MS: m/z 831.5 (M+H).

Example-17: (2S,4R)-4-hydroxy-1-((S)-2-(2-(4-((4-(6-(2-hydroxyphenyl)pyridazin-4-yl) phenyl) (methyl)amino)piperidin-1-yl)acetamido)-3,3-dimethylbutanoyl)-N—((S)-1-(4-(4-methylthiazol-5-yl) phenyl)ethyl)pyrrolidine-2-carboxamide (Compound 46)

Compound 46

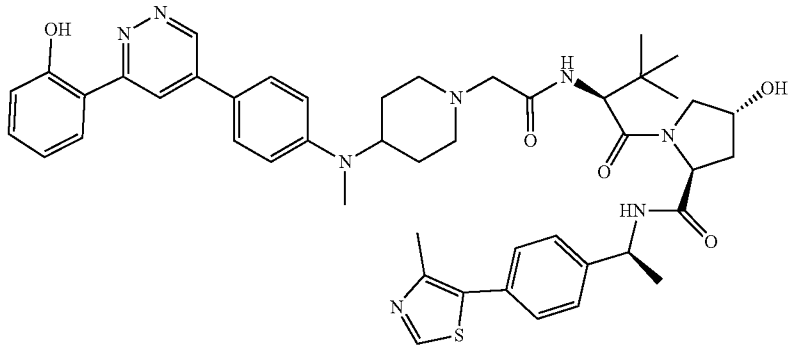

The Compound 46 was prepared by procedure similar to the one described in Example-16 with appropriate variations in reactants, quantities of reagents, protections and deprotections, solvents and reaction conditions.

$^1$H NMR (400 MHz, DMSO-$d_6$): δ 13.69 (s, 1H), 9.56-9.54 (m, 1H), 8.98 (s, 1H), 8.57-8.49 (m, 1H), 8.50-8.41 (m, 1H), 8.39-827 (m, 1H), 7.99 (d, J=12.0 Hz, 2H), 7.80-7.72 (m, 1H), 7.45-7.39 (m, 2H), 7.38-7.36 (m, 3H), 7.02-6.95 (m, 4H), 5.13-5.01 (m, 1H), 4.91-4.82 (m, 1H), 4.54 (s, 1H), 4.49-4.31 (m, 1H), 4.29-4.10 (m, 1H), 3.90-3.81 (m, 1H), 3.58 (s, 2H), 3.09 (s, 1H), 2.99 (s, 2H), 2.87 (s, 3H), 2.50-2.49 (m, 4H), 2.45 (s, 2H), 2.11-1.95 (m, 1H), 1.82-1.71 (m, 3H), 1.70-1.61 (m, 2H), 1.38 (d, J=8.0 Hz, 3H), 0.96 (s, 9H). LC-MS: m/z 845.3 (M+H).

-continued

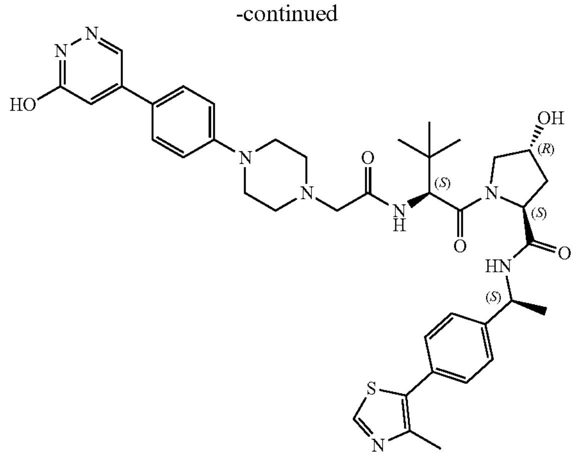

Compound 47

Example-18: (2S,4R)-4-hydroxy-1-((S)-2-(2-(4-(4-(6-hydroxypyridazin-4-yl)phenyl) piperazin-1-yl) acetamido)-3,3-dimethylbutanoyl)-N—((S)-1-(4-(4-methylthiazol-5-yl) phenyl)ethyl)pyrrolidine-2-carboxamide (Compound 47)

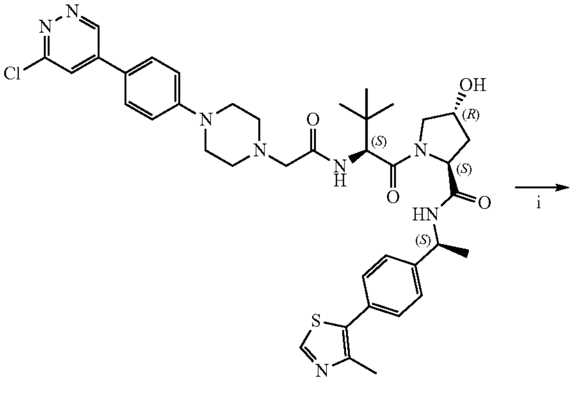

Step-i: Synthesis of (2S,4R)-4-hydroxy-1-((S)-2-(2-(4-(4-(6-hydroxypyridazin-4-yl)phenyl)piperazin-1-yl)acetamido)-3,3-dimethylbutanoyl)-N—((S)-1-(4-(4-methylthiazol-5-yl)phenyl)ethyl)pyrrolidine-2-carboxamide To a stirred solution of (2S,4R)-1-((S)-2-(2-(4-(4-(6-chloropyridazin-4-yl)phenyl)piperazin-1-yl)acetamido)-3,3-dimethylbutanoyl)-4-hydroxy-N—((S)-1-(4-(4-methylthiazol-5-yl)phenyl)ethyl)pyrrolidine-2-carboxamide (0.2 g, 0.26 mmol), in 1,4-dioxane (4 mL) and water (0.5 mL) was added $K_2CO_3$ (0.07 g, 0.52 mmol) and degassed with nitrogen for 5 min. Pd(dppf)$Cl_2$·DCM (0.02 g, 0.02d mmol) was added and the reaction mixture was microwaved for 1 h at 120° C. in microwave. Once the reaction was completed (monitored by TLC), the reaction mixture was diluted with EtOAc. The combined organic layer was washed with water, brine solution, dried over anhydrous sodium sulphate and concentrated under vacuum to give the residue which was purified by preparative HPLC to afford the title compound as pale-yellow solid (10 mg, 5%).

$^1$H NMR (400 MHz, DMSO-$d_6$): δ 12.9 (s, 1H), 8.98 (s, 1H), 8.44 (d, J=7.6 Hz, 1H), 8.30 (d, J=7.6 Hz, 1H), 7.71-7.79 (m, 2H), 7.33-7.45 (m, 4H), 7.06 (d, J=8.8 Hz, 2H), 7.01 (bs, 1H), 5.13 (d, J=3.2 Hz, 1H), 4.88 (t, J=8 Hz, 1H), 4.52 (d, J=9.6 Hz, 1H), 4.44 (t, J=8.4 Hz, 1H), 4.28 (bs, 1H), 3.59 (bs, 2H), 3.35 (m, 4H), 3.14 (d, J=16 hz, 1H), 3.02 (d, J=16 hz, 1H), 2.64 (m, 4H), 2.45 (s, 3H), 2.03 (m, 1H), 1.76 (m, 1H), 1.36 (d, J=7.2 Hz, 3H), 0.9 (s, 9H), LC-MS: m/z 741.3 (M+H).

Example-19: (2S,4R)-4-hydroxy-N—((R)-2-hydroxy-1-(4-(4-methylthiazol-5-yl)phenyl) ethyl)-1-((S)-2-(2-(4-(4-(6-(2-hydroxyphenyl)pyridazin-4-yl) phenyl)piperazin-1-yl) acetamido)-3,3-dimethylbutanoyl)pyrrolidine-2-carboxamide (Compound 48)

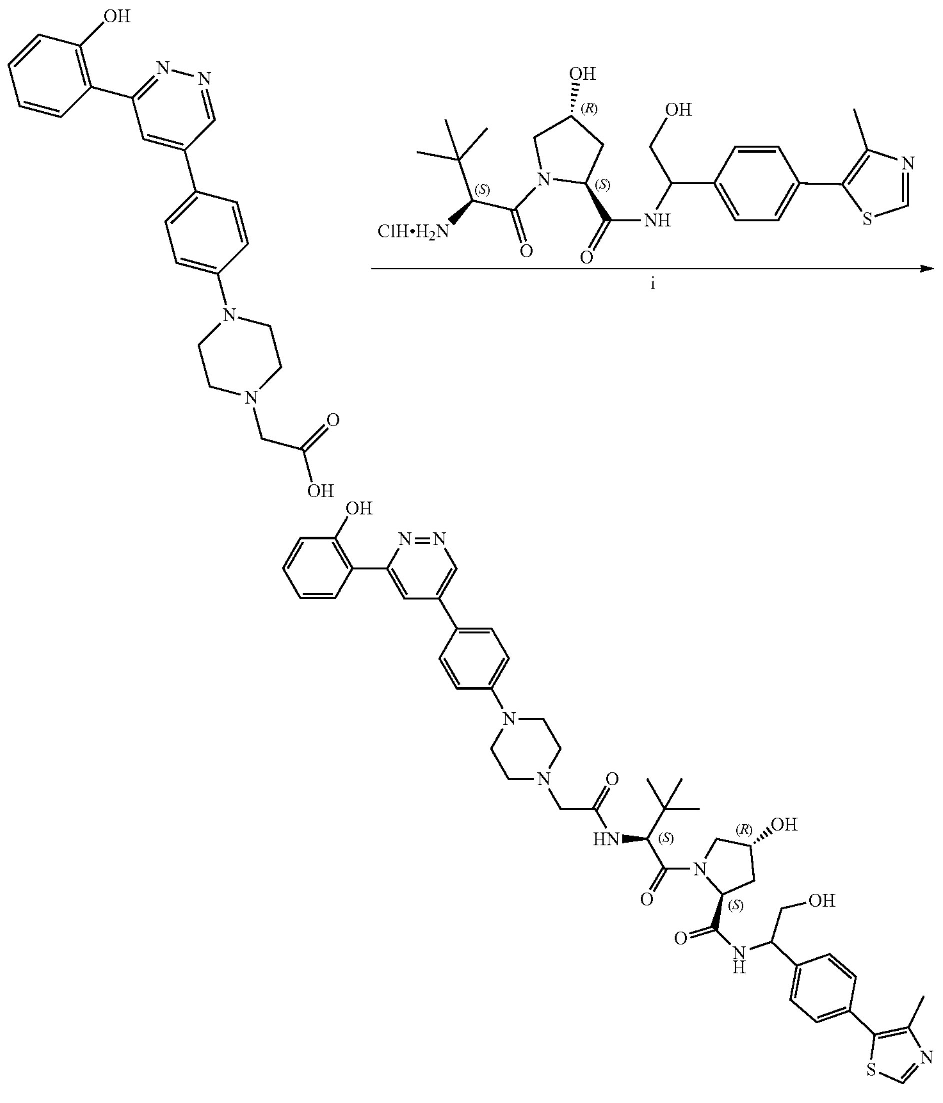

Compound 48

Step-i: Synthesis of (2S,4R)-4-hydroxy-N—((R)-2-hydroxy-1-(4-(4-methylthiazol-5-yl)phenyl)ethyl)-1-((S)-2-(2-(4-(4-(6-(2-hydroxyphenyl)pyridazin-4-yl) phenyl)piperazin-1-yl)acetamido)-3,3-dimethylbutanoyl)pyrrolidine-2-carboxamide To a solution of 2-(4-(4-(6-(2-hydroxyphenyl)pyridazin-4-yl)phenyl)piperazin-1-yl)acetic acid (0.13 g, 0.411 mmol) and (2S,4R)-1-((S)-2-Amino-3,3-dimethylbutanoyl)-4-hydroxy-N-(2-hydroxy-1-(4-(4-methylthiazol-5-yl)phenyl) ethyl)pyrrolidine-2-carboxamide hydrochloride (0.17 g, 0.34 mmol) in DMF (5 mL) at 0° C. was added HATU (0.19 g, 0.51 mmol) followed by the dropwise addition of DIPEA (0.2 mL, 1.02 mmol) and the reaction mixture was stirred for 4 h at RT. Then the reaction mixture was poured into ice cold water and extracted with ethyl acetate. The combined organic layer was washed with water, brine solution, dried over anhydrous sodium sulphate and concentrated under vacuum to get the crude product which was purified by combiflash column chromatography using 5% methanol in DCM as eluent to afford the title compound as yellow solid (10 mg, 3.5%).

$^1$H NMR (400 MHz, DMSO-d$_6$): δ 13.54 (bs, 1H), 9.59 (d, J=2 Hz, 1H), 8.98 (s, 1H), 8.63 (d, J=2 Hz, 1H), 8.46 (d, J=8 Hz, 1H), 8.26 (d, J=7.2 Hz, 1H), 8.03 (d, J=8.8 Hz, 2H), 7.80 (d, J=9.6 Hz, 2H), 7.36-7.44 (m, 5H), 7.15 (d, J=8.8 Hz, 2H), 7.02 (d, J=8 Hz, 2H), 5.15 (d, J=2.8 Hz, 1H), 4.80-4.86 (m, 2H), 4.47-4.54 (m, 2H), 4.29 (bs, 1H), 3.52-3.65 (m, 4H), 3.40 (m, 4H), 3.16 (d, J=16 hz, 1H), 3.04 (d, J=16 hz, 1H), 2.67 (m, 4H), 2.46 (s, 3H), 2.08 (m, 1H), 1.79 (m, 1H), 0.96 (s, 9H). LC-MS: m/z 833.4

Example-20: (2S,4R)—N-(2-(dimethylamino)-1-(4-(4-methylthiazol-5-yl)phenyl)ethyl)-4-hydroxy-1-((S)-2-(2-(4-(4-(6-(2-hydroxyphenyl)pyridazin-4-yl)phenyl)piperazin-1-yl) acetamido)-3,3-dimethylbutanoyl)pyrrolidine-2-carboxamide (Compound 49)

Compound 49

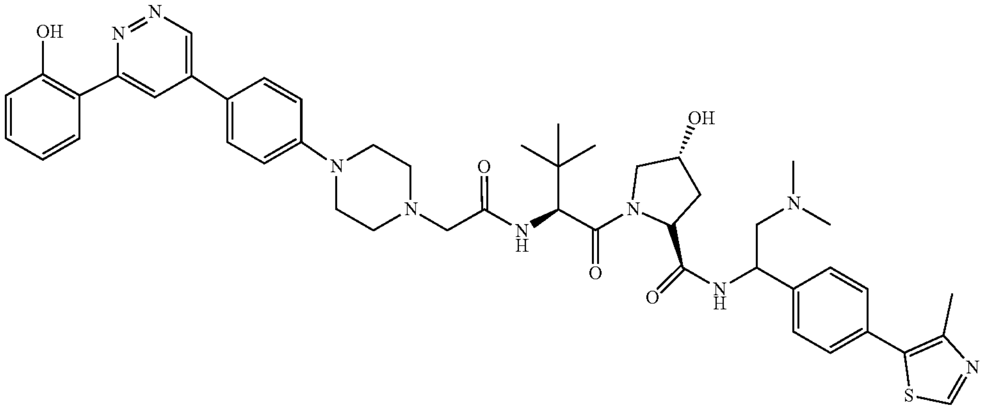

The Compound 49 was prepared by procedure similar to the one described in Example-15 with appropriate variations in reactants, quantities of reagents, protections and deprotections, solvents and reaction conditions.

$^1$H NMR (400 MHz, DMSO-$d_6$): δ 13.53 (s, 1H), 9.58 (d, J=2.0 Hz, 1H), 8.98-8.96 (m, 1H), 8.62 (s, 1H), 8.32-8.24 (m, 1H), 8.03 (t, J=3.2 Hz, 2H), 7.78-7.75 (m, 2H), 7.43-7.33 (m, 5H), 7.15 (t, J=6.4 Hz, 2H), 7.02 (t, J=6.4 Hz, 2H), 5.13-5.05 (m, 1H), 4.51-4.47 (m, 1H), 4.32-4.18 (m, 1H), 3.58-3.39 (m, 3H), 3.14-3.00 (m, 3H), 2.67-2.64 (m, 6H), 2.46 (s, 5H), 2.16-2.10 (m, 8H), 1.80 (s, 1H), 1.75-1.71 (m, 1H), 0.95 (s, 9H). LCMS: 860.7 (M+H).

Example-21: (2S,4R)-4-hydroxy-1-(2-(3-(2-((4-(6-(2-hydroxyphenyl)pyridazin-4-yl) phenyl)amino) ethoxy)isoxazol-5-yl)-3-methylbutanoyl)-N—((S)-1-(4-(4-methylthiazol-5-yl)phenyl)ethyl)pyrrolidine-2-carboxamide (Compound 50, Racemic)

Compound 50

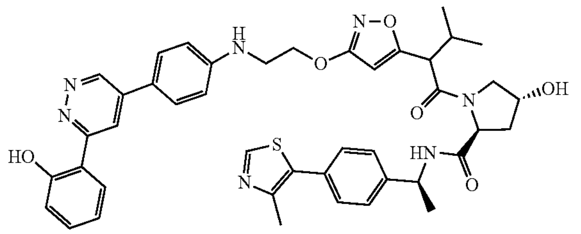

The Compound 50 was prepared by procedure similar to the one described in Example-13 with appropriate variations in reactants, quantities of reagents, protections and deprotections, solvents and reaction conditions.

$^1$H NMR (400 MHz, DMSO-$d_6$): δ 13.68 (br, 1H), 9.52 (brs, 1H), 8.96 (d, J=5.6 Hz, 1H), 8.55 (s, 1H), 8.42-8.35 (m, 1H), 8.26-8.24 (m, 1H), 7.95-7.91 (m, 2H), 7.42-7.32 (m, 4H), 7.01 (d, J=7.6 Hz, 2H), 6.55-6.52 (m, 2H), 6.63 (m, 1H), 6.11 (d, J=1.6 Hz, 1H), 5.10 (d, J=3.2 Hz, 1H), 4.92-4.87 (m, 1H), 4.45-4.26 (m, 4H), 3.77-3.58 (m, 2H), 3.53 (br, 2H), 3.47-3.42 (m, 1H), 2.45 (d, J=4.4 Hz, 3H), 2.28-2.23 (m, 1H), 2.06-1.98 (m, 1H), 1.80-1.76 (m, 1H), 1.45-1.43 (m, 1H), 1.38-1.32 (m, 3H), 0.97-0.94 (m, 3H), 0.83-0.79 (m, 3H). LCMS: 786.2 (M-1).

Example-P1: Determination of Anti Proliferative Activity of Compounds in Cell Lines A549 by Cell Titer Glo©(Promega) Assay A549 (ATCC CCL-185) cells were seeded in 96 well plate flat black clear bottom plates (Corning, Cat. No 3904) using complete F-12K Medium. Compounds of the present invention were added to cells from 10 mM stocks made in DMSO (Sigma Cat no. D2650) on the following day. Each concentration of compound was tested in triplicate with DMSO concentration at a final percentage not exceeding 0.3 in the cells. After the compound incubation (8 days for A549) assay was terminated using 50 μl of CellTiter Glo© reagent (Promega, Cat. no G7572). CellTiter-Glo© Luminescent reagent determines the number of viable cells based on quantitation of ATP present which is an indicator of cell number and metabolic activity. Luminescence readings were taken in Victor-3 instrument. Percent inhibition of proliferation was calculated using formula, % inhibition=100-(luminescence value of test/luminescence value of DMSO control)*100. DMSO control (0%)=Cells in complete media with DMSO; blank=Media alone containing DMSO. $IC_{50}$ was calculated using graph pad prism software.

From the experiment described in Example-P1, the selected compounds of the present invention were found to have $IC_{50}$ values of less than 1 μM.

Example-P2: Determination of SMARCA2 and SMARCA4 Degradation in VCaP Cells by Western Blot VCaP (ATCC CRL-2876) was plated in 6 well plates using complete Dulbecco's Modified Eagle's Medium. On the third day, compounds of present invention were added to cells from 10 mM stocks made in DMSO (Sigma Cat no. D2650). Each concentration of compound was tested with DMSO not exceeding final percentage of 0.3 in the cells. Cells were incubated with the compound for 16 hours followed by harvesting with 1×RIPA lysis buffer (Thermo Fischer, catalogue number #89900) containing protease inhibitor cocktail (Sigma catalogue number #P-8340). Equal amount of protein was loaded on SDS PAGE gel for electrophoresis. Western blot was carried out for detection of either SMARCA2 (Cell signalling technologies, catalogue number #11966) or SMARCA4 antibody (Cell signalling technologies, catalogue number #52251). Beta-Tubulin antibody (Cell signalling technologies, catalogue number #86298) was used as loading control. Percentage of SMARCA2 or SMARCA4 degradation was calculated using formula % Degradation=100−(normalized band intensity in treated sample/normalized band intensity in DMSO sample) *100.

| | Percent degradation (at 100 nM) | |
|---|---|---|
| Compound | SMARCA2 | SMARCA4 |
| 1 | 0 | 30 |
| 2 | 94 | 0 |
| 3 | 20 | 47 |
| 4 | 81 | 0 |
| 5 | 94 | 0 |
| 6 | 97 | 40 |
| 8 | 84 | 20 |
| 9 | 0 | 14 |
| 10 | 83 | 0 |
| 11 | 91 | 0 |
| 12 | 75 | 0 |
| 13 | 17 | 0 |
| 15 | 60 | 0 |
| 16 | 76 | 0 |
| 18 | 95 | 0 |
| 19 | 88 | 0 |
| 20 | 41 | 0 |
| 21 | 21 | 4 |
| 23 | 15 | 0 |
| 24 | 96 | 15 |
| 25 | 75 | 0 |
| 26 | 89 | 0 |
| 28 | 38 | 0 |
| 29 | 40 | 0 |
| 30 | 79 | 0 |
| 31 | 89 | 0 |
| 32 | 57 | 0 |
| 33 | 69 | 0 |
| 34 | 81 | 58 |
| 36 | 90 | 19 |
| 37 | 45 | 26 |
| 39 | 46 | 17 |
| 40 | 6 | 3 |
| 41 | 12 | 22 |
| 42 | 57 | 0 |
| 43 | 36 | 14 |
| 44 | 22 | 6 |
| 45 | 94 | 57 |
| 48 | 90 | 21 |
| 49 | 93 | 48 |

Example-P3: Determination of Anti Proliferative Activity of Compounds by Cell Titer Glo®(Promega) Assay Cells were seeded into 96-well plates and the plate was incubated in 37 degrees incubator overnight. The next day, compounds were diluted 3-fold to cover 9-point concentration range in DMSO. Intermediate plate dilution was prepared in media followed with compound treatment in cells. Retreatment of cells with compound dilutions was performed on Day 4 and assay was terminated on day 8 for SK-MEL-5 cells using CellTiter-Glo and the plate was kept on orbital shaker for 20 minutes at RT. Assay was terminated on day 6 for RERF-LC-A1 without a compound retreatment. Luminescence signal was recorded on VICTOR$^3$ instrument. Percent inhibition of proliferation was calculated at each concentration and plotted against the compound concentration. $EC_{50}$ value was calculated using GraphPad software.

Selected compounds of the present invention were screened in the above-mentioned assay procedures for determination of $EC_{50}$ (SK-MEL-5) values and the results are summarized into groups A, B and C in below table. Herein the group "A" refers to $EC_{50}$ values lower than 250 nM, "B" refers to $EC_{50}$ values between 250.01 nM-500 nM (both inclusive) and "C" refers to $EC_{50}$ values greater than 500 nM.

| Group | Compounds |
|---|---|
| A | 2, 5, 6, 11, 16, 18, 24, 30, 36 and 45. |
| B | 10, 20, 25, 28 and 31. |
| C | 12, 13, 14, 15, 17, 21, 22, 23, 27, 29 and 32. |

Further, RERF-LC-A1 cell line data for selected compounds of the present invention are summarized in table below. Herein the group "++" refers to $EC_{50}$ (RERF-LC-A1) values lower than 100 nM and "+" refers to $EC_{50}$ (RERF-LC-A1) values greater than 100 nM.

| Group | Compounds |
|---|---|
| ++ | 2, 6, 10, 11, 12, 14, and 24 |
| + | 5 and 42 |

We claim:

1. A compound of formula (I):

(I)

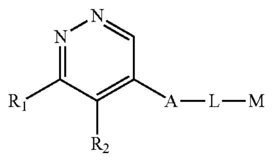

or a pharmaceutically acceptable salt or a stereoisomer or a tautomer thereof;

wherein

A is 5- to 6-membered heteroarylenyl or 6-membered arylenyl; wherein the arylenyl and heteroarylenyl are substituted with 1, 2 or 3 Ra substituents;

Ra is hydrogen, hydroxy, hydroxy($C_1$-$C_6$)alkyl, halogen, ($C_1$-$C_6$)alkoxy, ($C_1$-$C_6$)alkyl, halo($C_1$-$C_6$)alkyl, halo ($C_1$-$C_6$)alkoxy, amino, ($C_1$-$C_6$)alkylamino or cyano;

$R_1$ is halogen, ($C_1$-$C_6$)alkyl, halo($C_1$-$C_6$)alkyl, ($C_2$-$C_6$) alkenyl, ($C_1$-$C_6$)alkoxy, hydroxy, hydroxy($C_1$-$C_6$)alkyl, —COORb, —CON(Rb)$_2$, 6- to 10-membered aryl or 5- to 10-membered heteroaryl; wherein the aryl and heteroaryl are optionally substituted with 1, 2 or 3 groups that independently are hydroxy, ($C_1$-$C_6$)alkoxy, halogen, alkyl, haloalkyl, amino, —ONa, —COORc and —OCORc;

Rb and Rc independently are hydrogen, $(C_1-C_6)$alkyl or amino$(C_1-C_6)$alkyl;

$R_2$ is hydrogen, hydroxy, hydroxy$(C_1-C_6)$alkyl, halogen, $(C_1$-Celalkoxy, $(C_1-C_6)$alkyl, halo$(C_1-C_6)$alkyl or cyano;

L is —O—$(CH_2)$p-, —O—$(CH_2)$p-O—, —NRx-$(CH_2)$p-, —NRx-$(CH_2)$p-O—, —NRx-(3- to 10-membered heterocycloalkylenyl)-(CRxRy)n-, -(3- to 10-membered cycloalkylenyl)-(CRxRy)n-, -(3- to 10-membered heterocycloalkylenyl)-(CRxRy)n- or —O-(3- to 10-membered heterocycloalkylenyl)-(CRxRy)n-; wherein the cycloalkylenyl and heterocycloalkylenyl are substituted with 1, 2 or 3 Rd substituents;

Rd, at each occurrence, is independently selected from hydrogen, hydroxy, halogen, $(C_1-C_6)$alkoxy, $(C_1-C_6)$alkyl, halo$(C_1-C_6)$alkyl, amino, $(C_1-C_6)$alkylamino and cyano;

Rx and Ry, at each occurrence, are independently selected from hydrogen, $(C_1-C_6)$alkyl and halogen;

M is M-1 or M-2:

M-1

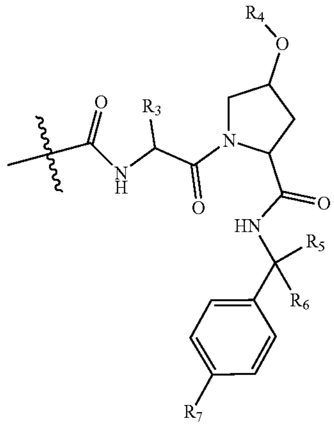

or

M-2

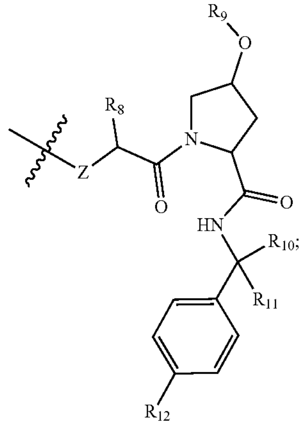

wherein,

Z is 5- to 6-membered heteroarylenyl optionally substituted with 1, 2 or 3 groups independently selected from hydroxy, halogen, $(C_1-C_6)$alkyl, halo$(C_1-C_6)$alkyl, hydroxy$(C_1-C_6)$alkyl, amino$(C_1-C_6)$alkyl and amino$(C_2-C_6)$alkynyl; wherein the aminoalkyl and amino$(C_2-C_6)$alkynyl are optionally substituted with 1 or 2 substituents selected from $(C_1-C_6)$alkyl and —$COCH_3$;

$R_3$ and $R_8$ independently are $(C_1-C_6)$alkyl, $(C_1-C_6)$acyl, halo$(C_1-C_6)$alkyl, hydroxy$(C_1-C_6)$alkyl or amino$(C_1-C_6)$alkyl;

$R_4$ and $R_9$ independently are hydrogen, $(C_1-C_6)$alkyl, hetero$(C_1-C_6)$alkyl, halo$(C_1-C_6)$alkyl, hydroxy$(C_1-C_6)$alkyl, amino$(C_1-C_6)$alkyl, —CO-amino$(C_1-C_6)$alkyl or $(C_1-C_6)$acyl;

wherein the alkyl is optionally substituted with —OCOR' or —OP(O)(OR")$_2$;

R' and R" are independently selected from hydrogen and $(C_1-C_6)$alkyl;

$R_5$, $R_6$, $R_{10}$ and $R_{11}$ independently are hydrogen, $(C_1-C_6)$alkyl, halogen, halo$(C_1-C_6)$alkyl, hydroxy$(C_1-C_6)$alkyl, amino$(C_1-C_6)$alkyl-, —CONRuRv, $(C_1-C_6)$acyl, and —$(C_1-C_6)$alkyl-heterocycloalkyl; wherein the aminoalkyl and heterocycloalkyl are optionally substituted with 1 or 2 substituents selected from $(C_1-C_6)$alkyl and —$COCH_3$; or $R_5$ and $R_6$ together combined with the C atom to which they are attached form a 4- to 6-membered heterocycloalkyl optionally substituted with $(C_1-C_6)$alkyl or —$COCH_3$; or $R_{10}$ and $R_{11}$ together combined with the C atom to which they are attached form a 4- to 6-membered heterocycloalkyl optionally substituted with $(C_1-C_6)$alkyl or —$COCH_3$;

Ru and Rv independently are hydrogen, alkyl, 4- to 6-membered cycloalkyl or 6-membered aryl;

$R_7$ and $R_{12}$ are thiazolyl substituted with $(C_1-C_6)$alkyl, hydroxy, amino or halo$(C_1-C_6)$alkyl;

p is an integer selected from 1, 2, 3 and 4; and n is an integer selected from 0, 1, 2 and 3.

2. The compound of claim 1, wherein $R_1$ is halogen, $(C_1-C_6)$alkyl, halo$(C_1-C_6)$alkyl, $(C_1-C_6)$alkoxy, hydroxy, hydroxy$(C_1-C_6)$alkyl, 6- to 10-membered aryl or 5- to 10-membered heteroaryl; wherein the aryl and heteroaryl are optionally substituted with 1, 2 or 3 groups independently selected from hydroxy, $(C_1-C_6)$alkoxy, halogen, $(C_1-C_6)$alkyl, halo$(C_1-C_6)$alkyl and amino.

3. The compound of claim 1, wherein A is phenylenyl or 5- to 6-membered heteroarylenyl each substituted with 1 or 2 Ra substituents.

4. The compound of claim 1, wherein A is phenylenyl, furanylenyl, thienylenyl, pyrrolylenyl, imidazolylenyl, oxazolylenyl, isoxazolylenyl, thiazolylenyl, isothiazolylenyl, 1H-tetrazolylenyl, oxadiazolylenyl, triazolylenyl, pyrazolylenyl, pyridylenyl, pyrimidinylenyl, pyrazinylenyl, pyridazinylenyl, 1,2,3-triazinylenyl, 1,2,4-triazinylenyl, or 1,3,5-triazinylenyl; wherein each group is substituted with 1 or 2 substituents that are hydrogen, hydroxy, hydroxy$(C_1-C_6)$alkyl, halogen, $(C_1-C_6)$alkoxy, $(C_1-C_6)$alkyl, halo$(C_1-C_6)$alkyl, halo$(C_1-C_6)$alkoxy, amino, $(C_1-C_6)$alkylamino or cyano.

5. The compound of claim 1, wherein L is —O—$(CH_2)$p-, —O—$(CH_2)$p-O—, —NRx-$(CH_2)$p-, —NRx-$(CH_2)$p-O—, —NRx-(3- to 10-membered heterocycloalkylenyl)-(CRxRy)n-, (3- to 10-membered cycloalkylenyl)-(CRxRy)n-, (3- to 10-membered heterocycloalkylenyl)-(CRxRy)n or —O-(3- to 10-membered heterocycloalkylenyl)-(CRxRy)n-; wherein the 3- to 10-membered cycloalkylenyl and the 3- to 10-membered heterocycloalkylenyl are substituted with 1 or 2 Rd substituents.

6. The compound of claim 5, wherein L is, —O—$CH_2$—, —O—$CH_2CH_2$—, —O—$CH_2CH_2CH_2$—, —O—$CH_2CH_2CH_2CH_2$—, —O—$CH_2$O—, —O—$CH_2CH_2$—O—, —O—$CH_2CH_2CH_2$—O—, —O—$CH_2CH_2CH_2CH_2$—O—, —NH—$CH_2$—, —NH—$CH_2CH_2$—, —NH—$CH_2CH_2CH_2$—, —NH—$CH_2CH_2CH_2CH_2$—, —$N(CH_3)$—$CH_2$—, —$N(CH_3)$—$CH_2CH_2$—, —$N(CH_3)$—$CH_2CH_2CH_2$—, —$N(CH_3)$—$CH_2CH_2CH_2CH_2$—, —NH—$CH_2$—O—, —NH—

$CH_2CH_2$—O—, —NH—$CH_2CH_2CH_2$—O—, —NH—$CH_2CH_2CH_2CH_2$—O—, —N($CH_3$)—$CH_2$—O—, —N($CH_3$)—$CH_2CH_2$—O—, —N($CH_3$)—$CH_2CH_2CH_2$—O— or —N($CH_3$)—$CH_2CH_2CH_2CH_2$—O—, —NRx-(3- to 10-membered heterocycloalkylenyl)-(CRxRy)n-, (3- to 10-membered heterocycloalkylenyl)-(CRxRy)n or —O-(3- to 10-membered heterocycloalkylenyl)-(CRxRy)n-heterocycloalkylenyl; wherein the heterocycloalkylenyl is piperidinylenyl, piperazinylenyl, azetidinylenyl, pyrolidinylenyl, tetrahydropyridinylenyl, diazobicyclooctanylenyl, azabicyclooctanylenyl, azaspiroheptanylenyl, tetrahydropyranyl, tetrahydropyridazinylenyl, morpholinylenyl, thiomorpholinylenyl, 1,4-dioxanylenyl, dioxidothiomorpholinylenyl, oxapiperazinylenyl, oxapiperidinylenyl, tetrahydropyranylenyl, dihydropyranylenyl or dihydropyrimidinylenyl; or (3- to 10-membered cycloalkylenyl)-(CRxRv)n-; wherein the cycloalkylenyl is cyclopropylenyl, cyclobutylenyl, cyclopentylenyl, cyclohexylenyl or cycloheptylenyl.

7. The compound of claim 1, wherein M is M-1; wherein $R_3$ is ($C_1$-$C_6$)alkyl, halo($C_1$-$C_6$)alkyl or hydroxy($C_1$-$C_6$)alkyl;

$R_4$ is hydrogen, ($C_1$-$C_6$)alkyl, hetero($C_1$-$C_6$)alkyl, halo($C_1$-$C_6$)alkyl, hydroxy($C_1$-$C_6$)alkyl or ($C_1$-$C_6$)acyl;

$R_5$ and $R_6$ independently are hydrogen, ($C_1$-$C_6$)alkyl, halogen, halo($C_1$-$C_6$)alkyl, hydroxy($C_1$-$C_6$)alkyl or (($C_1$-$C_6$)alkyl)aminoalkyl-; and $R_7$ is thiazolyl substituted with ($C_1$-$C_6$)alkyl.

8. The compound of claim 1, wherein M is M-2; wherein

Z is oxazolylenyl or isoxazolylenyl;

$R_8$ is ($C_1$-$C_6$)alkyl, halo($C_1$-$C_6$)alkyl or hydroxy($C_1$-$C_6$)alkyl;

$R_9$ is hydrogen, ($C_1$-$C_6$)alkyl, halo($C_1$-$C_6$)alkyl, hydroxy($C_1$-$C_6$)alkyl or ($C_1$-$C_6$)acyl;

$R_{10}$ and $R_{11}$ independently are hydrogen, ($C_1$-$C_6$) alkyl, halogen, halo($C_1$-$C_6$)alkyl, hydroxy($C_1$-$C_6$)alkyl or (($C_1$-$C_6$)alkyl)aminoalkyl-; and $R_{12}$ is thiazolyl substituted with ($C_1$-$C_6$)alkyl.

9. The compound of claim 1, wherein the compound is of formula (IA):

(IA)

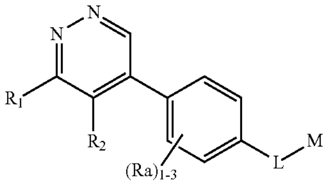

10. The compound of claim 9, wherein $R_1$ is halogen, hydroxy, 6- to 10-membered aryl or 5- to 10-membered heteroaryl; wherein the aryl and the heteroaryl are each optionally substituted with 1 or 2 groups independently selected from ($C_1$-$C_6$)alkyl, hydroxy, ($C_1$-$C_6$)alkoxy, halogen and halo($C_1$-$C_6$)alkyl.

11. The compound of claim 9, wherein L is —O—($CH_2$)p-, —O—($CH_2$)p-O—, —NRx-($CH_2$)p-, —NRx-($CH_2$)p-O—, —NRx-(3- to 10-membered heterocycloalkylenyl)-(CRxRy)n-, (3- to 10-membered cycloalkylenyl)-(CRxRy)n-, (3- to 10-membered heterocycloalkylenyl)-(CRxRy)n or —O-(3- to 10-membered heterocycloalkylenyl)-(CRxRy)n-.

12. The compound of claim 9, wherein M is

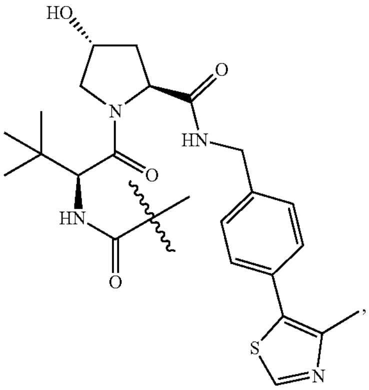

,

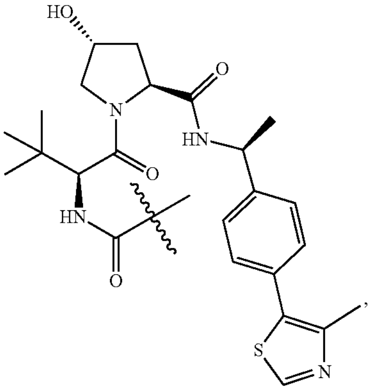

,

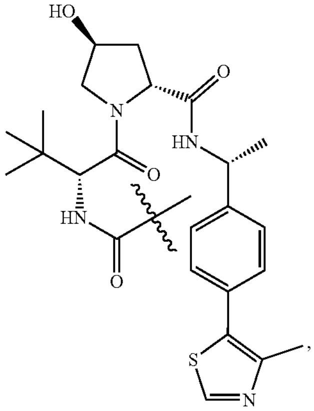

,

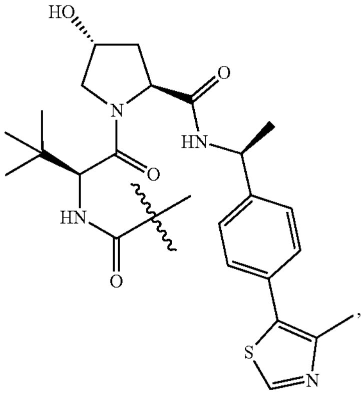

,

-continued

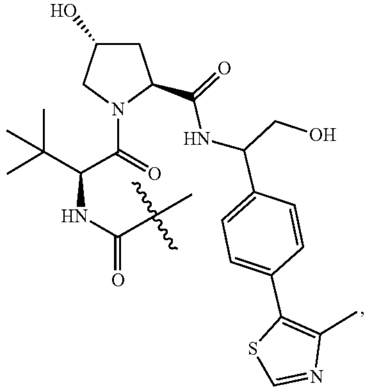

,

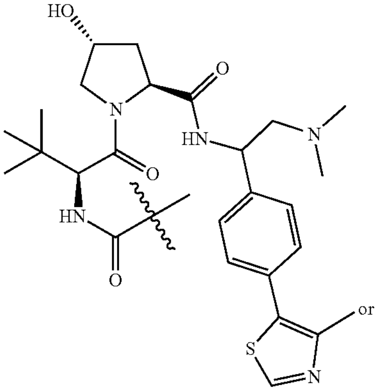

or

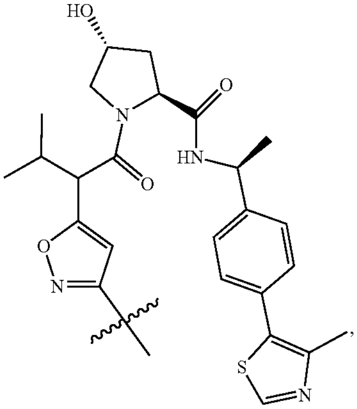

,

13. The compound of claim 9, wherein $R_1$ is —Cl, —OH,

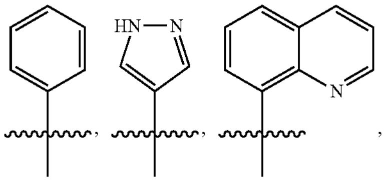

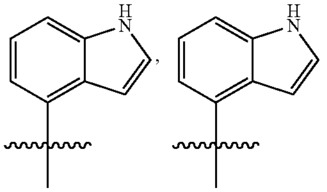

or

-continued

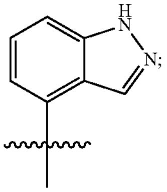

wherein each ring is optionally substituted with 1, 2 or 3 groups independently selected from $(C_1-C_6)$alkyl, hydroxy, $(C_1-C_6)$alkoxy, halogen and halo$(C_1-C_6)$alkyl;

$R_2$ is hydrogen or halogen;

Ra is hydrogen or halogen;

L is $—O—CH_2CH_2CH_2—$, $—O—CH_2CH_2CH_2CH_2—$, $—O—CH_2CH_2—O—$, $—O—CH_2CH_2CH_2—O—$, $—NH—CH_2CH_2CH_2CH_2—$, $—N(CH_3)—CH_2CH_2—O—$, $—N(CH_3)—CH_2CH_2CH_2CH_2—$, $—NH—CH_2CH_2—O—$

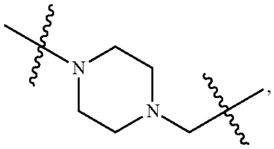

,

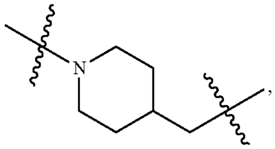

,

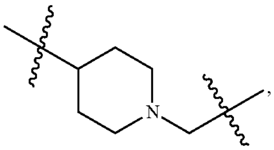

,

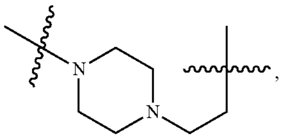

,

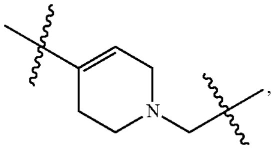

,

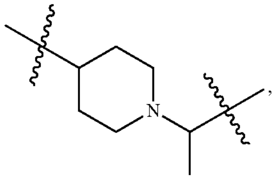

,

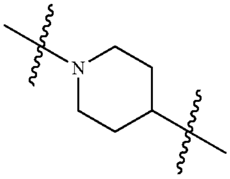

,

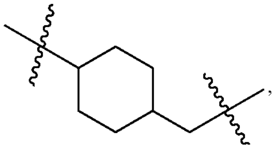

,

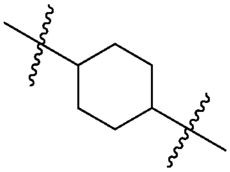

,

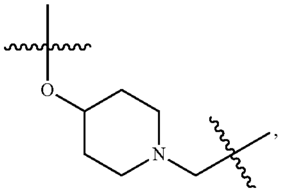

,

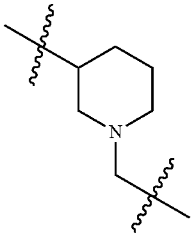

,

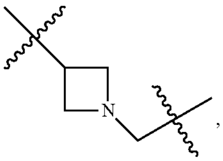

,

-continued
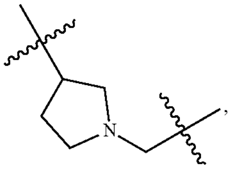,
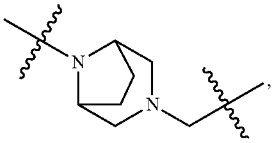,
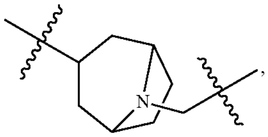,
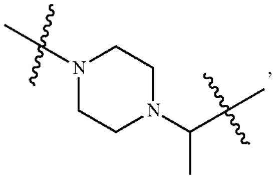,
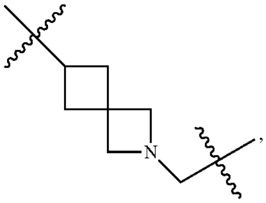,
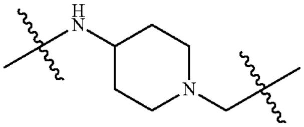
or
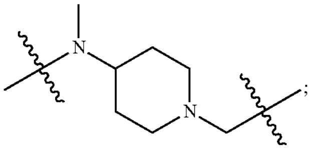;
wherein each ring is substituted with 1 or 2 Rd substituents;
M represents
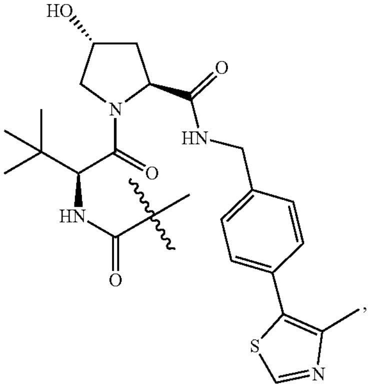,
-continued
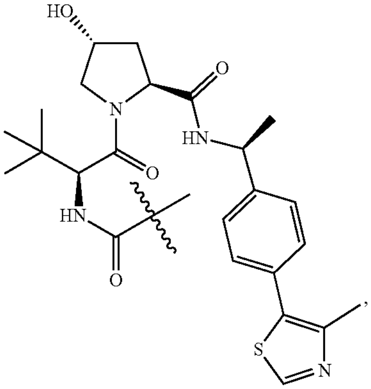,
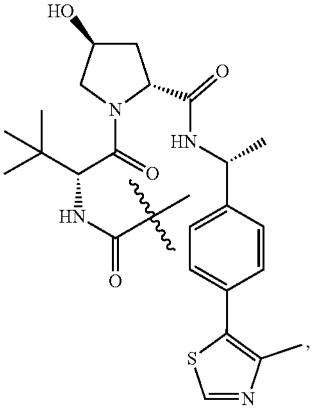,
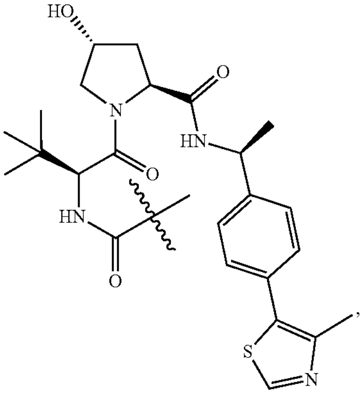,
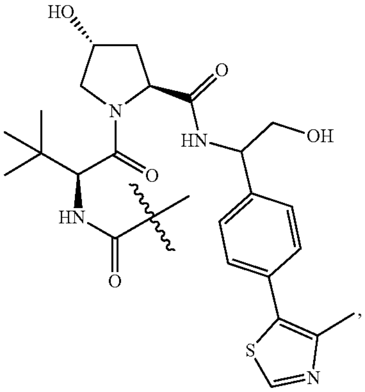, -continued

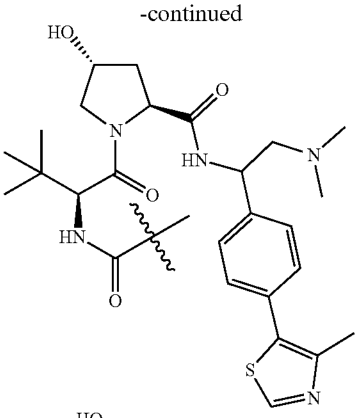

or

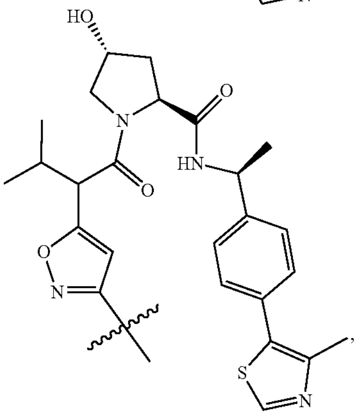

14. The compound of claim 1, wherein the compound is of formula (IB):

(IB)

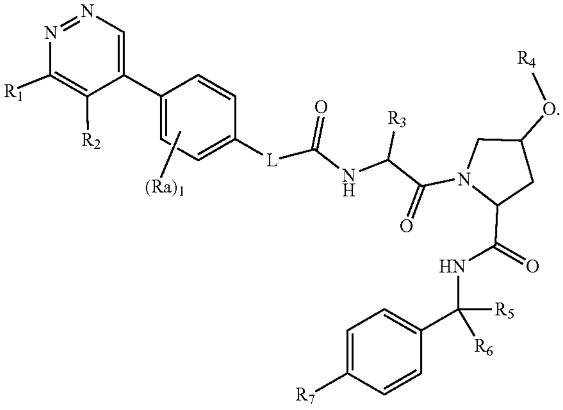

15. The compound of claim 14, wherein $R_1$ is —Cl, —OH,

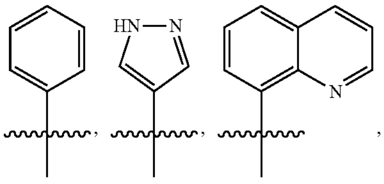

,

-continued

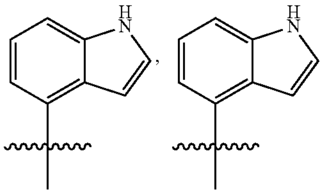

or

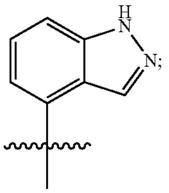

wherein each ring is optionally substituted with 1 or 2 groups independently selected from $(C_1-C_6)$alkyl, hydroxy and halogen.

16. The compound of claim 14, wherein L is —O—$(CH_2)$p-, —O—$(CH_2)$p-O—, —NRx-$(CH_2)$p-, —NRx-$(CH_2)$p-O—, —NRx-(3- to 10-membered heterocycloalkylenyl)-(CRxRy)n-, (3- to 10-membered cycloalkylenyl)-(CRxRy)n-, (3- to 10-membered heterocycloalkylenyl)-(CRxRy)n or —O-(3- to 10-membered heterocycloalkylenyl)-(CRxRy)n-.

17. The compound of claim 14, wherein $R_1$ is —Cl, —OH,

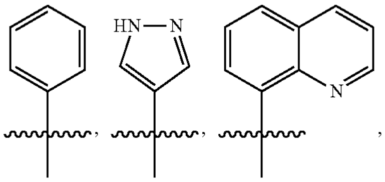

,

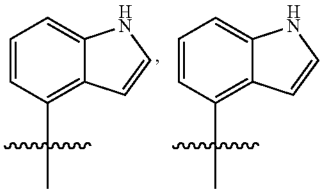

or

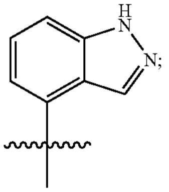

wherein each ring is optionally substituted with 1 or 2 groups independently selected from alkyl, hydroxy and halogen;

$R_2$ is hydrogen or halogen;

Ra is hydrogen or halogen;

L is —O—$CH_2CH_2CH_2$—, —O—$CH_2CH_2CH_2CH_2$—, —O—$CH_2CH_2$—O—, —O—$CH_2CH_2CH_2$—O—, —NH—$CH_2CH_2CH_2CH_2$—, —$N(CH_3)$—$CH_2CH_2$—O—, —$N(CH_3)$—$CH_2CH_2CH_2CH_2$—, —NH—$CH_2CH_2$—O—

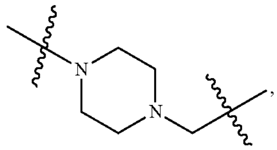,
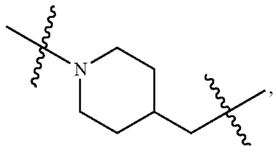,
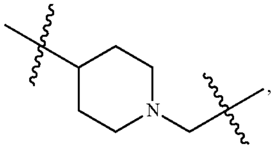,
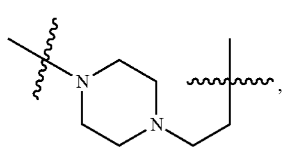,
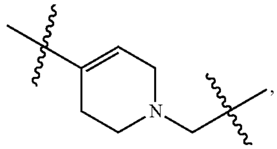,
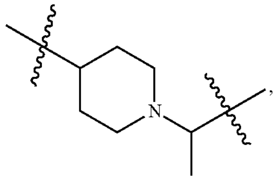,
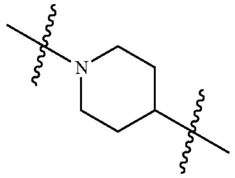,
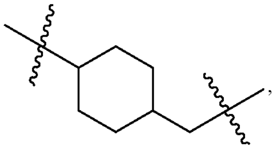,
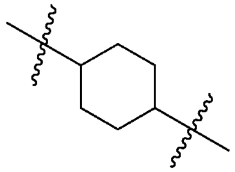,
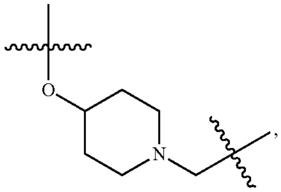,
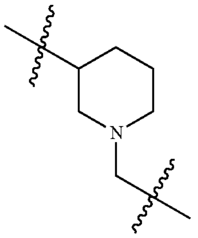,
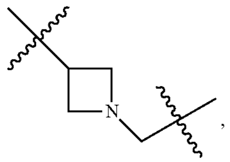,
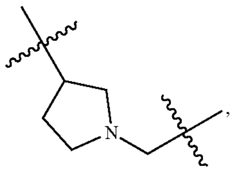,
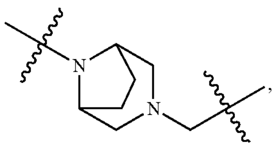,
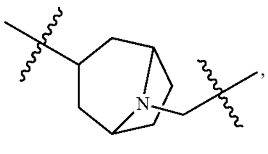,
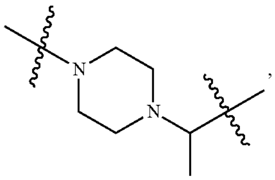,
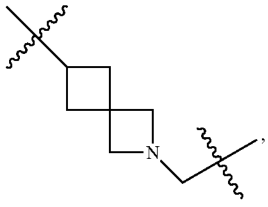, -continued

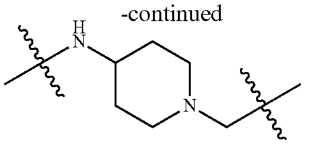
or
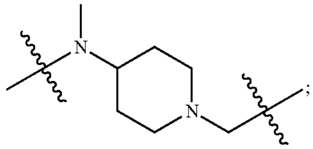;

wherein each ring is substituted with 1 or 2 Rd substituents;

$R_3$ is $(C_1\text{-}C_6)$alkyl;

$R_4$ is hydrogen or $(C_1\text{-}C_6)$alkyl;

$R_5$ is hydrogen;

$R_6$ is $(C_1\text{-}C_6)$alkyl, halogen, halo$(C_1\text{-}C_6)$alkyl, hydroxy $(C_1\text{-}C_6)$alkyl or $((C_1\text{-}C_6)$alkyl)amino$(C_1\text{-}C_6)$alkyl-; and $R_7$ is thiazolyl substituted with $(C_1\text{-}C_6)$alkyl.

18. The compound of claim 1, wherein the compound is of formula (IC):

(IC)

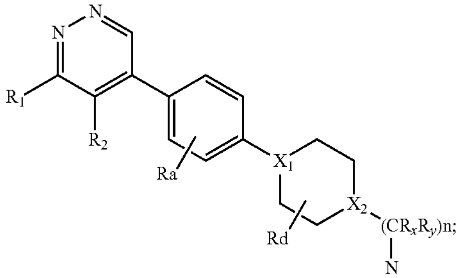;

wherein $X_1$ and $X_2$ independently are N or C.

19. The compound of claim 6, wherein $X_1$ and $X_2$ independently are N or C;

$R_1$ is —Cl, —OH,

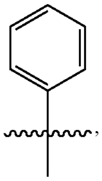, 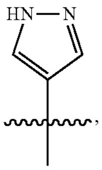, 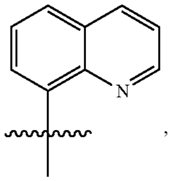,
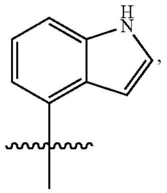, 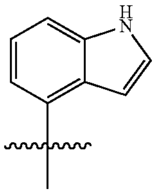 or
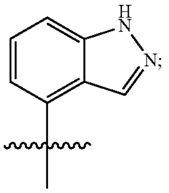;

wherein each ring is optionally substituted with 1 or 2 groups independently selected from $(C_1\text{-}C_6)$alkyl, hydroxy and halogen;
$R_2$ is hydrogen or halogen;
Ra is hydrogen or halogen;
Rd is hydrogen or hydroxy;
Rx is hydrogen;
Ry is hydrogen or $(C_1\text{-}C_6)$alkyl;
M is
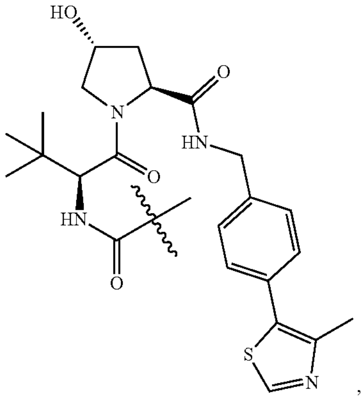
,
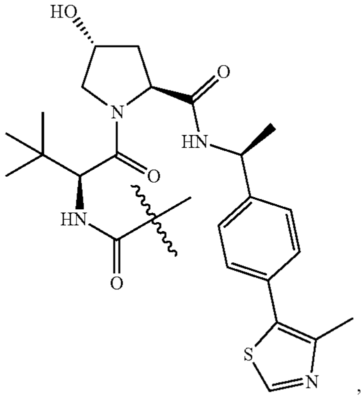
,
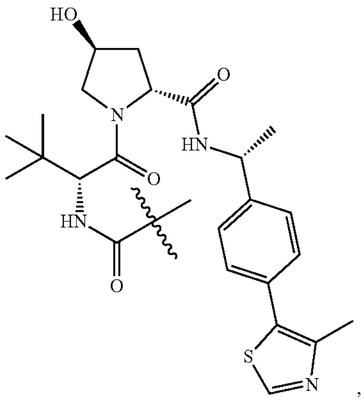
,
-continued
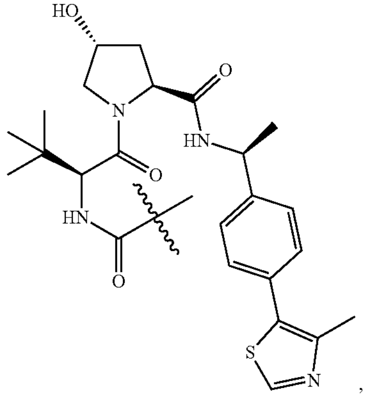
,
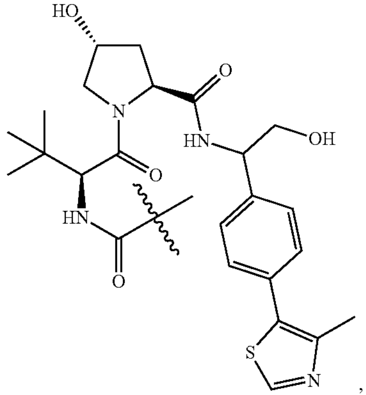
,
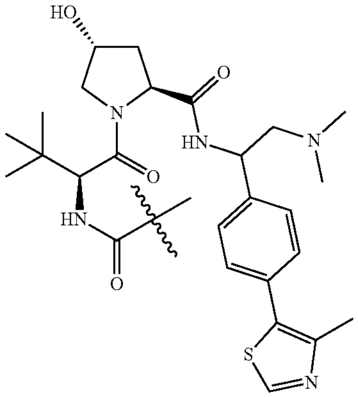
or
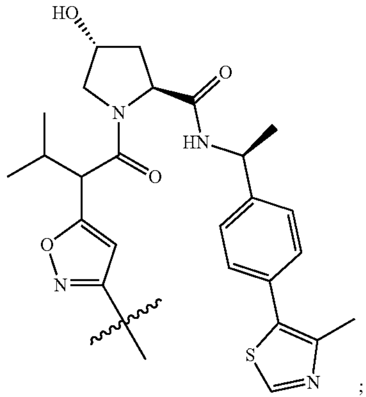
;
n is 0, 1, 2 or 3.
20. The compound of claim 1, wherein the compound is of formula (ID)

(ID)

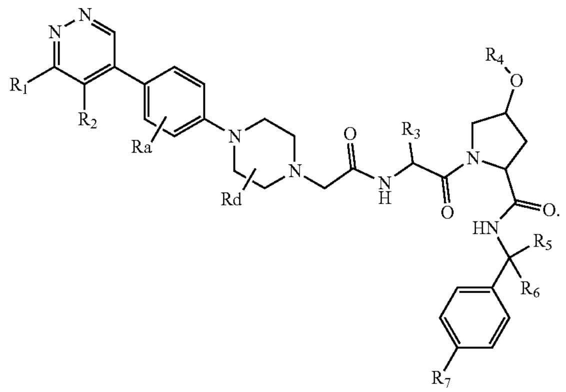

21. The compound of claim 20, wherein $R_1$ is halogen, hydroxy, 6- to 10-membered aryl or 5- to 10-membered heteroaryl; wherein, the aryl and heteroaryl are optionally substituted with hydroxy, halogen, Q-$C_6$)alkyl or halo($C_1$-$C_6$)alkyl;

$R_2$ is hydrogen or halogen;

Ra is hydrogen or halogen;

Rd is hydrogen or hydroxy;

$R_3$ is ($C_1$-$C_6$)alkyl, ($C_1$-$C_6$)acyl or halo($C_1$-$C_6$)alkyl;

$R_4$ is hydrogen or ($C_1$-$C_6$)alkyl;

$R_5$ is hydrogen;

$R_6$ is hydrogen, ($C_1$-$C_6$)alkyl, halogen, hydroxy($C_1$-$C_6$)alkyl or (($C_1$-$C_3$)alkyl)amino($C_1$-$C_6$)alkyl-;

$R_7$ is thiazolyl substituted with ($C_1$-$C_6$)alkyl; and n is 0, 1, 2 or 3.

22. A compound, that is selected from

| Compound | IUPAC |
|---|---|
| 1 | (2S,4R)-4-hydroxy-1-(2-(3-(4-(6-(2-hydroxyphenyl)pyridazin-4-yl)phenyl)isoxazol-5-yl)-3-methylbutanoyl)-N-((S)-1-(4-(4-methylthiazol-5-yl)phenyl)ethyl)pyrrolidine-2-carboxamide; |
| 2 | (2S,4R)-4-hydroxy-1-((S)-2-(2-(4-(4-(6-(2-hydroxyphenyl)pyridazin-4-yl)phenyl)piperazin-1-yl)acetamido)-3,3-dimethylbutanoyl)-N-((S)-1-(4-(4-methylthiazol-5-yl)phenyl)ethyl)pyrrolidine-2-carboxamide; |
| 3 | (2S,4R)-1-((S)-2-(2-(4-(4-(6-chloropyridazin-4-yl)phenyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide; |
| 4 | (2S,4R)-1-((S)-2-(2-(4-(4-(6-(5-fluoro-2-hydroxyphenyl)pyridazin-4-yl)phenyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide; |
| 5 | (2S,4R)-4-hydroxy-1-((S)-2-(2-(4-(5-(6-(2-hydroxyphenyl)pyridazin-4-yl)pyridin-2-yl)piperazin-1-yl)acetamido)-3,3-dimethylbutanoyl)-N-((S)-1-(4-(4-methylthiazol-5-yl)phenyl)ethyl)pyrrolidine-2-carboxamide; |
| 6 | (2S,4R)-4-hydroxy-1-((S)-2-(2-(1-(4-(6-(2-hydroxyphenyl)pyridazin-4-yl)phenyl)piperidin-4-yl)acetamido)-3,3-dimethylbutanoyl)-N-((S)-1-(4-(4-methylthiazol-5-yl)phenyl)ethyl)pyrrolidine-2-carboxamide; |
| 7 | (2S,4R)-1-((S)-2-(2-(4-(4-(6-(2-fluorophenyl)pyridazin-4-yl)phenyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide; |
| 8 | (2S,4R)-4-hydroxy-1-((S)-2-(3-(4-(4-(6-(2-hydroxyphenyl)pyridazin-4-yl)phenyl)piperazin-1-yl)propanamido)-3,3-dimethylbutanoyl)-N-((S)-1-(4-(4-methylthiazol-5-yl)phenyl)ethyl)pyrrolidine-2-carboxamide; |
| 9 | (2S,4R)-1-((S)-3,3-dimethyl-2-(2-(4-(4-(6-(1-methyl-1H-pyrazol-4-yl)pyridazin-4-yl)phenyl)piperazin-1-yl)acetamido)butanoyl)-4-hydroxy-N-((S)-1-(4-(4-methylthiazol-5-yl)phenyl)ethyl)pyrrolidine-2-carboxamide; |
| 10 | (2S,4R)-4-hydroxy-1-((S)-2-(2-(4-(4-(6-(2-hydroxyphenyl)pyridazin-4-yl)phenyl)-3,6-dihydropyridin-1(2H)-yl)acetamido)-3,3-dimethylbutanoyl)-N-((S)-1-(4-(4-methylthiazol-5-yl)phenyl)ethyl)pyrrolidine-2-carboxamide; |
| 11 | (2S,4R)-4-hydroxy-1-((S)-2-(2-(4-(4-(6-(2-hydroxyphenyl)pyridazin-4-yl)phenyl)piperidin-1-yl)acetamido)-3,3-dimethylbutanoyl)-N-((S)-1-(4-(4-methylthiazol-5-yl)phenyl)ethyl)pyrrolidine-2-carboxamide; |
| 12 | (2S,4R)-4-hydroxy-1-((S)-2-(2-(4-(4-(6-(2-hydroxyphenyl)pyridazin-4-yl)phenyl)piperidin-1-yl)acetamido)-3,3-dimethylbutanoyl)-N-(4-(4-methylthiazol-5-yl)benzyl)pyrrolidine-2-carboxamide; |
| 13 | (2S,4R)-1-((S)-2-(2-(4-(4-(6-(5-fluoro-2-hydroxyphenyl)pyridazin-4-yl)phenyl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide; |
| 14 | (2S,4R)-4-hydroxy-1-((2S)-2-(2-(4-(4-(6-(2-hydroxyphenyl)pyridazin-4-yl)phenyl)piperidin-1-yl)propanamido)-3,3-dimethylbutanoyl)-N-((S)-1-(4-(4-methylthiazol-5-yl)phenyl)ethyl)pyrrolidine-2-carboxamide; |
| 15 | (2S,4R)-1-((S)-2-(2-(4-(2-fluoro-4-(6-(2-hydroxyphenyl)pyridazin-4-yl)phenyl)piperidin-1-yl)acetamido)-3,3-dimethylbutanoyl)-4-hydroxy-N-((S)-1-(4-(4-methylthiazol-5-yl)phenyl)ethyl)pyrrolidine-2-carboxamide; |

-continued

| Compound | IUPAC |
|---|---|
| 16 | N-((S)-1-((2S,4R)-4-hydroxy-2-(((S)-1-(4-(4-methylthiazol-5-yl)phenyl)ethyl)carbamoyl)pyrrolidin-1-yl)-3,3-dimethyl-1-oxobutan-2-yl)-1-(4-(6-(2-hydroxyphenyl)pyridazin-4-yl)phenyl)piperidine-4-carboxamide; |
| 17 | (2S,4R)-4-hydroxy-1-((S)-2-(2-(4-(4-(6-(2-hydroxyphenyl)pyridazin-4-yl)phenyl)cyclohexyl)acetamido)-3,3-dimethylbutanoyl)-N-((S)-1-(4-(4-methylthiazol-5-yl)phenyl)ethyl)pyrrolidine-2-carboxamide; |
| 18 | (2S,4R)-4-hydroxy-1-((S)-2-(4-(4-(6-(2-hydroxyphenyl)pyridazin-4-yl)phenyl)cyclohexane-1-carboxamido)-3,3-dimethylbutanoyl)-N-((S)-1-(4-(4-methylthiazol-5-yl)phenyl)ethyl)pyrrolidine-2-carboxamide; |
| 19 | (2S,4R)-4-hydroxy-1-((S)-2-(2-(4-(4-(6-(2-hydroxyphenyl)pyridazin-4-yl)phenoxy)piperidin-1-yl)acetamido)-3,3-dimethylbutanoyl)-N-((S)-1-(4-(4-methylthiazol-5-yl)phenyl)ethyl)pyrrolidine-2-carboxamide; |
| 20 | (2S,4R)-4-hydroxy-1-((2S)-2-(2-(3-(4-(6-(2-hydroxyphenyl)pyridazin-4-yl)phenyl)piperidin-1-yl)acetamido)-3,3-dimethylbutanoyl)-N-((S)-1-(4-(4-methylthiazol-5-yl)phenyl)ethyl)pyrrolidine-2-carboxamide; |
| 21 | (2S,4R)-4-hydroxy-1-((S)-2-(2-(3-(4-(6-(2-hydroxyphenyl)pyridazin-4-yl)phenyl)azetidin-1-yl)acetamido)-3,3-dimethylbutanoyl)-N-((S)-1-(4-(4-methylthiazol-5-yl)phenyl)ethyl)pyrrolidine-2-carboxamide; |
| 22 | (2S,4R)-4-hydroxy-1-((2S)-2-(2-(3-(4-(6-(2-hydroxyphenyl)pyridazin-4-yl)phenyl)pyrrolidin-1-yl)acetamido)-3,3-dimethylbutanoyl)-N-((S)-1-(4-(4-methylthiazol-5-yl)phenyl)ethyl)pyrrolidine-2-carboxamide; |
| 23 | (2S,4R)-4-hydroxy-1-((S)-2-(2-(4-(3-(6-(2-hydroxyphenyl)pyridazin-4-yl)phenyl)piperidin-1-yl)acetamido)-3,3-dimethylbutanoyl)-N-((S)-1-(4-(4-methylthiazol-5-yl)phenyl)ethyl)pyrrolidine-2-carboxamide; |
| 24 | (2S,4R)-4-hydroxy-1-((2S)-2-(2-(8-(4-(6-(2-hydroxyphenyl)pyridazin-4-yl)phenyl)-3,8-diazabicyclo[3.2.1]octan-3-yl)acetamido)-3,3-dimethylbutanoyl)-N-((S)-1-(4-(4-methylthiazol-5-yl)phenyl)ethyl)pyrrolidine-2-carboxamide; |
| 25 | (2S,4R)-4-hydroxy-1-((2S)-2-(2-(3-(4-(6-(2-hydroxyphenyl)pyridazin-4-yl)phenyl)-8-azabicyclo[3.2.1]octan-8-yl)acetamido)-3,3-dimethylbutanoyl)-N-((S)-1-(4-(4-methylthiazol-5-yl)phenyl)ethyl)pyrrolidine-2-carboxamide; |
| 26 | (2S,4R)-1-((S)-2-(2-(4-(2-fluoro-4-(6-(2-hydroxyphenyl)pyridazin-4-yl)phenyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide; |
| 27 | (2S,4R)-4-hydroxy-1-((S)-2-(2-(4-(5-(6-(2-hydroxyphenyl)pyridazin-4-yl)pyridin-2-yl)piperidin-1-yl)acetamido)-3,3-dimethylbutanoyl)-N-((S)-1-(4-(4-methylthiazol-5-yl)phenyl)ethyl)pyrrolidine-2-carboxamide; |
| 28 | 2S,4R)-4-hydroxy-1-((2S)-2-(2-(4-(4-(6-(2-hydroxyphenyl)pyridazin-4-yl)phenyl)piperazin-1-yl)propanamido)-3,3-dimethylbutanoyl)-N-((S)-1-(4-(4-methylthiazol-5-yl)phenyl)ethyl)pyrrolidine-2-carboxamide; |
| 29 (Isomer-1) | (2S,4R)-4-hydroxy-1-((2S)-2-(2-(4-(4-(6-(2-hydroxyphenyl)pyridazin-4-yl)phenyl)piperazin-1-yl)propanamido)-3,3-dimethylbutanoyl)-N-((S)-1-(4-(4-methylthiazol-5-yl)phenyl)ethyl)pyrrolidine-2-carboxamide; |
| 30 (Isomer-2) | (2S,4R)-4-hydroxy-1-((2S)-2-(2-(4-(4-(6-(2-hydroxyphenyl)pyridazin-4-yl)phenyl)piperazin-1-yl)propanamido)-3,3-dimethylbutanoyl)-N-((S)-1-(4-(4-methylthiazol-5-yl)phenyl)ethyl)pyrrolidine-2-carboxamide; |
| 31 | (2S,4R)-4-hydroxy-1-((S)-2-(2-(6-(4-(6-(2-hydroxyphenyl)pyridazin-4-yl)phenyl)-2-azaspiro[3.3]heptan-2-yl)acetamido)-3,3-dimethylbutanoyl)-N-((S)-1-(4-(4-methylthiazol-5-yl)phenyl)ethyl)pyrrolidine-2-carboxamide; |
| 32 | (2S,4R)-4-hydroxy-1-((S)-2-(2-(4-hydroxy-4-(4-(6-(2-hydroxyphenyl)pyridazin-4-yl)phenyl)piperidin-1-yl)acetamido)-3,3-dimethylbutanoyl)-N-((S)-1-(4-(4-methylthiazol-5-yl)phenyl)ethyl)pyrrolidine-2-carboxamide; |
| 33 | (2S,4R)-4-hydroxy-1-((S)-2-(2-(4-(4-(6-(2-hydroxyphenyl)pyridazin-4-yl)-1H-pyrazol-1-yl)piperidin-1-yl)acetamido)-3,3-dimethylbutanoyl)-N-((S)-1-(4-(4-methylthiazol-5-yl)phenyl)ethyl)pyrrolidine-2-carboxamide; |
| 34 | (2S,4R)-4-hydroxy-1-((S)-2-(5-(4-(6-(2-hydroxyphenyl)pyridazin-4-yl)phenoxy)pentanamido)-3,3-dimethylbutanoyl)-N-((S)-1-(4-(4-methylthiazol-5-yl)phenyl)ethyl)pyrrolidine-2-carboxamide; |
| 35 | (2S,4R)-4-hydroxy-1-((S)-2-(4-(4-(6-(2-hydroxyphenyl)pyridazin-4-yl)phenoxy)butanamido)-3,3-dimethylbutanoyl)-N-((S)-1-(4-(4-methylthiazol-5-yl)phenyl)ethyl)pyrrolidine-2-carboxamide; |
| 36 | (2S,4R)-4-hydroxy-1-((S)-2-(5-((4-(6-(2-hydroxyphenyl)pyridazin-4-yl)phenyl)amino)pentanamido)-3,3-dimethylbutanoyl)-N-((S)-1-(4-(4-methylthiazol-5-yl)phenyl)ethyl)pyrrolidine-2-carboxamide; |
| 37 | (2S,4R)-1-((S)-2-(2-(4-(4-(6-(2-(difluoromethyl)phenyl)pyridazin-4-yl)phenyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide; |

-continued

| Compound | IUPAC |
|---|---|
| 38 | (2S,4R)-1-((S)-3,3-dimethyl-2-(2-(4-(4-(6-(quinolin-8-yl)pyridazin-4-yl)phenyl)piperazin-1-yl)acetamido)butanoyl)-4-hydroxy-N-((S)-1-(4-(4-methylthiazol-5-yl)phenyl)ethyl)pyrrolidine-2-carboxamide; |
| 39 | (2S,4R)-1-((S)-2-(2-(4-(4-(6-(1H-indol-7-yl)pyridazin-4-yl)phenyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide; |
| 40 | (2S,4R)-1-((S)-2-(2-(4-(4-(6-(benzofuran-7-yl)pyridazin-4-yl)phenyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide; |
| 41 | (2S,4R)-1-((S)-2-(2-(4-(4-(6-(1H-indazol-7-yl)pyridazin-4-yl)phenyl)piperazin-1-yl)acetamido)-3,3-dimethylbutanoyl)-4-hydroxy-N-((S)-1-(4-(4-methylthiazol-5-yl)phenyl)ethyl)pyrrolidine-2-carboxamide; |
| 42 | (2S,4R)-4-hydroxy-1-(2-(3-(2-(4-(6-(2-hydroxyphenyl)pyridazin-4-yl)phenoxy)ethoxy)isoxazol-5-yl)-3-methylbutanoyl)-N-((S)-1-(4-(4-methylthiazol-5-yl)phenyl)ethyl)pyrrolidine-2-carboxamide; |
| 43 | (2S,4R)-4-hydroxy-1-(2-(3-(3-(4-(6-(2-hydroxyphenyl)pyridazin-4-yl)phenoxy)propoxy)isoxazol-5-yl)-3-methylbutanoyl)-N-((S)-1-(4-(4-methylthiazol-5-yl)phenyl)ethyl)pyrrolidine-2-carboxamide; |
| 44 | (2S,4R)-4-hydroxy-1-(2-(3-(2-((4-(6-(2-hydroxyphenyl)pyridazin-4-yl)phenyl)(methyl)amino)ethoxy)isoxazol-5-yl)-3-methylbutanoyl)-N-((S)-1-(4-(4-methylthiazol-5-yl)phenyl)ethyl)pyrrolidine-2-carboxamide; |
| 45 | (2S,4R)-4-hydroxy-1-((S)-2-(2-(4-((4-(6-(2-hydroxyphenyl)pyridazin-4-yl)phenyl)amino)piperidin-1-yl)acetamido)-3,3-dimethylbutanoyl)-N-((S)-1-(4-(4-methylthiazol-5-yl)phenyl)ethyl)pyrrolidine-2-carboxamide; |
| 46 | (2S,4R)-4-hydroxy-1-((S)-2-(2-(4-((4-(6-(2-hydroxyphenyl)pyridazin-4-yl)phenyl)(methyl)amino)piperidin-1-yl)acetamido)-3,3-dimethylbutanoyl)-N-((S)-1-(4-(4-methylthiazol-5-yl)phenyl)ethyl)pyrrolidine-2-carboxamide; |
| 47 | (2S,4R)-4-hydroxy-1-((S)-2-(2-(4-(4-(6-hydroxypyridazin-4-yl)phenyl)piperazin-1-yl)acetamido)-3,3-dimethylbutanoyl)-N-((S)-1-(4-(4-methylthiazol-5-yl)phenyl)ethyl)pyrrolidine-2-carboxamide; |
| 48 | (2S,4R)-4-hydroxy-N-((R)-2-hydroxy-1-(4-(4-methylthiazol-5-yl)phenyl)ethyl)-1-((S)-2-(2-(4-(4-(6-(2-hydroxyphenyl)pyridazin-4-yl)phenyl)piperazin-1-yl)acetamido)-3,3-dimethylbutanoyl)pyrrolidine-2-carboxamide; |
| 49 | (2S,4R)-N-(2-(dimethylamino)-1-(4-(4-methylthiazol-5-yl)phenyl)ethyl)-4-hydroxy-1-((S)-2-(2-(4-(4-(6-(2-hydroxyphenyl)pyridazin-4-yl)phenyl)piperazin-1-yl)acetamido)-3,3-dimethylbutanoyl)pyrrolidine-2-carboxamide; and |
| 50 | (2S,4R)-4-hydroxy-1-(2-(3-(2-((4-(6-(2-hydroxyphenyl)pyridazin-4-yl)phenyl)amino)ethoxy)isoxazol-5-yl)-3-methylbutanoyl)-N-((S)-1-(4-(4-methylthiazol-5-yl)phenyl)ethyl)pyrrolidine-2-carboxamide; |

or pharmaceutically acceptable salt or a stereoisomer or a tautomer thereof.

23. A pharmaceutical composition comprising the compound of claim 1 or a pharmaceutically acceptable salt or a stereoisomer or a tautomer thereof and a pharmaceutically acceptable carrier or excipient.

24. A method for degrading a target protein comprising administering to a subject a therapeutically effective amount of the compound of claim 1 or a pharmaceutically acceptable salt or a stereoisomer or a tautomer thereof, wherein the compound is effective for degrading the target protein, wherein the target protein is SMARCA2 or SMARCA4 or a combination thereof.

25. A method for treating or delaying progression of a cancer dependent upon at least one of SMARCA2 or SMARCA4 in a subject in need thereof comprising administering to the subject a therapeutically effective amount of the compound of claim 1.

26. The method of claim 25, wherein the cancer is hematologic cancers, non-small cell lung cancer, acoustic neuroma, acute leukemia, acute lymphocytic leukemia, acute myelocytic leukemia, adenocarcinoma, angiosarcoma, astrocytoma, acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, diffuse large B-cell lymphoma, dysproliferative changes, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, head and neck cancer, hemangioblastoma, hepatoma, hepatocellular cancer, hormone insensitive prostate cancer, leiomyosarcoma, leukemia, liposarcoma, liver cancer, lymphagioendotheliosarcoma, lymphangiosarcoma, lymphoblastic leukemia, lymphoma, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, malignant rhabdoid tumor (MRT), rhabdomyosarcoma, sarcoma, sebaceous gland carcinoma, seminoma, skin cancer, small cell lung carcinoma, small cell lung cancer, stomach cancer, squamous cell carcinoma, synovioma, sweat gland carcinoma, thyroid cancer, Waldenstrom's macroglobulinemia, testicular tumors, uterine cancer or Wilms' tumor.

27. A method for inhibiting tumor growth in a subject afflicted with cancer in need thereof comprising administering to the subject a therapeutically effective amount of a compound of claim 1; wherein the cancer is hematologic cancers, non-small cell lung cancer, acoustic neuroma, acute leukemia, acute lymphocytic leukemia, acute myelocytic leukemia, adenocarcinoma, angiosarcoma, astrocytoma, acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, diffuse large B-cell lymphoma, dysproliferative changes, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, head and neck cancer, hemangioblastoma, hepatoma, hepatocellular cancer, hormone insensitive prostate cancer, leiomyosarcoma, leukemia, liposarcoma, liver cancer, lymphagioendotheliosarcoma, lymphangiosarcoma, lymphoblastic leukemia, lymphoma, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, malignant rhabdoid tumor (MRT), rhabdomyosarcoma, sarcoma, sebaceous gland carcinoma, seminoma, skin cancer, small cell lung carcinoma, small cell lung cancer, stomach cancer, squamous cell carcinoma, synovioma, sweat gland carcinoma, thyroid cancer, Waldenstrom's macroglobulinemia, testicular tumors, uterine cancer or Wilms' tumor.

* * * * *